United States Patent
Hatakeyama et al.

(10) Patent No.: US 10,864,366 B2
(45) Date of Patent: Dec. 15, 2020

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Osamu Watanabe, Joetsu (JP); Keisuke Niida, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 113 days.

(21) Appl. No.: 16/169,321

(22) Filed: Oct. 24, 2018

(65) Prior Publication Data

US 2019/0151648 A1    May 23, 2019

(30) Foreign Application Priority Data

Nov. 21, 2017 (JP) .................................. 2017-223618

(51) Int. Cl.
 *A61N 1/04* (2006.01)
 *A61L 27/50* (2006.01)
 (Continued)

(52) U.S. Cl.
 CPC .......... *A61N 1/0472* (2013.01); *A61B 5/0408* (2013.01); *A61L 27/50* (2013.01);
 (Continued)

(58) Field of Classification Search
 CPC .. A61N 1/0472; A61N 1/0496; A61N 1/0408; A61B 5/0408; A61B 2562/0209;
 (Continued)

(56) References Cited

U.S. PATENT DOCUMENTS

| | | | |
|---|---|---|---|
| 2004/0116641 A1 | 6/2004 | Mather et al. | |
| 2010/0119970 A1* | 5/2010 | Ohsawa ............... | C07D 307/93 430/270.1 |
| 2016/0155530 A1 | 6/2016 | Someya et al. | |

FOREIGN PATENT DOCUMENTS

| JP | H05-095924 A | 4/1993 |
|---|---|---|
| JP | H10-087834 A | 4/1998 |

(Continued)

*Primary Examiner* — Shane Fang
(74) *Attorney, Agent, or Firm* — Oliff PLC

(57) ABSTRACT

The present invention provides a bio-electrode composition including: a resin containing a urethane bond in a main chain and a silsesquioxane in a side chain; and an electro-conductive material, wherein the electro-conductive material is a polymer compound having one or more repeating units selected from fluorosulfonic acid salts shown by the following general formulae (1)-1 and (1)-2, sulfonimide salts shown by the following general formula (1)-3, and sulfonamide salts shown by the following general formula (1)-4. This can form a living body contact layer for a bio-electrode that is excellent in electric conductivity and biocompatibility, light in weight, manufacturable at low cost, and free from large lowering of the electric conductivity even when it is wetted with water or dried. The present invention also provides a bio-electrode in which the living body contact layer is formed from the bio-electrode composition, and a method for manufacturing the bio-electrode.

(1)-1

(Continued)

-continued

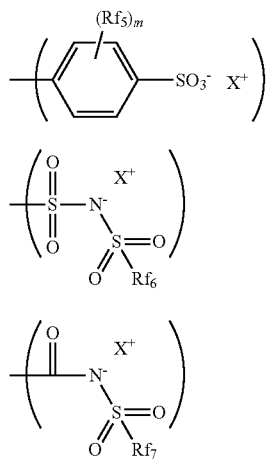

20 Claims, 2 Drawing Sheets

(51) Int. Cl.
| | |
|---|---|
| A61L 31/12 | (2006.01) |
| A61L 31/14 | (2006.01) |
| C07C 381/12 | (2006.01) |
| H01B 1/24 | (2006.01) |
| C08G 18/48 | (2006.01) |
| C08G 18/61 | (2006.01) |
| C08G 18/71 | (2006.01) |
| C08L 71/02 | (2006.01) |
| H05K 1/09 | (2006.01) |
| C08G 18/38 | (2006.01) |
| C08G 18/73 | (2006.01) |
| H01B 1/12 | (2006.01) |
| A61B 5/0408 | (2006.01) |
| C08G 18/79 | (2006.01) |
| C08G 18/66 | (2006.01) |
| C08L 43/04 | (2006.01) |
| C08G 18/32 | (2006.01) |
| C08G 18/75 | (2006.01) |

(52) U.S. Cl.
CPC ............ *A61L 31/126* (2013.01); *A61L 31/14* (2013.01); *A61N 1/0496* (2013.01); *C07C 381/12* (2013.01); *C08G 18/3206* (2013.01); *C08G 18/3212* (2013.01); *C08G 18/3893* (2013.01); *C08G 18/4825* (2013.01); *C08G 18/4833* (2013.01); *C08G 18/4854* (2013.01); *C08G 18/61* (2013.01); *C08G 18/6666* (2013.01); *C08G 18/718* (2013.01); *C08G 18/73* (2013.01); *C08G 18/755* (2013.01); *C08G 18/758* (2013.01); *C08G 18/792* (2013.01); *C08L 43/04* (2013.01); *C08L 71/02* (2013.01); *H01B 1/12* (2013.01); *H01B 1/24* (2013.01); *H05K 1/09* (2013.01); *H05K 1/095* (2013.01); *A61B 2562/0209* (2013.01); *A61B 2562/125* (2013.01); *A61N 1/0408* (2013.01); *H05K 2201/026* (2013.01); *H05K 2201/0209* (2013.01); *H05K 2201/0221* (2013.01); *H05K 2201/0257* (2013.01); *H05K 2201/0323* (2013.01)

(58) Field of Classification Search
CPC . A61B 2562/125; A61L 27/50; A61L 31/126; A61L 31/14; C07C 381/12; C08G 18/3206; C08G 18/3212; C08G 18/3893; C08G 18/4825; C08G 18/4833; C08G 18/4854; C08G 18/61; C08G 18/6666; C08G 18/718; C08G 18/73; C08G 18/755; C08G 18/758; C08G 18/792; C08L 43/04; C08L 71/02; H01B 1/12; H01B 1/24; H05K 1/09; H05K 1/095; H05K 2201/0209; H05K 2201/0221; H05K 2201/0257; H05K 2201/026; H05K 2201/0323
See application file for complete search history.

(56) References Cited

FOREIGN PATENT DOCUMENTS

| | | |
|---|---|---|
| JP | 2003-225217 A | 8/2003 |
| JP | 2004-033468 A | 2/2004 |
| JP | 2005-320418 A | 11/2005 |
| JP | 2006-503170 A | 1/2006 |
| JP | 2010-113209 A | 5/2010 |
| JP | 2011-201955 A | 10/2011 |
| JP | 2012-152725 A | 8/2012 |
| JP | 2015-019806 A | 2/2015 |
| JP | 2015-100673 A | 6/2015 |
| WO | 2013/039151 A1 | 3/2013 |

* cited by examiner

BIO-ELECTRODE COMPOSITION, BIO-ELECTRODE, AND METHOD FOR MANUFACTURING BIO-ELECTRODE

TECHNICAL FIELD

The present invention relates to: a bio-electrode, which is in contact with living skin and can detect physical conditions such as a heart rate on the basis of electric signals from the skin, and a method for manufacturing the same, as well as a bio-electrode composition that is usable for a bio-electrode suitably.

BACKGROUND ART

In recent years, wearable devices have been developed progressively with the spread of Internet of Things (IoT). Representative examples thereof include a watch and eyeglasses that can be connected with internet. Wearable devices that can always monitor physical conditions are also necessary in a medical field and a sports field, and are expected to be a growth field in the future.

In the medical field, for example, wearable devices to monitor organic conditions have been investigated as in an electrocardiogram measurement, which detects heart beats by concentration change of ions released from skin in synchronism with the heart beats. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, bio-electrodes used for a medical wearable device have to keep the electric conductivity unchanged and not to cause skin allergies even when being used for a long time. In addition to these, it is desirable that the bio-electrode is light in weight and can be manufactured at low cost.

Medical wearable devices include a type in which the device is attached to a body and a type in which the device is incorporated into clothes. As the type in which the device is attached to a body, it has been proposed a bio-electrode using water soluble gel containing water and electrolyte, which are materials of the foregoing electro-conductive paste (Patent Literature 1). On the other hand, as the type in which the device is incorporated into clothes, it has been proposed a means to use cloth in which an electro-conductive polymer such as poly-3,4-ethylenedioxythiophene-polystyrenesulfonate (PEDOT-PSS) or silver paste is incorporated into the fibers for electrodes (Patent Literature 2).

When using the foregoing water soluble gel containing water and electrolyte, however, the electric conductivity is lost as the water is lost due to drying. On the other hand, some people can suffer from skin allergies by the use of metal with high ionization tendency such as copper. The use of an electro-conductive polymer such as PEDOT-PSS also has a higher risk of skin allergies due to the strong acidity of the electro-conductive polymer.

One of the roles of bio-electrodes includes conversion of concentration change of ions released from skin to electric signals. Accordingly, they have to have higher ionic conductivity. The bio-electrode of water-soluble gel electrolyte has higher ionic conductivity. On the other hand, the use of metal having higher electron conductivity such as silver or gold as a bio-electrode causes inferior electric conductance and higher resistance between the bio-electrode and skin. It has been investigated to use metal nanowire, carbon black, carbon nanotube, etc., which have excellent electron conductivity, as an electrode material (Patent Literatures 3, 4, and 5). These bio-electrodes, however, fails to exhibit high performance of bio-electrodes by the reason described above.

To improve the ionic conductivity of solid-state batteries and so forth, it has been investigated to combine ionic electrolyte and polyethylene glycol. The ionic conduction is brought by ions hopping on the polyethylene glycol chain.

It has started to use silicone for use such as medical tubes and so on since silicone is excellent in biocompatibility and repels water such as perspiration. However, it is difficult to use silicone for bio-electrodes since silicone is an insulating material.

Urethane may be usable for bio-electrodes since urethane is also excellent in biocompatibility, and the electric insulation property is not so high as that of silicone. Urethane, however, has higher hydrophilicity and is hydrolysable, thereby being unsuitable for uses that involve contact with skin for a long time.

In order to prevent the hydrolysis of polyurethane, polyurethane having a silicone main chain has been investigated (Patent Literature 6). Urethane resins having a ladder- or cage-type silsesquioxane have also been proposed (Patent Literatures 7, 8). It is demonstrated that hybridizing a glassy silsesquioxane and a stretchable urethane can provide shape memory properties.

When the bio-electrode is away from skin, it becomes impossible to obtain information from the body. Just the change of contact area fluctuates the quantity of electricity to be conducted, thereby fluctuating the baseline of an electrocardiogram (electric signals). Accordingly, the bio-electrode has to be in contact with skin continually without changing the contact area in order to obtain stable electric signals from a body. For that purpose, the bio-electrode preferably has tackiness. It also needs stretchability and flexibility to cope with expansion and contraction as well as change of bending of skin.

Urethane is processible to a soft gel state after curing. Water-containing bio-electrodes based on urethane gel have been proposed for the bio-electrode use described above (Patent Literature 9).

CITATION LIST

Patent Literatures

Patent Literature 1: International Patent Laid-Open Publication No. WO 2013-039151
Patent Literature 2: Japanese Unexamined Patent Application Publication No. 2015-100673
Patent Literature 3: Japanese Unexamined Patent Application Publication No. H5-095924
Patent Literature 4: Japanese Unexamined Patent Application Publication No. 2003-225217
Patent Literature 5: Japanese Unexamined Patent Application Publication No. 2015-019806
Patent Literature 6: Japanese Unexamined Patent Application Publication No. 2005-320418
Patent Literature 7: Japanese Unexamined Patent Application Publication No. H10-87834
Patent Literature 8: Japanese PCT National Publication No. 2006-503170
Patent Literature 9: Japanese Unexamined Patent Application Publication No. 2011-201955

SUMMARY OF THE INVENTION

Technical Problem

The present invention has been accomplished to solve the foregoing problems, and an object thereof is to provide a bio-electrode composition capable of forming a living body contact layer for a bio-electrode that is excellent in electric conductivity and biocompatibility, light in weight, manufacturable at low cost, and free from large lowering of the electric conductivity even when it is wetted with water or dried; a bio-electrode in which the living body contact layer is formed from the bio-electrode composition; and a method for manufacturing the bio-electrode.

Solution to Problem

To solve the above problems, the present invention provides a bio-electrode composition comprising:
a resin containing a urethane bond in a main chain and a silsesquioxane in a side chain; and
an electro-conductive material,
wherein the electro-conductive material is a polymer compound having one or more repeating units selected from the group consisting of fluorosulfonic acid salts shown by the following general formulae (1)-1 and (1)-2, sulfonimide salts shown by the following general formula (1)-3, and sulfonamide salts shown by the following general formula (1)-4,

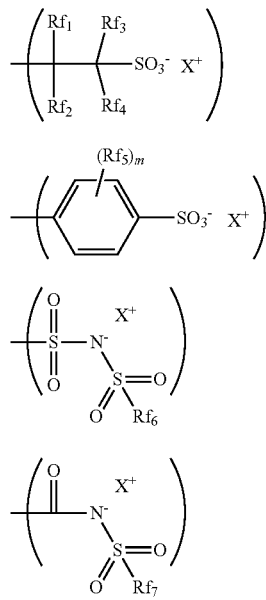

wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

wherein $R^1$ to $R^4$ each represent a hydrogen atom, a linear, branched, or cyclic alkyl group having 1 to 20 carbon atoms, an ether group, a thiol group, an ester group, a carbonyl group, a sulfonyl group, a cyano group, an amino group, a nitro group, or an alkenyl group having 6 to 10 carbon atoms, optionally having a halogen atom, and optionally bonded to each other to form a ring.

The inventive bio-electrode composition is capable of forming a living body contact layer for a bio-electrode that is excellent in electric conductivity and biocompatibility, light in weight, manufacturable at low cost, and free from large lowering of the electric conductivity even when it is wetted with water or dried.

It is preferable that the one or more repeating units selected from the group consisting of fluorosulfonic acid salts shown by the general formulae (1)-1 and (1)-2, sulfonimide salts shown by the general formula (1)-3, and sulfonamide salts shown by the general formula (1)-4 be one or more repeating units selected from repeating units a1 to a7 shown by the following general formulae (2),

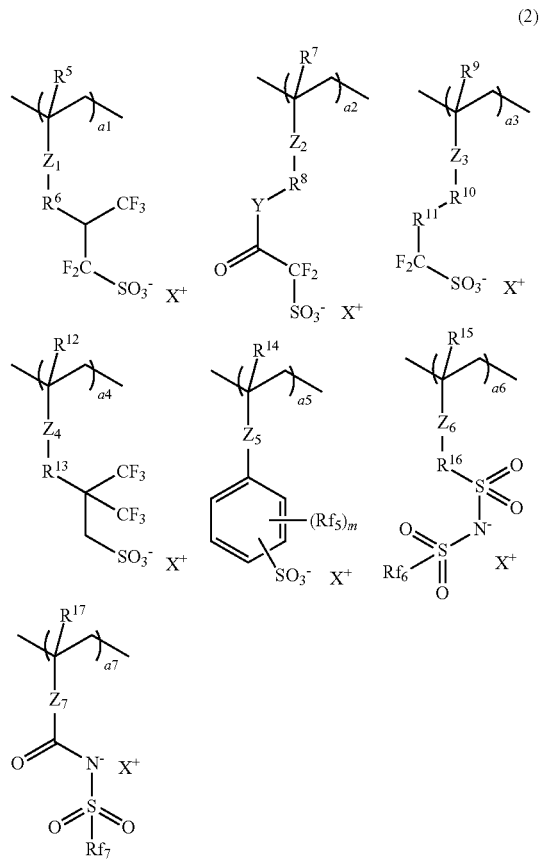

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, and $R^{16}$ each independently represent any of a single bond, an ester group, and a linear, branched, or cyclic hydrocarbon group having 1 to 12 carbon atoms and optionally having either or both of an ether group and an ester group; $R^{11}$ represents a linear or branched alkylene group having 1 to 4 carbon atoms, and one or two of the hydrogen atoms in $R^{11}$ are each optionally substituted with a fluorine atom; $Z_1$, $Z_2$, $Z_3$ $Z_4$, and $Z_6$ each independently represent any of a single bond, a phenylene group, a naphthylene group, an ether group, an ester group, and an amide group; $Z_5$ represents any of a single bond, an ether group, and an ester group; $Z_7$ represents a single bond, an arylene group having 6 to 12 carbon atoms, or —C(=O)—O—$Z^8$—; $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{18}$— group; $R^{18}$ represents a hydrogen atom, or a linear or branched alkyl group having 1 to 4 carbon atoms, optionally bonded to $R^8$ to form a ring; "m" is an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 \leq a1+a2+a3+a4+a5+a6+a7$ 1.0; and $Rf_5$, $Rf_6$, $Rf_7$, and $X^1$ have the same meanings as defined above.

With the bio-electrode composition using an electro-conductive material that has the repeating unit like this, the effect of the present invention can be more improved.

The electro-conductive material is preferably a polymer compound having a repeating unit of a sulfonamide salt shown by the general formula (1)-4.

The bio-electrode composition using an electro-conductive material that has the repeating unit like this is favorably used for a bio-electrode with lower irritant to skin.

It is preferable that the resin containing a urethane bond in a main chain and a silsesquioxane in a side chain have a structure shown by the following general formula (3),

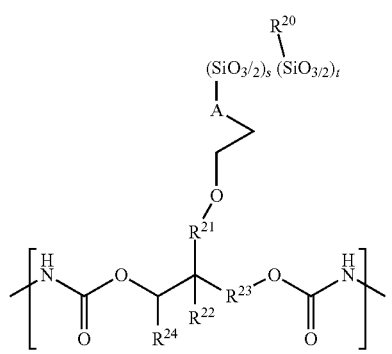

(3)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0 < s \leq 0.2$ and $0.8 \leq t < 1.0$.

The bio-electrode composition that contains a resin containing a urethane bond in a main chain and a silsesquioxane in a side chain like this is favorably used for bio-electrode with really excellent repellency.

It is preferable that the resin containing a urethane bond in a main chain and a silsesquioxane in a side chain have a structure containing a polyether main chain shown by the following general formula (4),

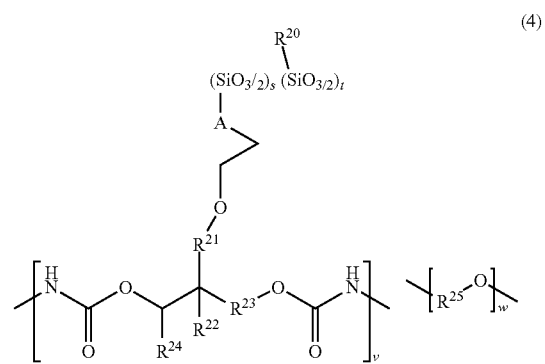

(4)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; "s" and "t" satisfy $0 < s \leq 0.2$ and $0.8 \leq t < 1.0$; $R^{25}$ represents a linear, branched, or cyclic alkylene group having 2 to 12 carbon atoms; and "v" and "w" satisfy $0 < v < 1.0$ and $0 < w < 1.0$.

The bio-electrode composition that contains a resin containing a urethane bond in a main chain and a silsesquioxane in a side chain like this is favorably used for a bio-electrode that is more flexible and excellent in ionic conductivity.

It is preferable that the resin containing a urethane bond in a main chain and a silsesquioxane in a side chain be a reaction product of a diol compound shown by the following general formula (5), a polyether compound having a hydroxy group at a terminal, and a compound having an isocyanate group,

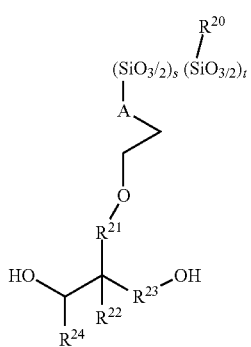

(5)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0<s\leq0.2$ and $0.8\leq t<1.0$.

It is preferable that the resin containing a urethane bond in a main chain and a silsesquioxane in a side chain be a reaction product of a diol compound shown by the following general formula (6) and a compound having an isocyanate group,

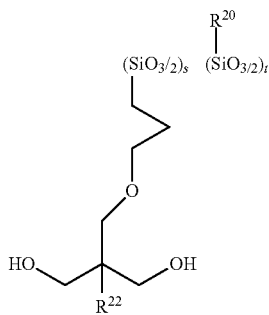

(6)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{22}$ represents a hydrogen atom or a linear alkyl group having 1 to 4 carbon atoms; and "s" and "t" satisfy $0<s\leq0.2$ and $0.8\leq t<1.0$.

The bio-electrode composition that contains a resin containing a urethane bond in a main chain and a silsesquioxane in a side chain like this facilitates to form a living body contact layer for a bio-electrode that is excellent in electric conductivity and biocompatibility, light in weight, manufacturable at low cost, and free from large lowering of the electric conductivity even when it is wetted with water or dried.

It is preferable that the diol compound shown by the general formula (6) be a reaction product of substances shown by the following general formulae (7)-1 and (7)-2,

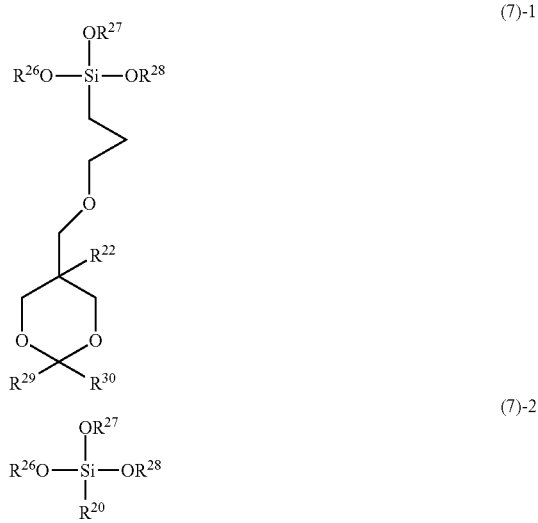

wherein $R^{20}$ and $R^{22}$ have the same meanings as defined above; $R^{26}$ to $R^{28}$ each represent an alkyl group having 1 to 6 carbon atoms; and $R^{29}$ and $R^{30}$ each represent a hydrogen atom, a linear, branched, or cyclic alkyl group having 1 to 20 carbon atoms and optionally bonded to the other to form a ring, or an aryl group having 6 to 10 carbon atoms.

The bio-electrode composition that contains a resin containing a urethane bond in a main chain and a silsesquioxane in a side chain like this can be produced more easily.

It is preferable that the bio-electrode composition further comprise an organic solvent.

This further improves the coating properties of the bio-electrode composition.

It is preferable that the bio-electrode composition further comprise a carbon material.

The bio-electrode composition like this is capable of forming a living body contact layer with more improved electric conductivity.

It is preferable that the carbon material be either or both of carbon black and carbon nanotube.

In the bio-electrode composition of the present invention, it is possible to use these carbon materials particularly favorably.

The present invention also provides a bio-electrode comprising an electro-conductive base material and a living body contact layer formed on the electro-conductive base material, wherein the living body contact layer is a cured material of the bio-electrode composition described above.

The inventive bio-electrode is excellent in electric conductivity and biocompatibility, light in weight, manufacturable at low cost, and free from large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

In the bio-electrode of the present invention, it is possible to use the electro-conductive base material like this particularly favorably.

The present invention also provides a method for manufacturing a bio-electrode having an electro-conductive base material and a living body contact layer formed on the electro-conductive base material, comprising:

applying the bio-electrode composition described above onto the electro-conductive base material; and curing the bio-electrode composition; thereby forming the living body contact layer.

The inventive method for manufacturing a bio-electrode makes it possible to easily manufacture a bio-electrode that is excellent in electric conductivity and biocompatibility, light in weight, manufacturable at low cost, and free from large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

The electro-conductive base material like this is usable for the inventive method for manufacturing a bio-electrode particularly favorably.

Advantageous Effects of Invention

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. The electric conductivity can be more improved by adding a carbon material. It is possible to manufacture a bio-electrode with high flexibility and stretchability to be always in contact with skin by combining flexible urethane gel. Accordingly, the inventive bio-electrode, with the living body contact layer being formed by using the inventive bio-electrode composition like this, is particularly suitable as a bio-electrode used for a medical wearable device. Moreover, the inventive method for manufacturing a bio-electrode makes it possible to manufacture such a bio-electrode easily at low cost.

DESCRIPTION OF EMBODIMENTS

Figure 1:
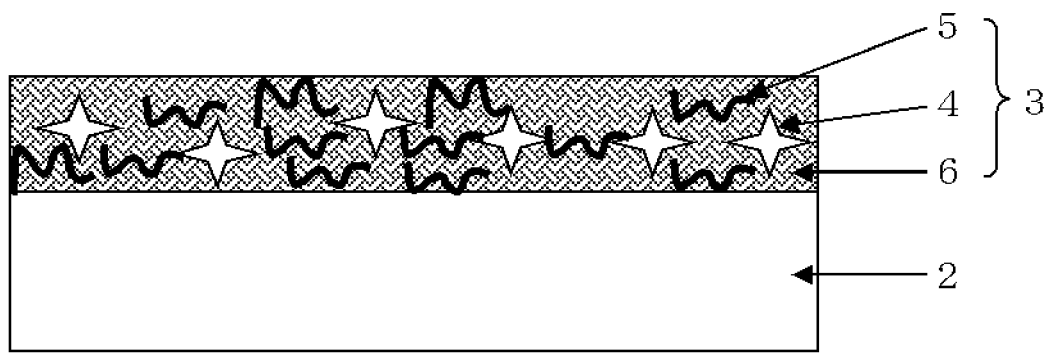
FIG. 1 is a schematic sectional view showing an example of the inventive bio-electrode.

As described above, it has been desired to develop a bio-electrode composition capable of forming a living body contact layer for a bio-electrode that is excellent in electric conductivity and biocompatibility, light in weight, manufacturable at low cost, and free from large lowering of the electric conductivity even when it is wetted with water or dried; a bio-electrode in which the living body contact layer is formed from the bio-electrode composition; and a method for manufacturing the same.

The bio-electrode has a function to convert concentration change of ions released from skin to electric signals. Accordingly, it is necessary to increase the ionic conductivity in the film. Metal films have very high electron conductivity, but have lower performance as a bio-electrode. This is due to lower ionic conductivity of metal films. Water or polar solvent that contains ions has higher ionic conductivity, and bio-electrodes of water-soluble gel that contain hydrous water-soluble polymers and ions have been used widely. However, it has a drawback of lowering the ionic conductivity when the water is dried as described above. It has been required for a dry bio-electrode with high ionic conductivity without containing water or organic solvent.

The method for improving the ionic conductivity other than the addition of a salt of ion electrolyte includes combining polyether or polycarbonate and a salt. The ions move on the oxygen functional groups of these polymers such that they are hopping. In comparison between polyether and polycarbonate, polyether has stretchability, but polycarbonate does not have stretchability. Since the bio-electrode adhered on skin has to stretch along with the expansion and contraction of skin, polyether is more preferable.

The bio-electrode film composed of a bio-electrode composition is required to be always in contact with skin without fluctuating the area. Fluctuation of contact area is not preferable since it changes the electric conductivity. Accordingly, the bio-electrode film has to be a soft film. A film that is not only soft but also tacky can stably obtain information from skin all the time. A soft and tacky bio-electrode in a gel state can be always in contact with skin to give stable biological signals. Polyurethane in which a polyether group is introduced is excellent in flexibility. In this case, the urethane resin is formed by the reaction of an isocyanate compound and polyether having hydroxy groups at the terminals. A soft urethane resin with tackiness in a gel state can be produced by reducing the crosslinking density.

Illustrative examples of the salt of ion electrolyte include ionic liquid. Ionic liquids are characterized by high thermal and chemical stability as well as excellent electric conductivity, thereby having been widely used for battery uses. Illustrative examples of known ionic liquid include hydrochloric acid salt, hydrobromic acid salt, hydroiodic acid salt, tri fluoromethanesulfonic acid salt, nonafluorobutanesulfonic acid salt, bis(trifluoromethanesulfonyl)imidic acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate. Therefore, in a bio-electrode in which the living body contact layer is formed from an adhesive composition with these salts added, there is a defect of lowering the electric conductivity due to extraction of the salt with perspiration or by washing. In addition, there are problems that the tetrafluoroborate salt is highly toxic, and the other salts have high solubility in water to easily permeate into skin, each of which causes rough dry skin (i.e., highly irritative to skin).

Additionally, urethane resins have higher hydrophilicity and are degraded by gradual hydrolysis of the urethane bonds. To decrease the hydrolysis, it is effective to increase the hydrophobicity. Accordingly, silicone-urethanes having a silicone bond have been investigated. A urethane resin in which silicone is introduced into the main chain has both of a silicone part and a urethane part in the main chain. In this case, introduction of silicone lowers the stretchability and the strength. This is because silicone has lower strength compared to urethane. However, when silicone of a silsesquioxane is introduced into the side chain, the strength is rather improved far from being lowered. This is probably due to increased hydrogen bonding of the urethane bond caused by introduction of the side chain type silicone. The side chain silicone is capable of increasing the repellency more effectively. Introducing silsesquioxane silicone into the side chain not only increases the tensile strength but also improves the tackiness.

For highly-sensitive bio-electrodes, which can detect weak biological signals, higher ionic conductivity is necessary. Silicones are insulators, but urethanes are allowed to have improved ionic conductivity by introducing polyether into the chain extending part. From this viewpoint, urethanes that have polyethers introduced into the main chain are preferable rather than urethanes that have polysiloxanes introduced into the main chain. Among the polyethers, polyethylene glycol chains have highest electric conductivity and are preferable.

Accordingly, the inventors have diligently investigated the above problems to find that bio-electrode compositions that contain a resin containing a urethane bond in a main chain and a silsesquioxane in a side chain excel in repellency, electric conductivity, and tackiness. Further, the inventors have found that bio-electrode compositions with the electro-conductive material being a polymeric salt do not cause lowering of electric conductivity due to water extraction or passing through skin to irritate the skin; thereby bringing the present invention to completion.

That is, the present invention is a bio-electrode composition comprising:

a resin containing a urethane bond in a main chain and a silsesquioxane in a side chain; and an electro-conductive material, wherein the electro-conductive material is a polymer compound having one or more repeating units selected from the group consisting of fluorosulfonic acid salts shown by the following general formulae (1)-1 and (1)-2, sulfonimide salts shown by the following general formula (1)-3, and sulfonamide salts shown by the following general formula (1)-4,

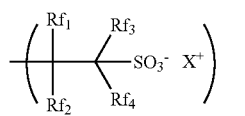
(1)-1

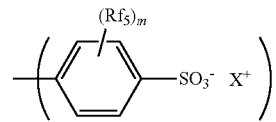
(1)-2

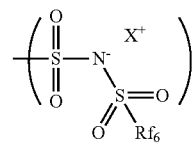
(1)-3

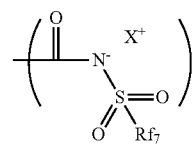
(1)-4 wherein $Rf_1$ and $Rf_2$ each represent a hydrogen atom, a fluorine atom, a trifluoromethyl group, or an oxygen atom, provided that when $Rf_2$ represents an oxygen atom, $Rf_2$ also represents an oxygen atom to form a carbonyl group together with a carbon atom bonded therewith; $Rf_2$ and $Rf_4$ each represent a hydrogen atom, a fluorine atom, or a trifluoromethyl group, provided that one or more fluorine atoms are contained in $Rf_2$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

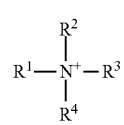
(1)-5 wherein $R^1$ to $R^4$ each represent a hydrogen atom, a linear, branched, or cyclic alkyl group having 1 to 20 carbon atoms, an ether group, a thiol group, an ester group, a carbonyl group, a sulfonyl group, a cyano group, an amino group, a nitro group, or an alkenyl group having 6 to 10 carbon atoms, optionally having a halogen atom, and optionally bonded to each other to form a ring.

Hereinafter, the present invention will be described specifically, but the present invention is not limited thereto.

<Bio-Electrode Composition>

The inventive bio-electrode composition contains an electro-conductive material (polymeric ionic material) and a resin containing a urethane bond on a main chain and a silsesquioxane group on a side chain. Hereinafter, each component will be described more specifically.

[Electro-Conductive Material (Salt)]

The salt to be added to the inventive bio-electrode composition as an electro-conductive material is a polymer compound having one or more repeating units selected from the group consisting of fluorosulfonic acid salts shown by the following general formulae (1)-1 and (1)-2, sulfonimide salts shown by the following general formula (1)-3, and sulfonamide salts shown by the following general formula (1)-4,

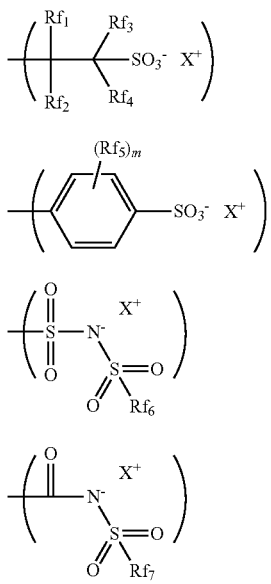

(1)-1

(1)-2

(1)-3

(1)-4 wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

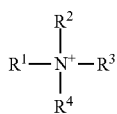

(1)-5 wherein $R^1$ to $R^4$ each represent a hydrogen atom, a linear, branched, or cyclic alkyl group having 1 to 20 carbon atoms, an ether group, a thiol group, an ester group, a carbonyl group, a sulfonyl group, a cyano group, an amino group, a nitro group, or an alkenyl group having 6 to 10 carbon atoms, optionally having a halogen atom, and optionally bonded to each other to form a ring.

The electro-conductive material used for the inventive bio-electrode composition, being the salt as described above, is excellent in electric conductivity, and being a polymeric salt (ionic polymer), has extremely low water solubility and does not pass through skin.

The irritation to skin is higher as the acid is stronger before neutralization with sodium, potassium, ammonium, etc. Among the electro-conductive materials described above, the sulfonamide shown by the formula (1)-4 has the lowest acidity and thereby lowest irritation to skin, and is preferably used.

It is preferable that the one or more repeating units selected from the group consisting of fluorosulfonic acid salts shown by the formulae (1)-1 and (1)-2, sulfonimide salts shown by the formula (1)-3, and sulfonamide salts shown by the formula (1)-4 be one or more repeating units selected from repeating units a1 to a7 shown by the following formulae (2),

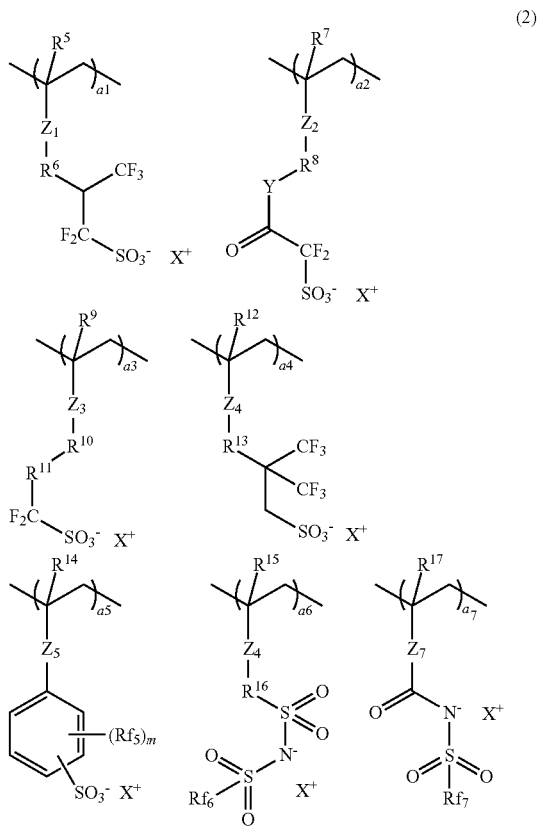

(2)

In the formula, $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, and $R^{16}$ each independently represent any of a single bond, an ester group, and a linear, branched, or cyclic hydrocarbon group having 1 to 12 carbon atoms and optionally having either or both of an ether group and an ester group; $R^{11}$ represents a linear or branched alkylene group having 1 to 4 carbon atoms, and one or two of the hydrogen atoms in $R^{11}$ are each optionally substituted with a fluorine atom; $Z_1$, $Z_2$, $Z_3$, $Z_4$, and $Z_6$ each independently represent any of a single bond, a phenylene group, a naphthylene group, an ether group, an ester group, and an amide group; $Z_5$ represents any of a single bond, an ether group, and an ester group; $Z_7$ represents a single bond, an arylene group having 6 to 12 carbon atoms, or —C(=O)—O—$Z^8$—; $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{18}$-group; $R^{18}$ represents a hydrogen atom, or a linear or branched alkyl group having 1 to 4 carbon atoms, optionally bonded to $R^8$ to form a ring; "m" is an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \le a5 \le 1.0$, $0 \le a6 \le 1.0$, $0 \le a7 \le 1.0$, and $0 < a1+a2+a3+a4+a5+a6+a7 \le 1.0$; and $Rf_5$, $Rf_6$, $Rf_7$, and $X^+$ have the same meanings as defined above.
The fluorosulfonic acid salt monomer to obtain the repeating unit a1 in the formulae (2) is not particularly limited, and specific illustrative examples thereof include the following.
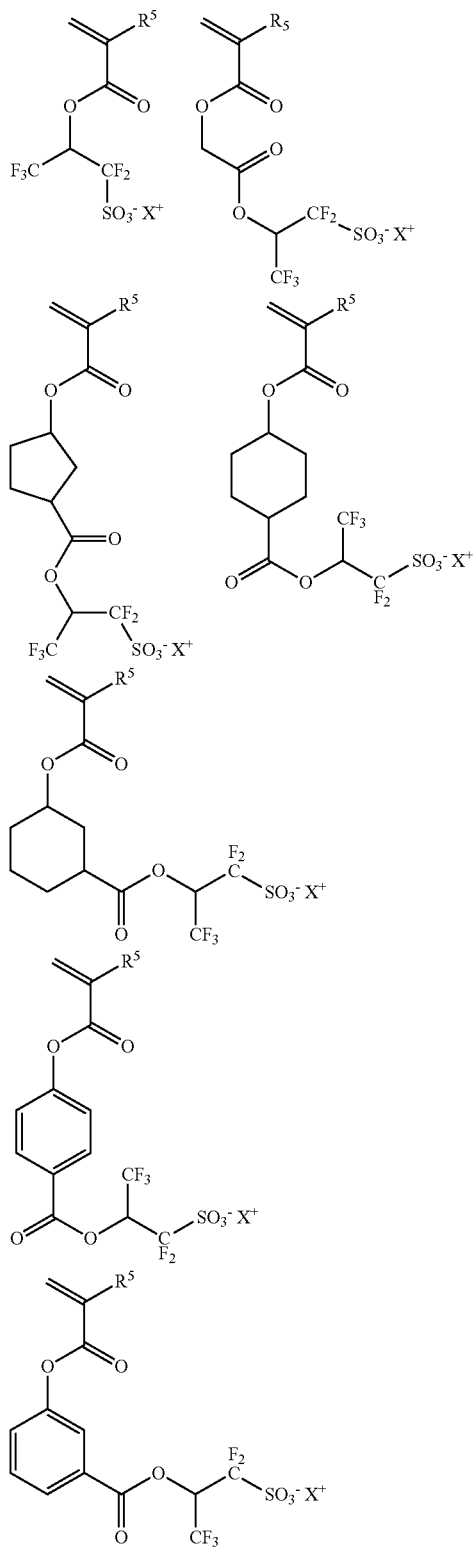
-continued
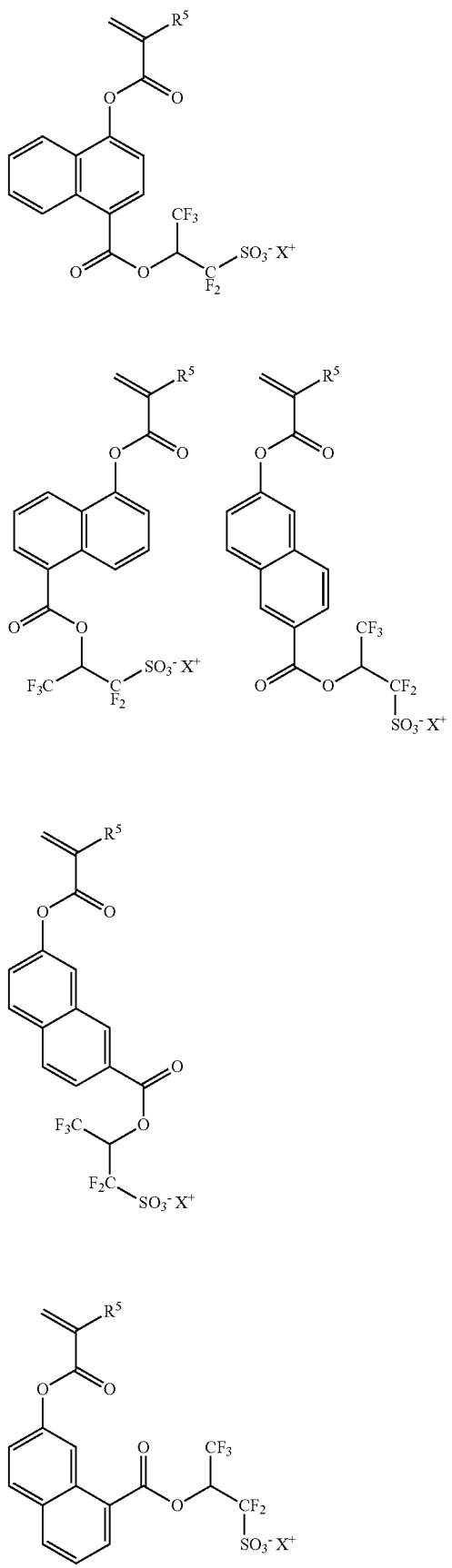

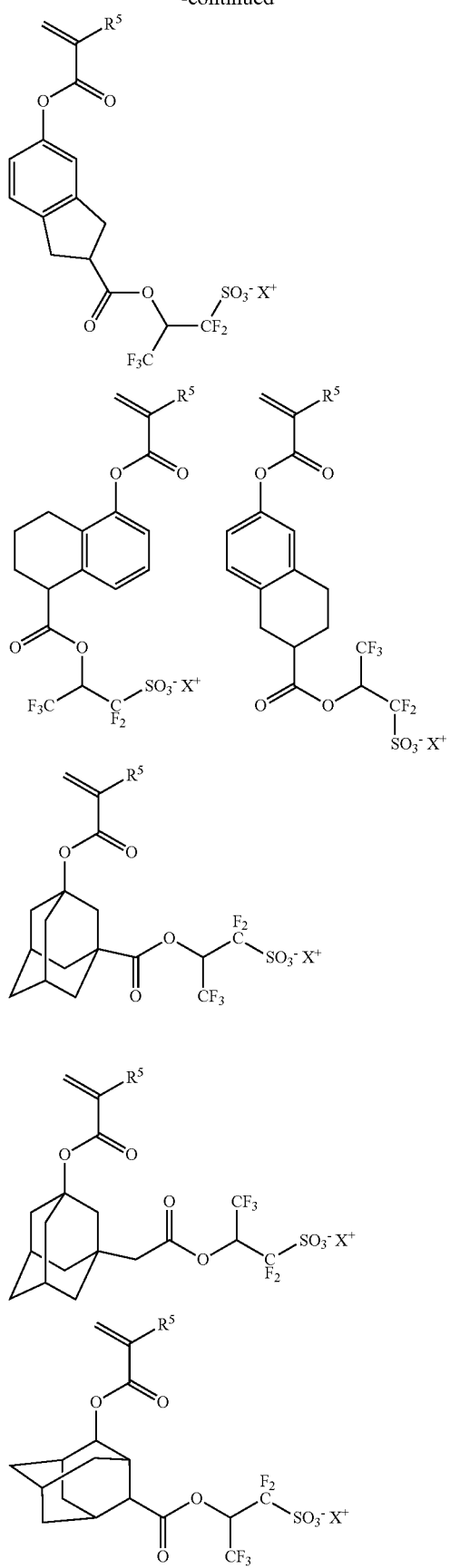
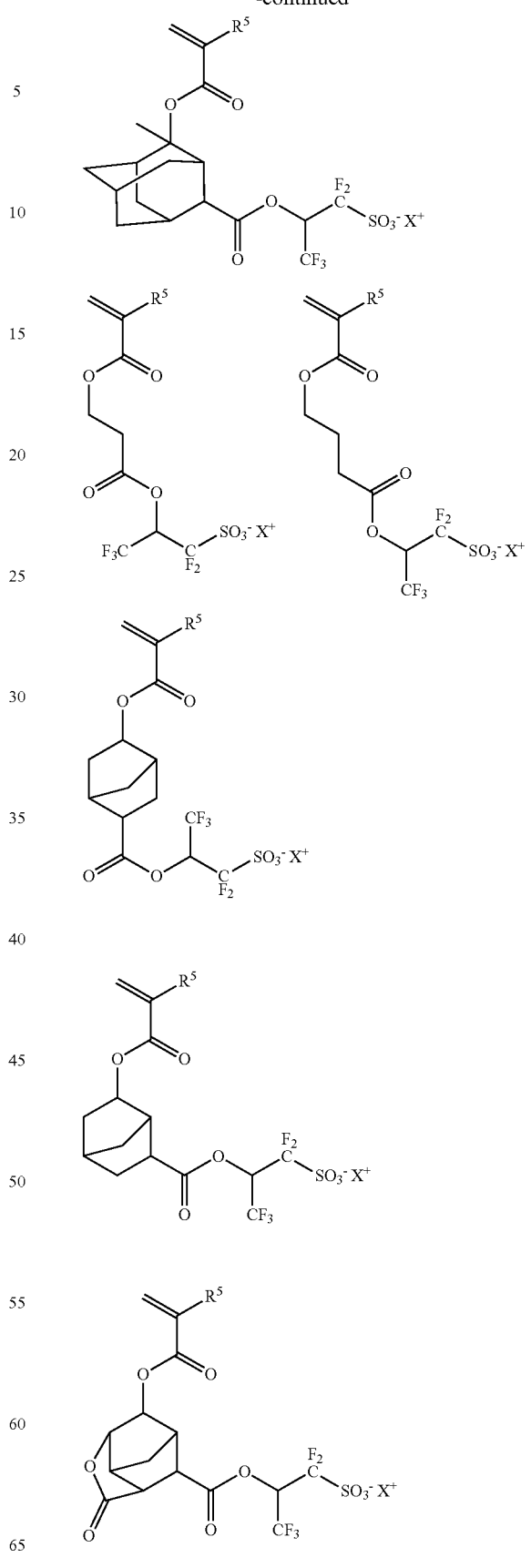

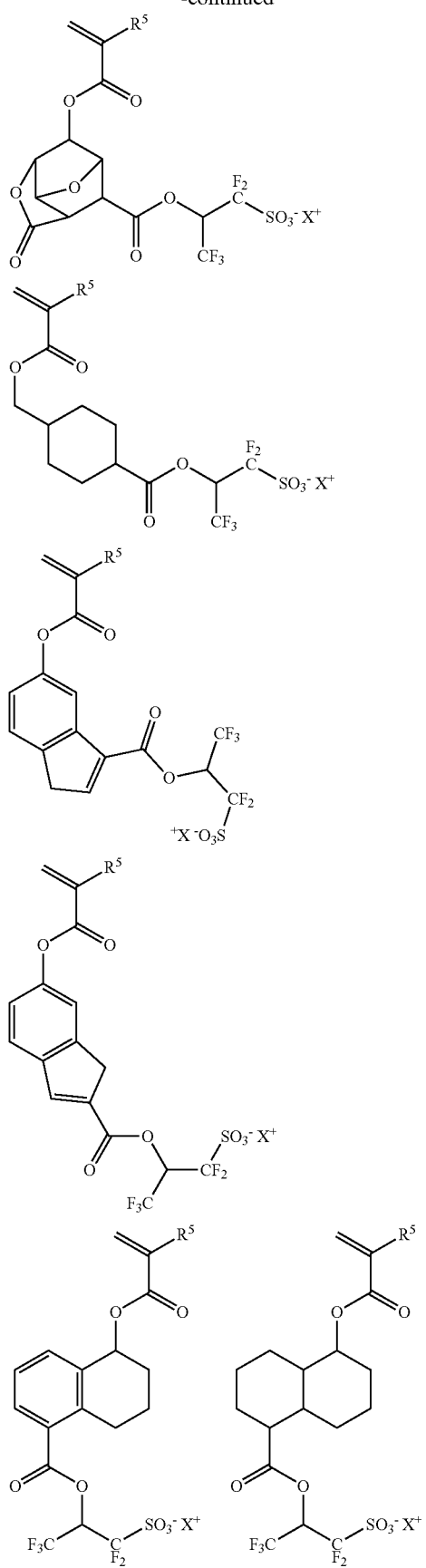
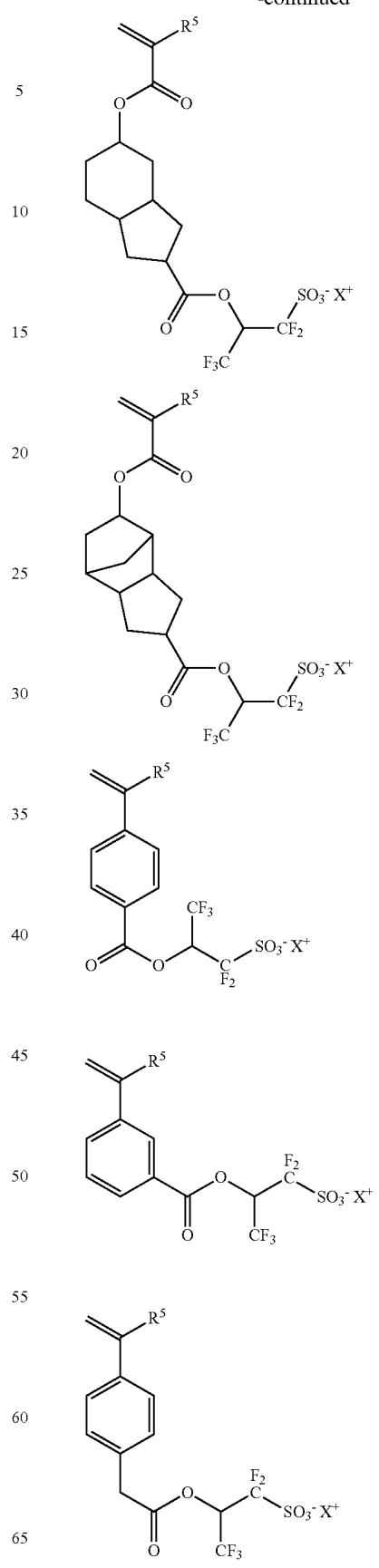

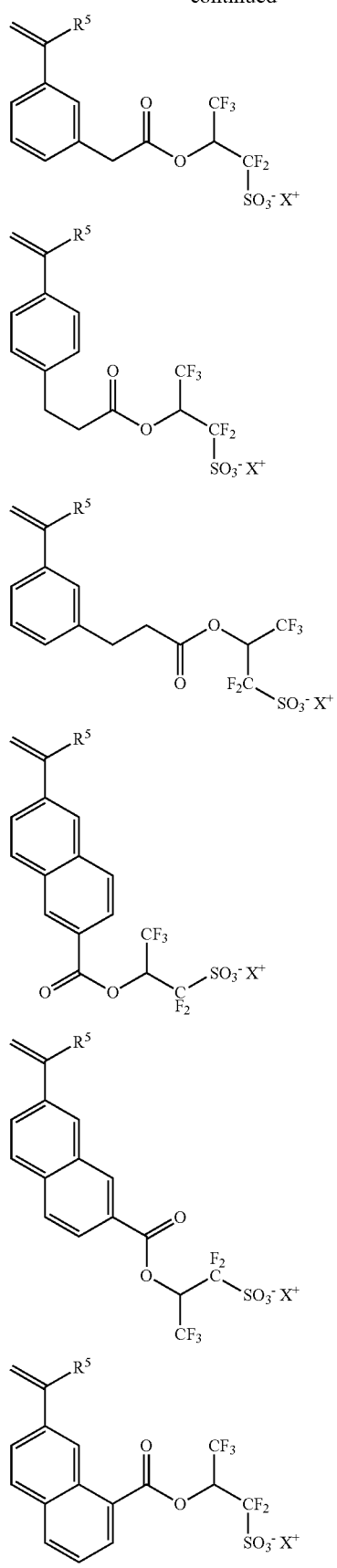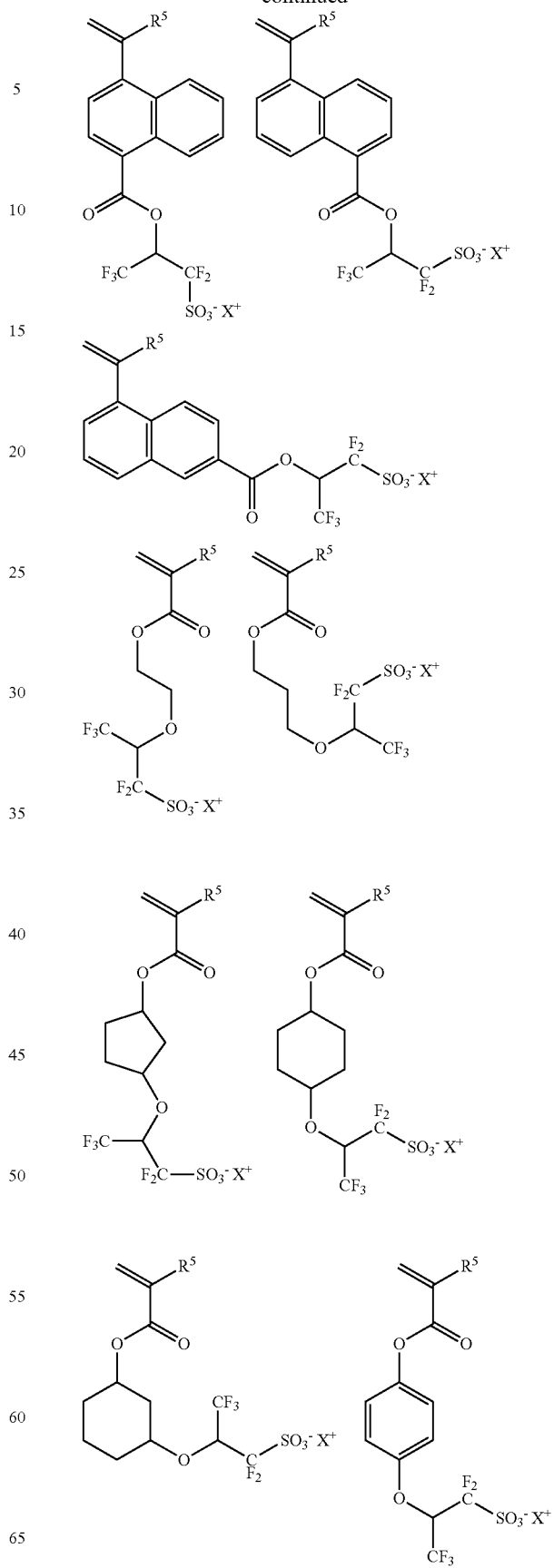

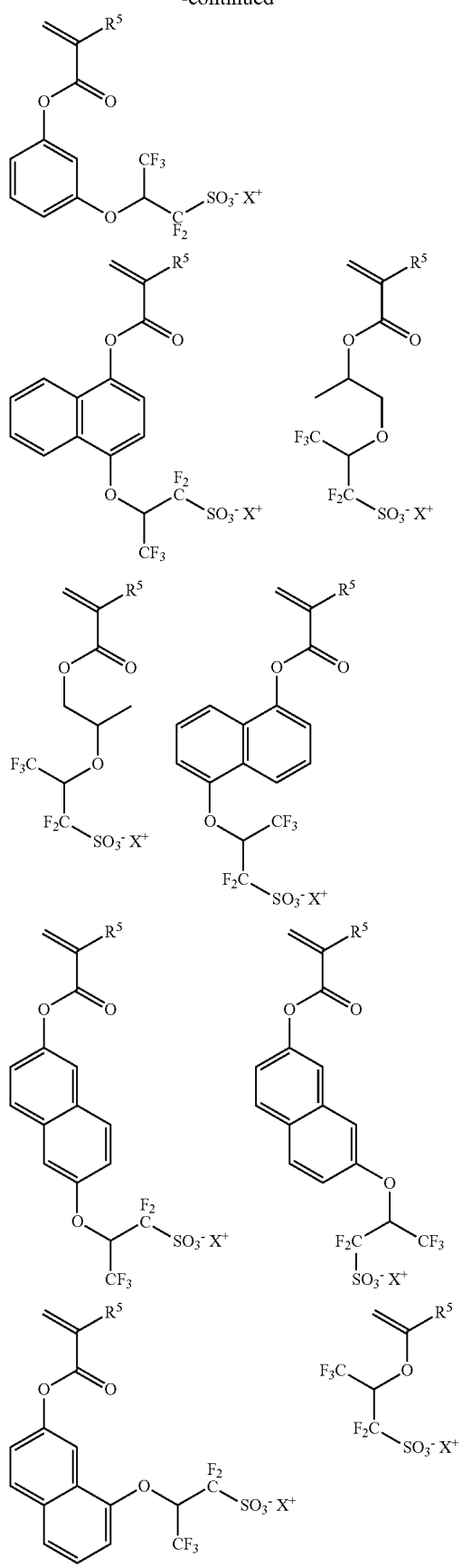
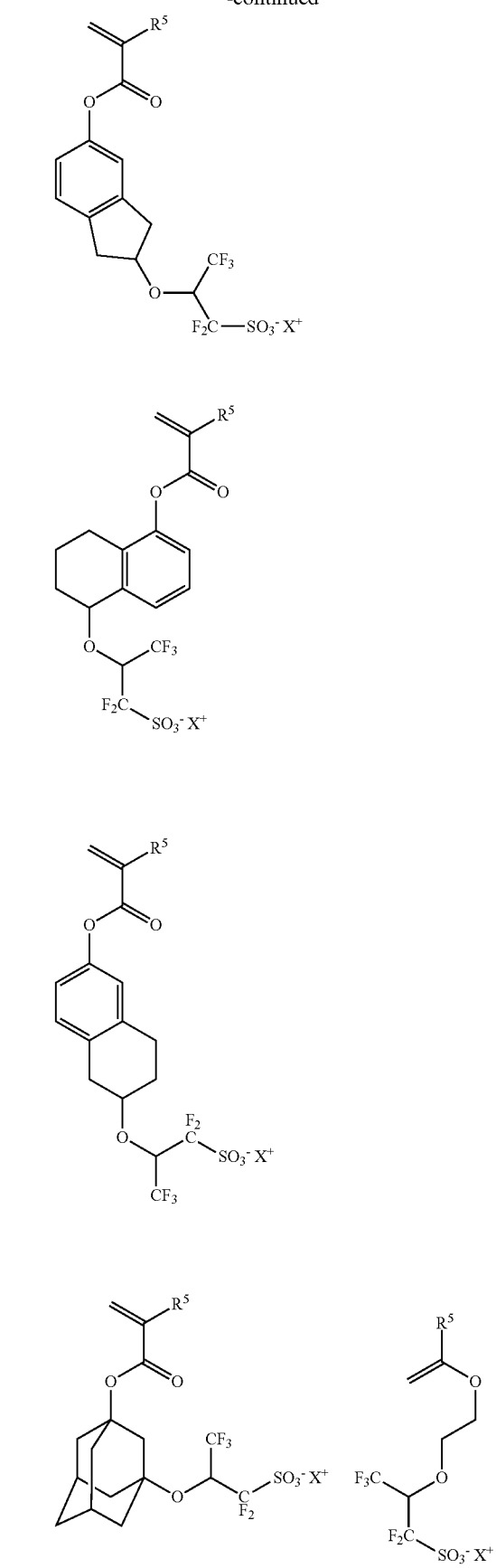

-continued
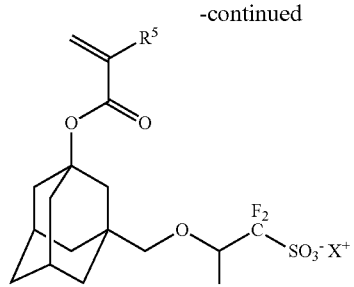
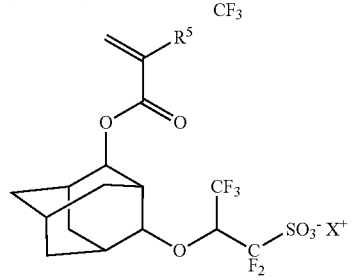
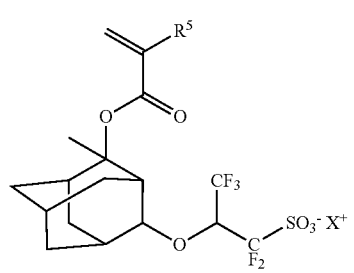
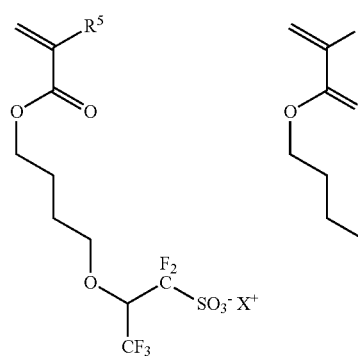
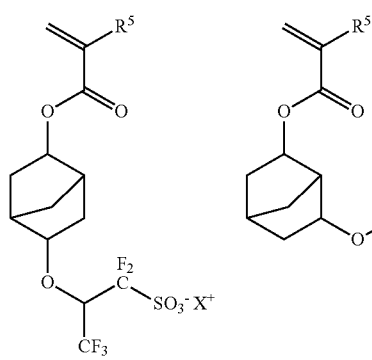
-continued
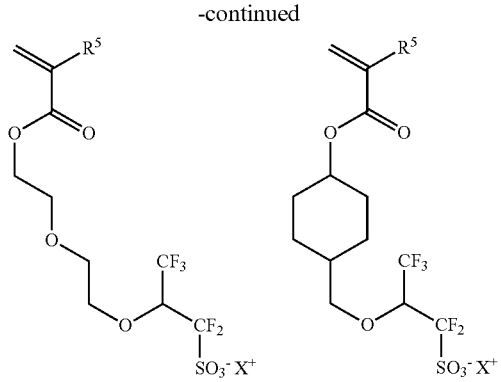
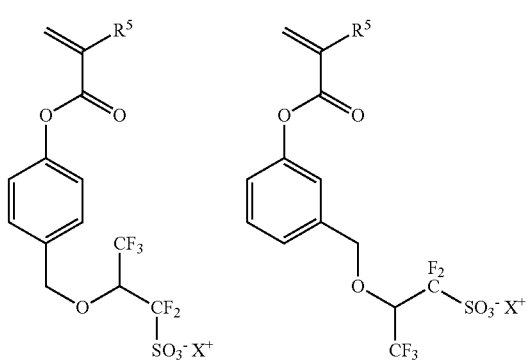
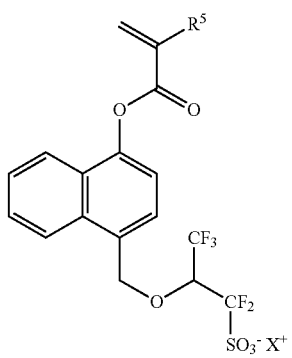
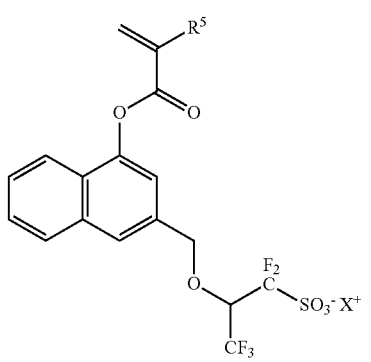

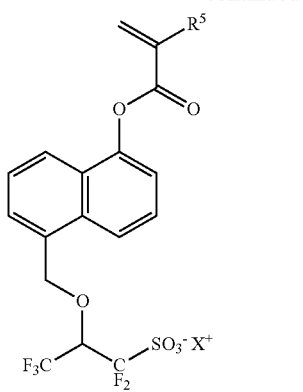
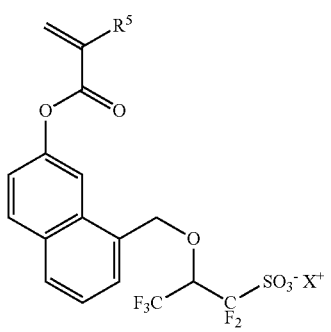
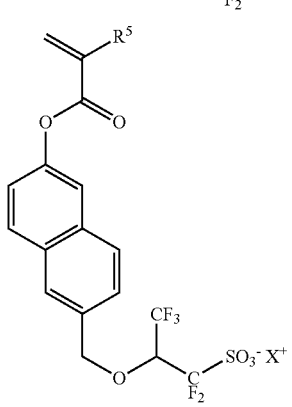
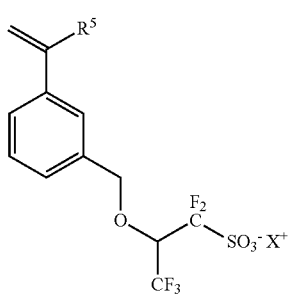
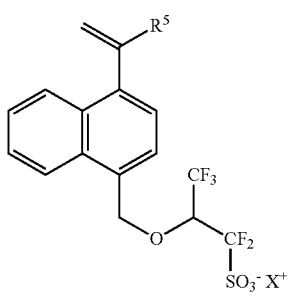
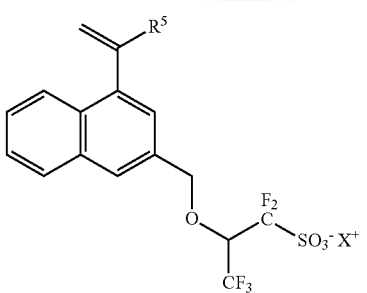
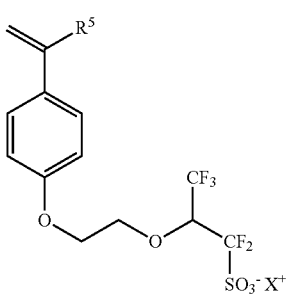
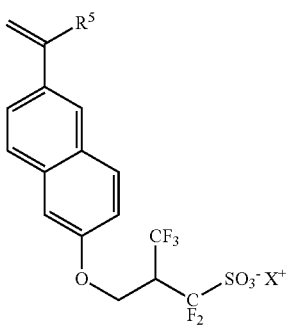
In the formulae, $R^5$ and X have the same meanings as defined above.
The fluorosulfonic acid salt monomer to obtain the repeating unit a2 in the formulae (2) is not particularly limited, and specific illustrative examples thereof include the following.
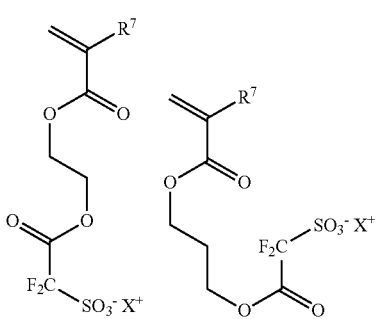

-continued
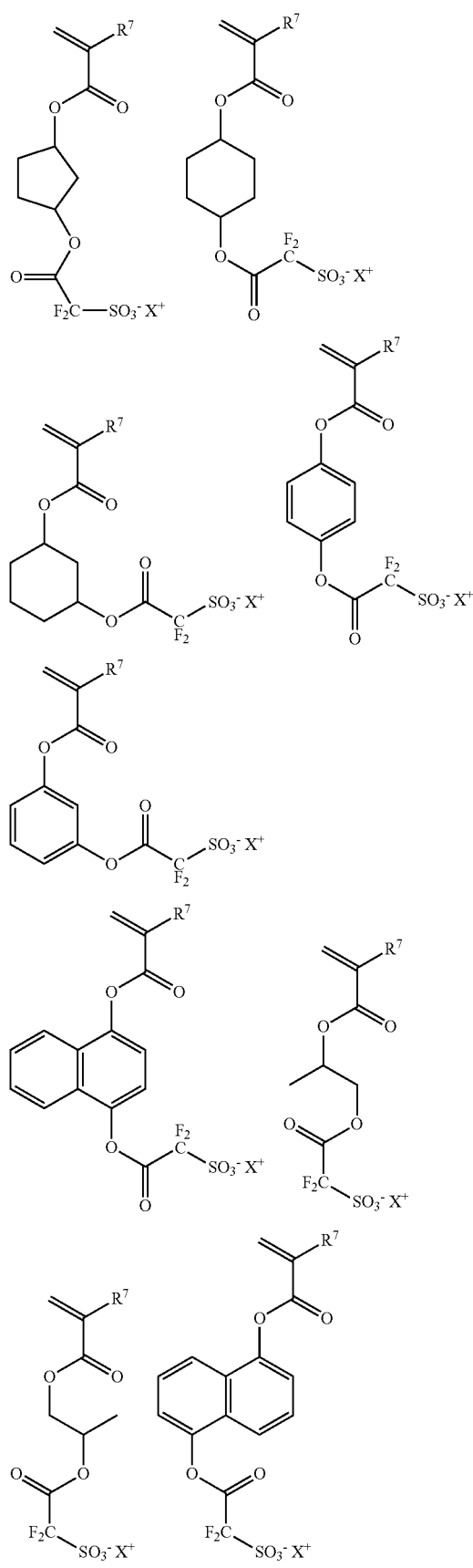
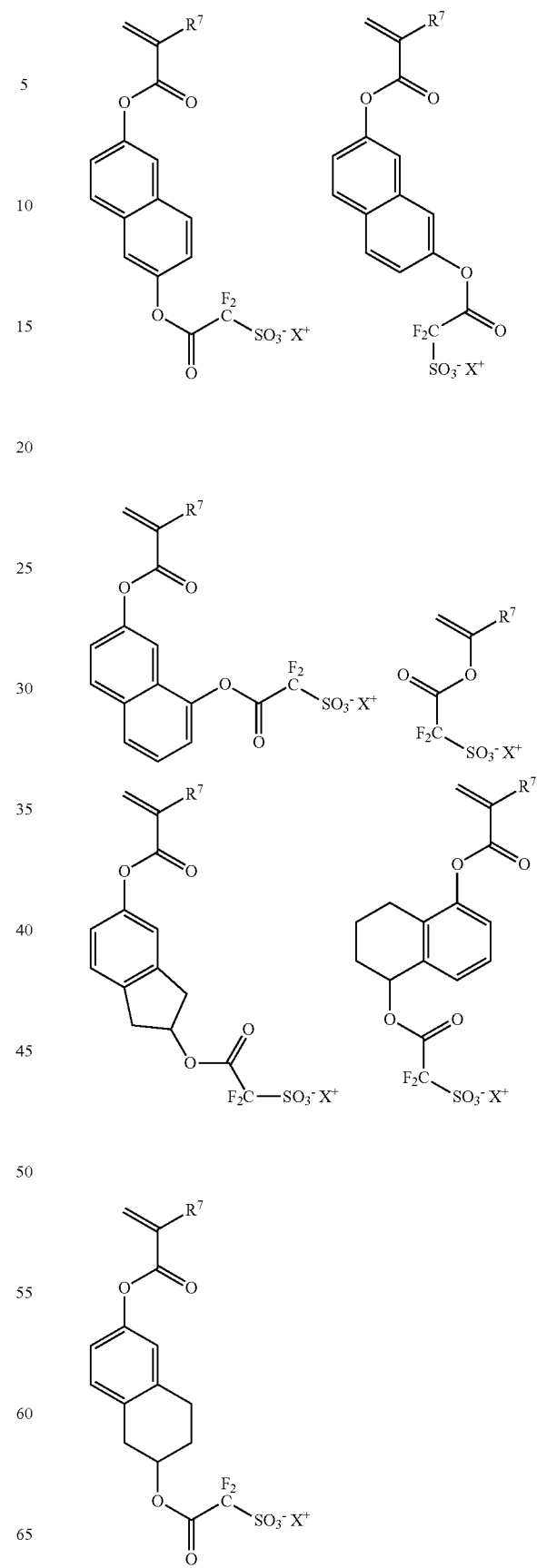

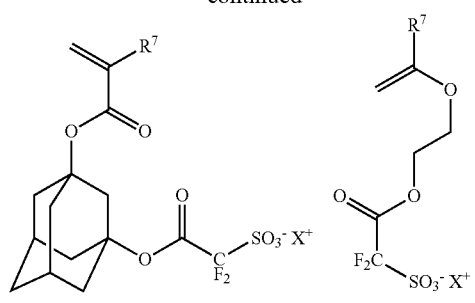
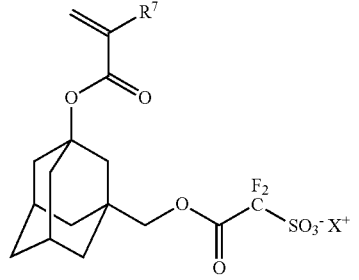
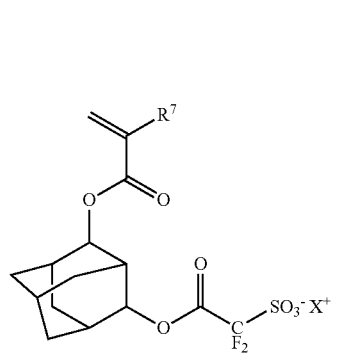
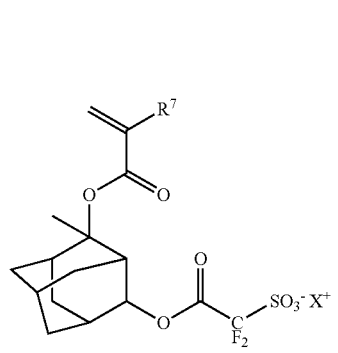
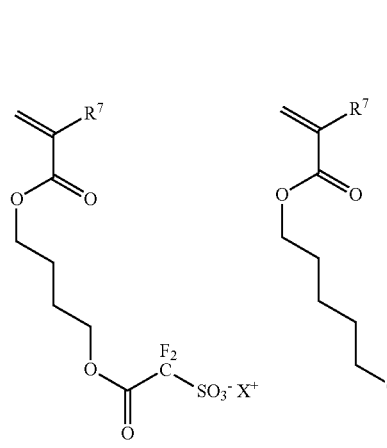
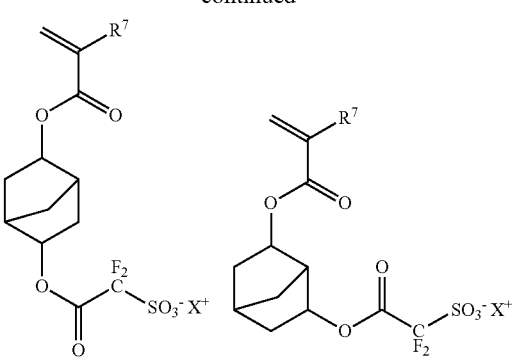
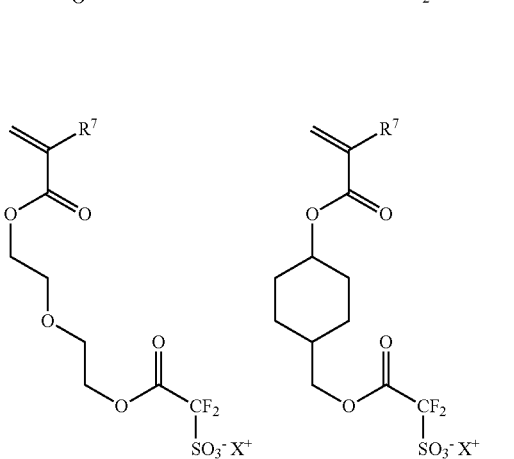

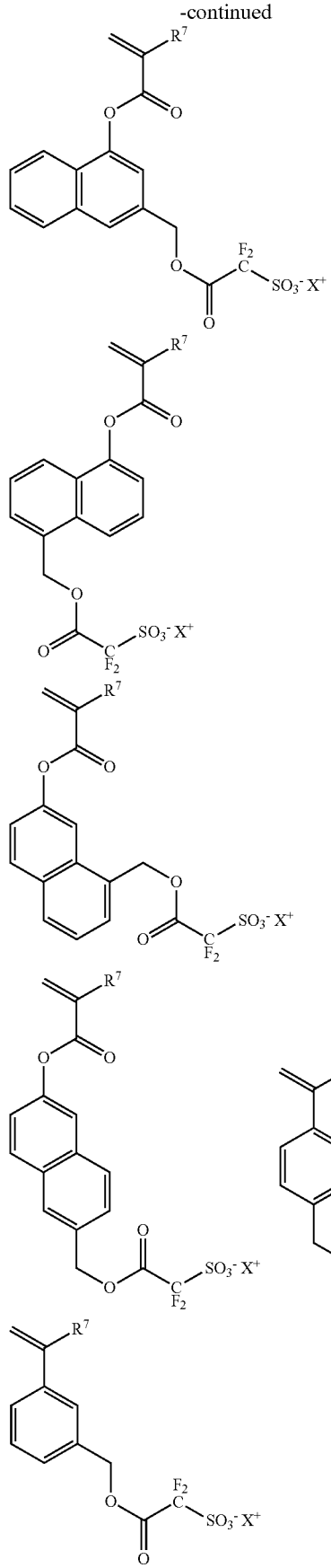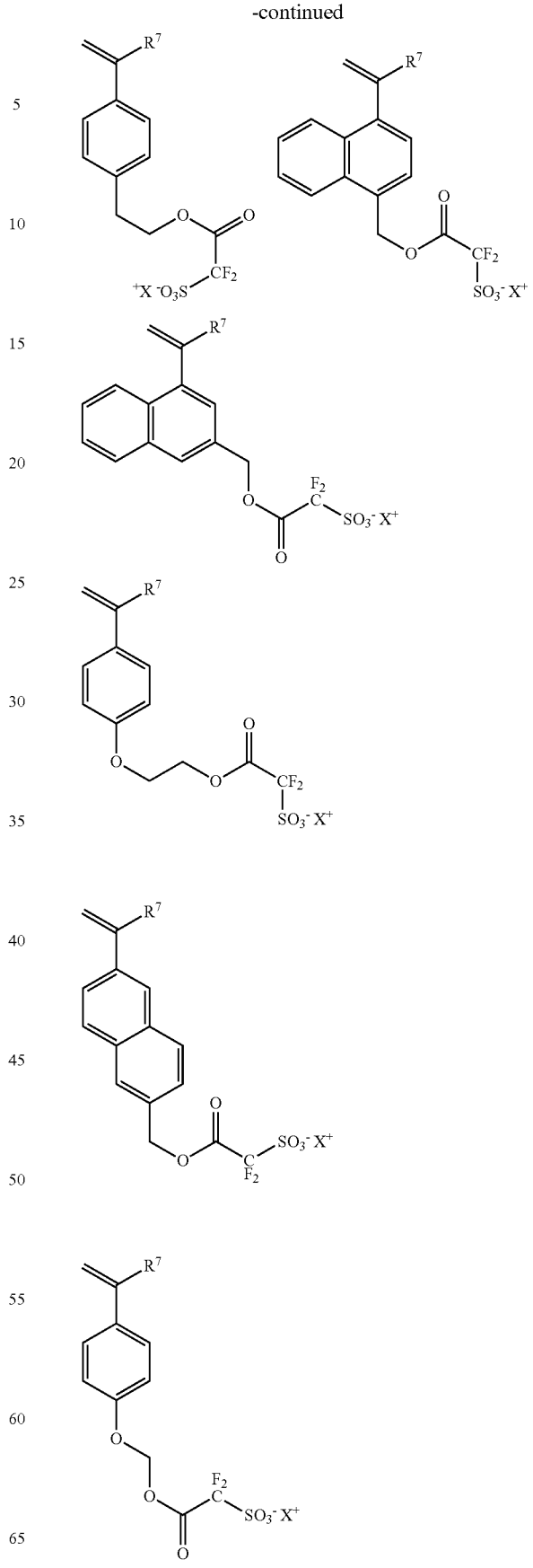

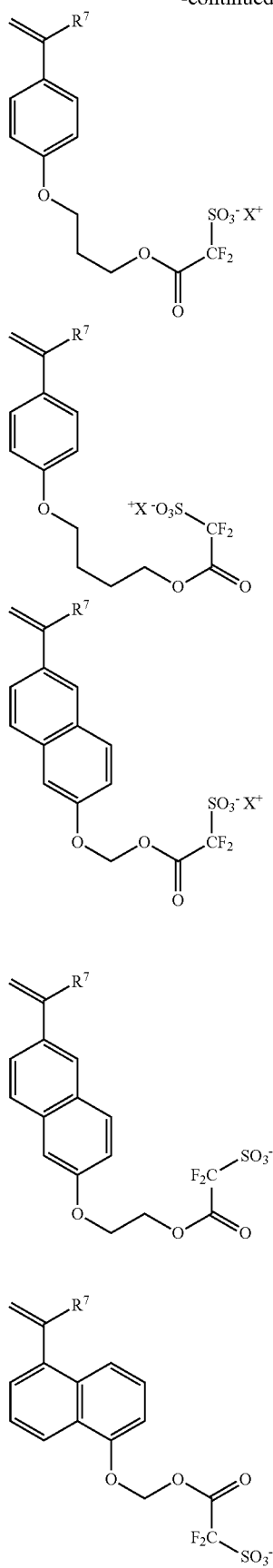
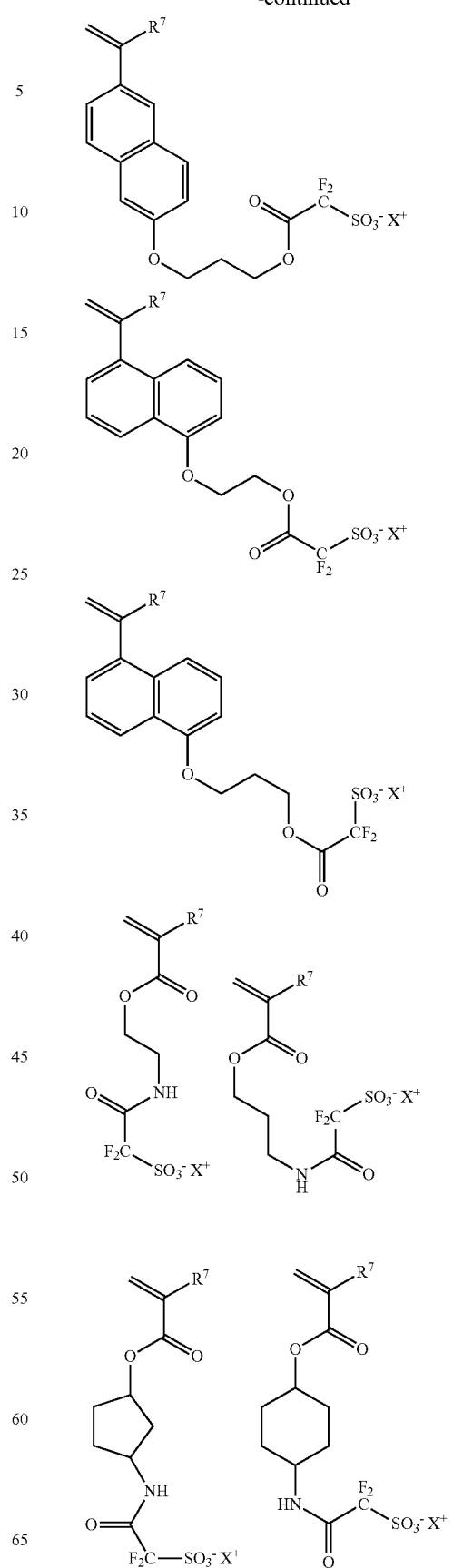

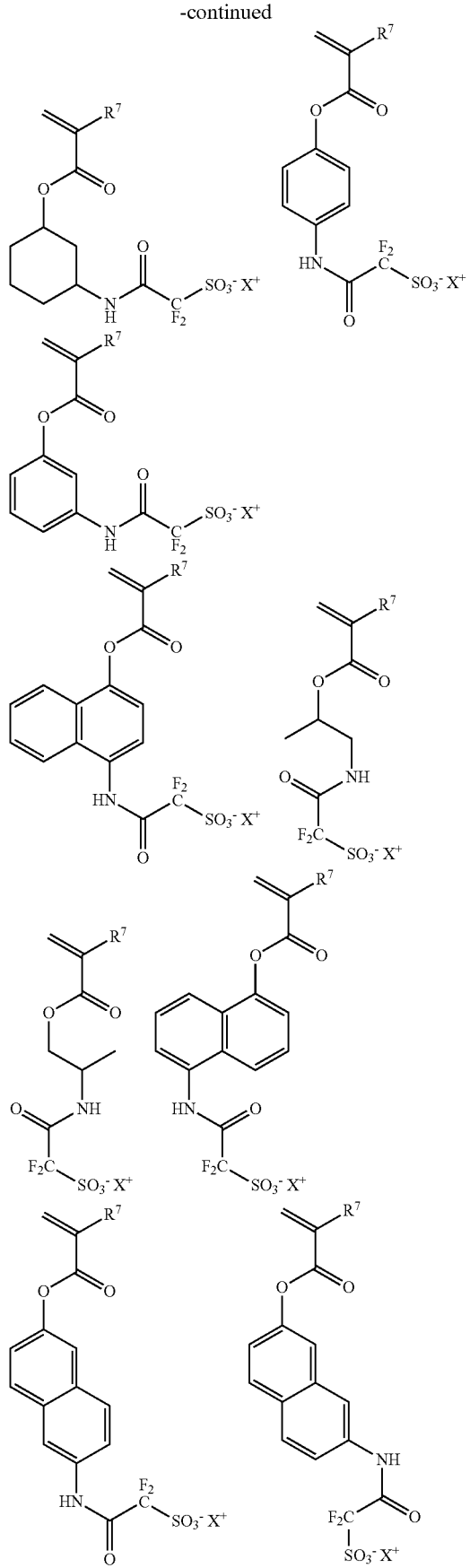
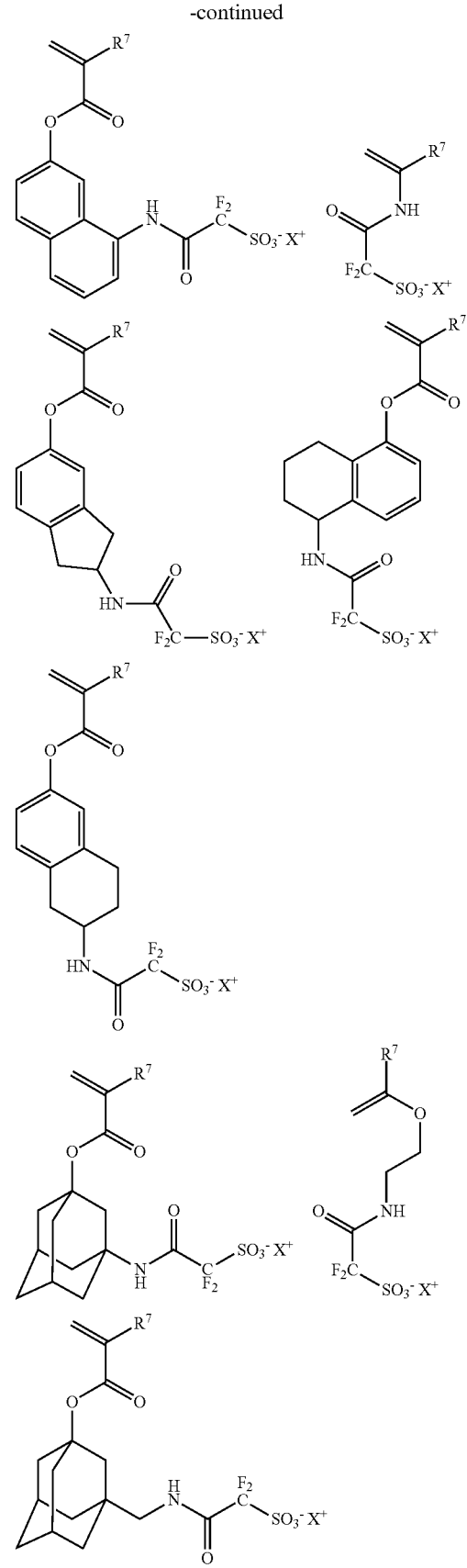

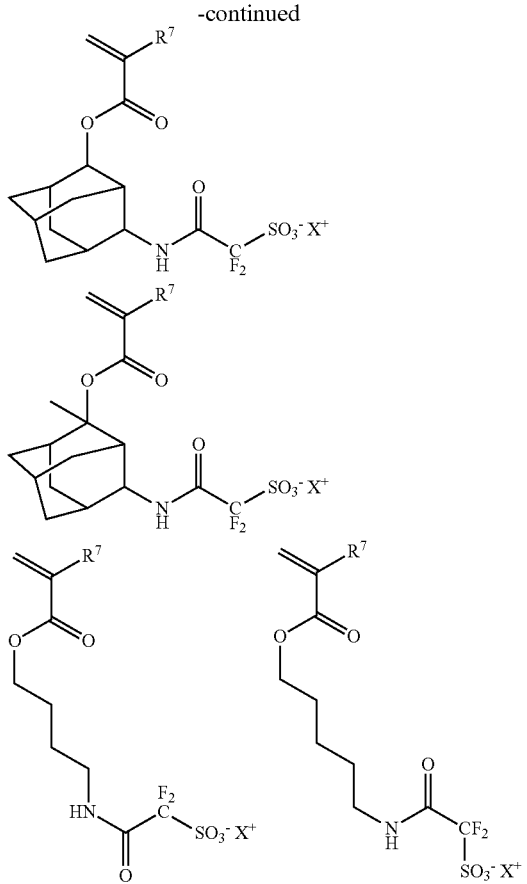
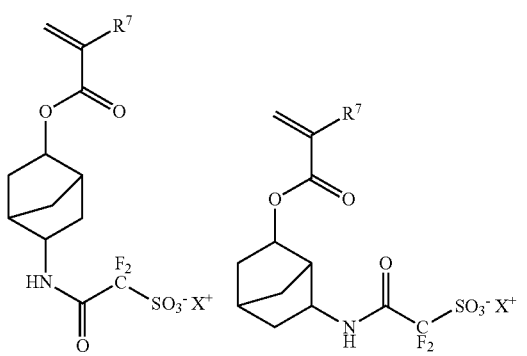
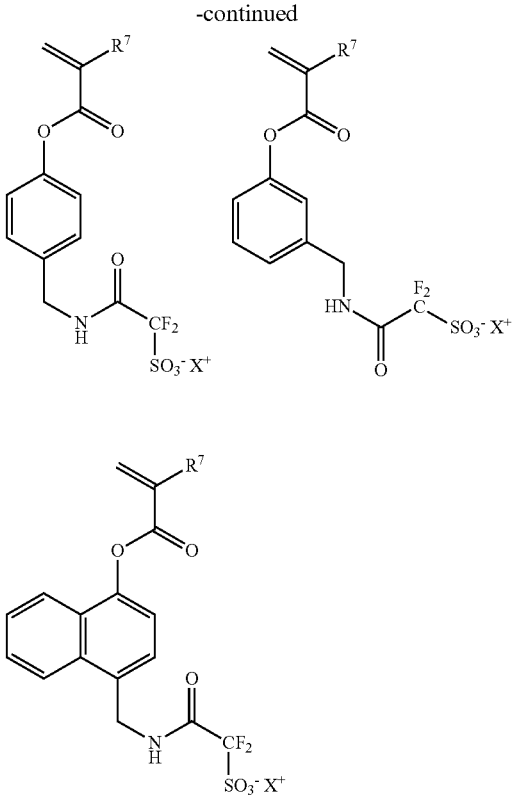
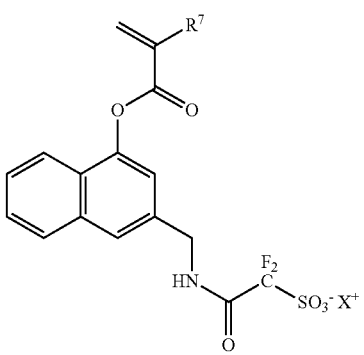
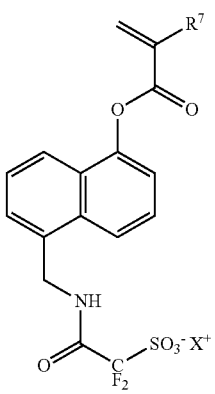

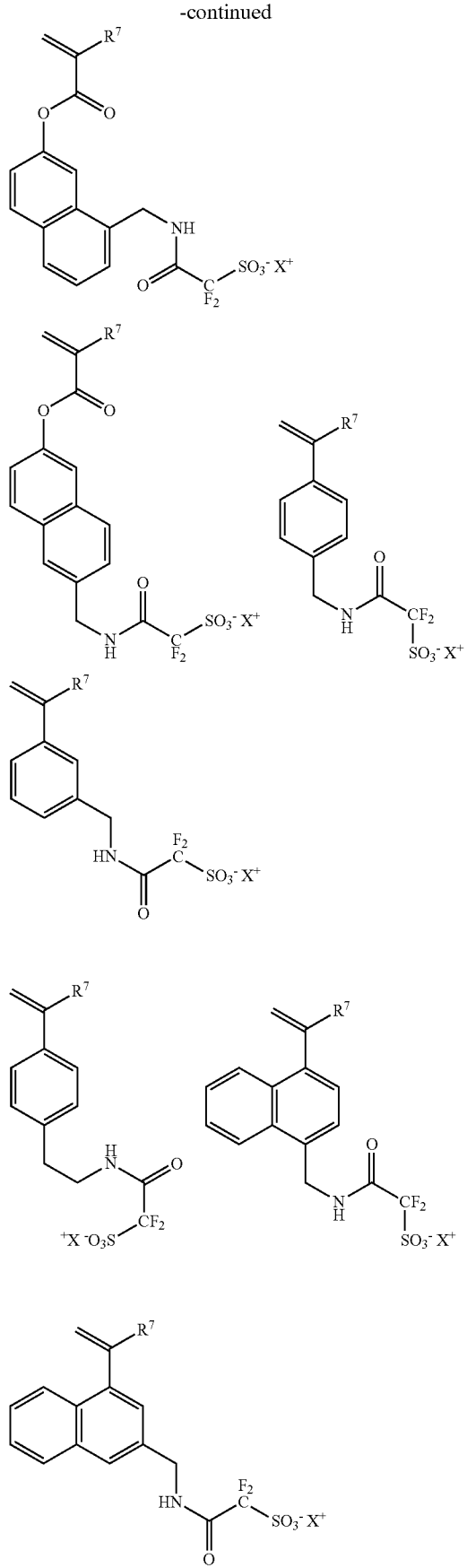
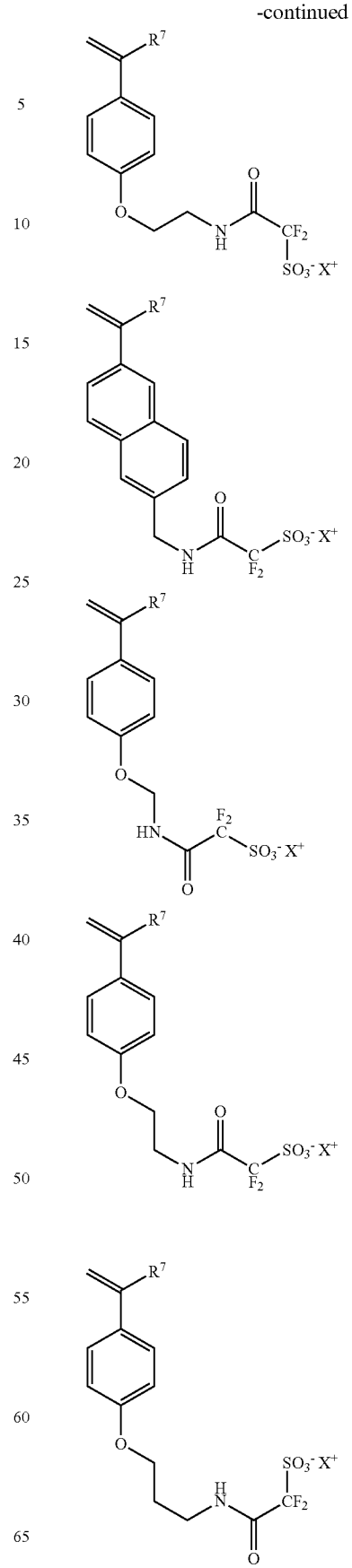

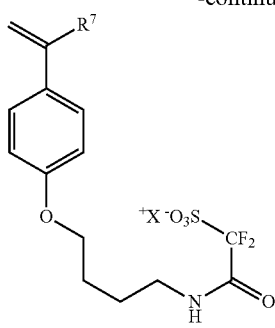
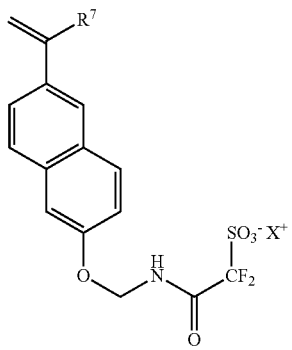
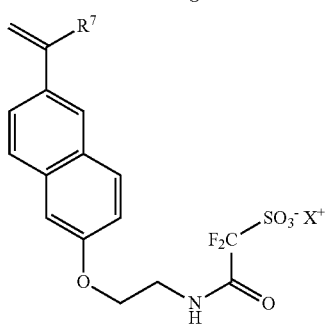
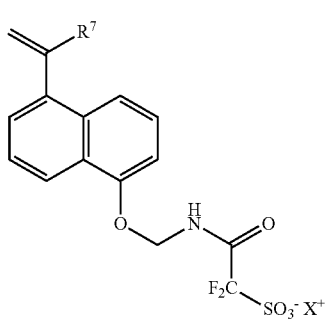
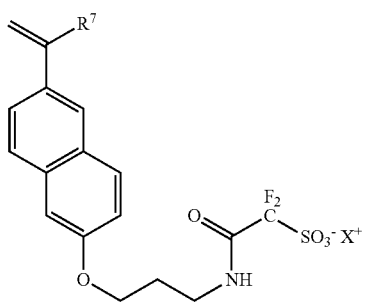
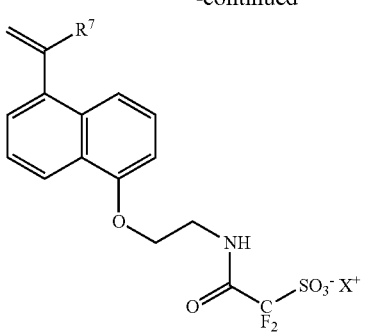
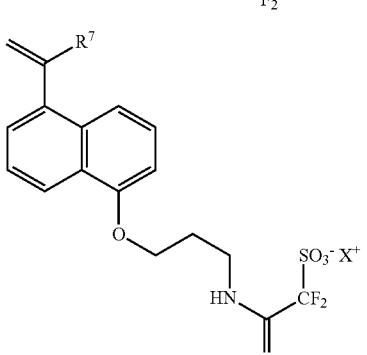
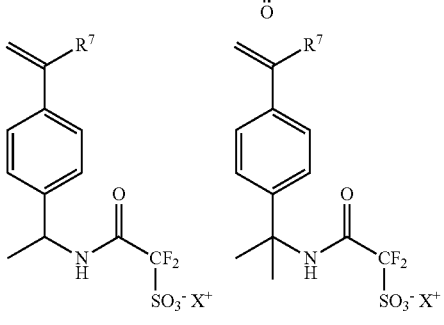
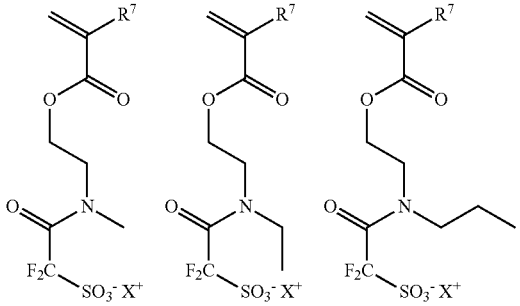
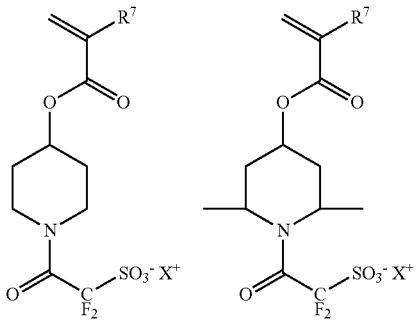

-continued
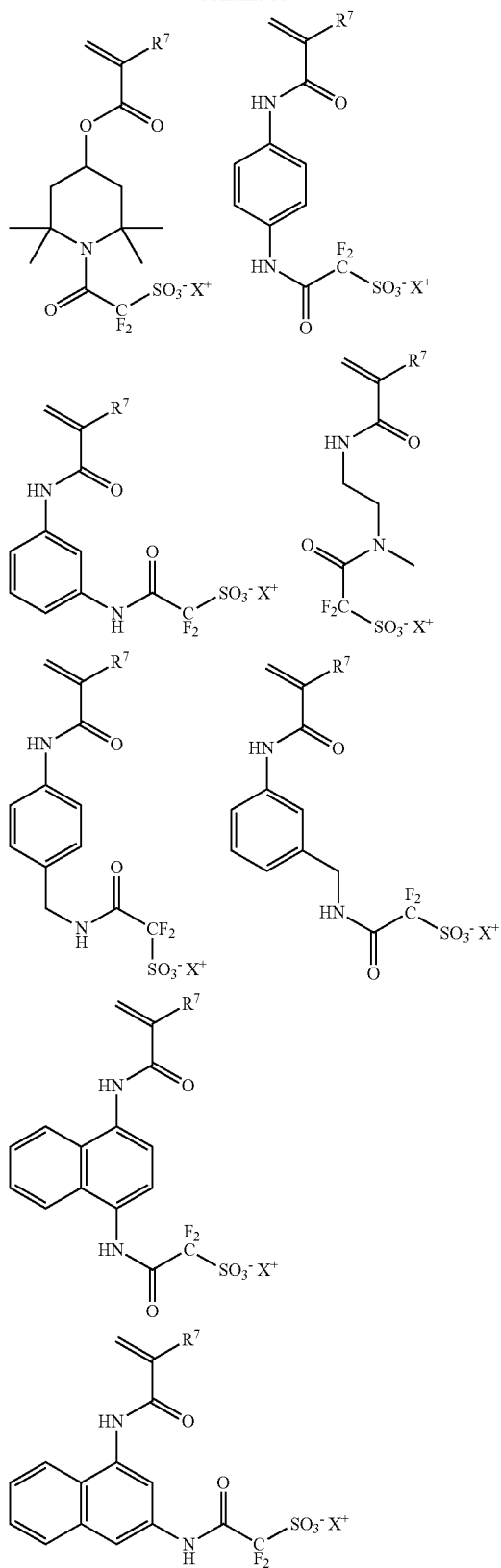
In the formulae, $R^7$ and X have the same meanings as defined above.
The fluorosulfonic acid salt monomer to obtain the repeating unit a3 in the formulae (2) is not particularly limited, and specific illustrative examples thereof include the following.
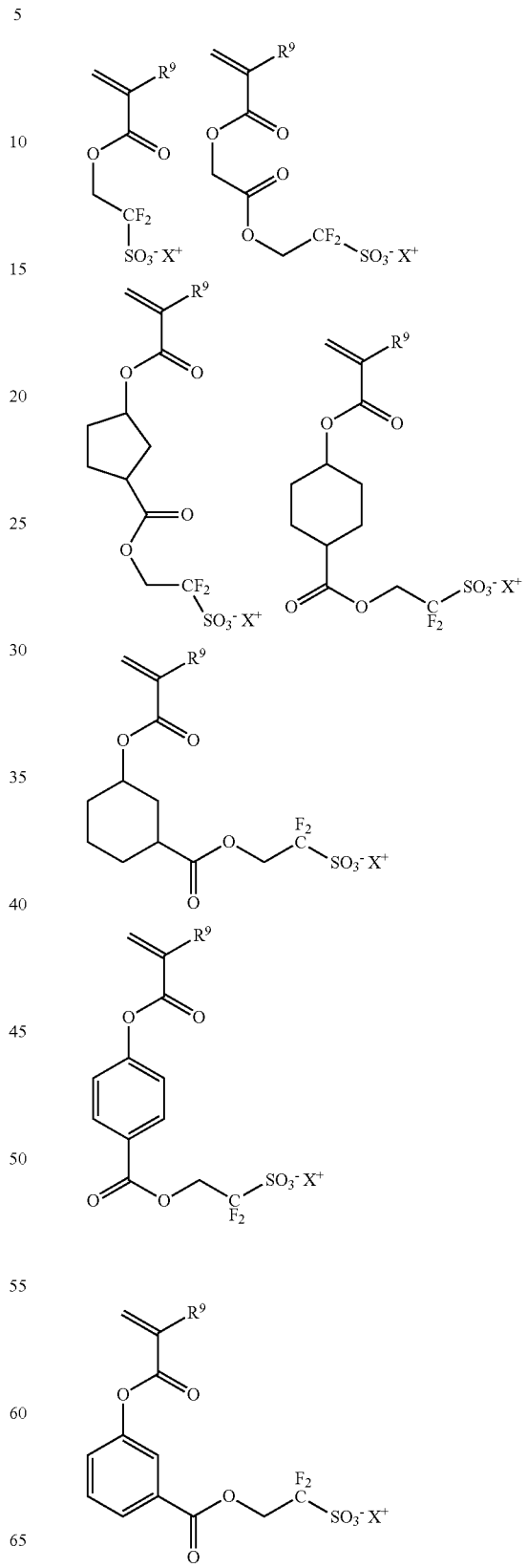

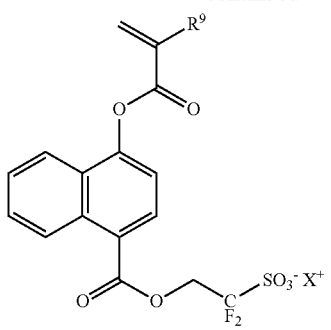
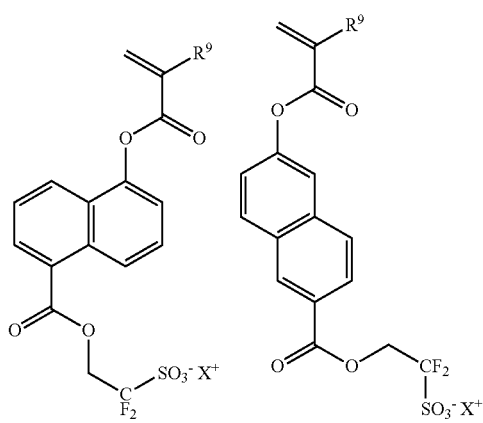
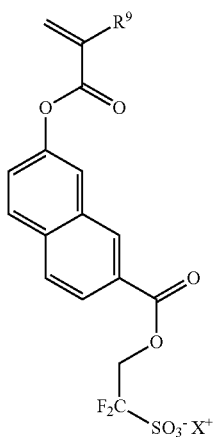
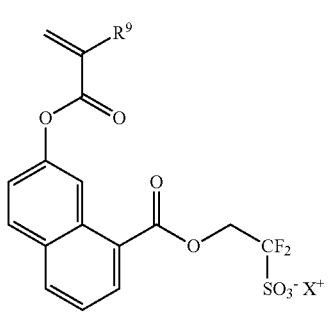
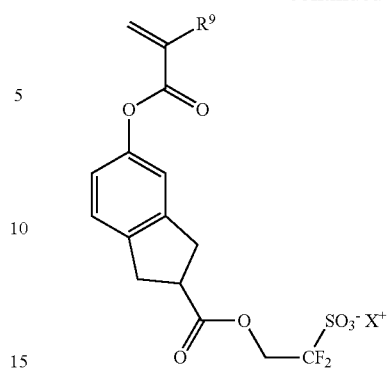
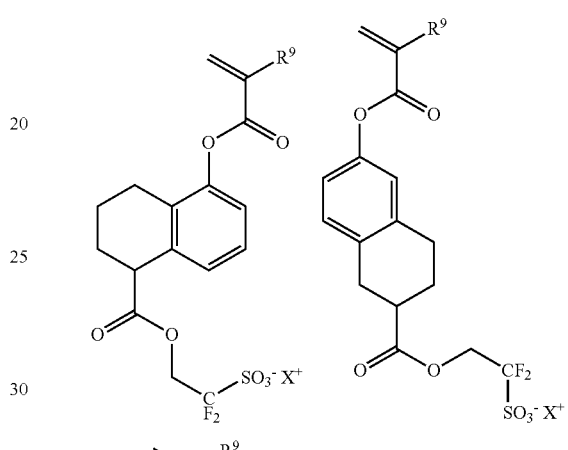
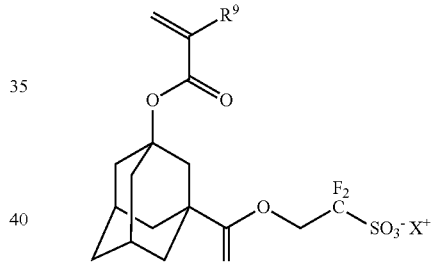
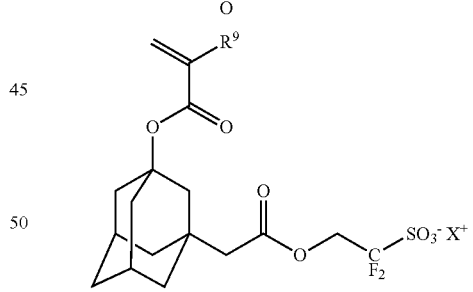
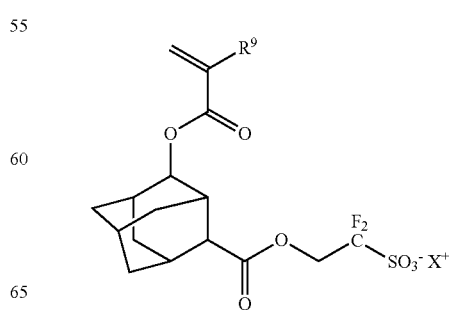

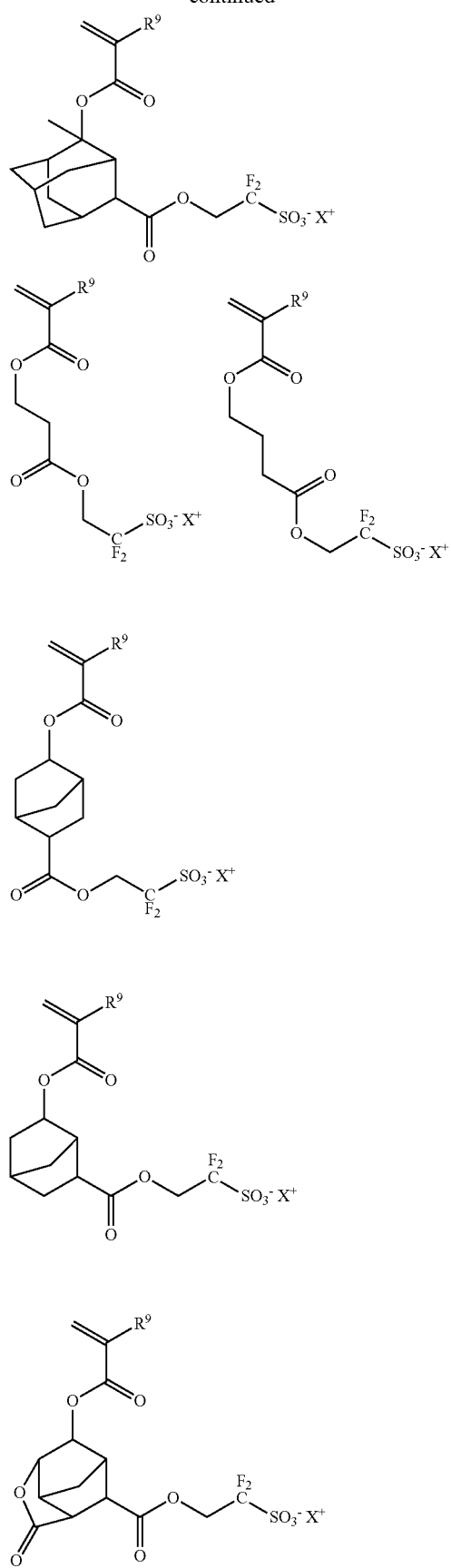
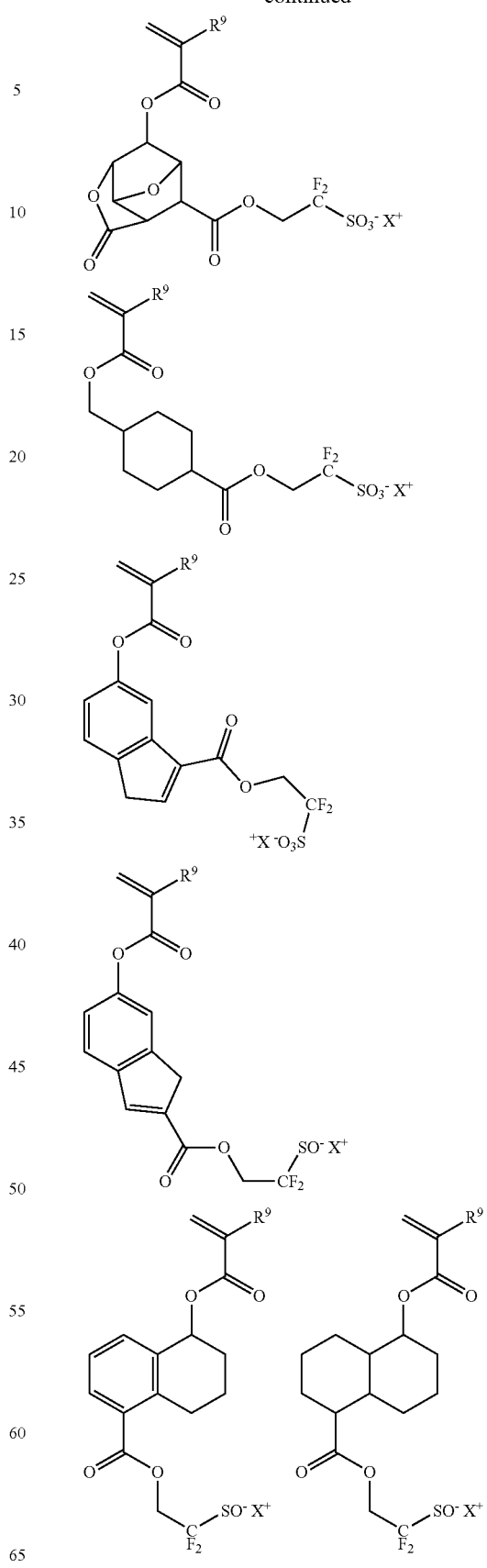

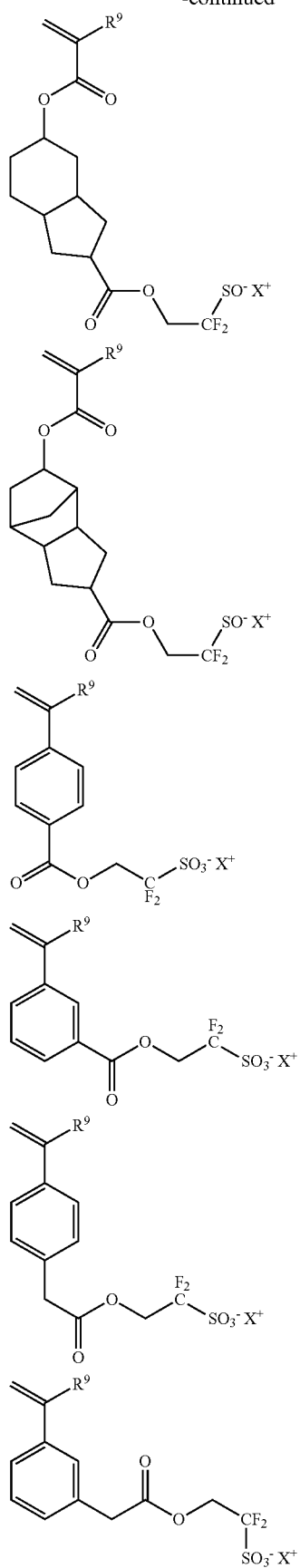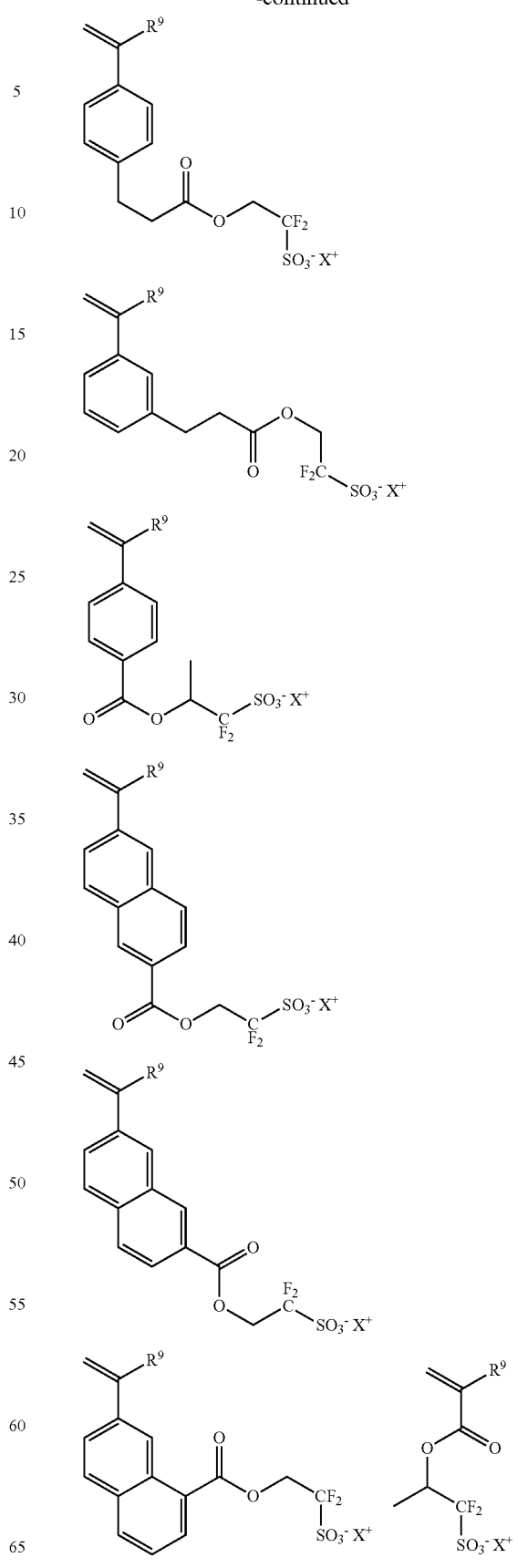

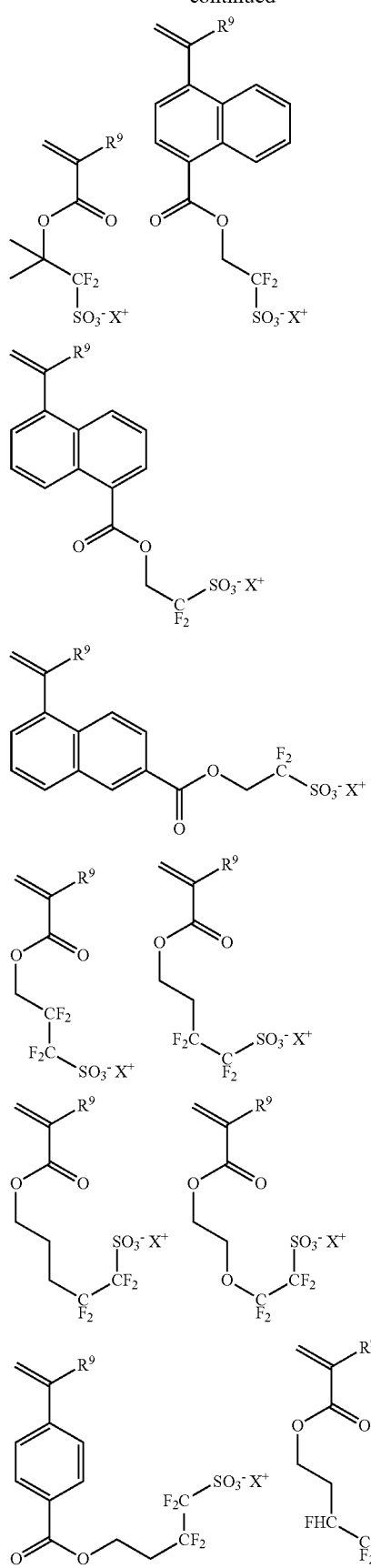
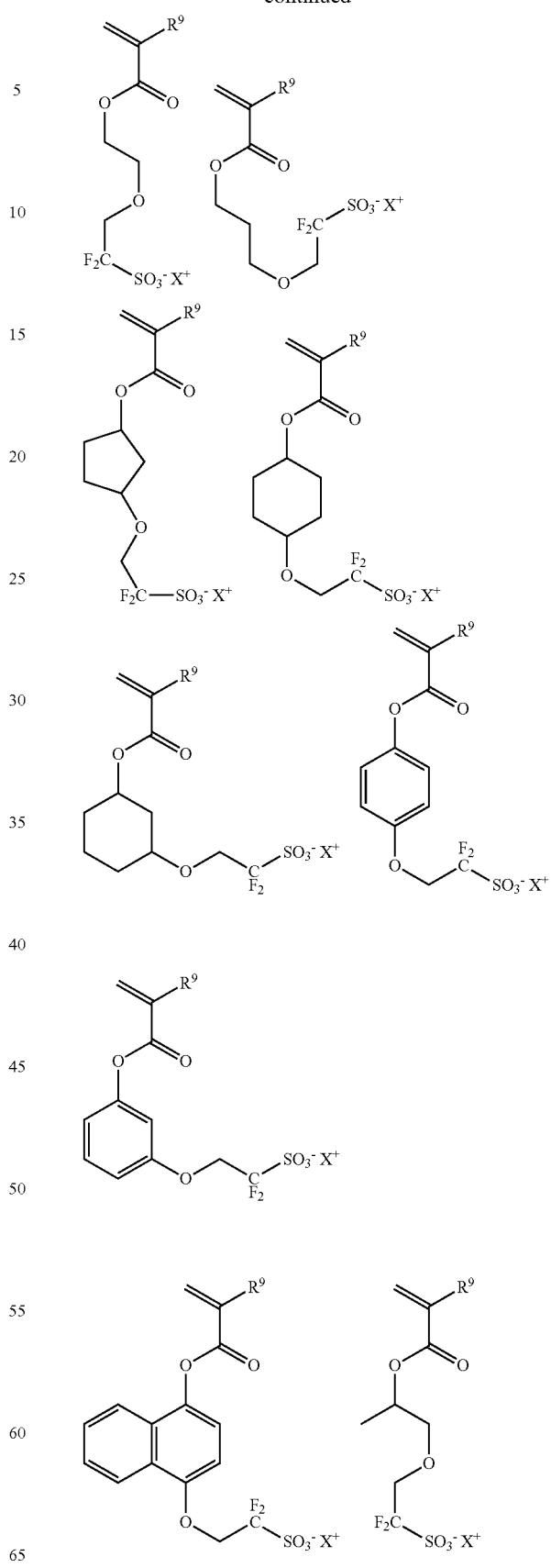

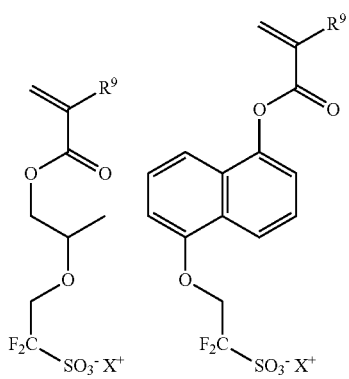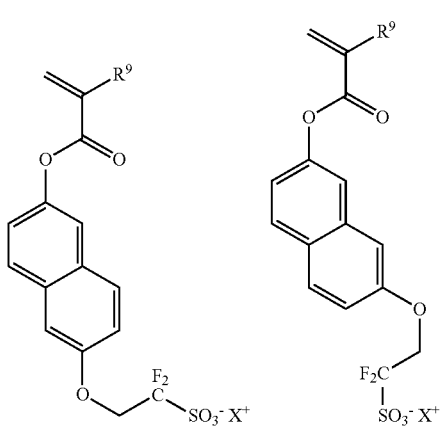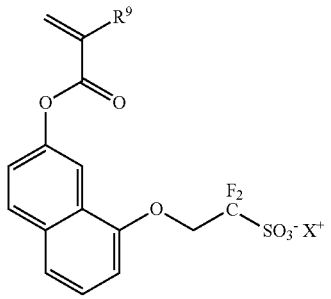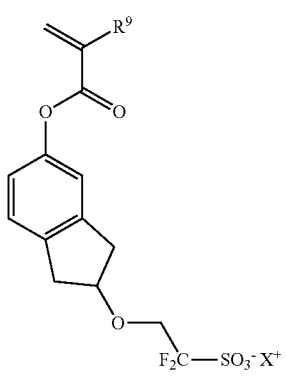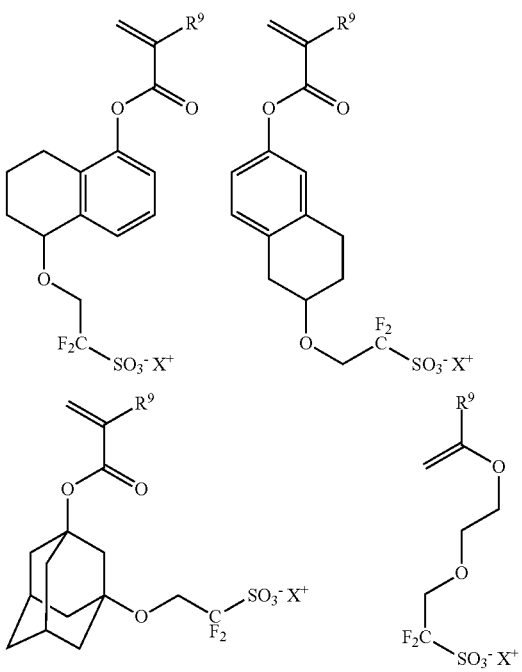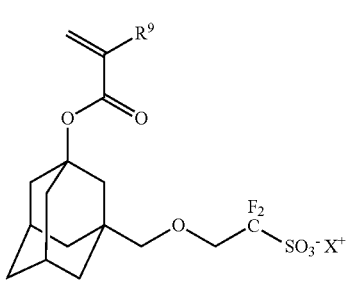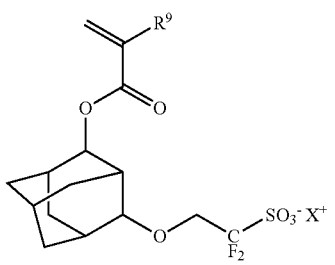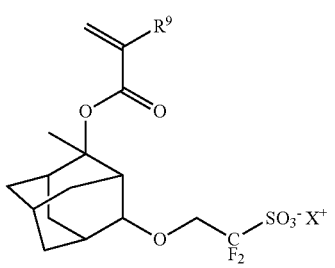

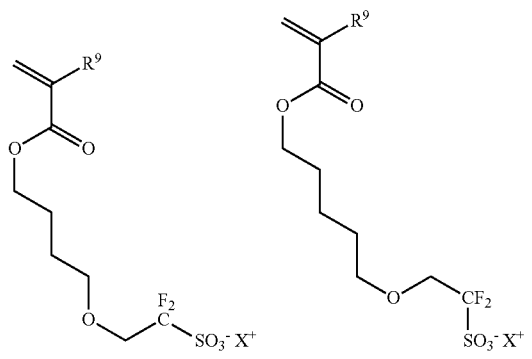
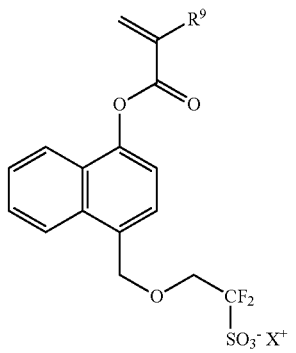
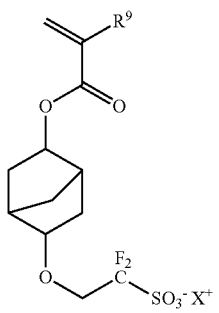
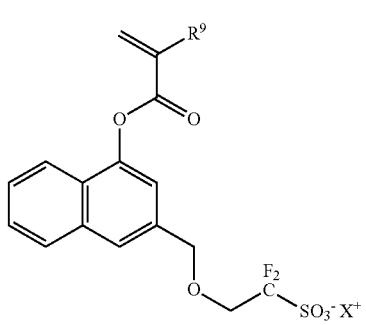
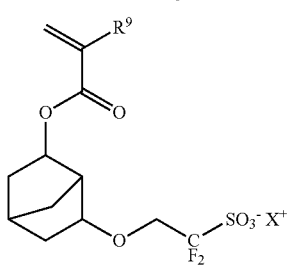
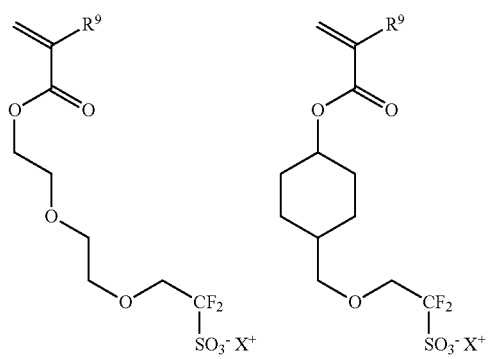
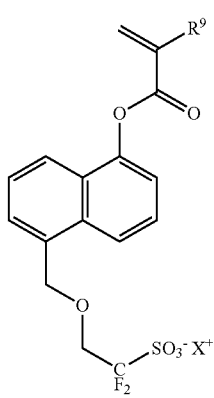
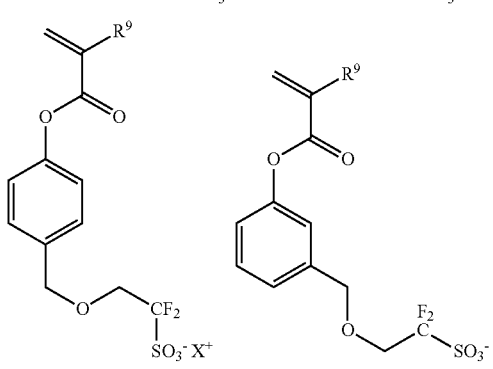
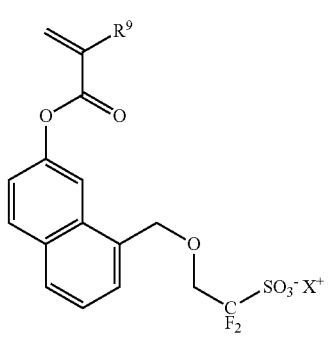

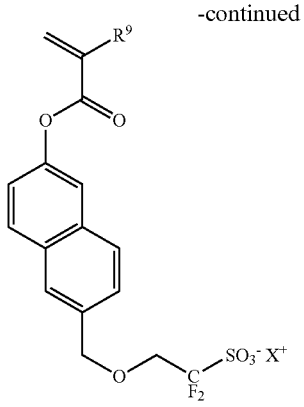
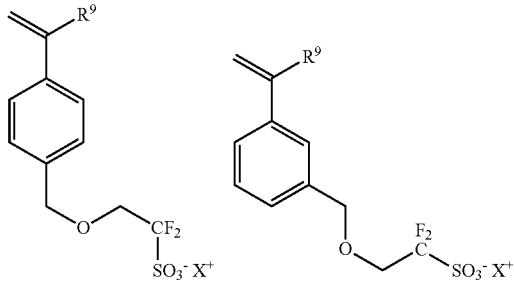
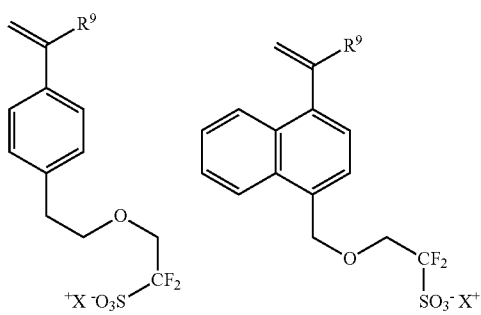
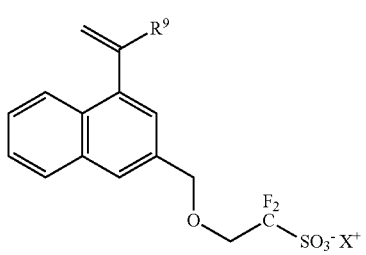
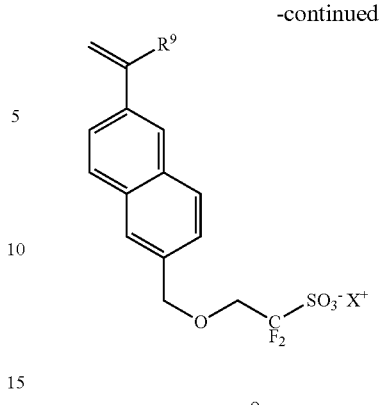
In the formulae, $R^9$ and X have the same meanings as defined above.
The fluorosulfonic acid salt monomer to obtain the repeating unit a4 in the formulae (2) is not particularly limited, and specific illustrative examples thereof include the following.
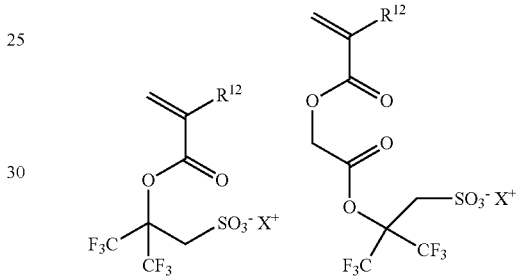
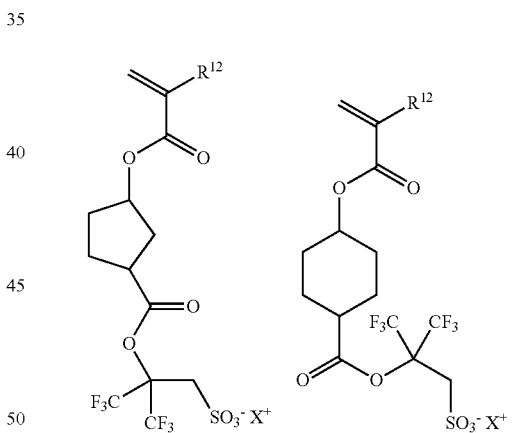
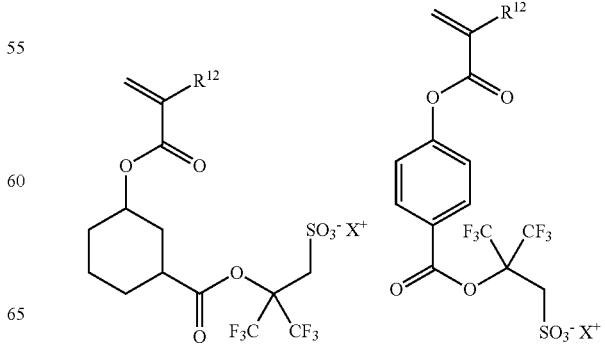
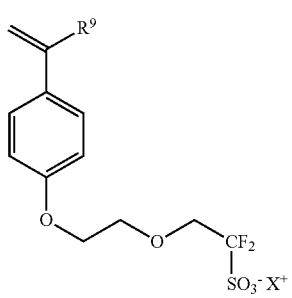

-continued
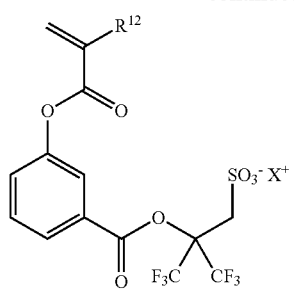
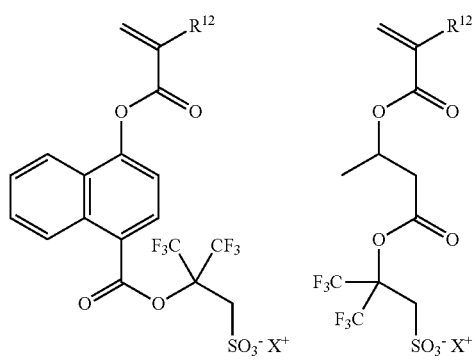
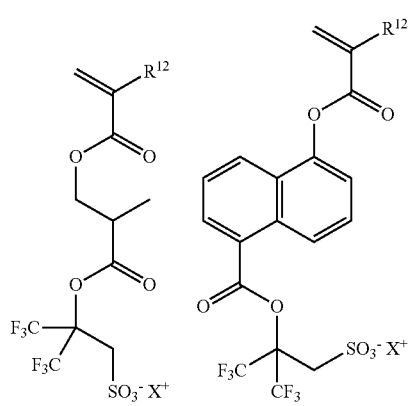
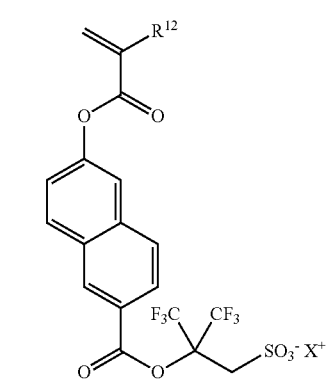
-continued
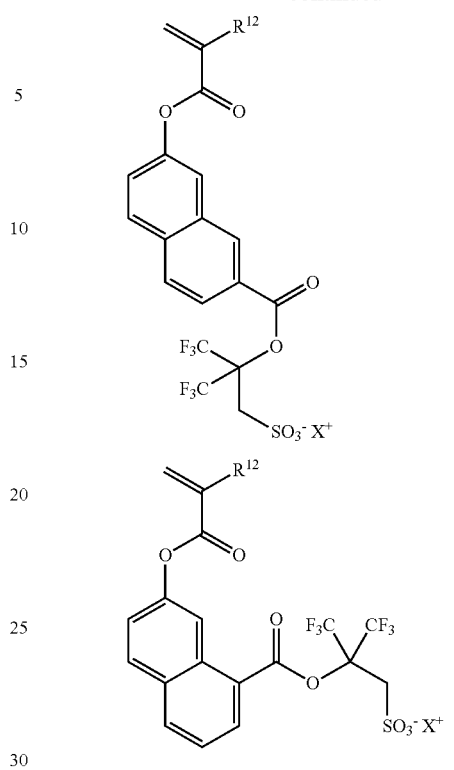
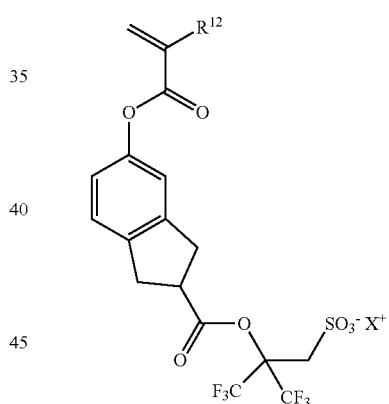
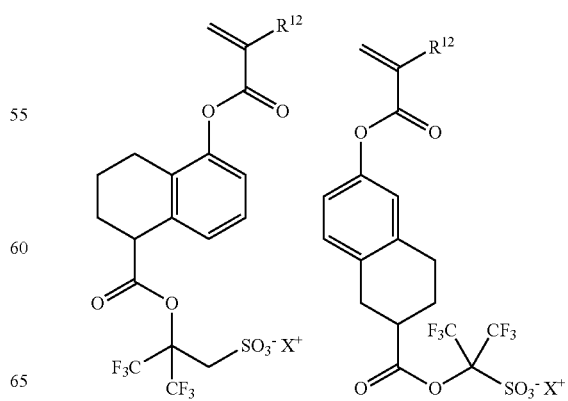

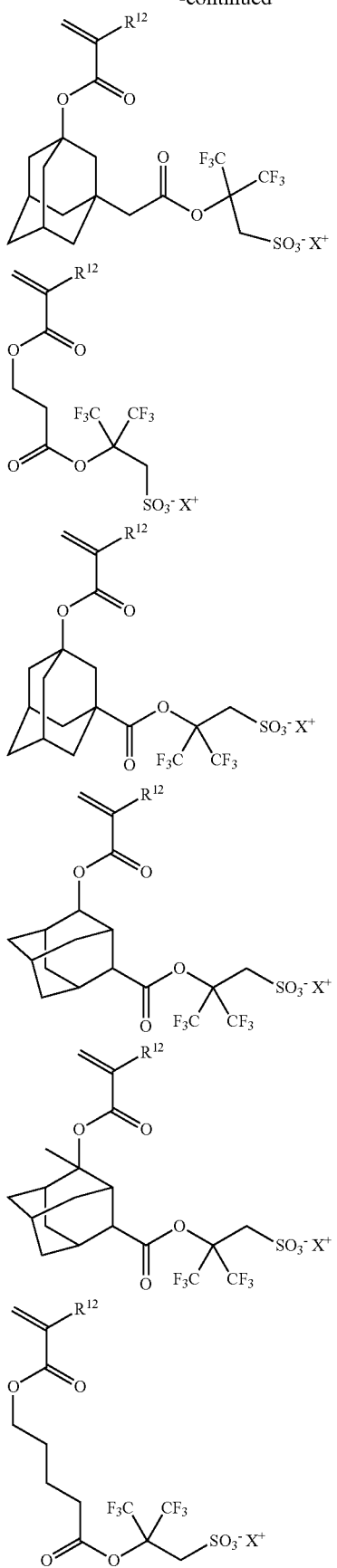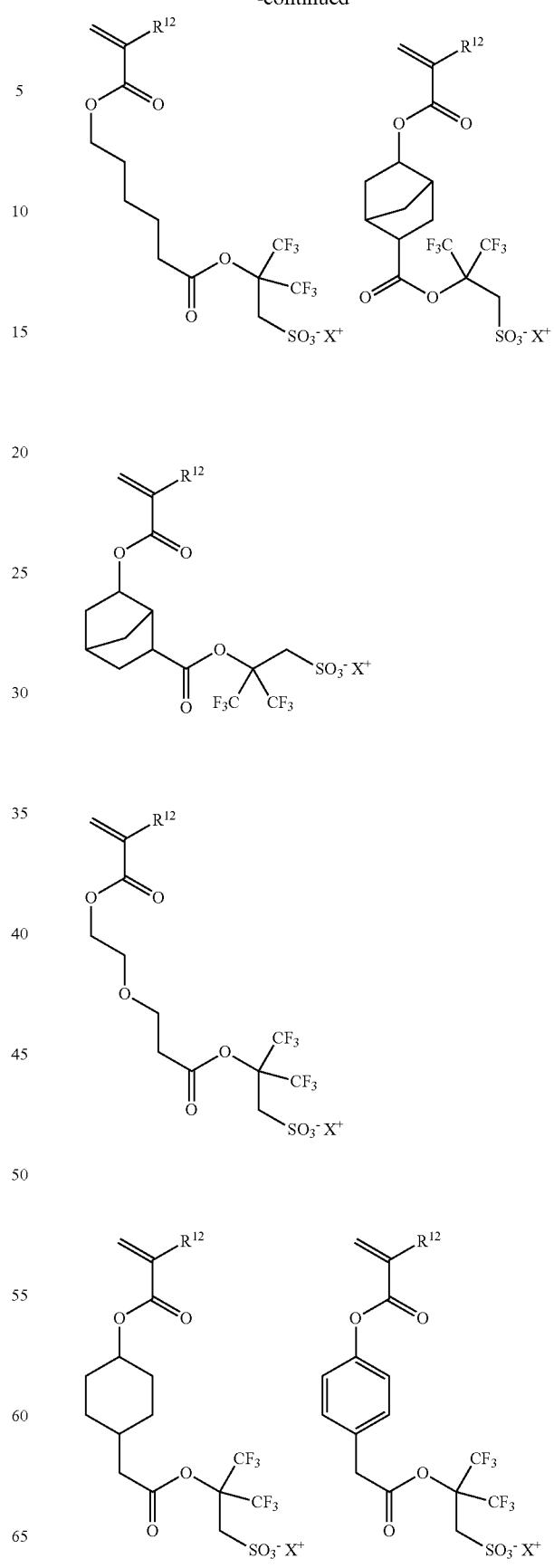

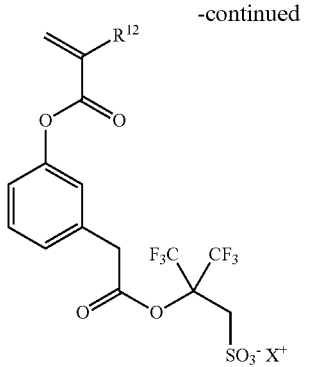
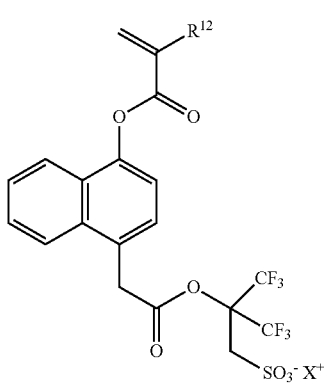
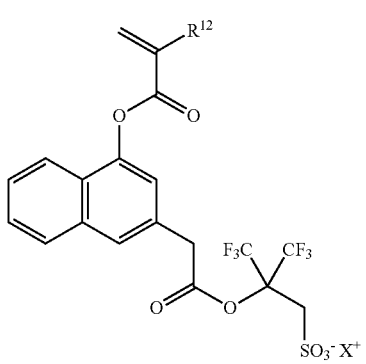
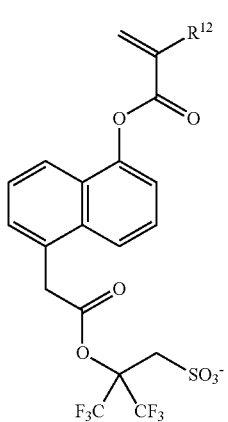
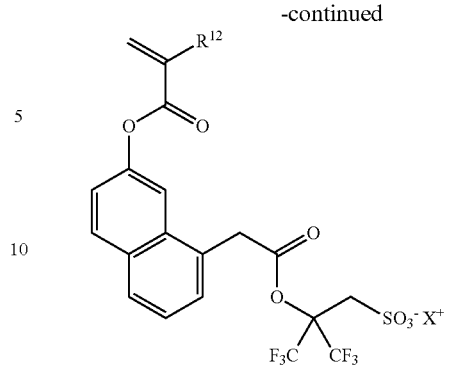
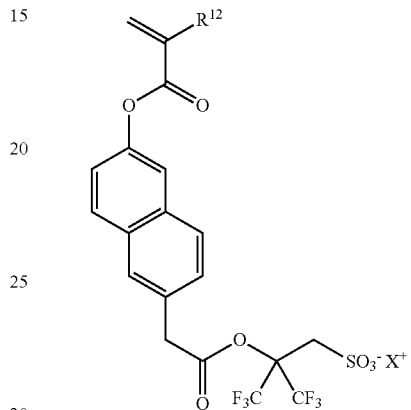
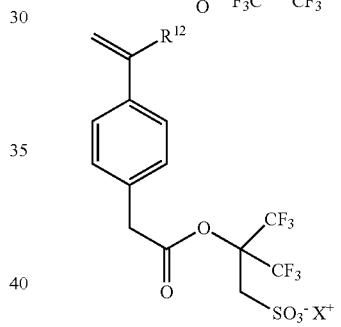
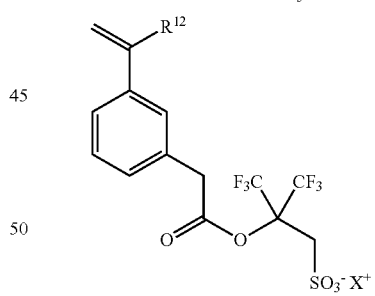
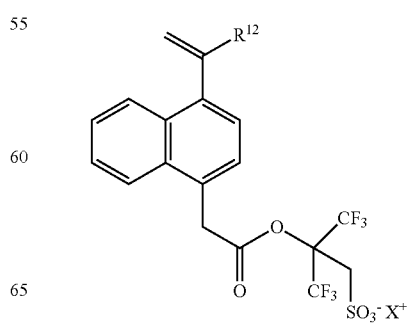

67
-continued
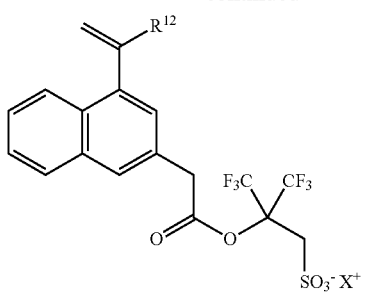
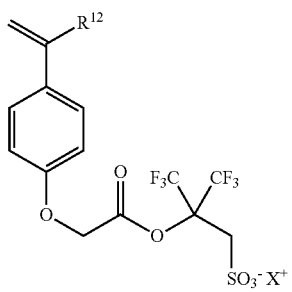
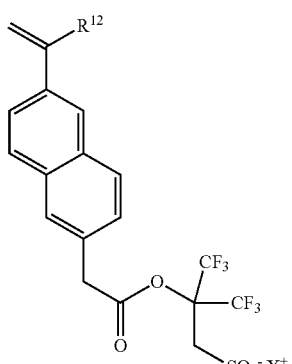
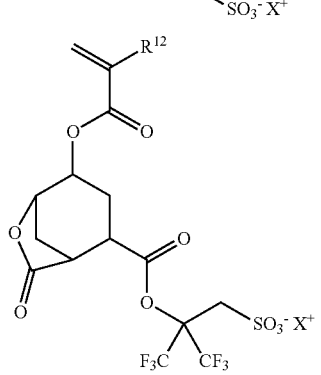
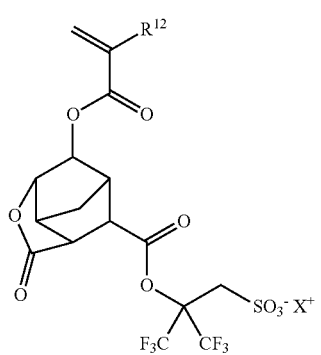
68
-continued
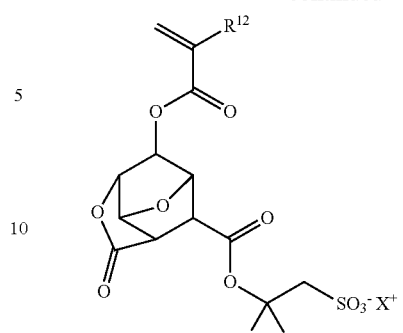
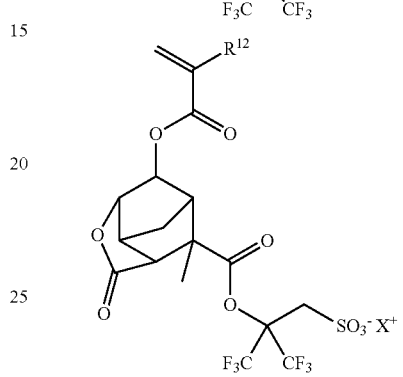
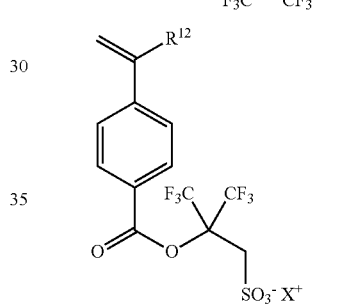
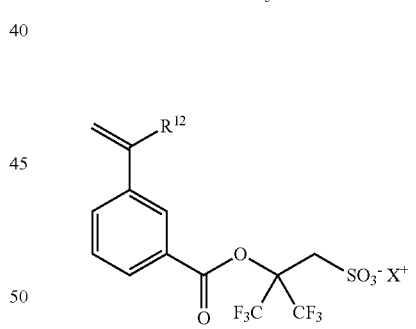
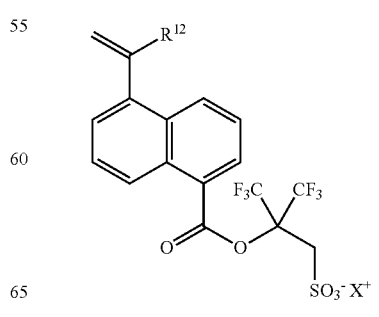

-continued

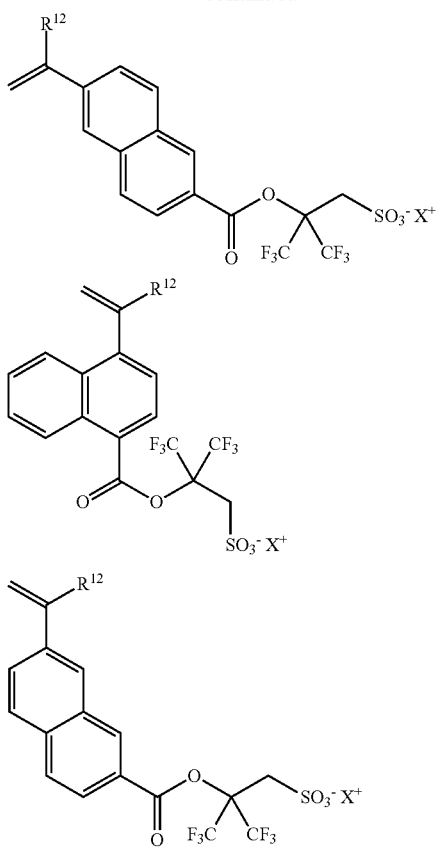

In the formulae, $R^{12}$ and X have the same meanings as defined above.

The fluorosulfonic acid salt monomer to obtain the repeating unit a5 in the formulae (2) is not particularly limited, and specific illustrative examples thereof include the following.

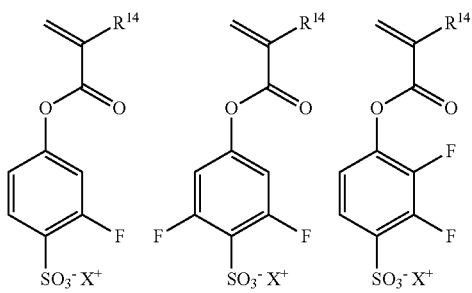

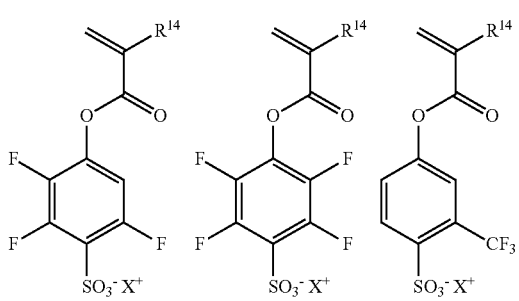

-continued

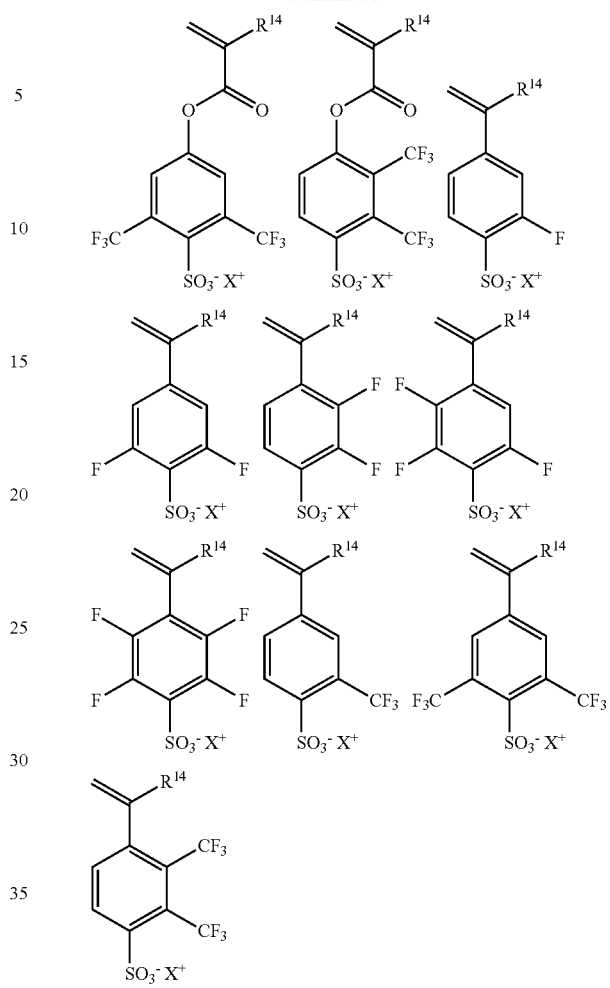

In the formulae, $R^{14}$ and X have the same meanings as defined above.

The sulfonimide salt monomer to obtain the repeating unit a6 in the formulae (2) is not particularly limited, and specific illustrative examples thereof include the following.

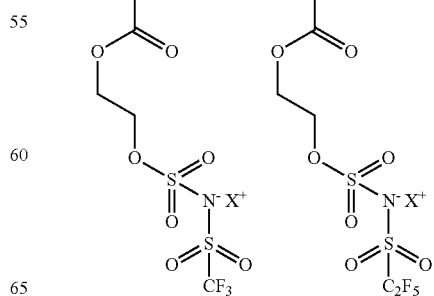

71
-continued
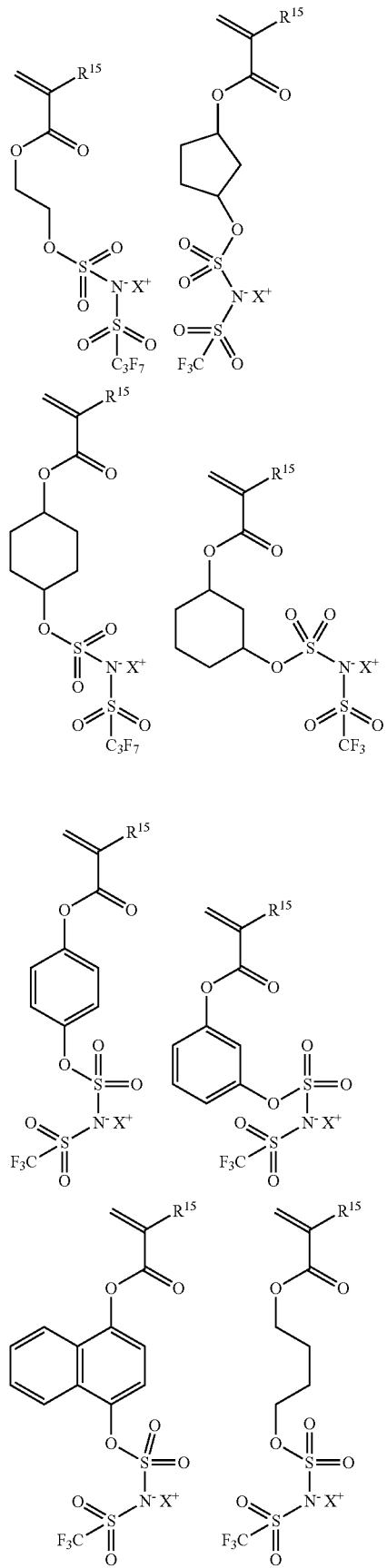
72
-continued
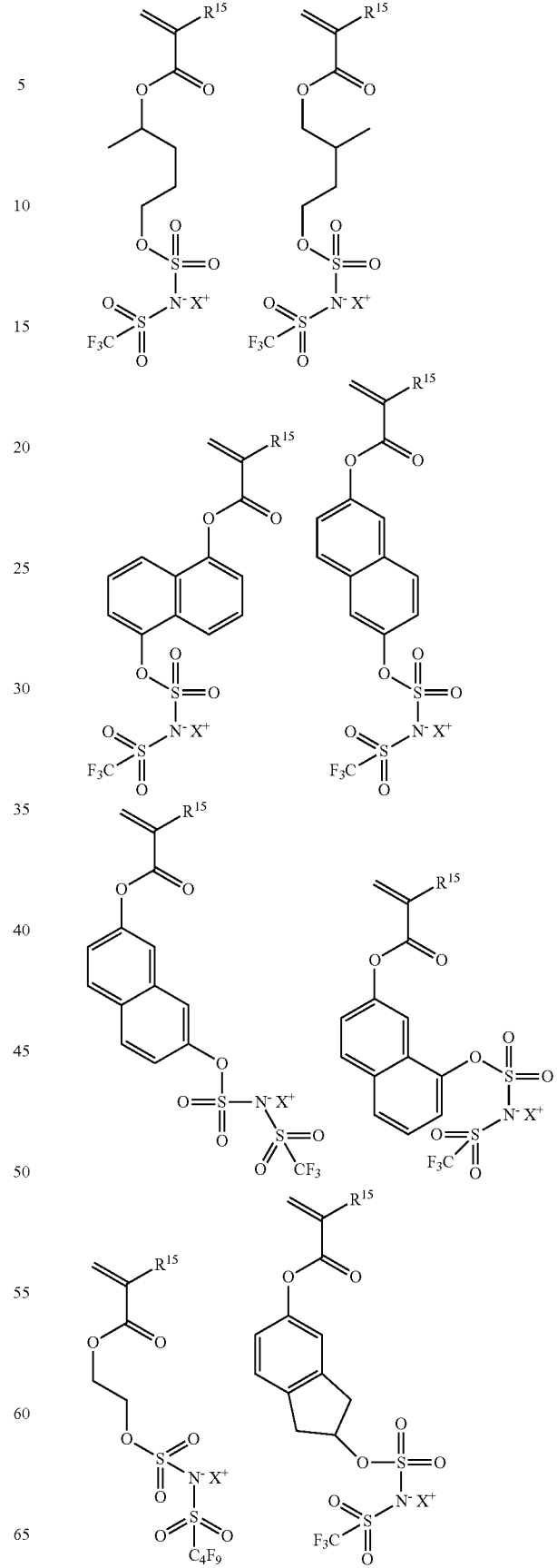

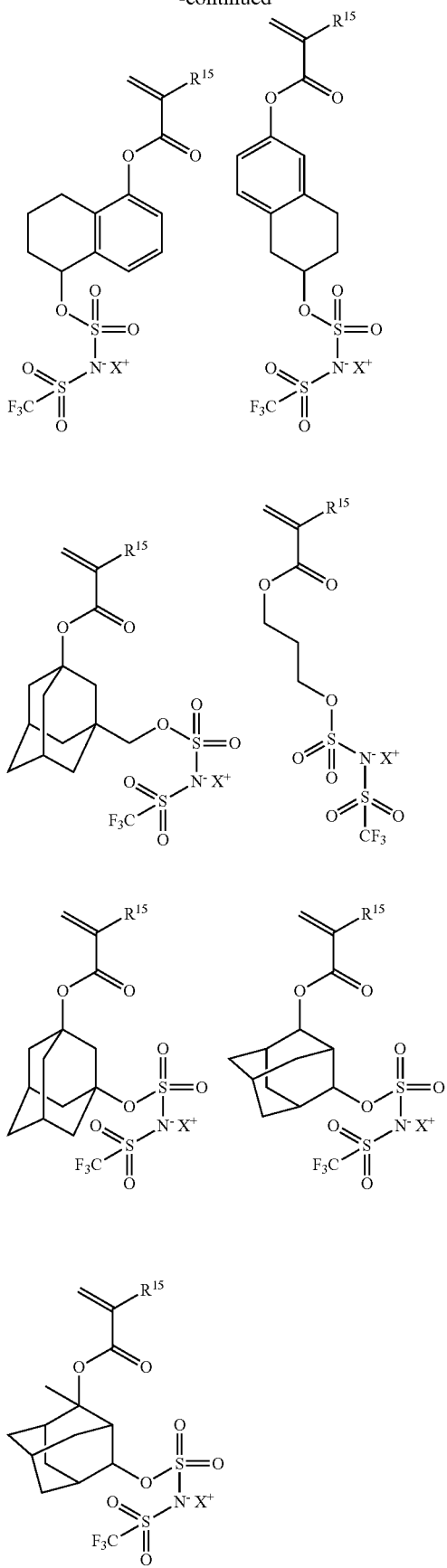
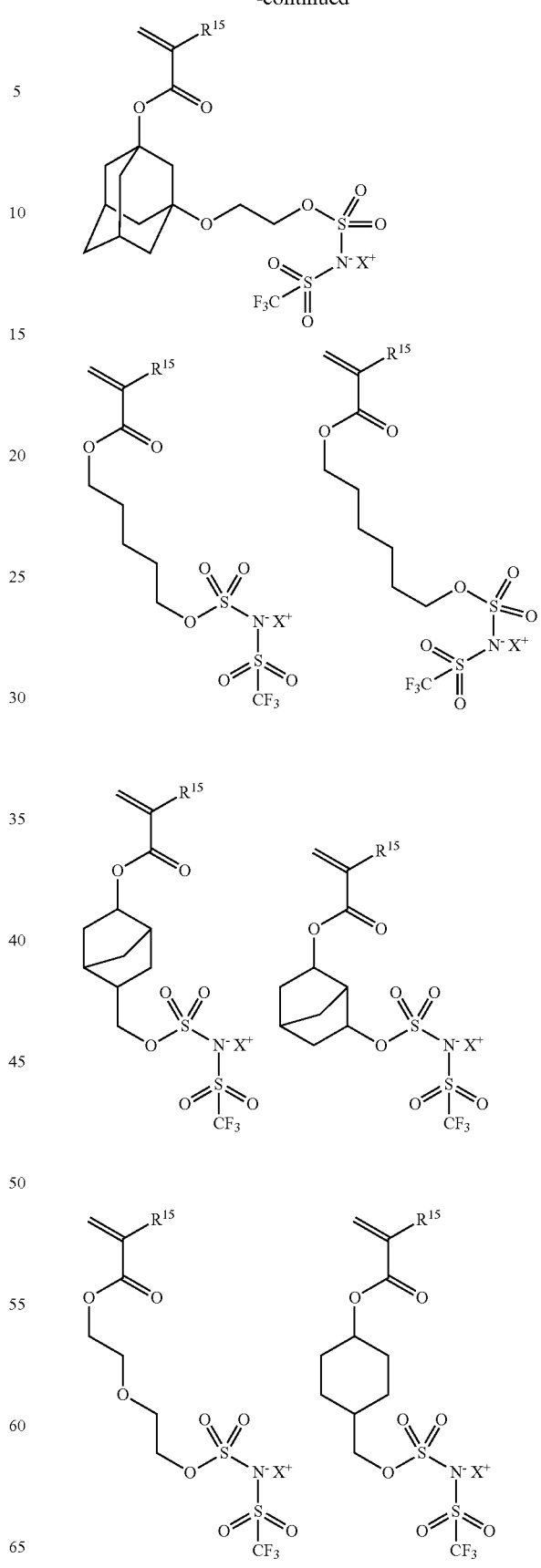

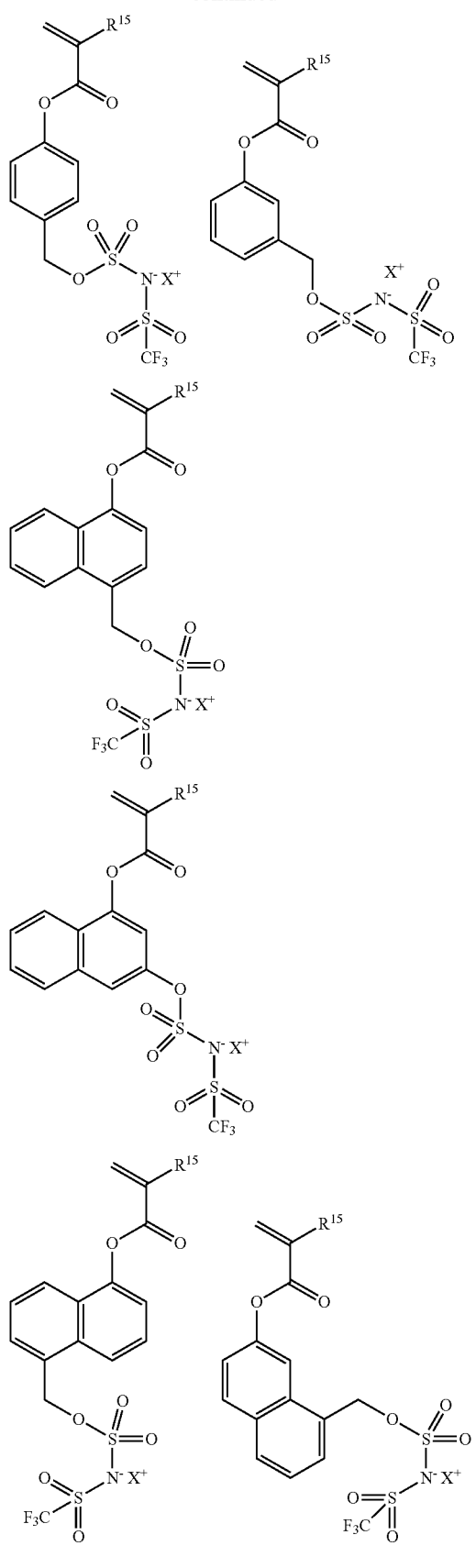
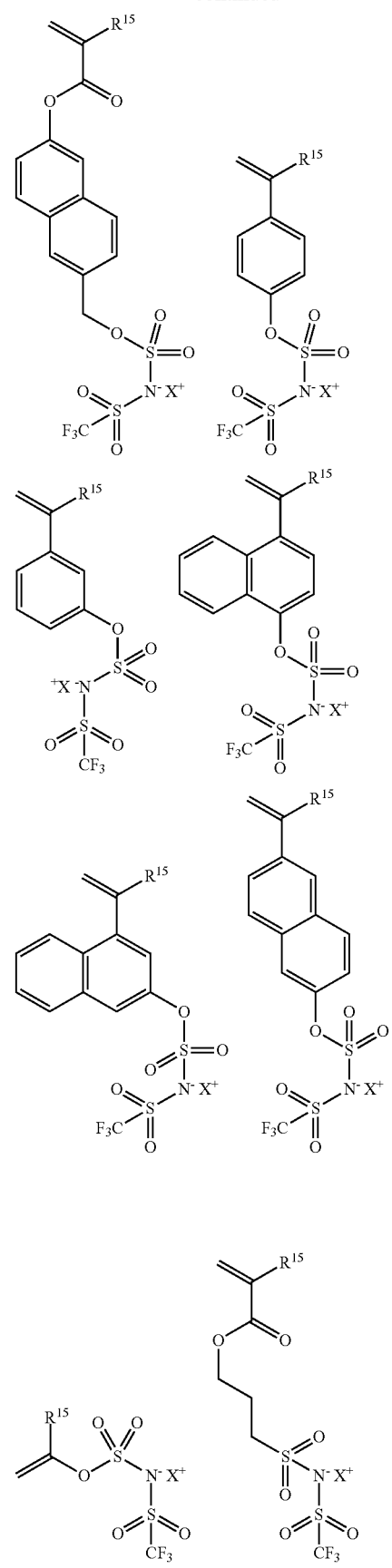

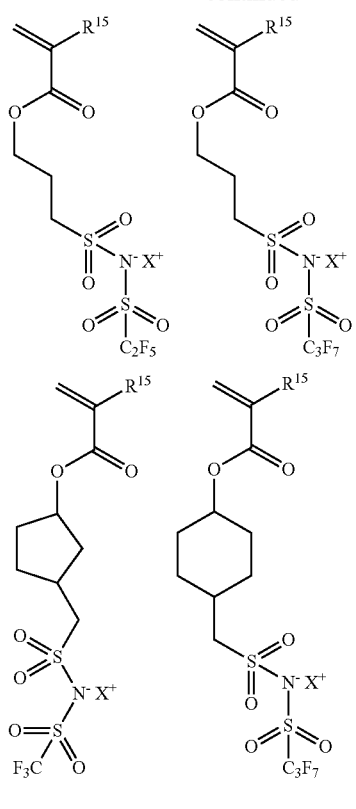
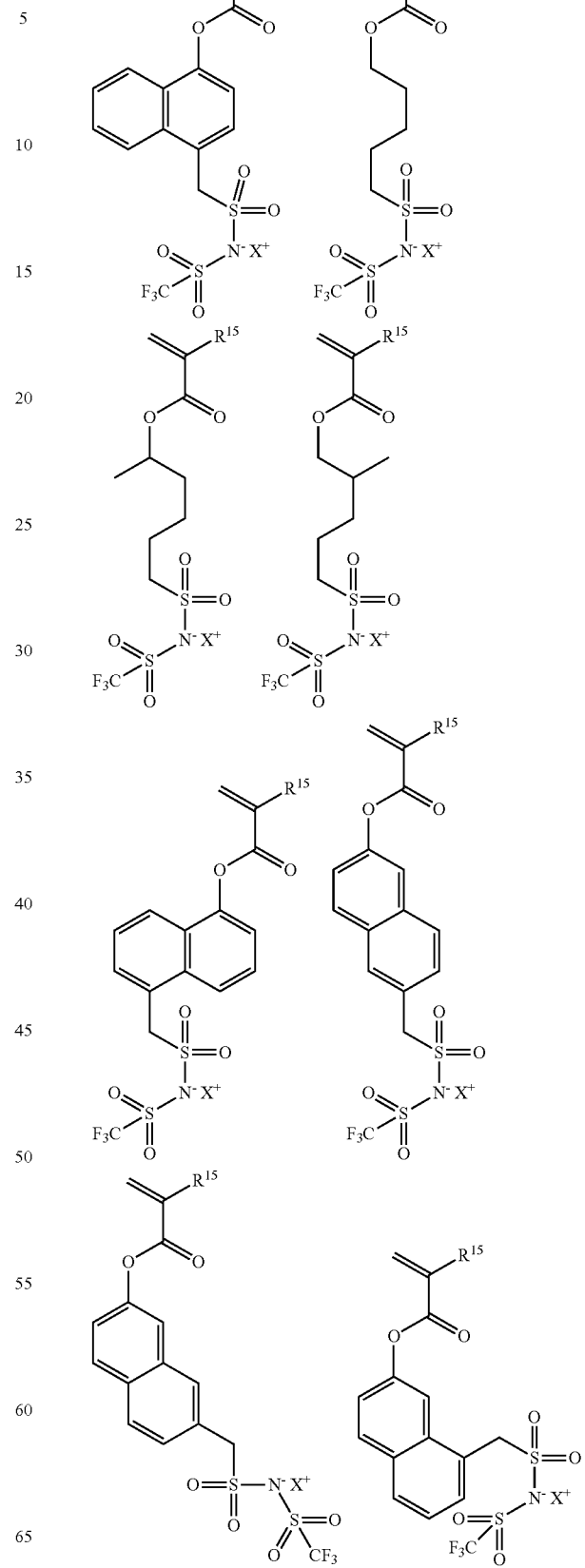

-continued
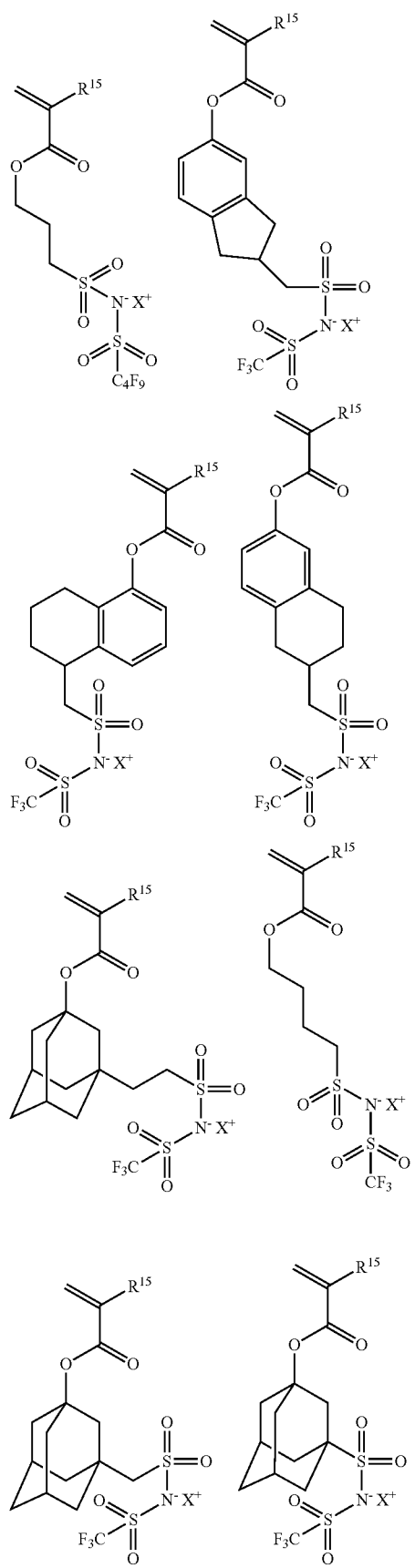
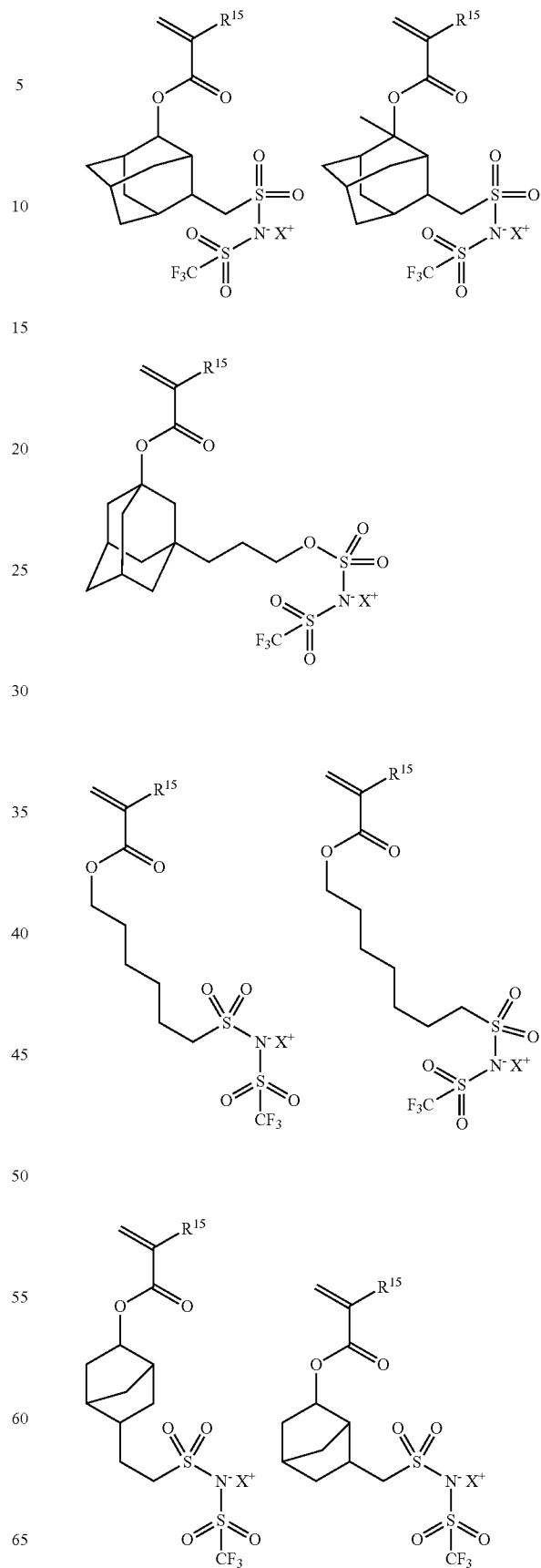

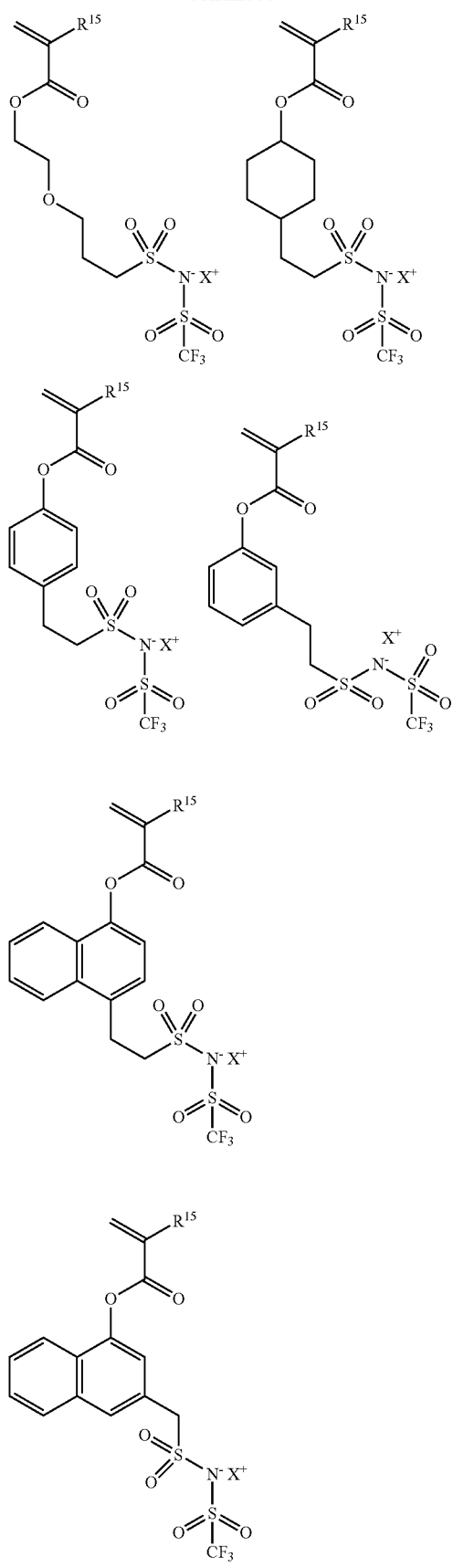
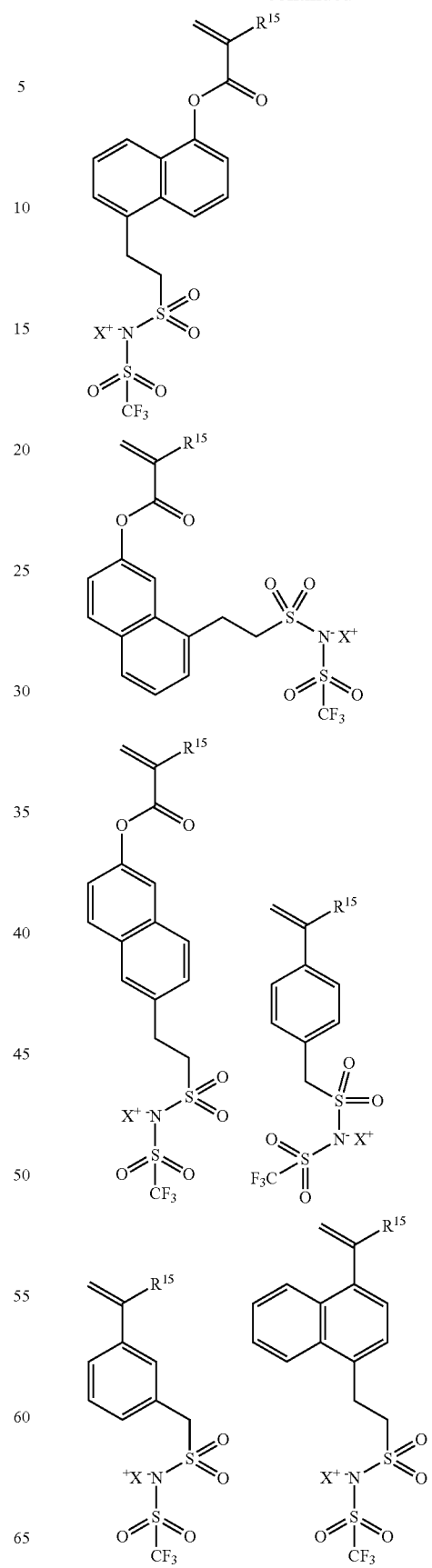

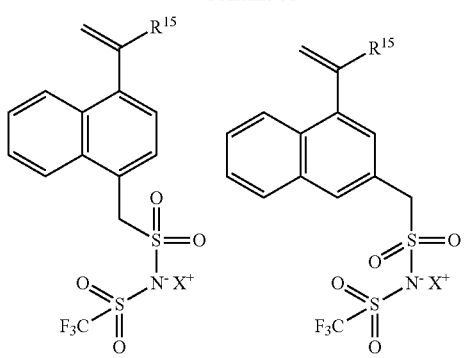
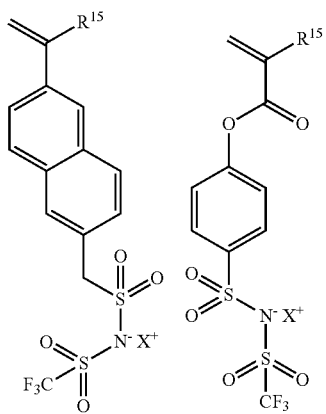
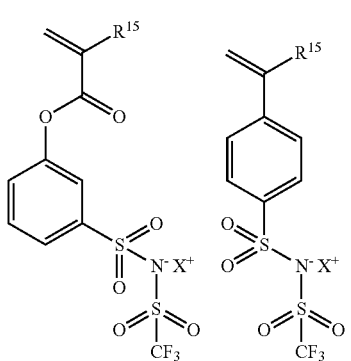
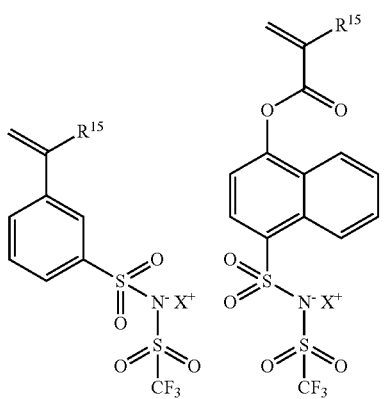
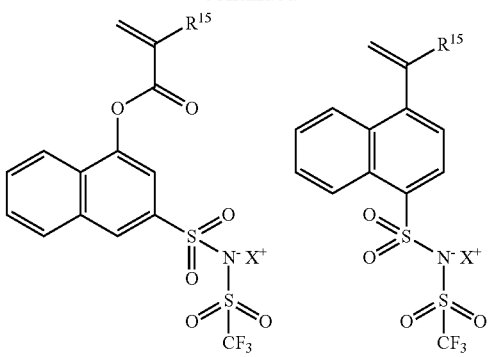
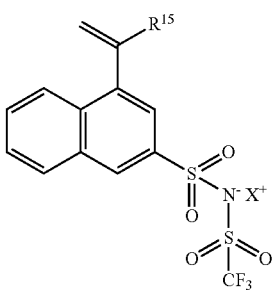
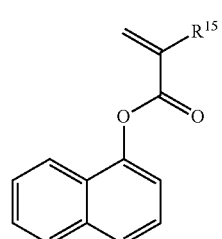
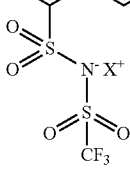
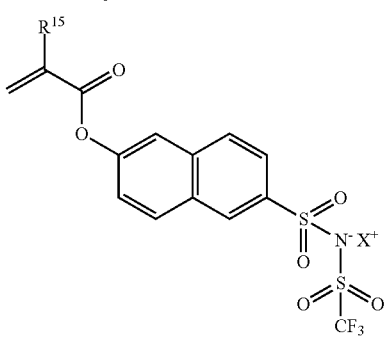
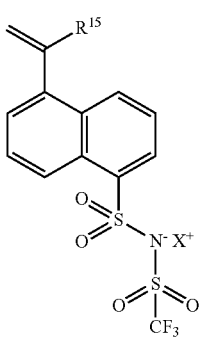

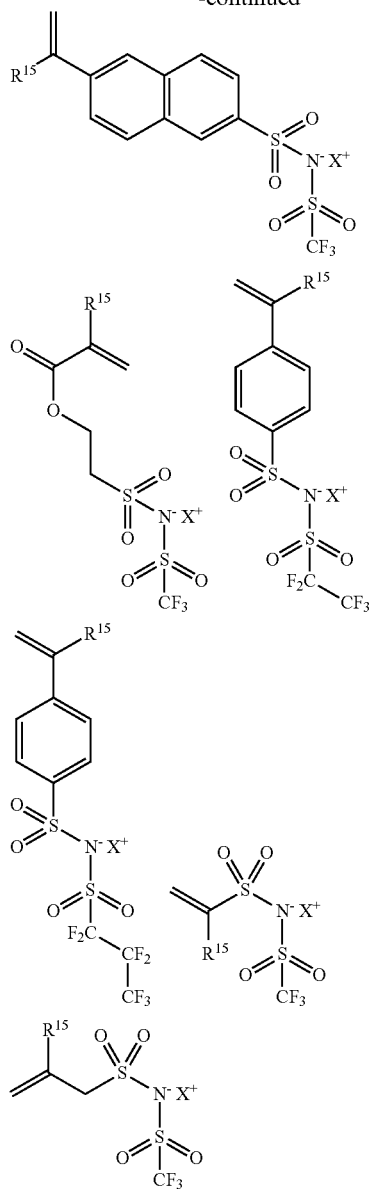
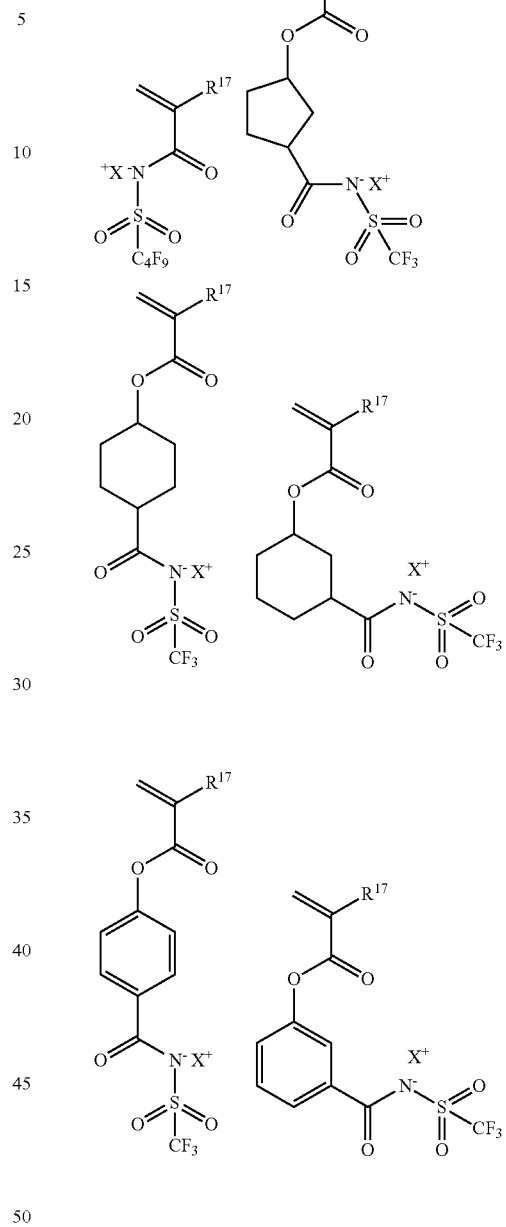
In the formulae, $R^{15}$ and X have the same meanings as defined above.
The sulfonamide salt monomer to obtain the repeating unit a7 in the formulae (2) is not particularly limited, and specific illustrative examples thereof include the following.
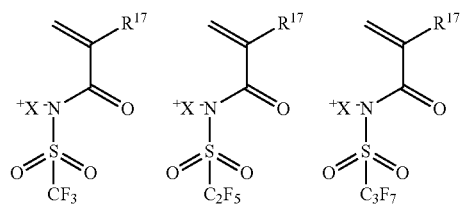
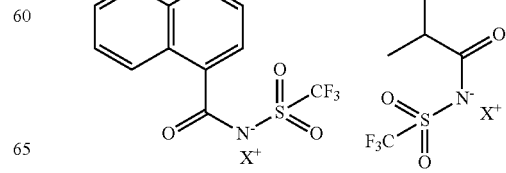

87
-continued
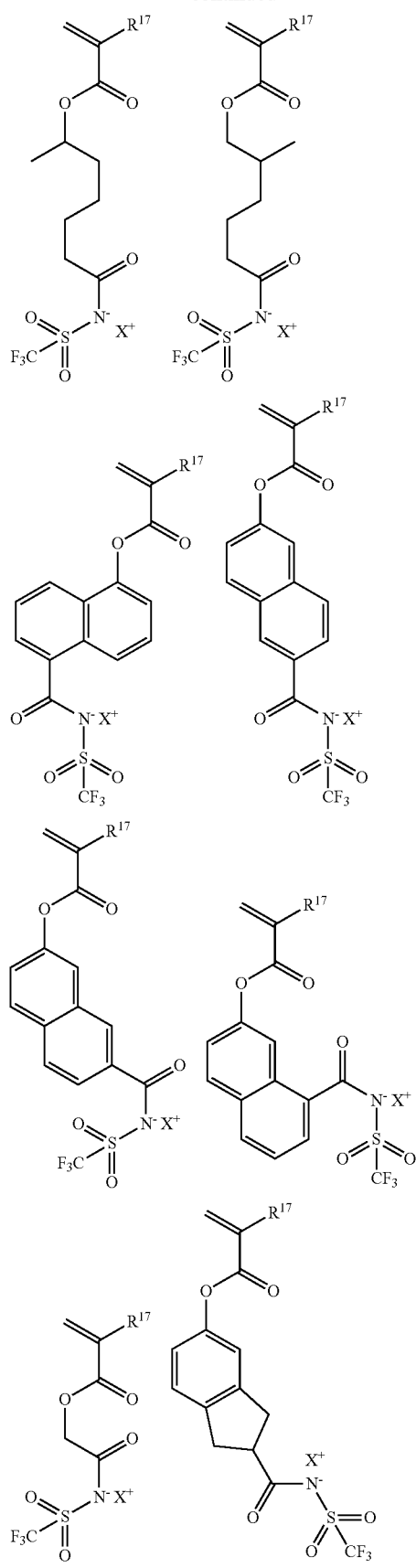
88
-continued
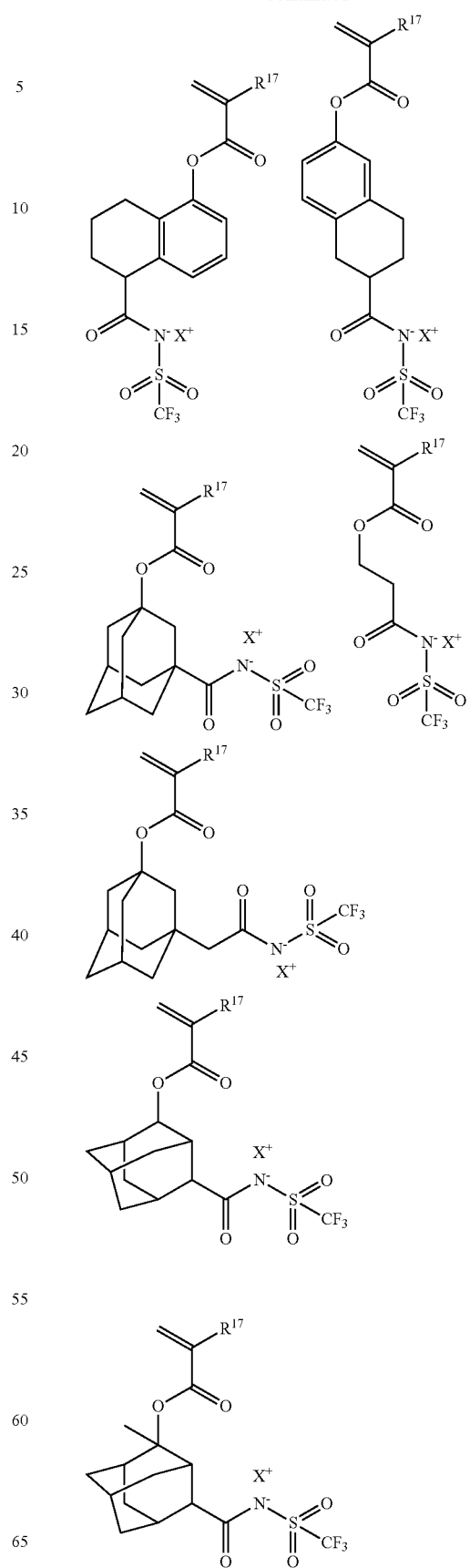

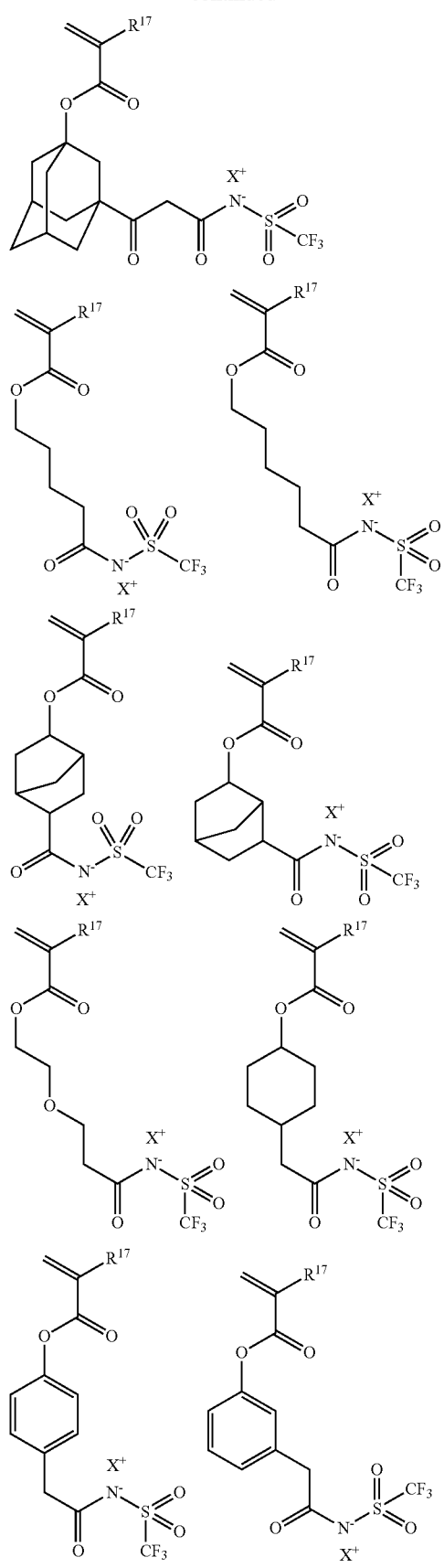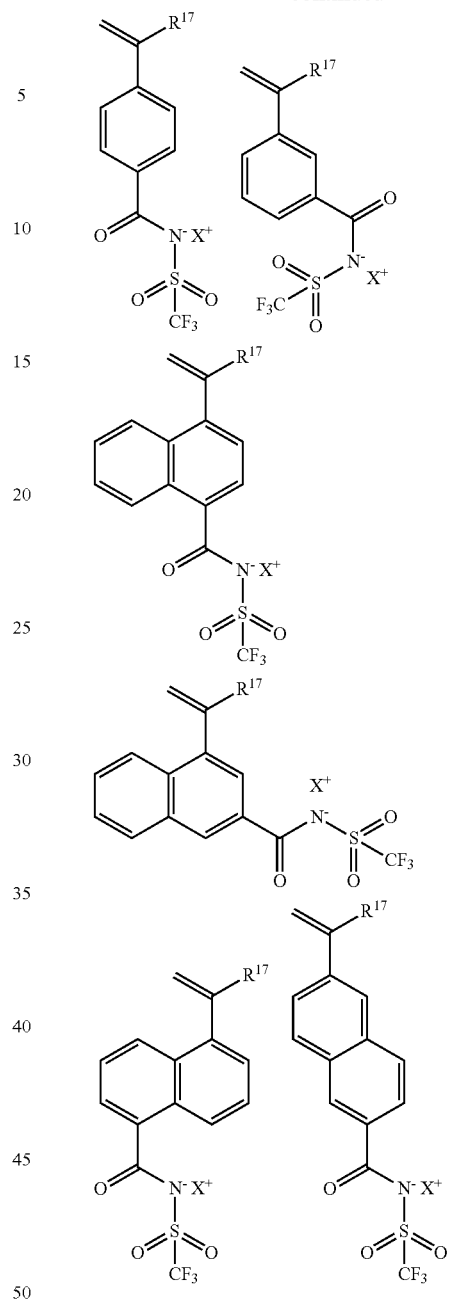
In the formulae, $R^{17}$ and X have the same meanings as defined above.
The ammonium cation structure shown by the formula (1)-5 is not particularly limited, and specific illustrative examples thereof include the following.
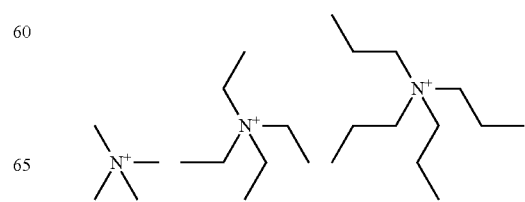

91
-continued
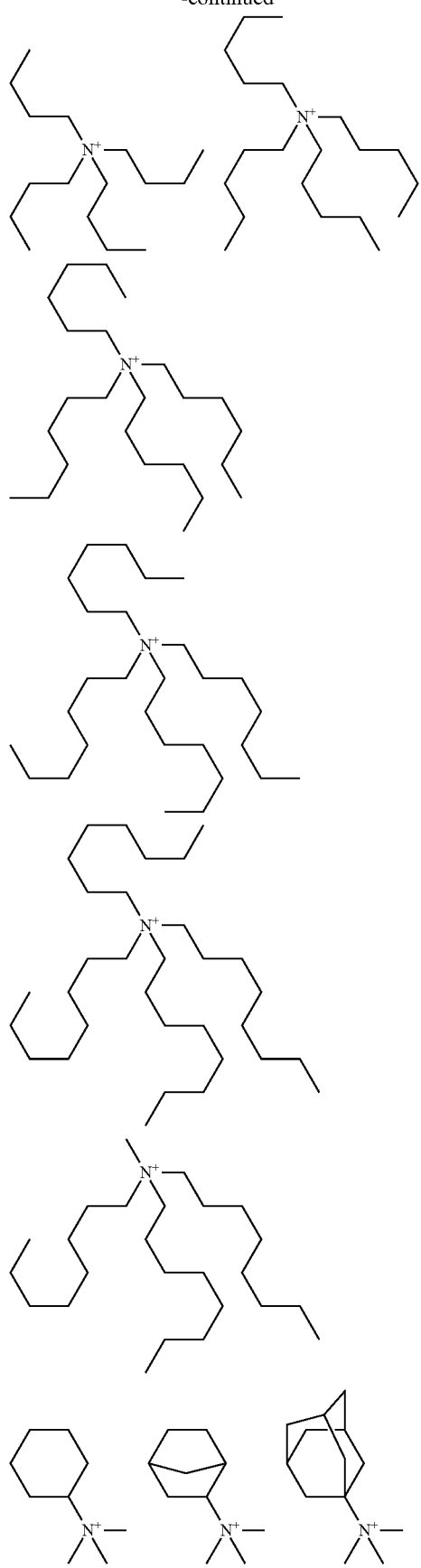
92
-continued
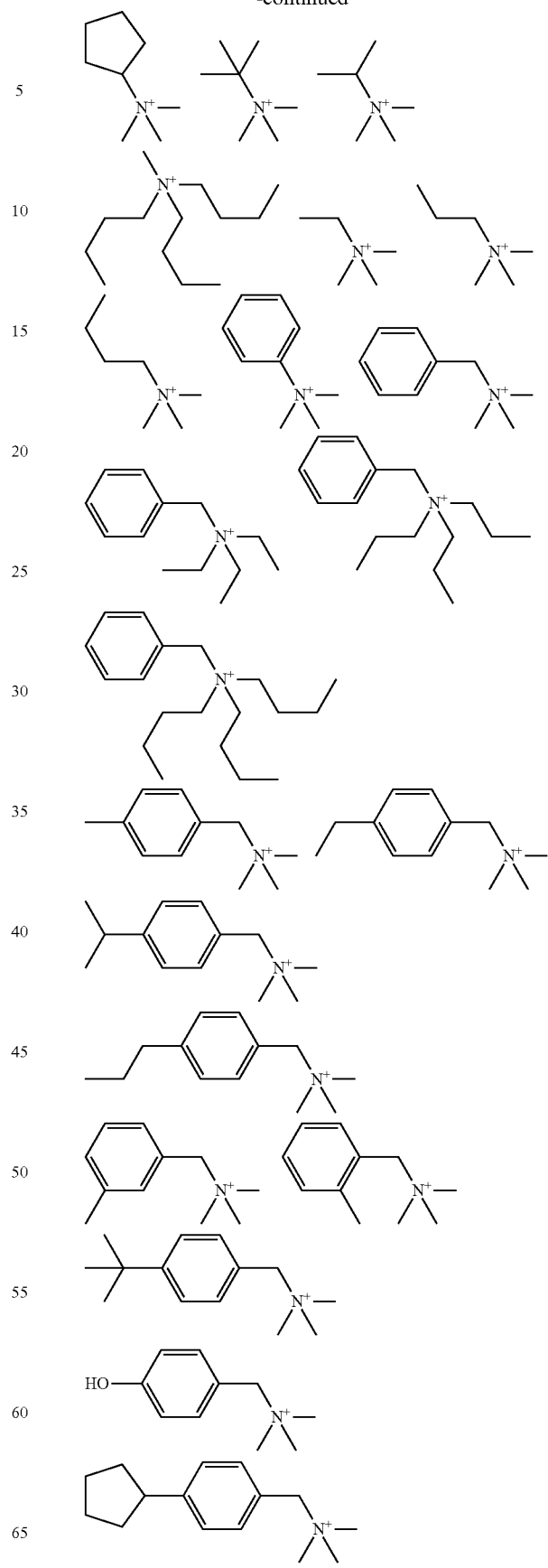

-continued
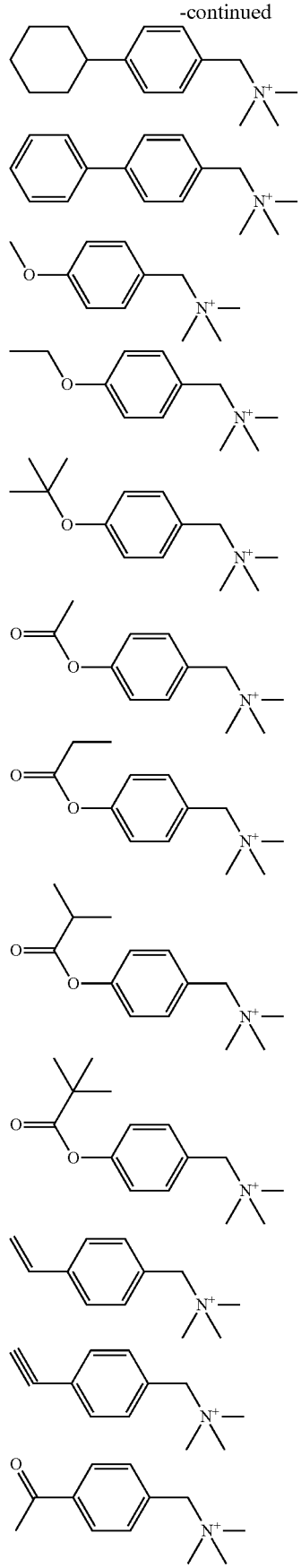
-continued
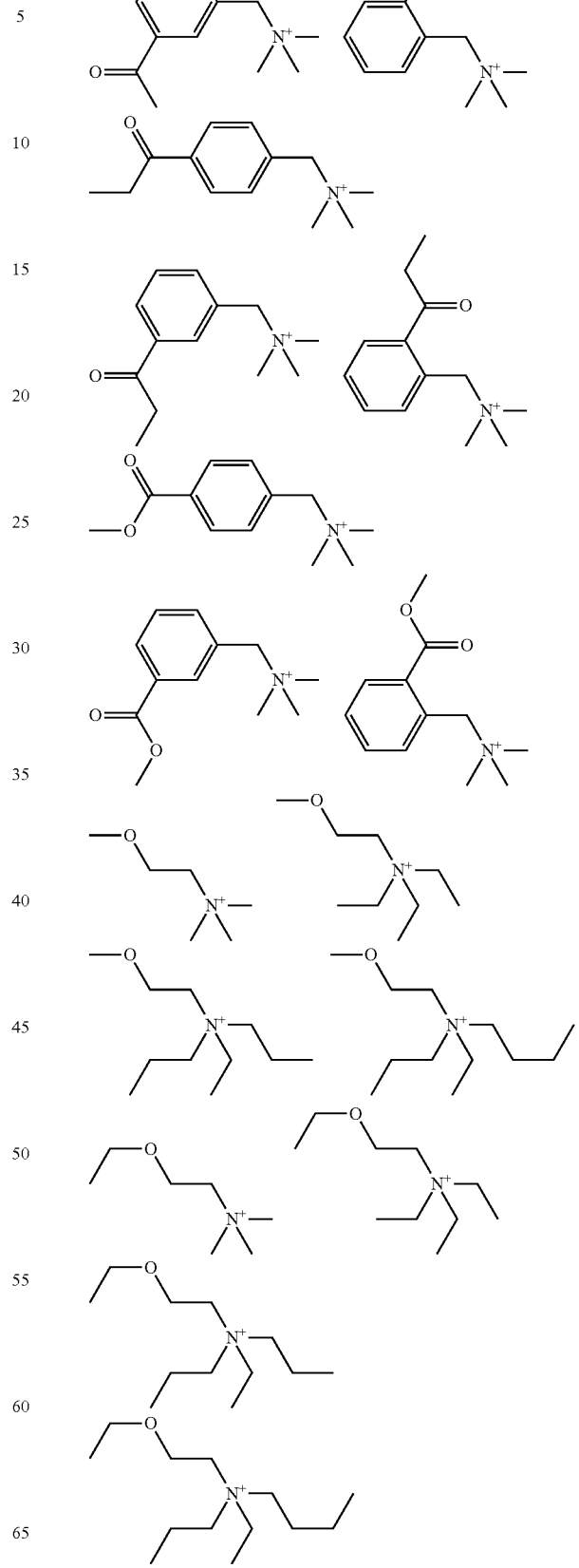

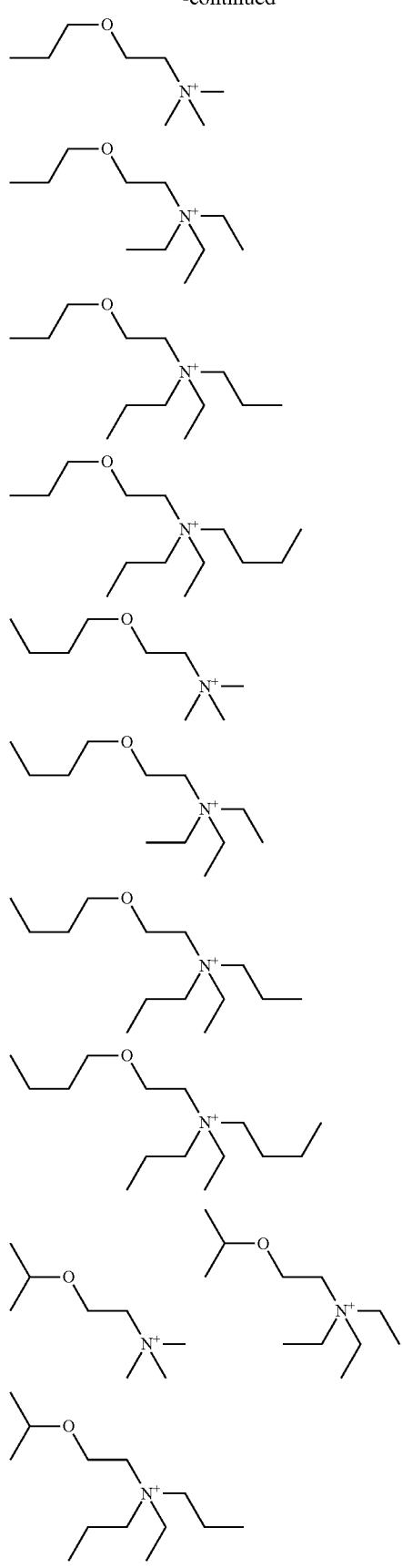
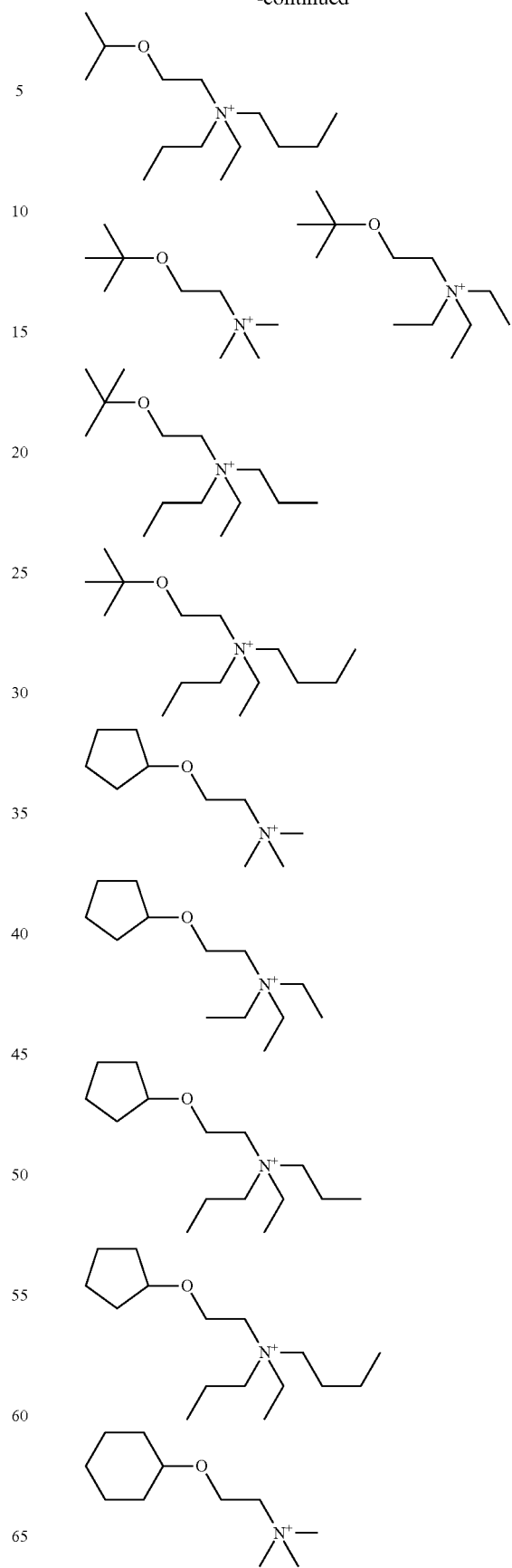

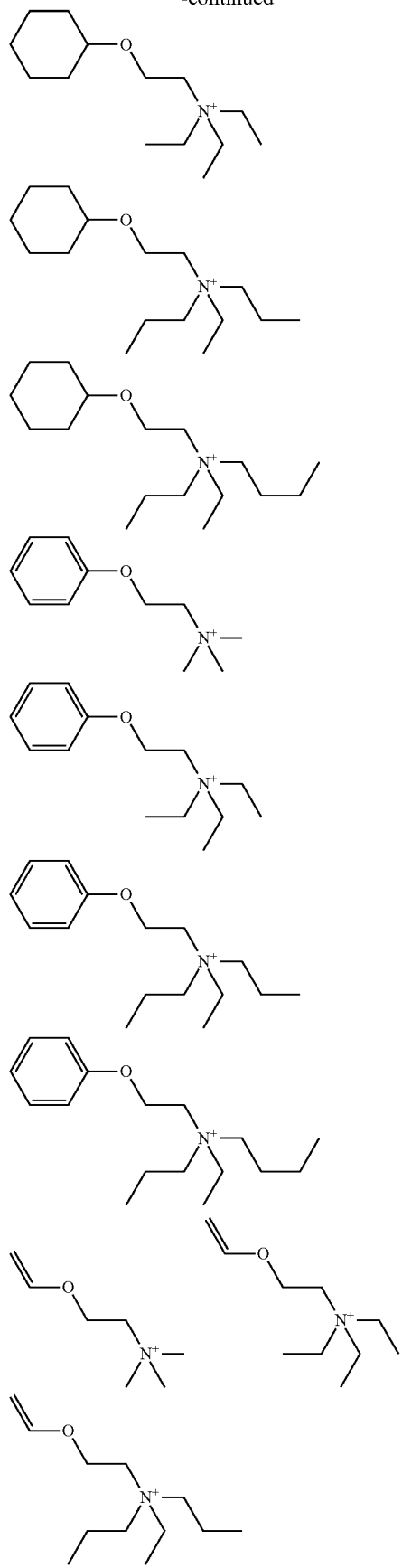
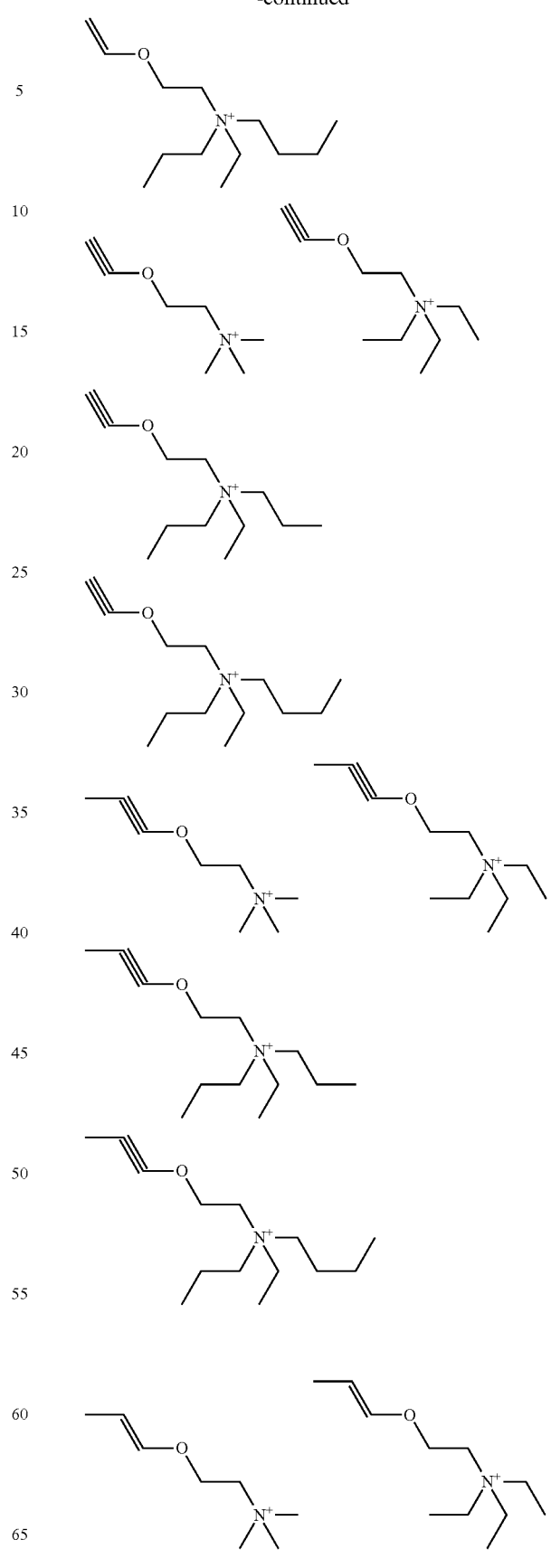

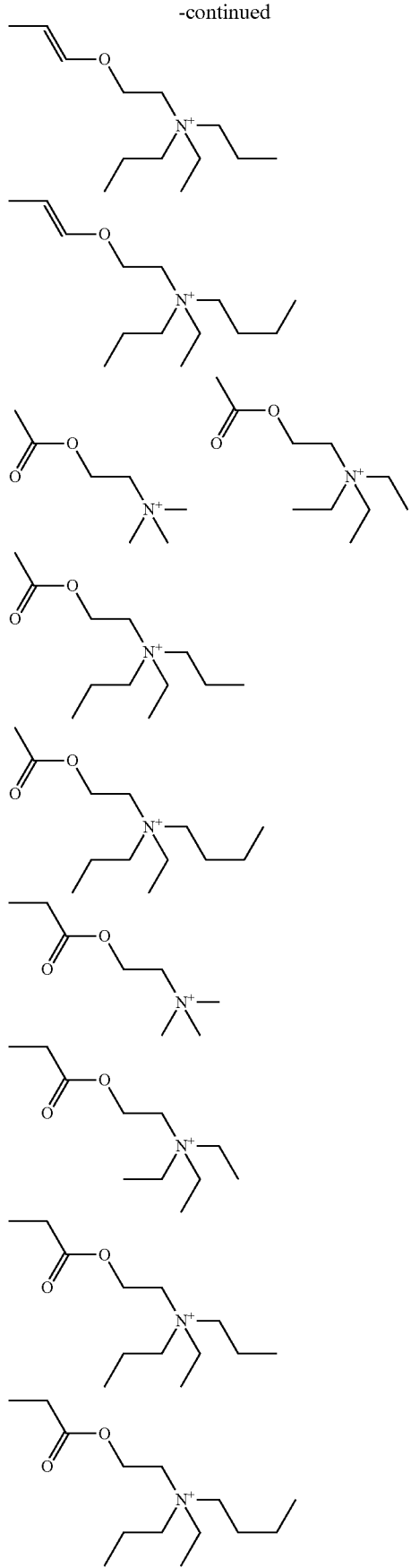
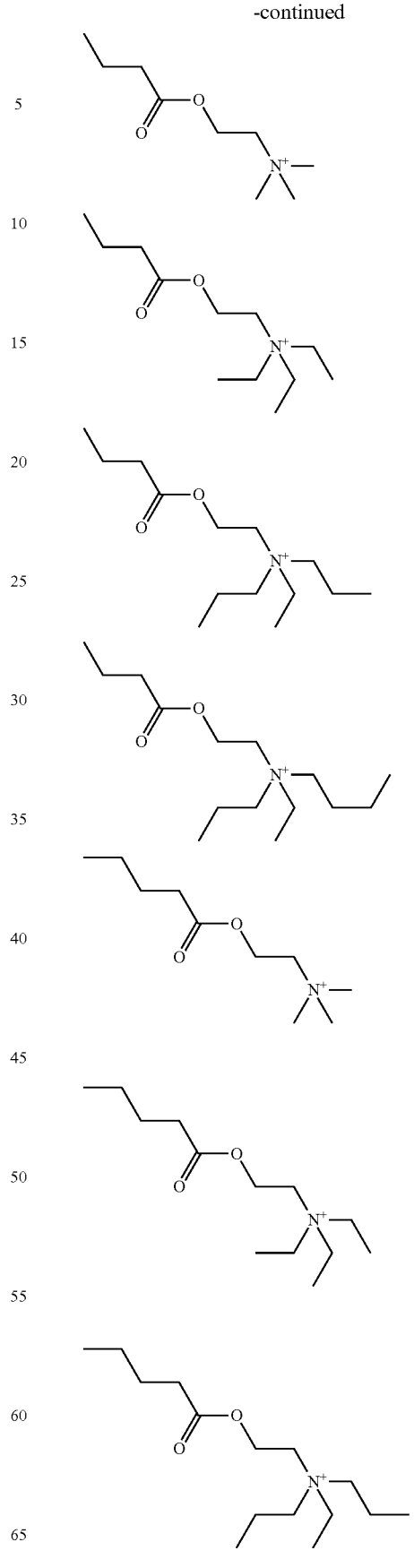

101
-continued
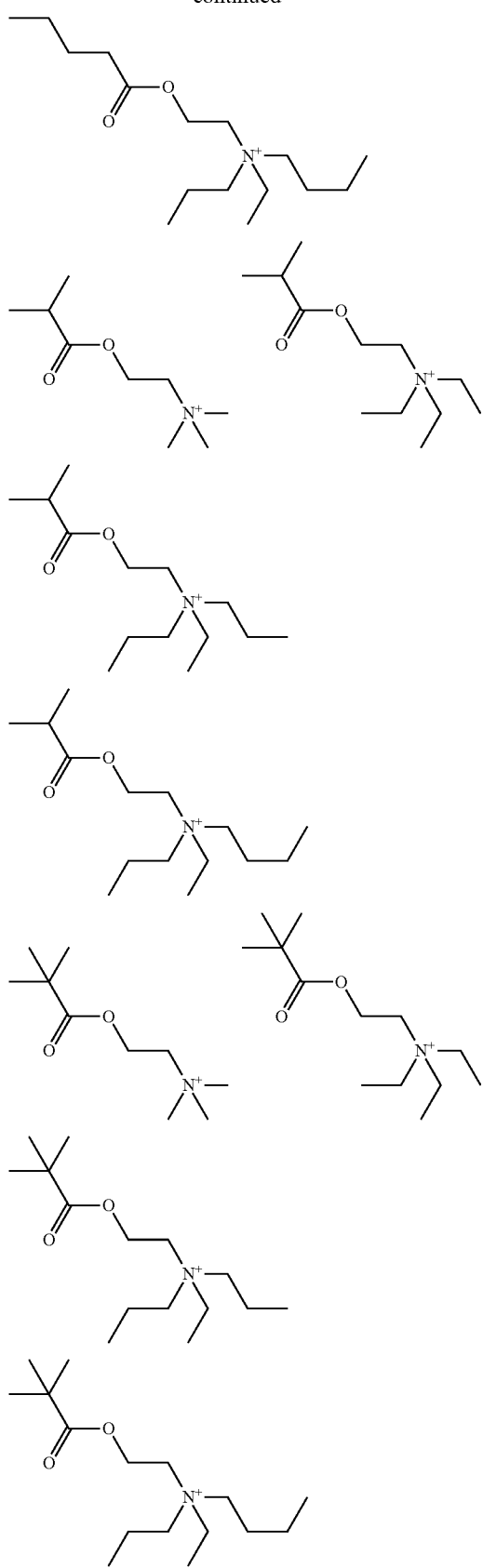
102
-continued
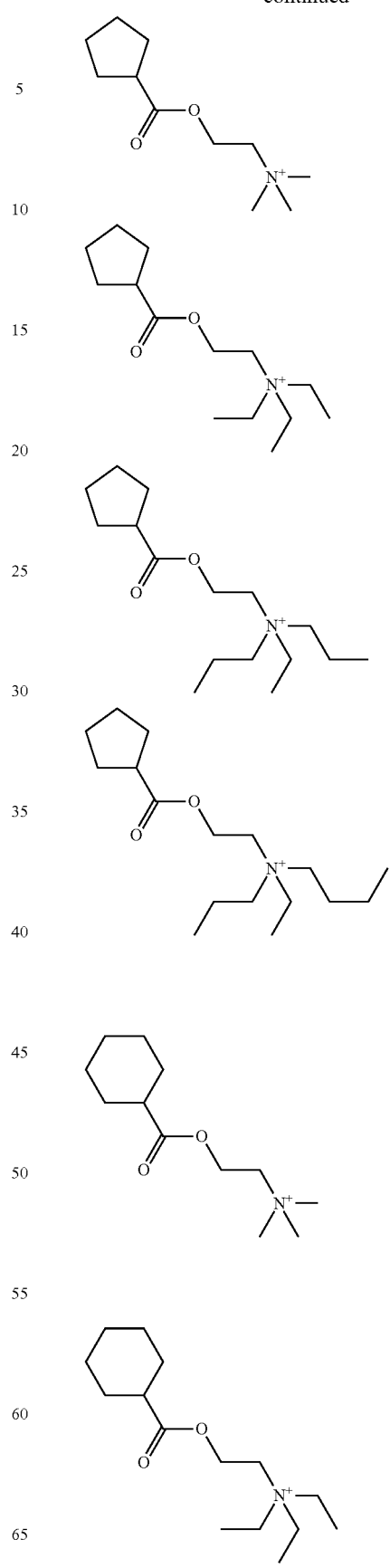

103
-continued
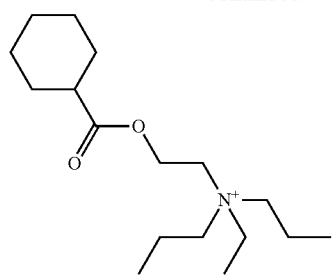
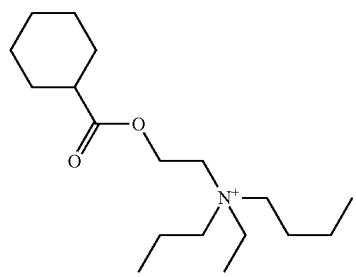
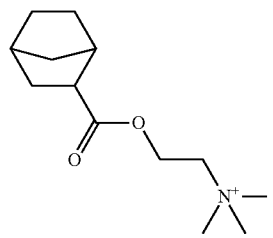
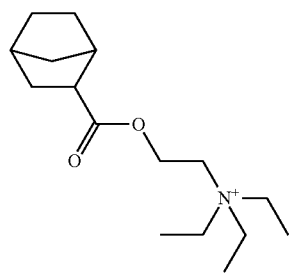
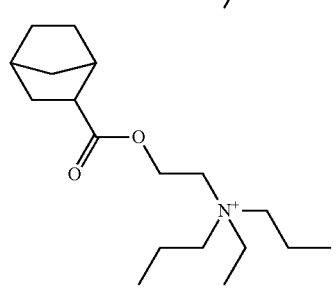
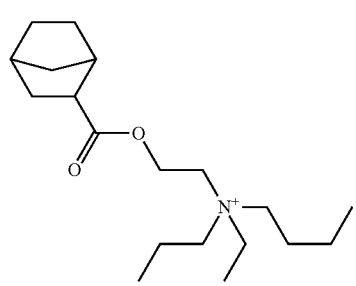
104
-continued
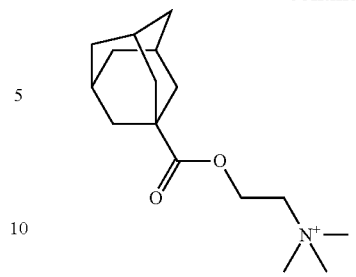
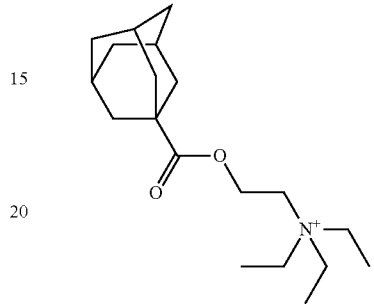
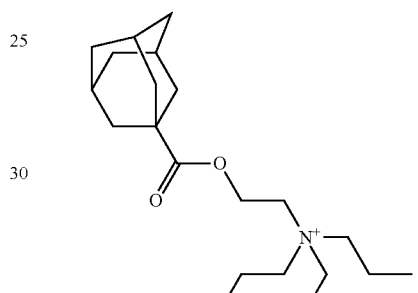
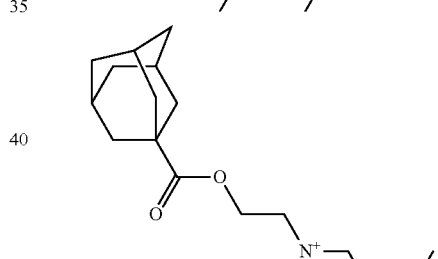
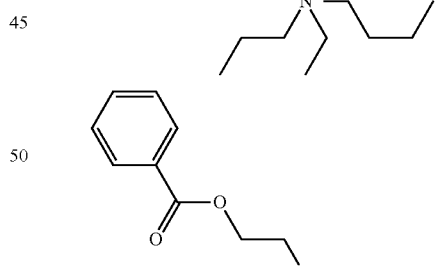
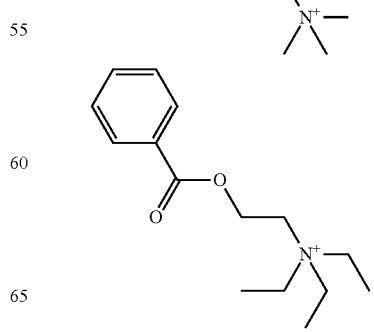
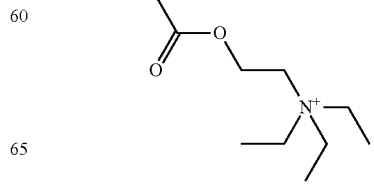

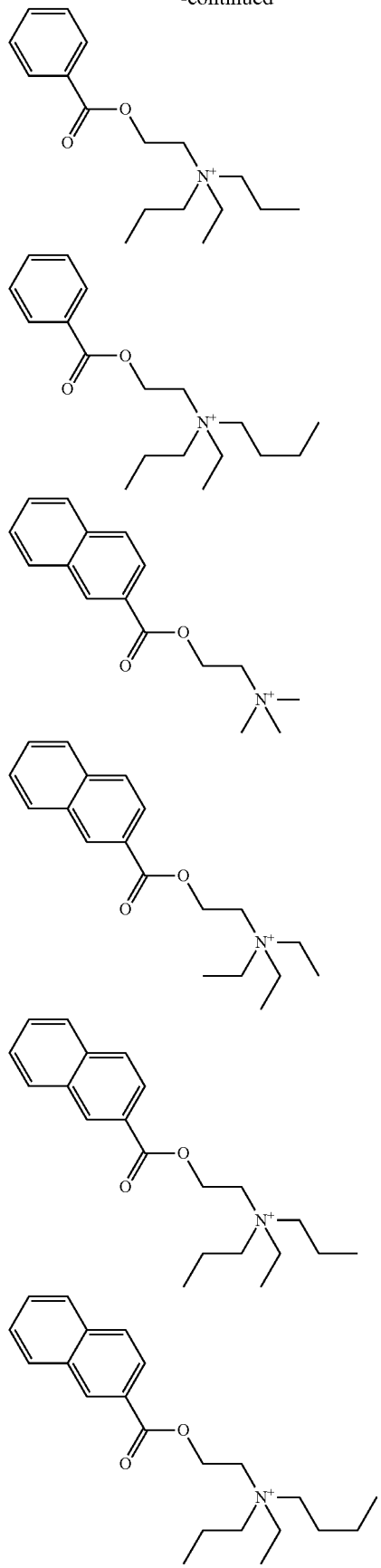
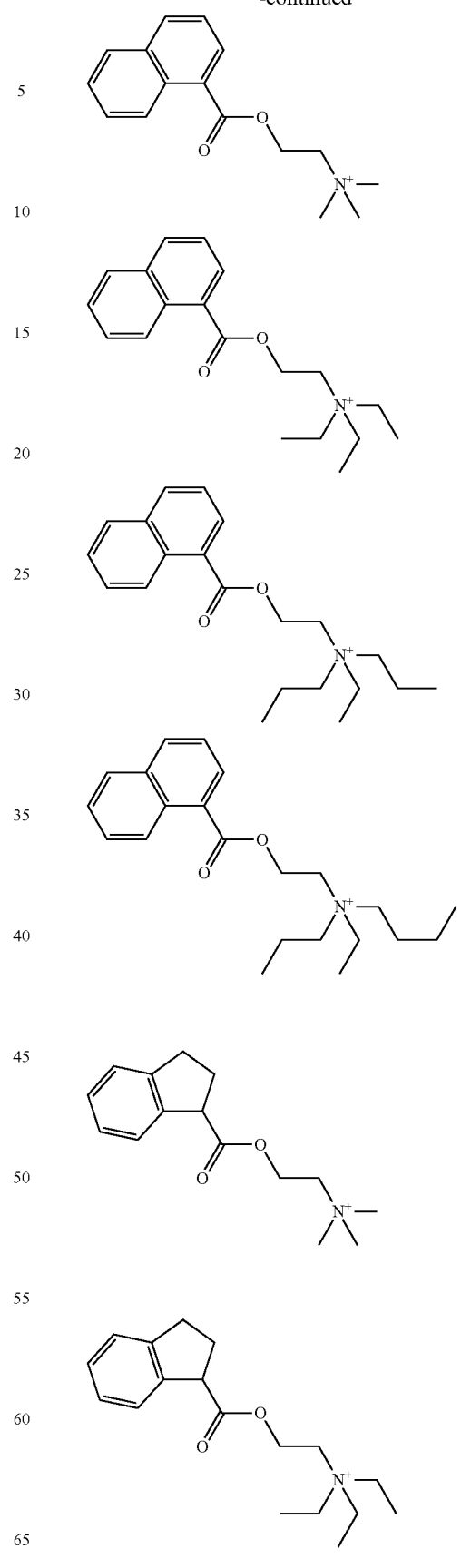

107
-continued
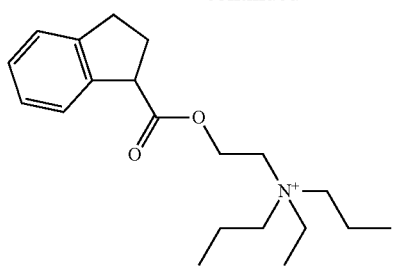
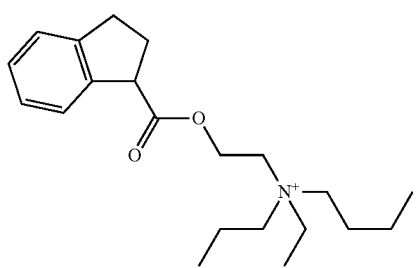
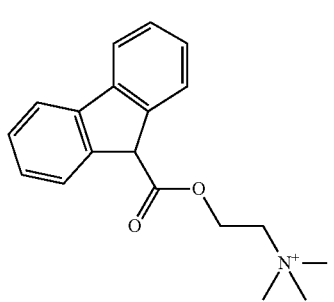
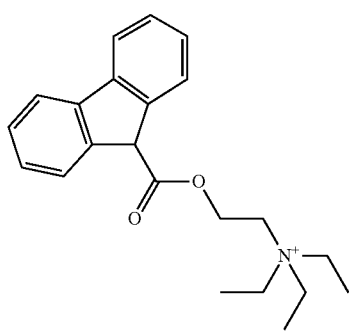
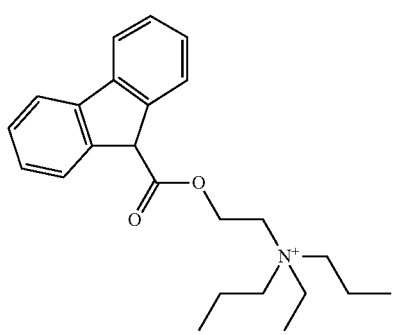
108
-continued
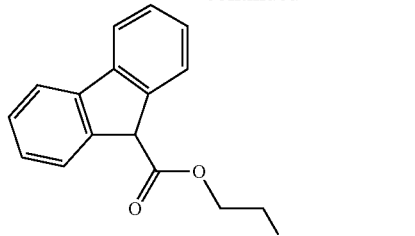
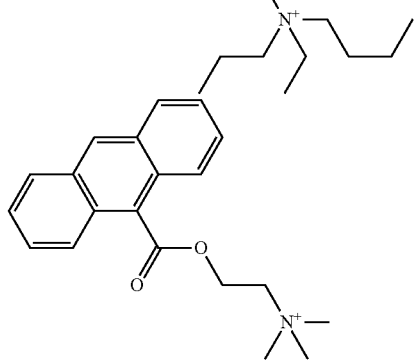
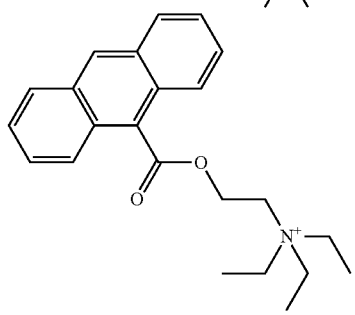
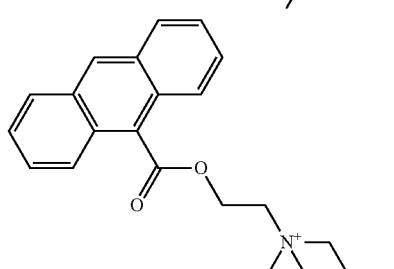
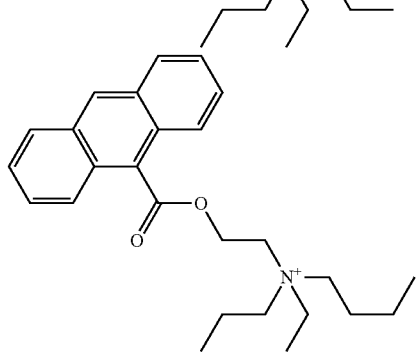
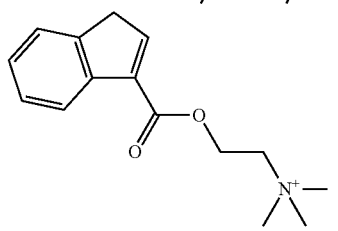

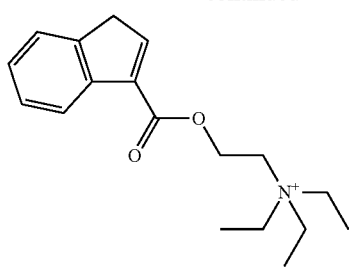
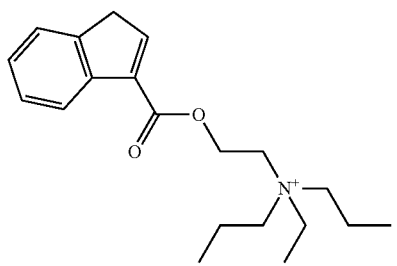
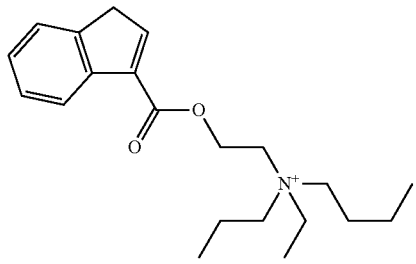
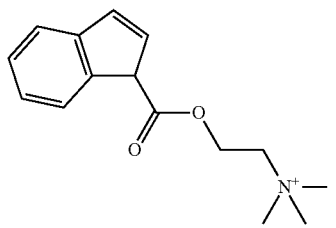
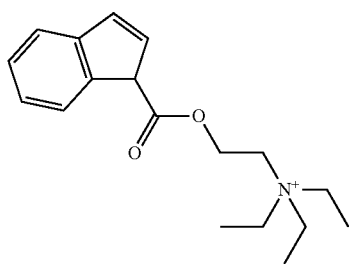
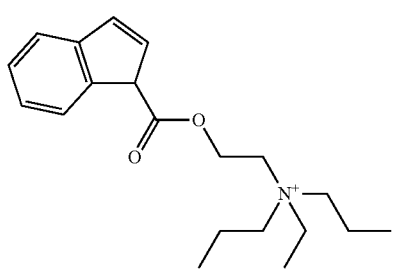
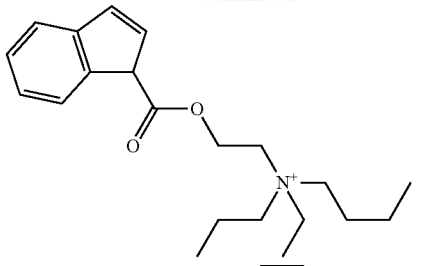
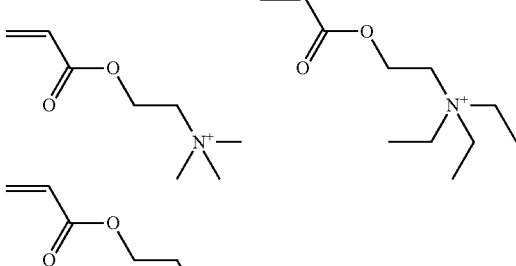
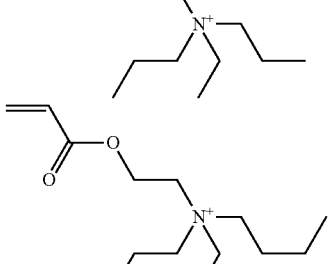
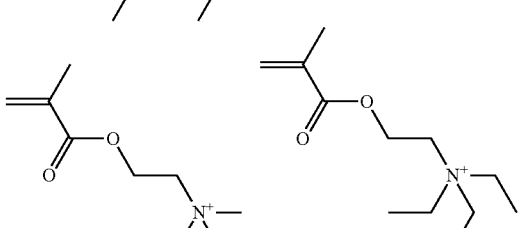
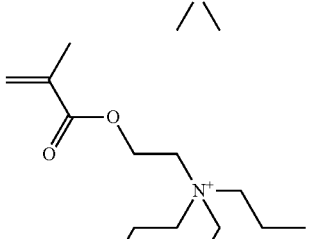
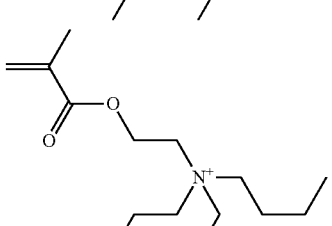
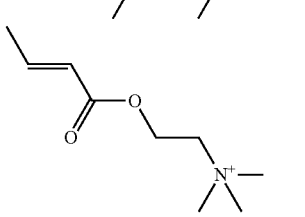

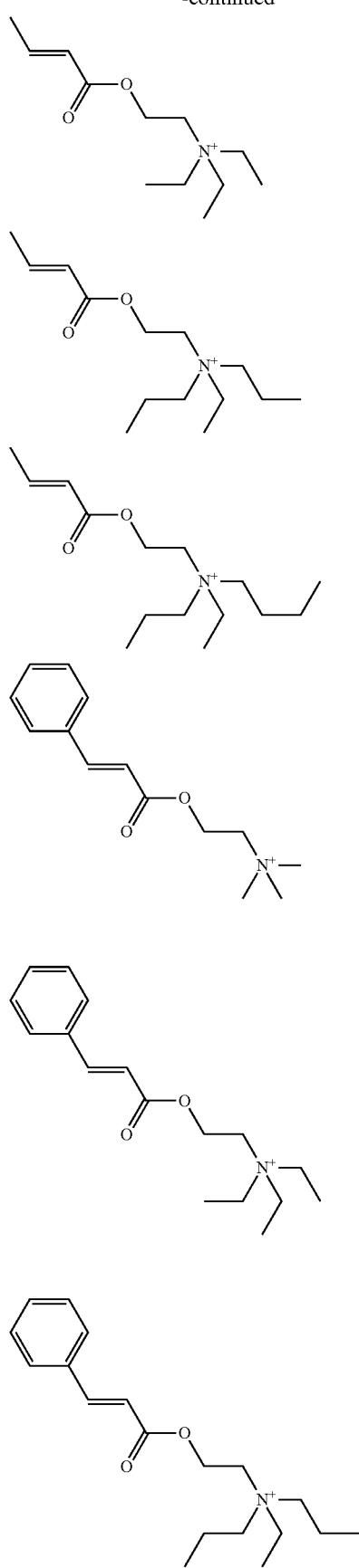
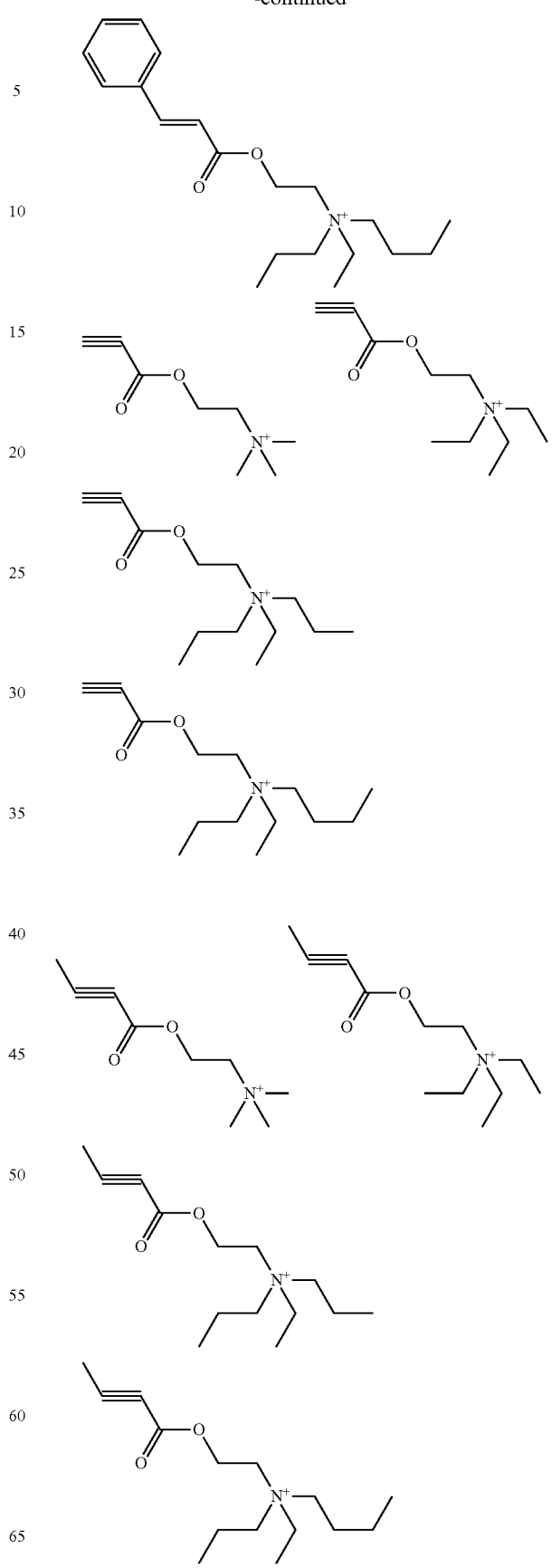

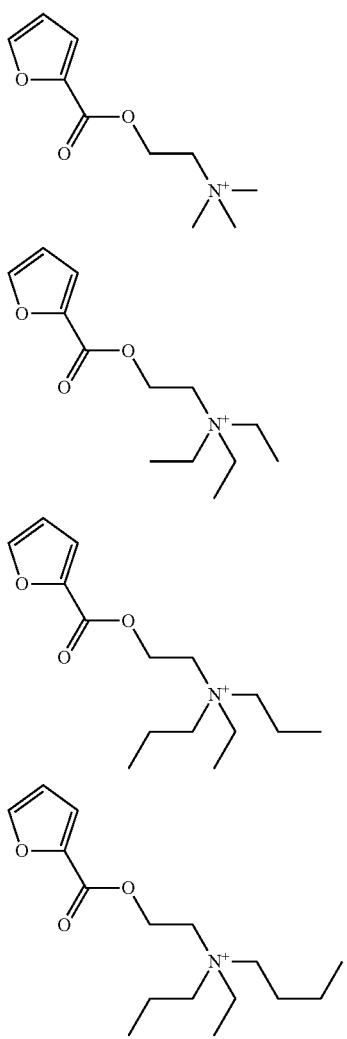
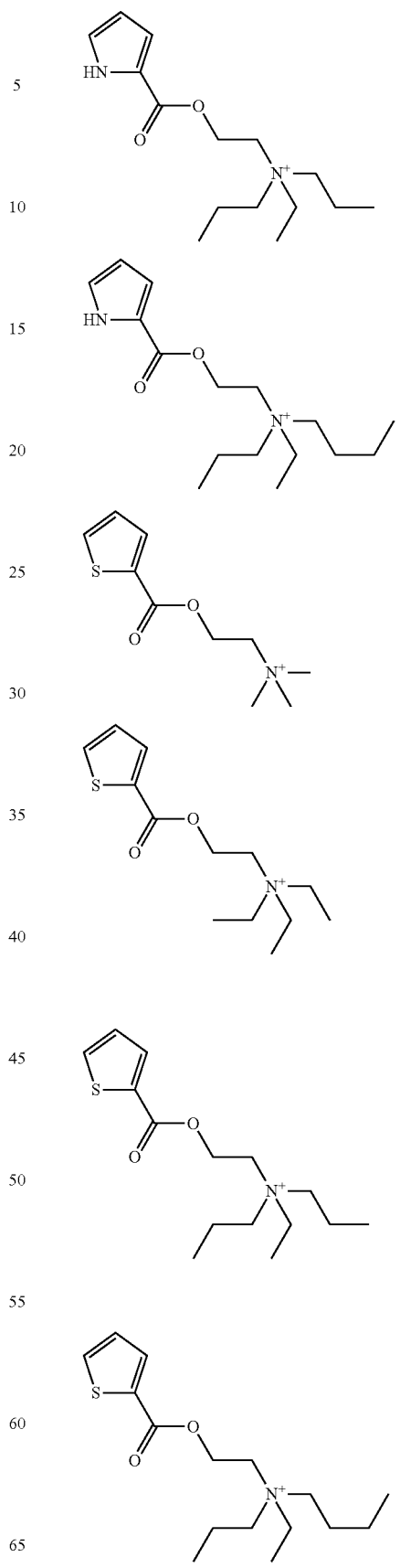

115
-continued
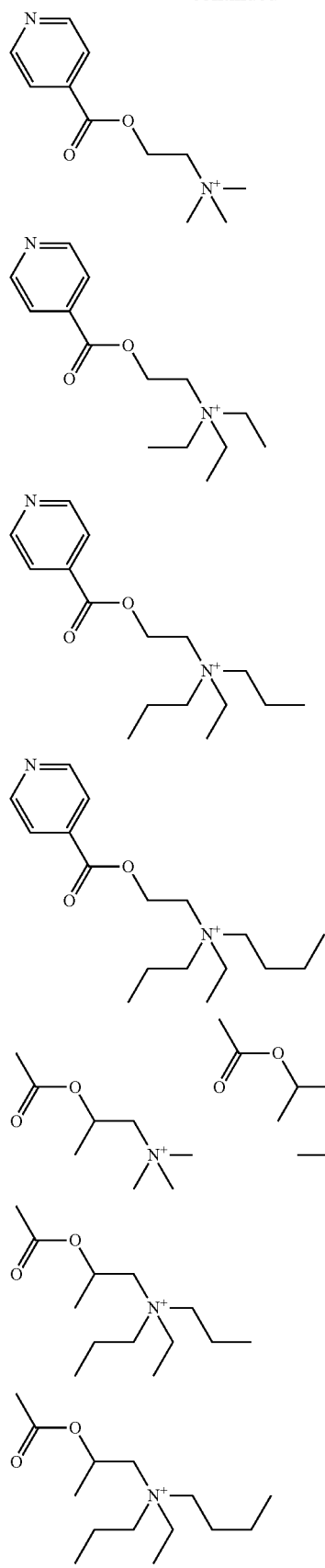
116
-continued
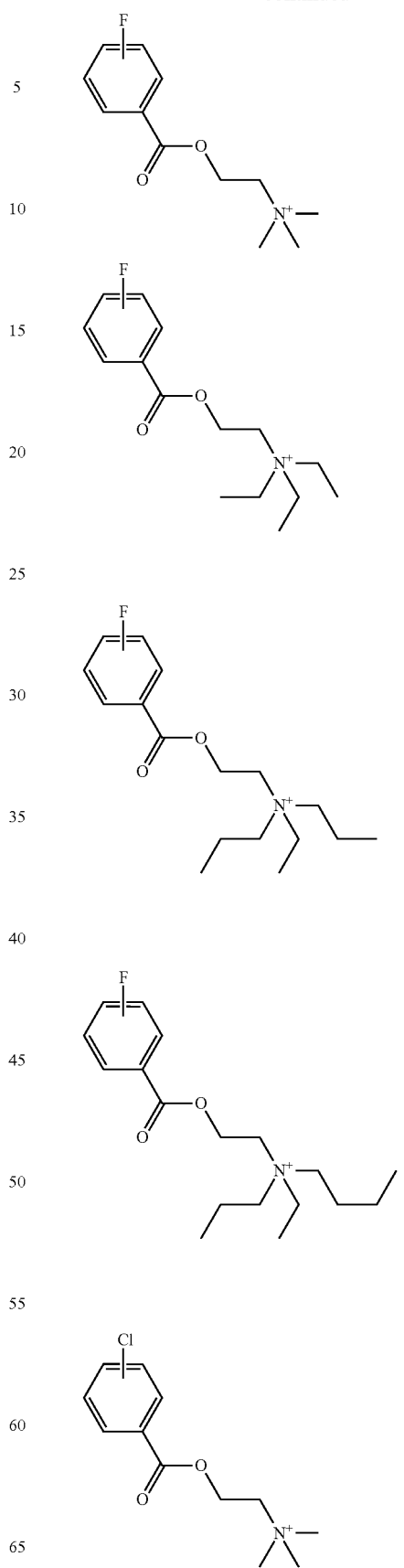

117
-continued
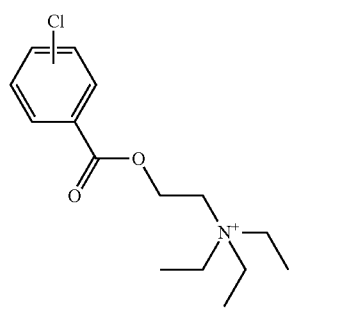
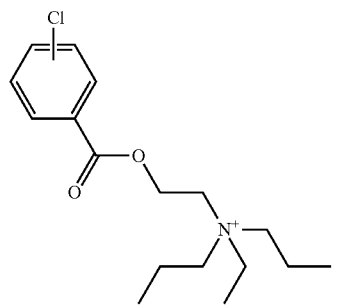
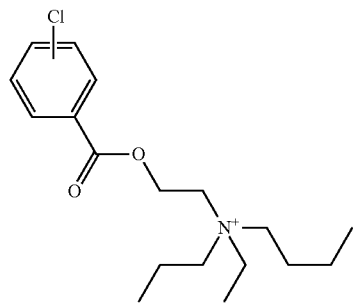
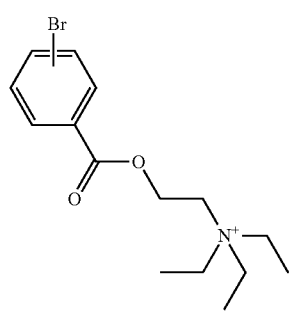
118
-continued
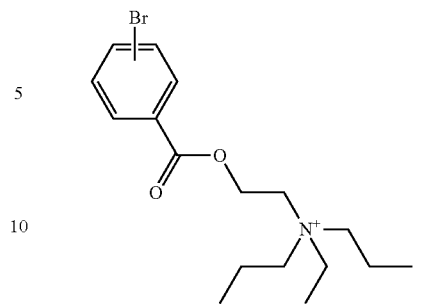
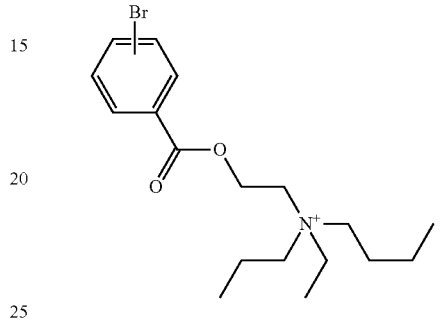
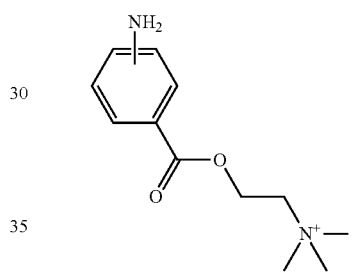
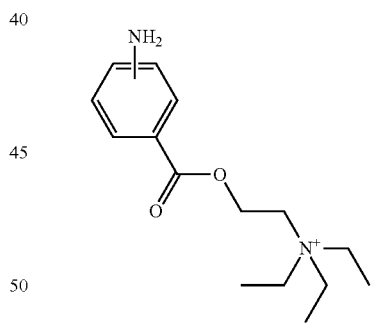
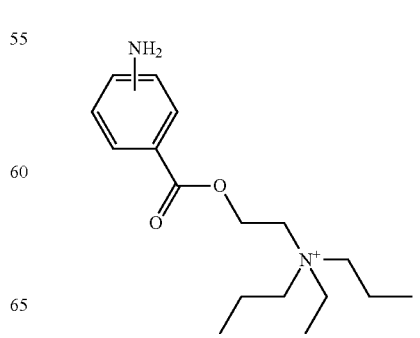

119
-continued
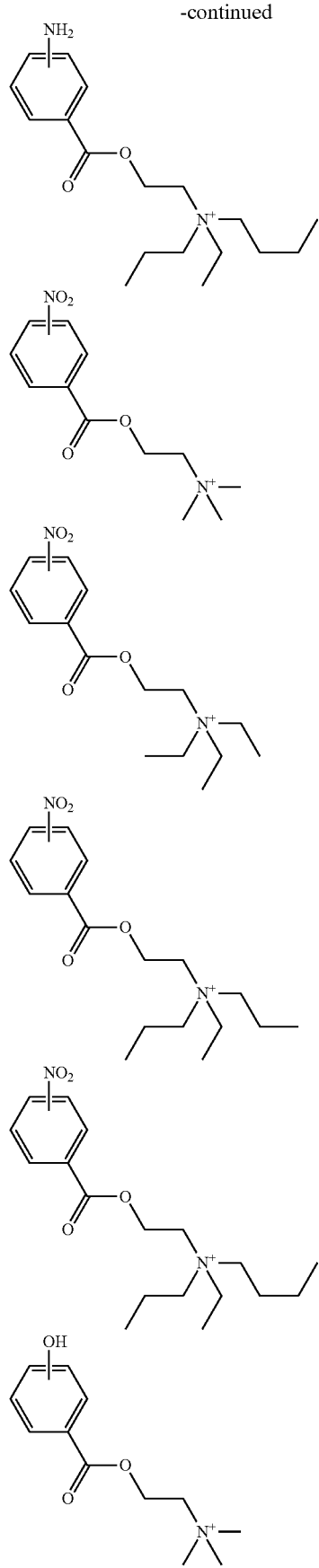
120
-continued
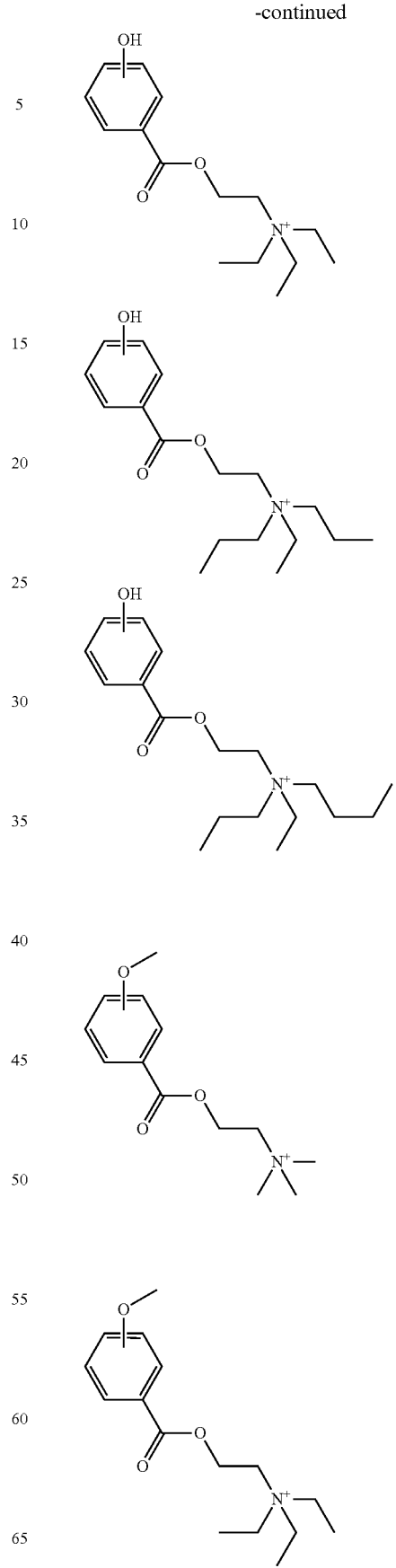

121
-continued
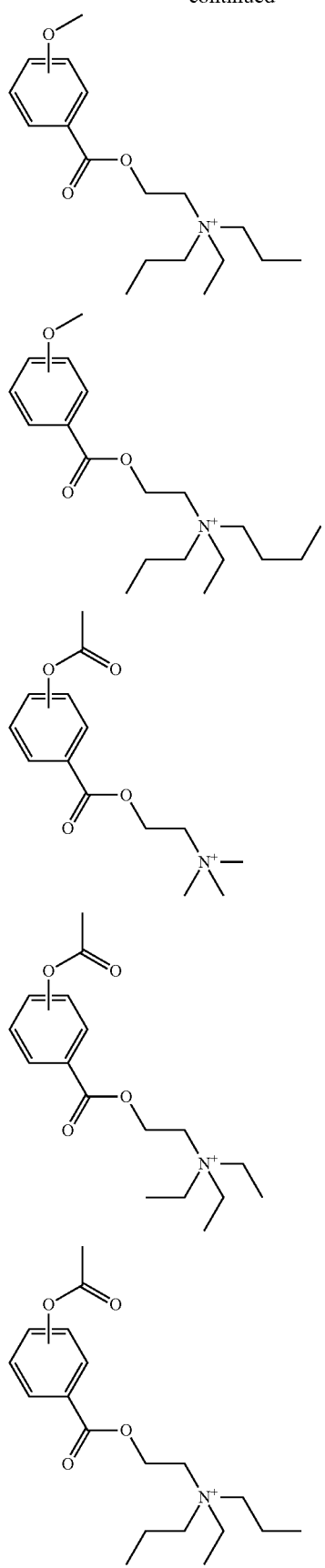
122
-continued
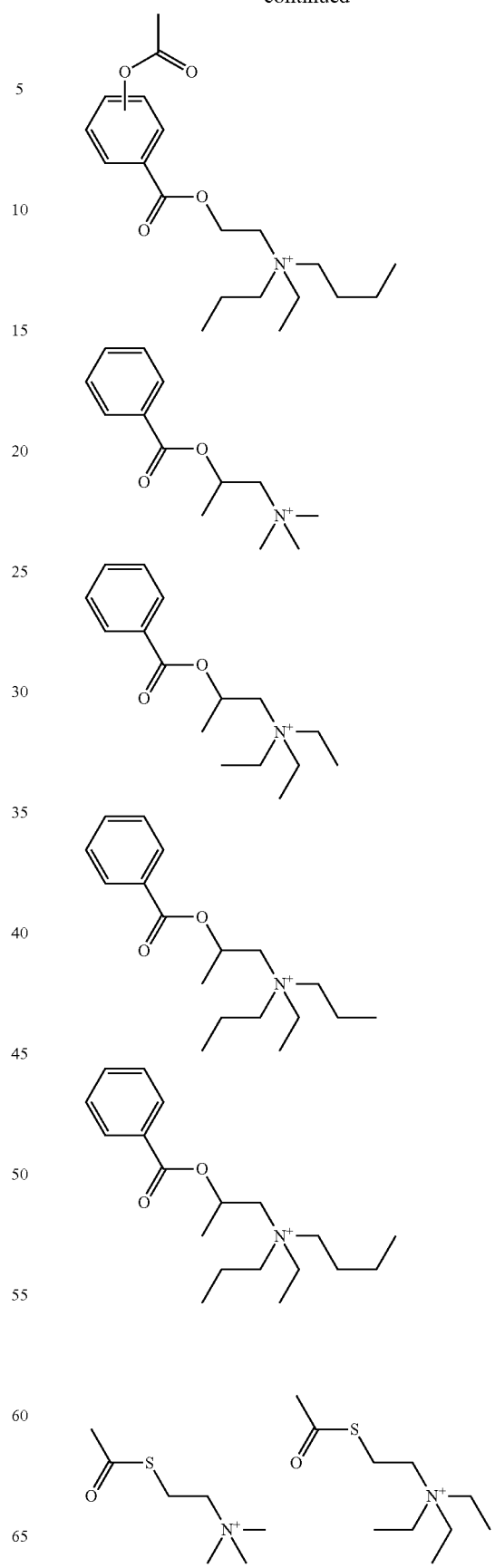

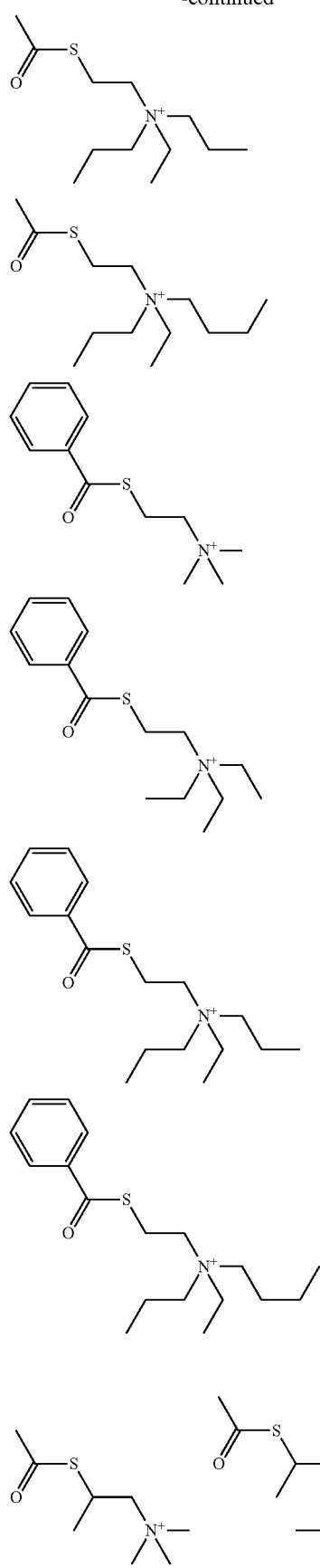
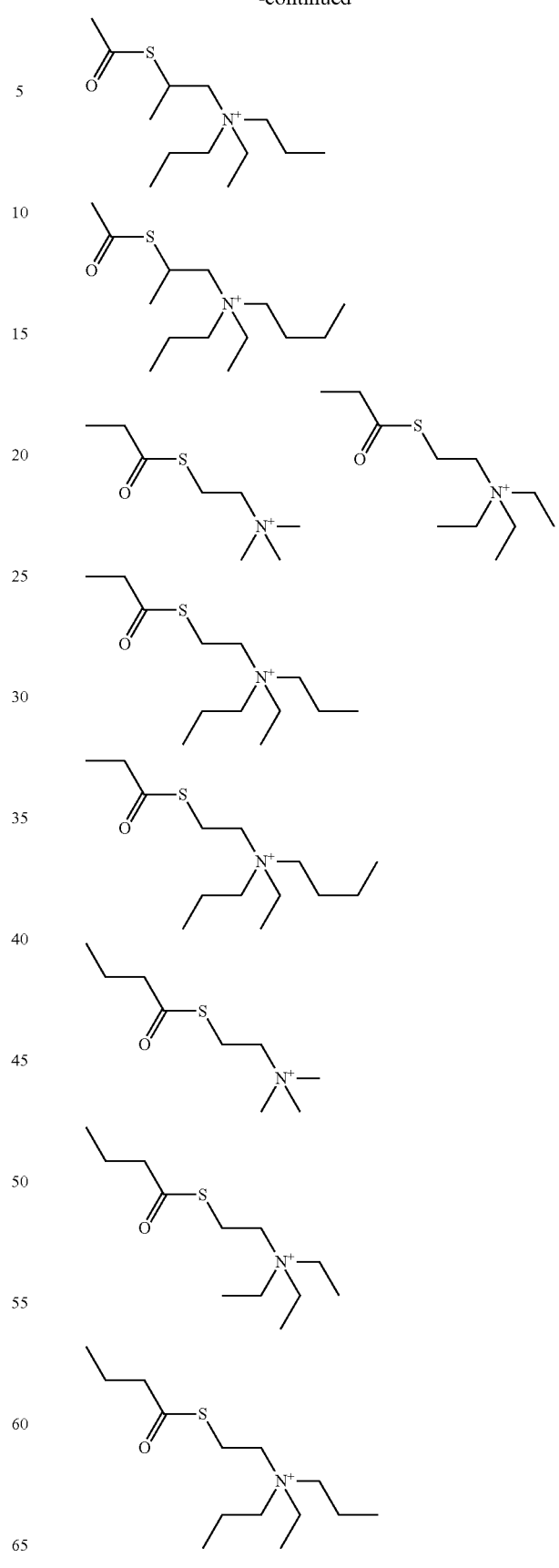

125
-continued
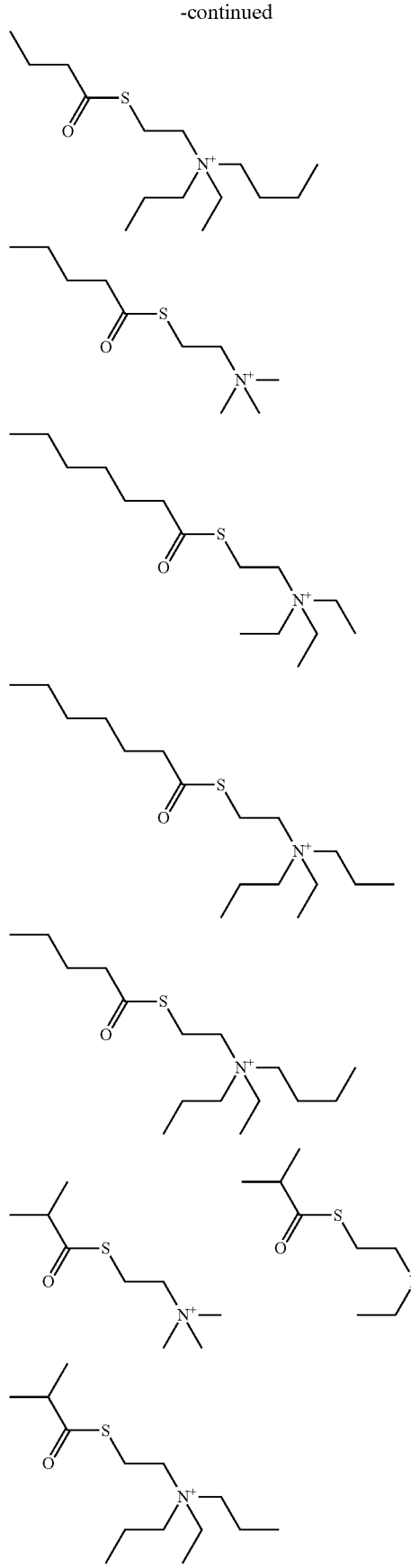
126
-continued
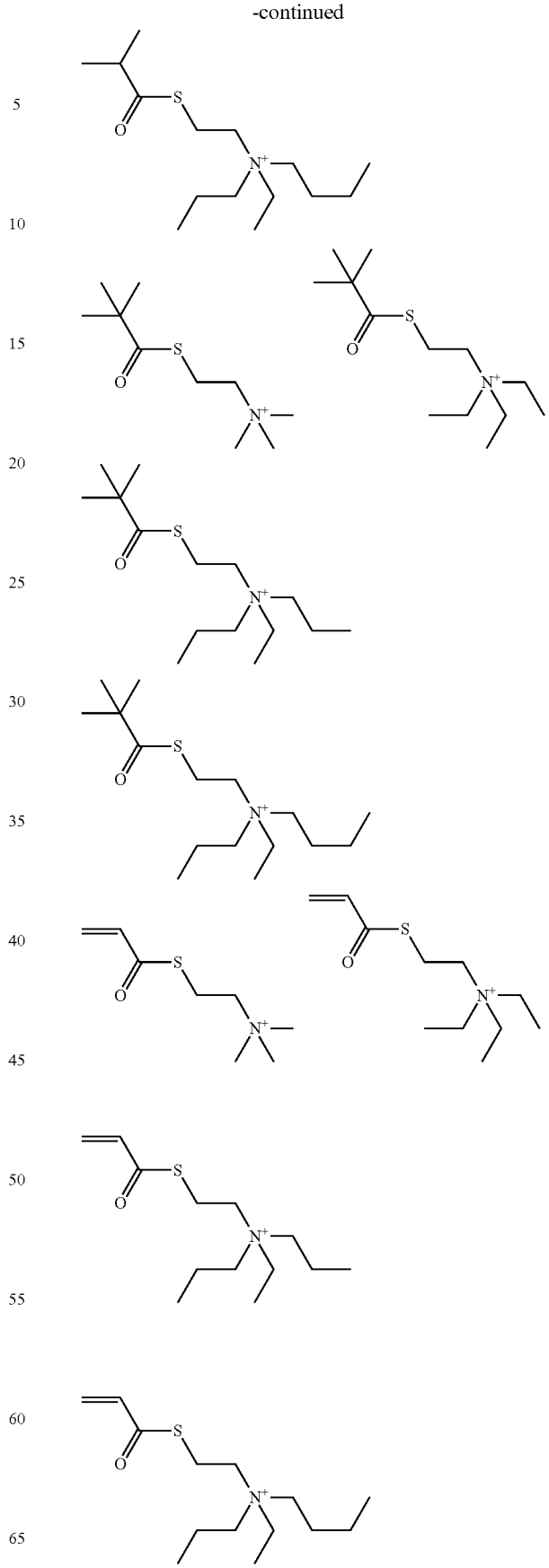

127
-continued
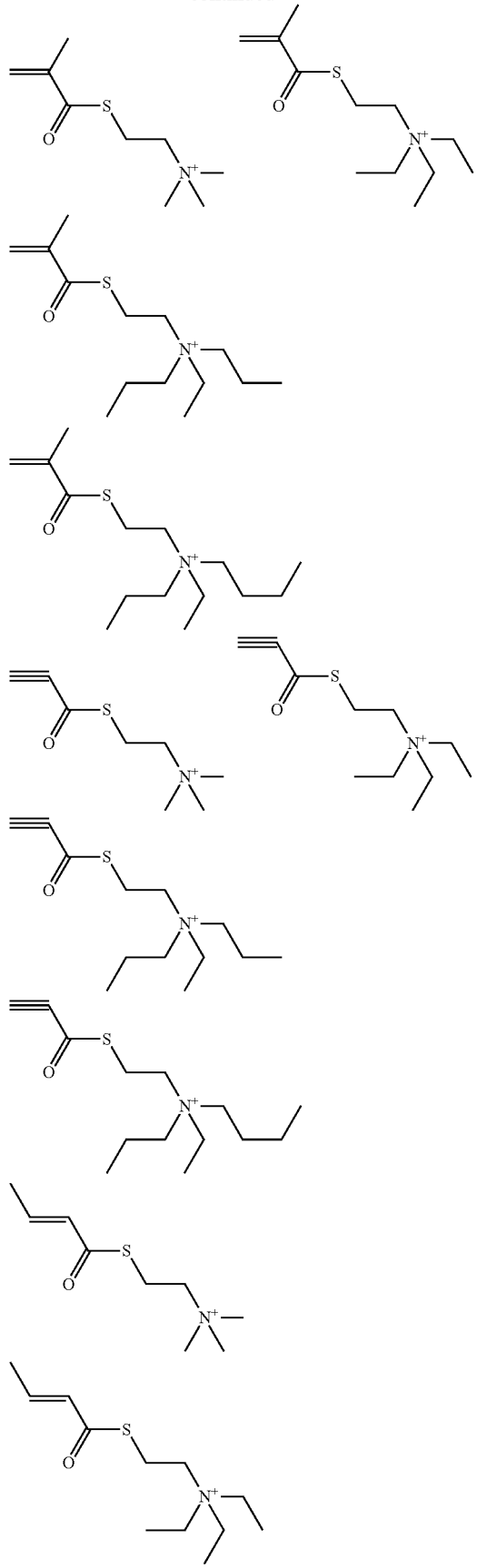
128
-continued
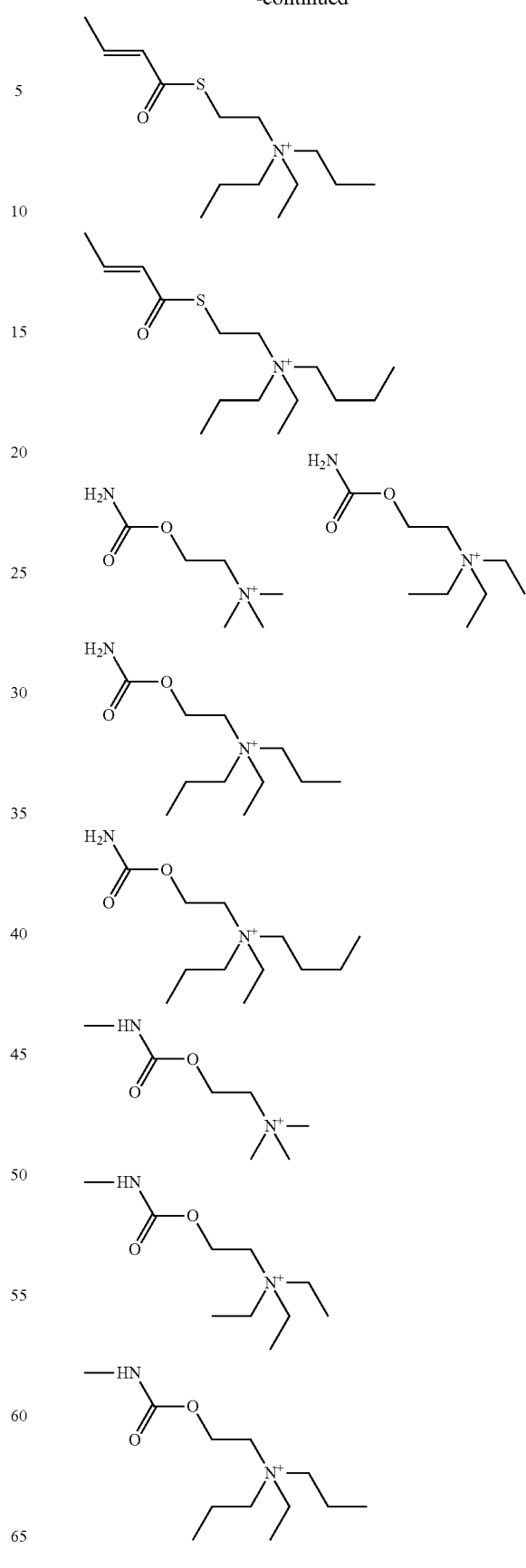

-continued
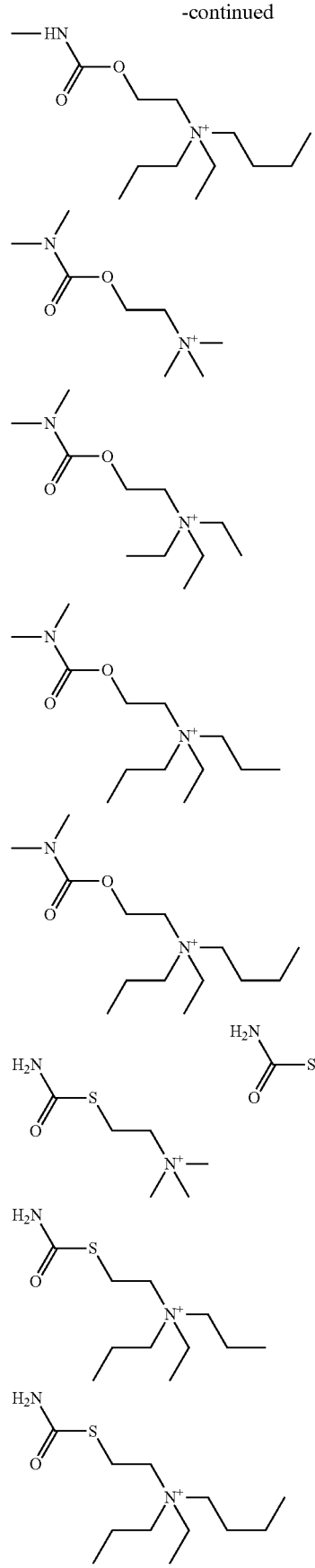
-continued
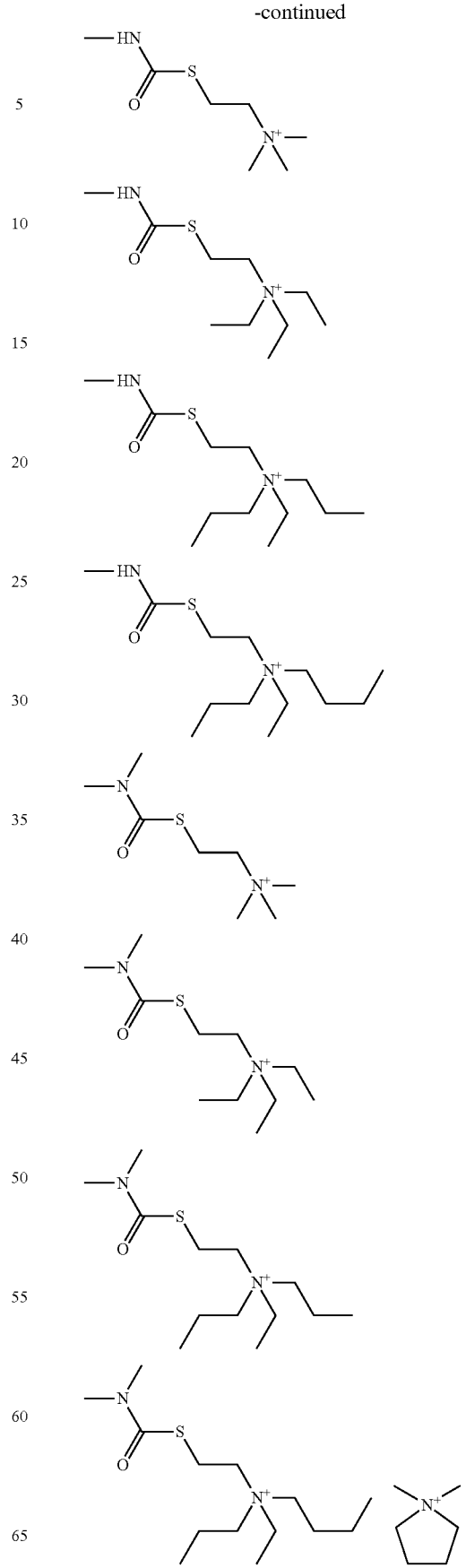

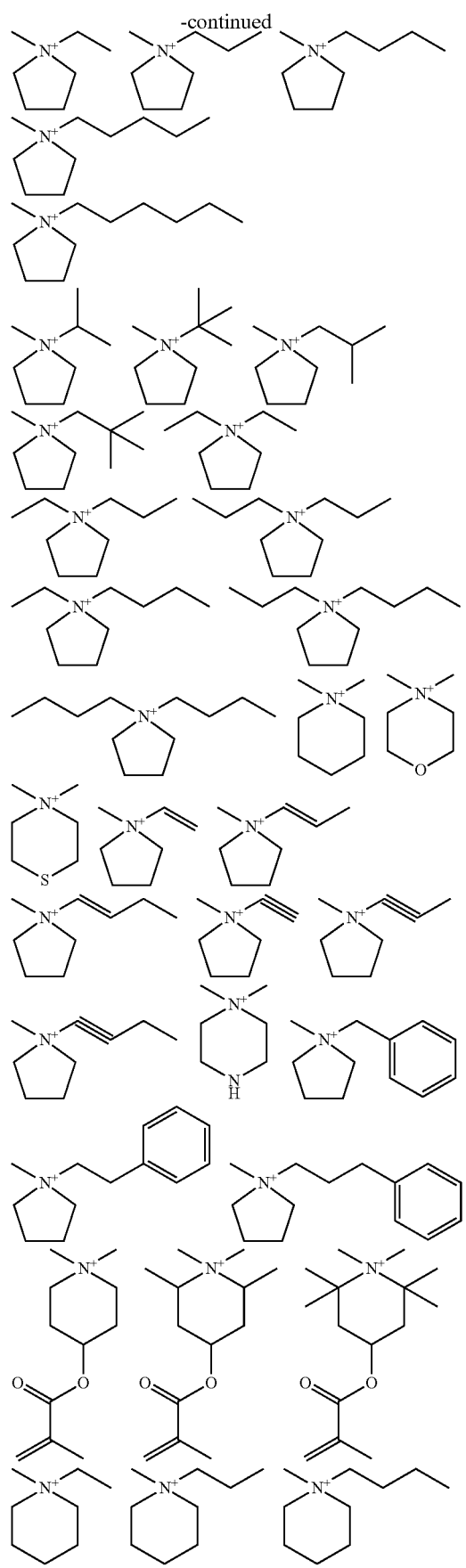
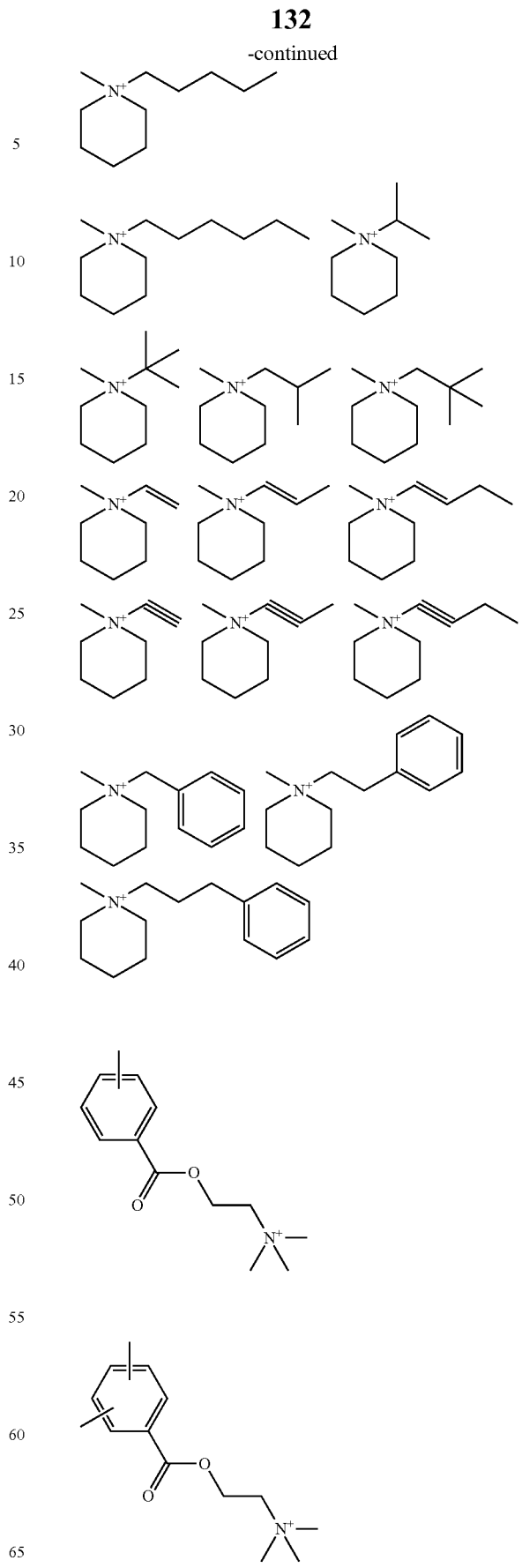

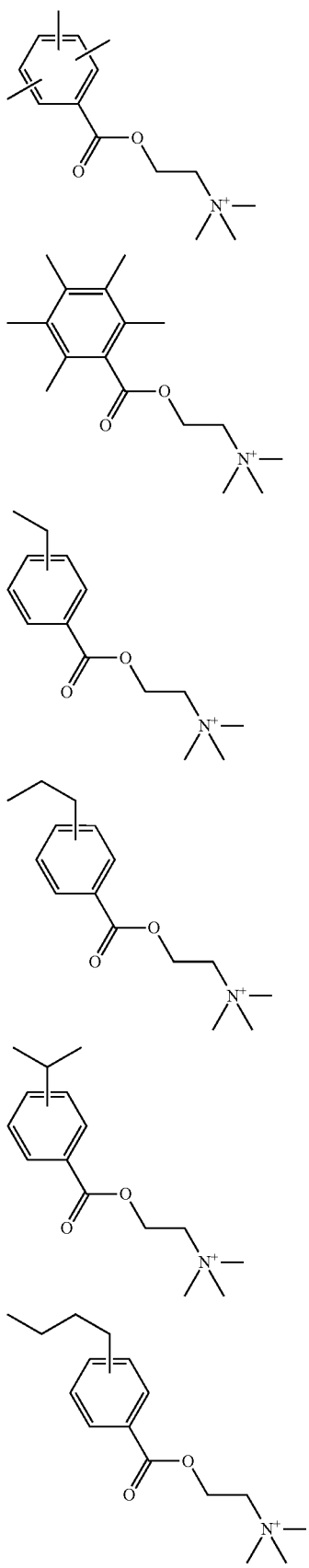
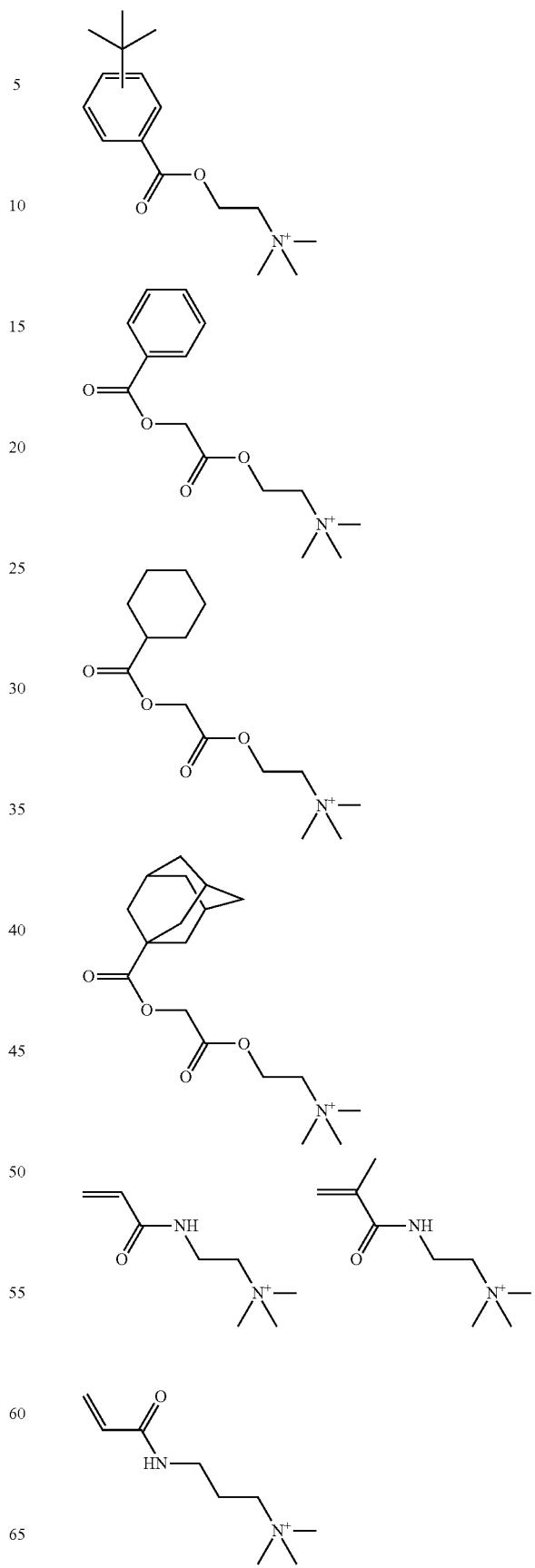

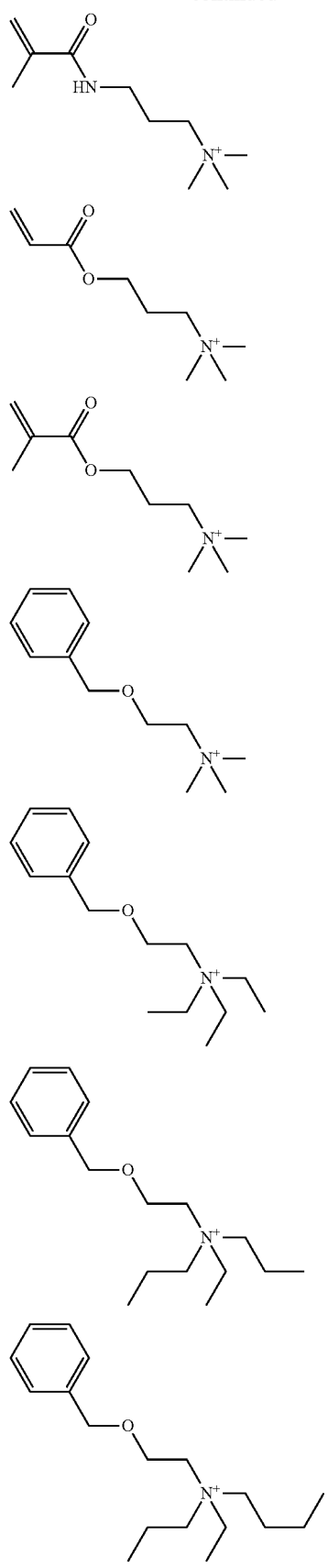
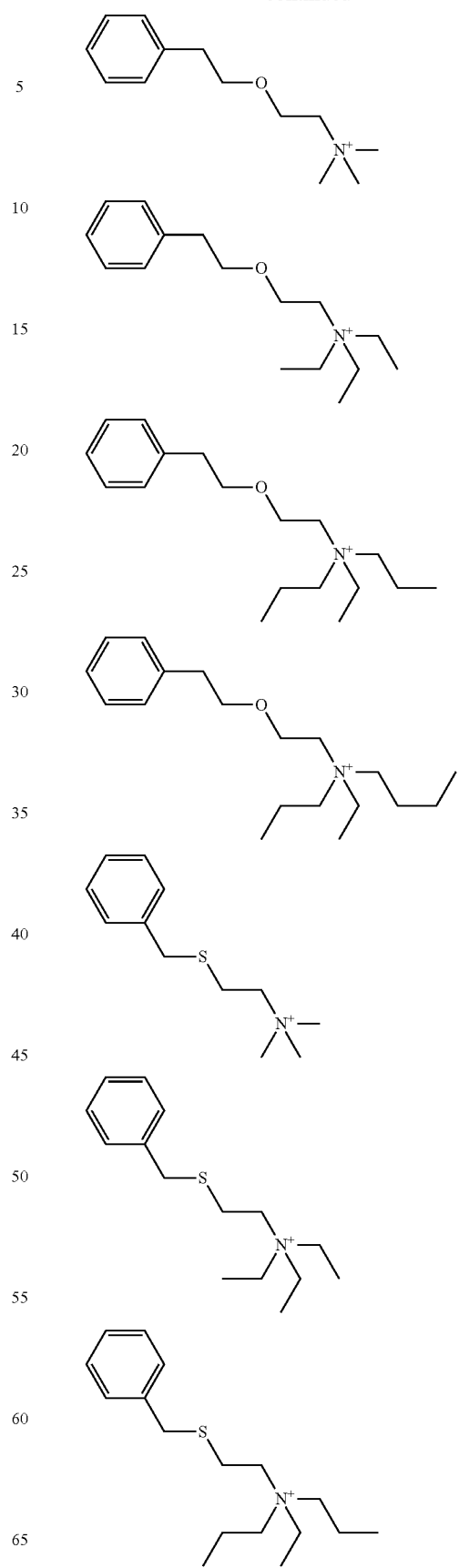

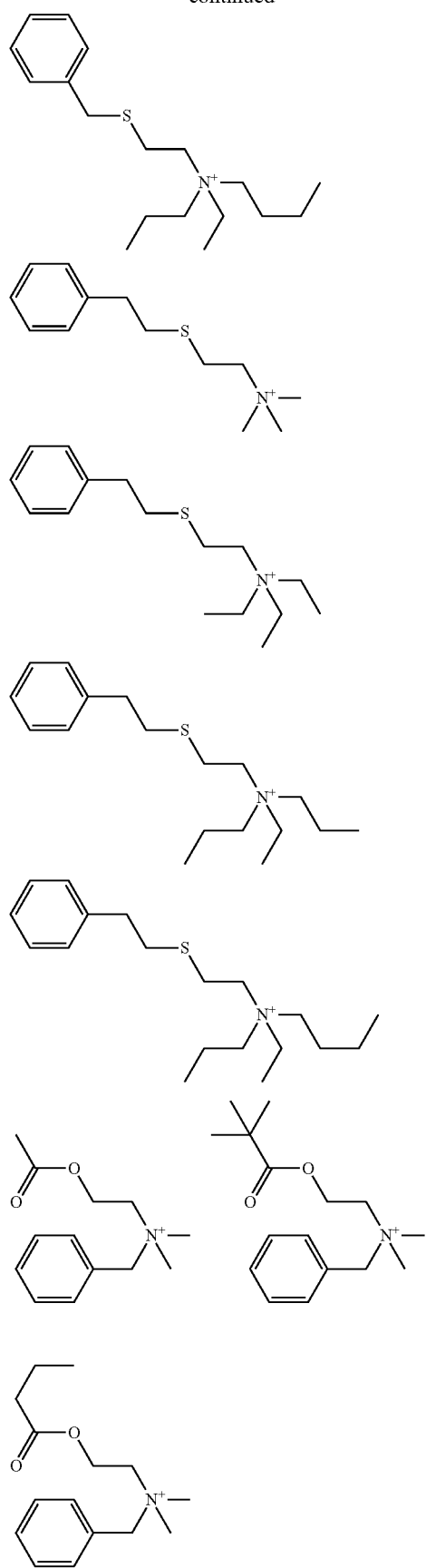
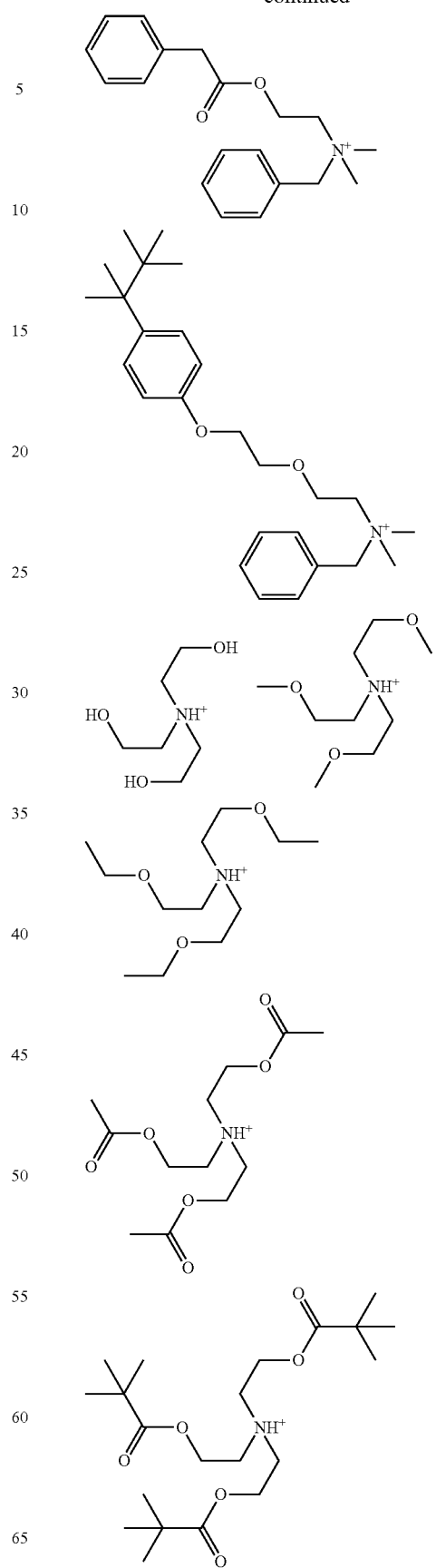

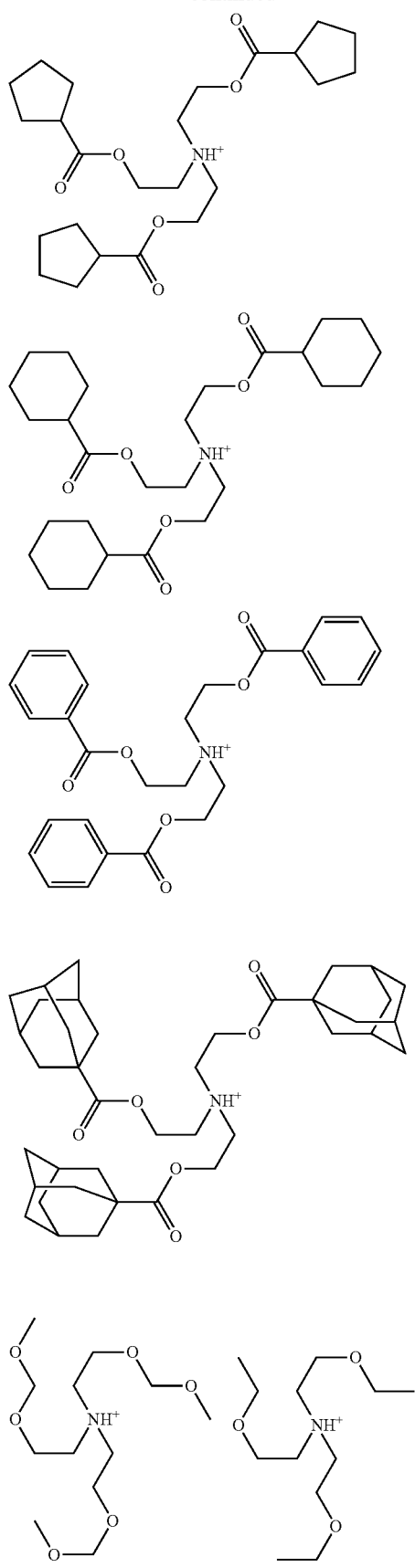
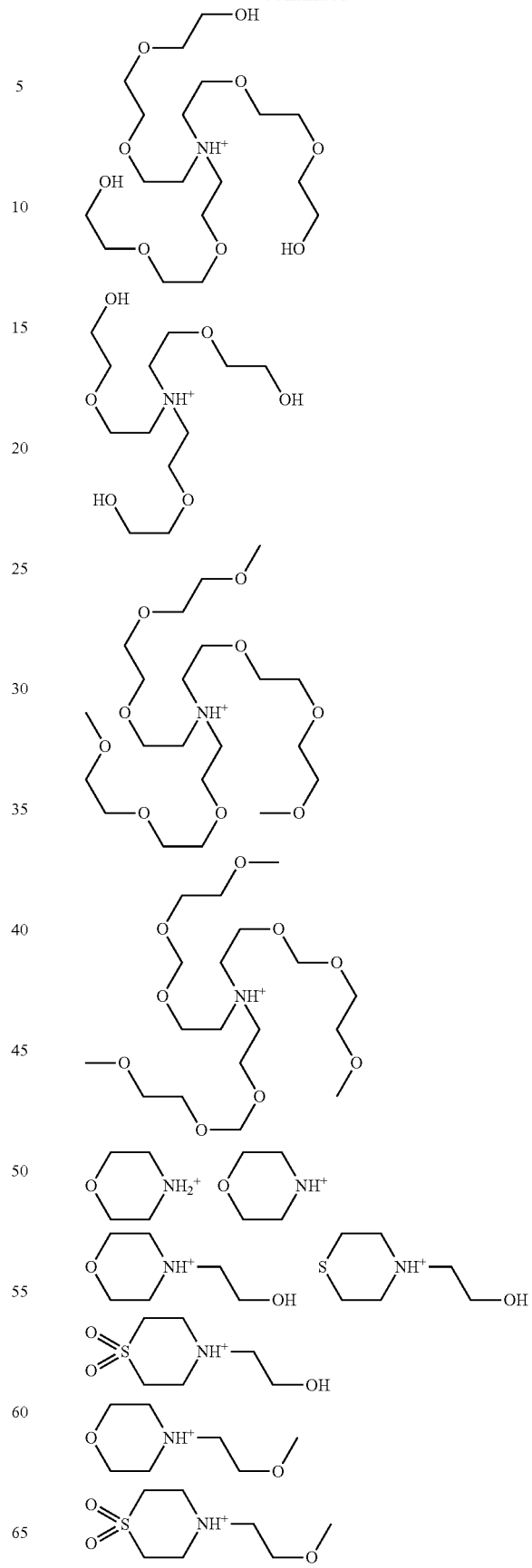

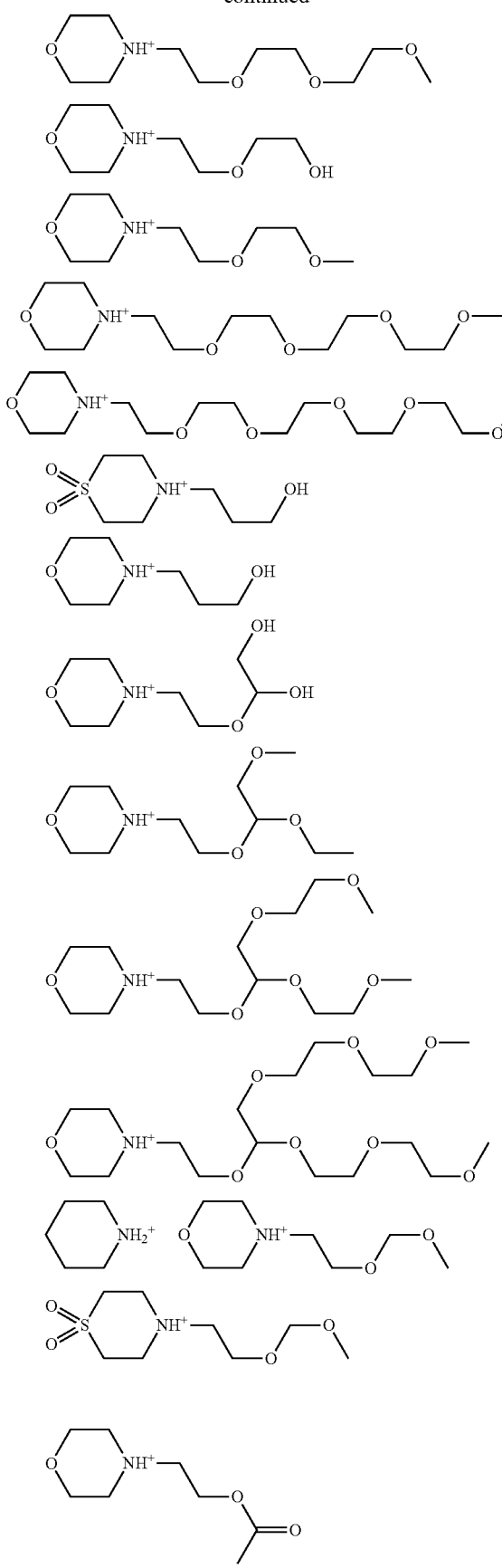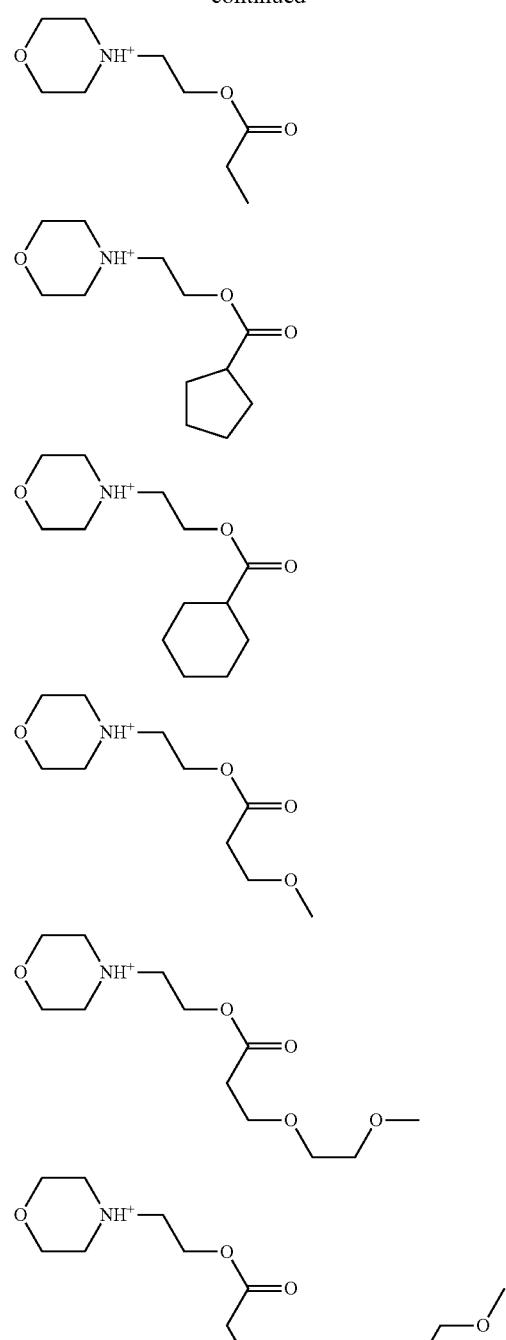

The bio-electrode composition used for the present invention preferably contains an ionic polymer that has a repeating unit(s) of an ionic monomer shown by a1 to a7, but the ionic polymer may also be copolymerized with a repeating unit b having tackiness function. The monomer for obtaining the repeating unit b that brings tackiness is not particularly limited, and specific illustrative examples thereof include the following.

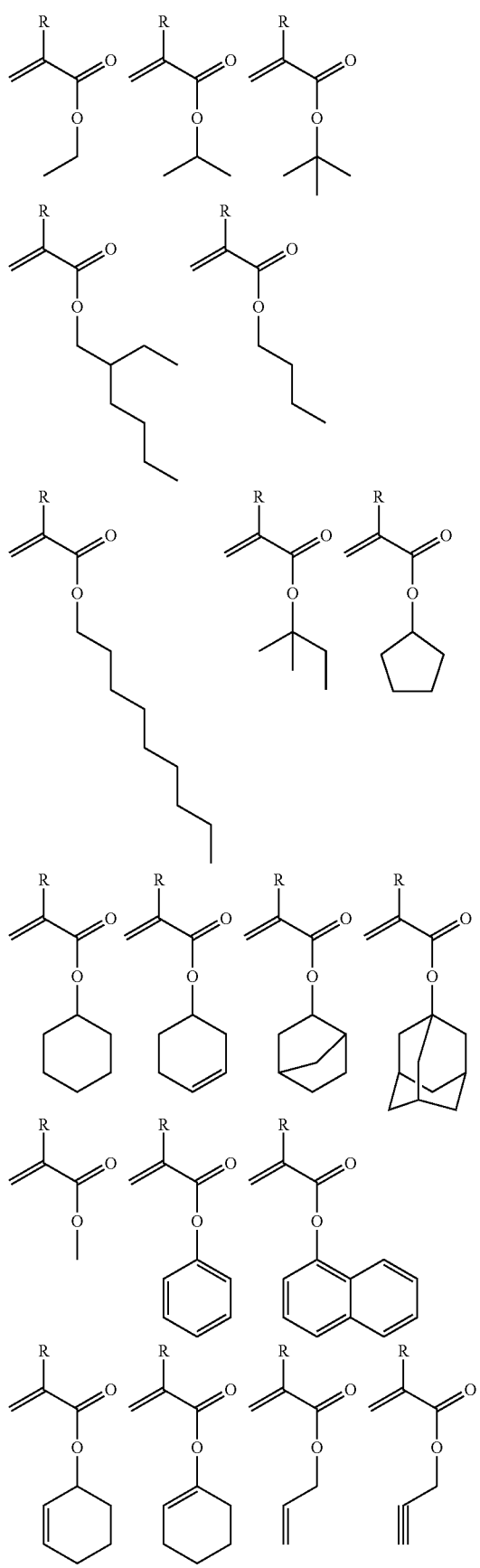
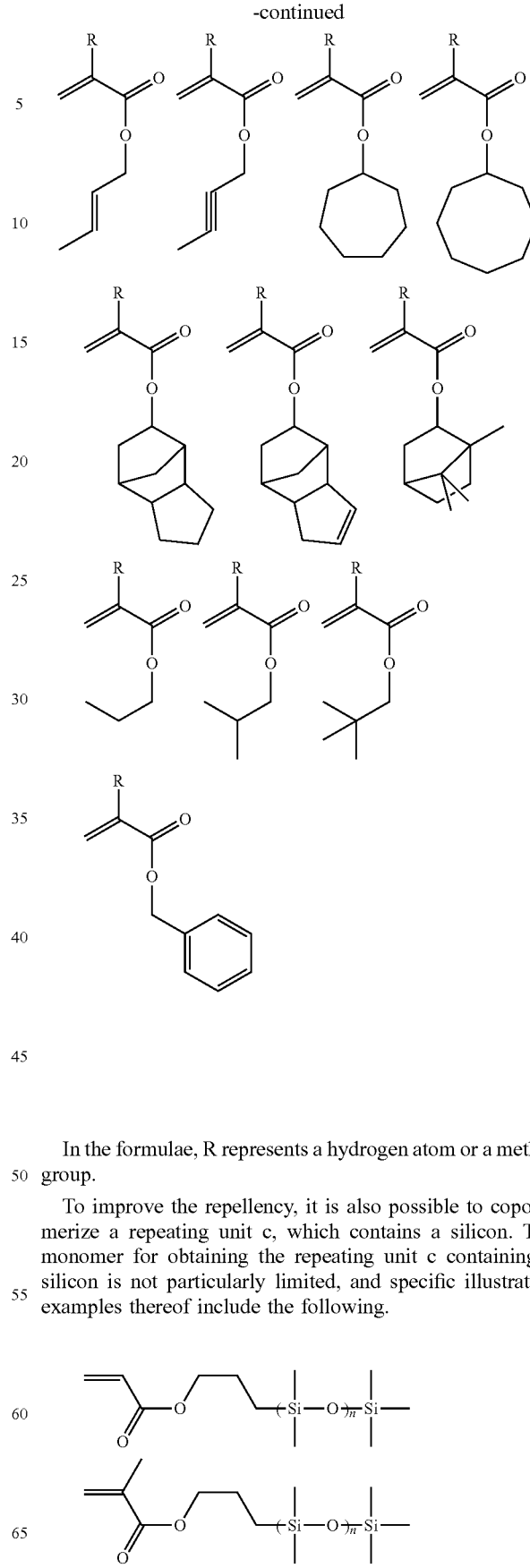
In the formulae, R represents a hydrogen atom or a methyl group.
To improve the repellency, it is also possible to copolymerize a repeating unit c, which contains a silicon. The monomer for obtaining the repeating unit c containing a silicon is not particularly limited, and specific illustrative examples thereof include the following.
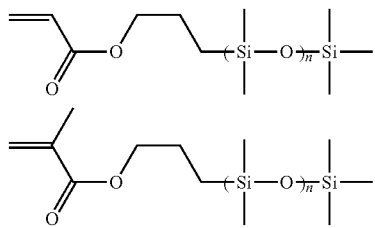

145
-continued
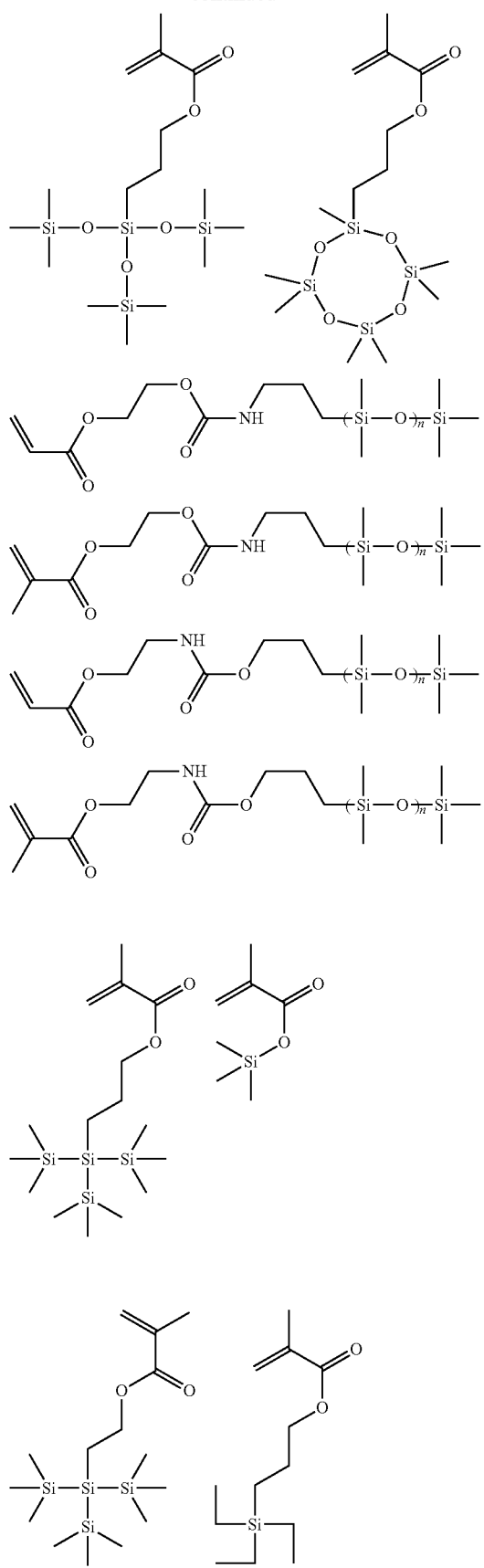
146
-continued
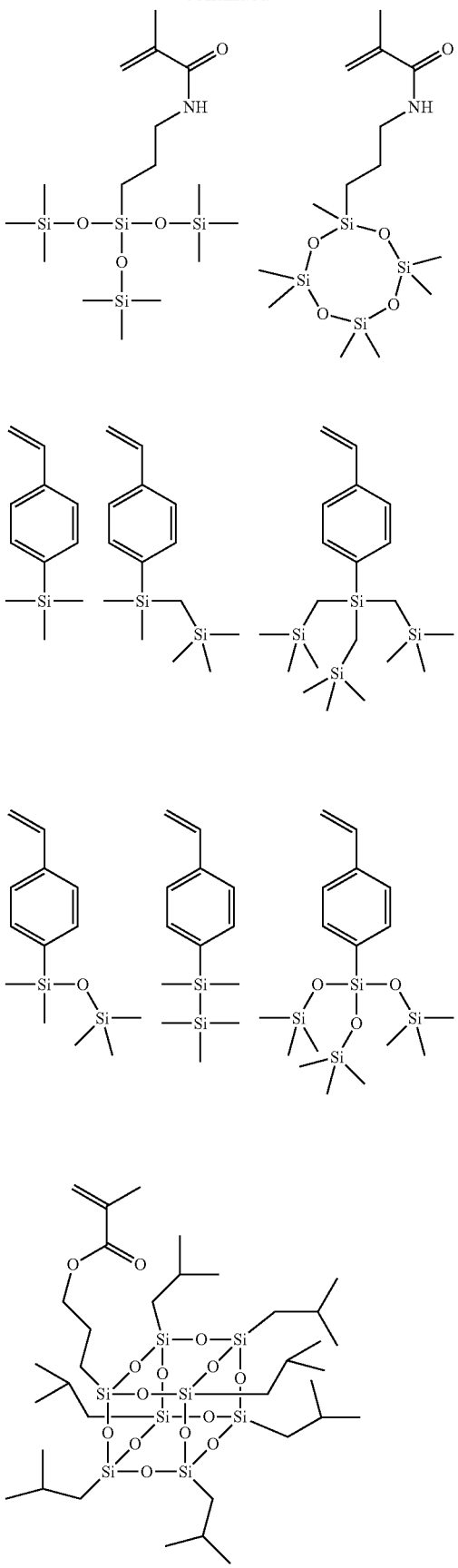

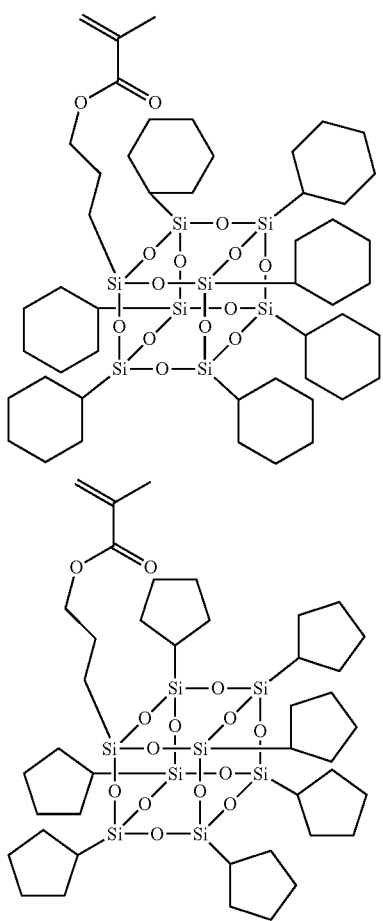
In the formulae, "n" is an integer of 0 to 100.
Additionally, it is also possible to copolymerize a repeating unit d, which has a glyme chain, to improve the electric conductivity. The monomer for obtaining the repeating unit d having a glyme chain is not particularly limited, and specific illustrative examples thereof include the following.
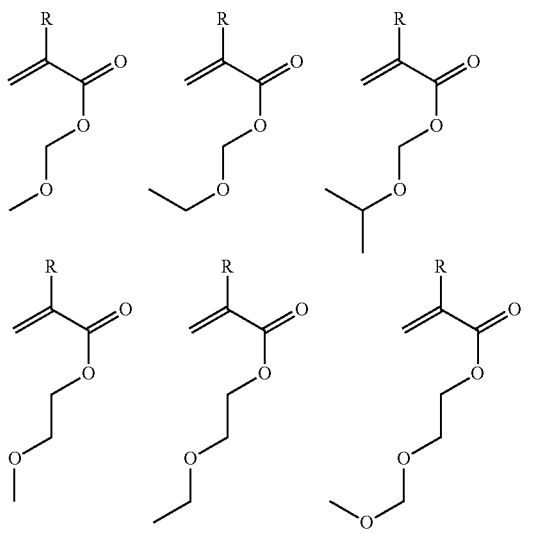
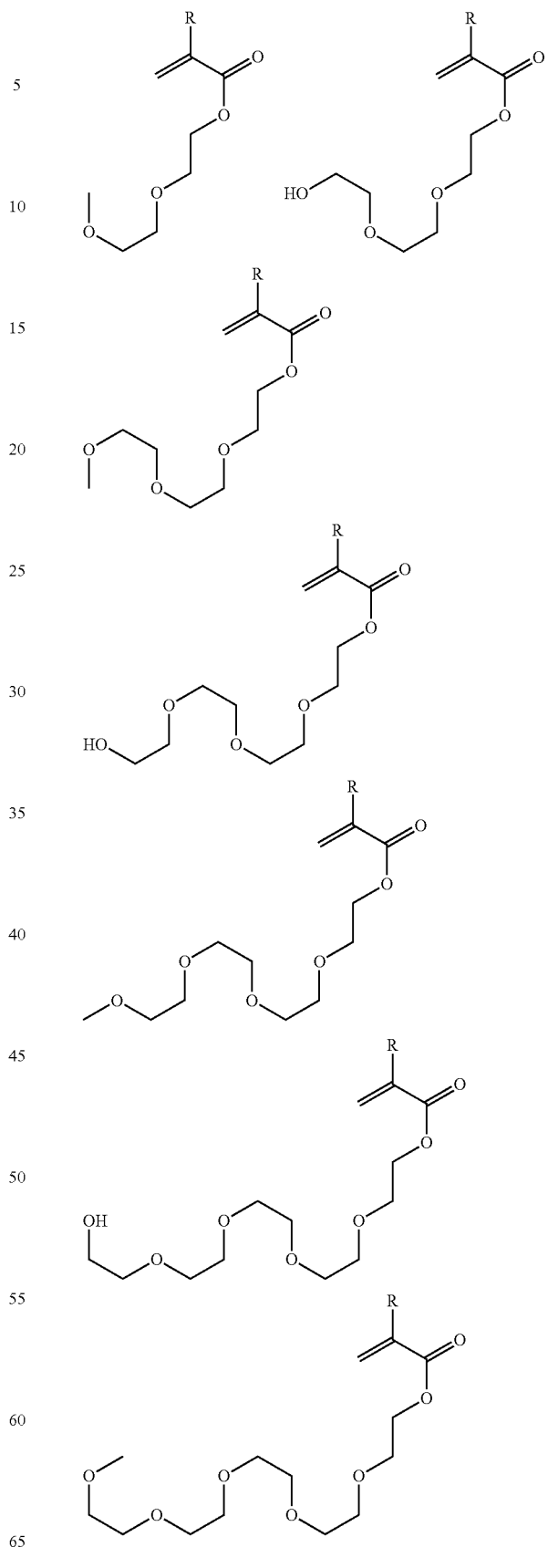

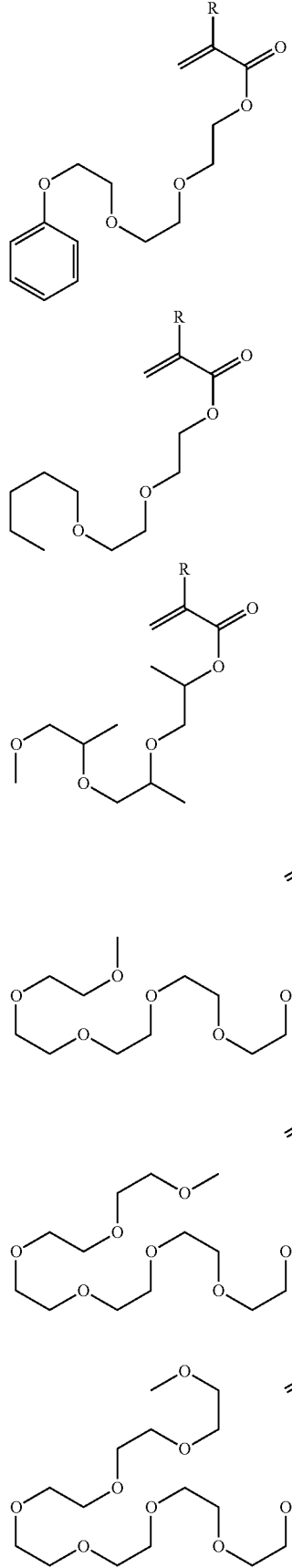
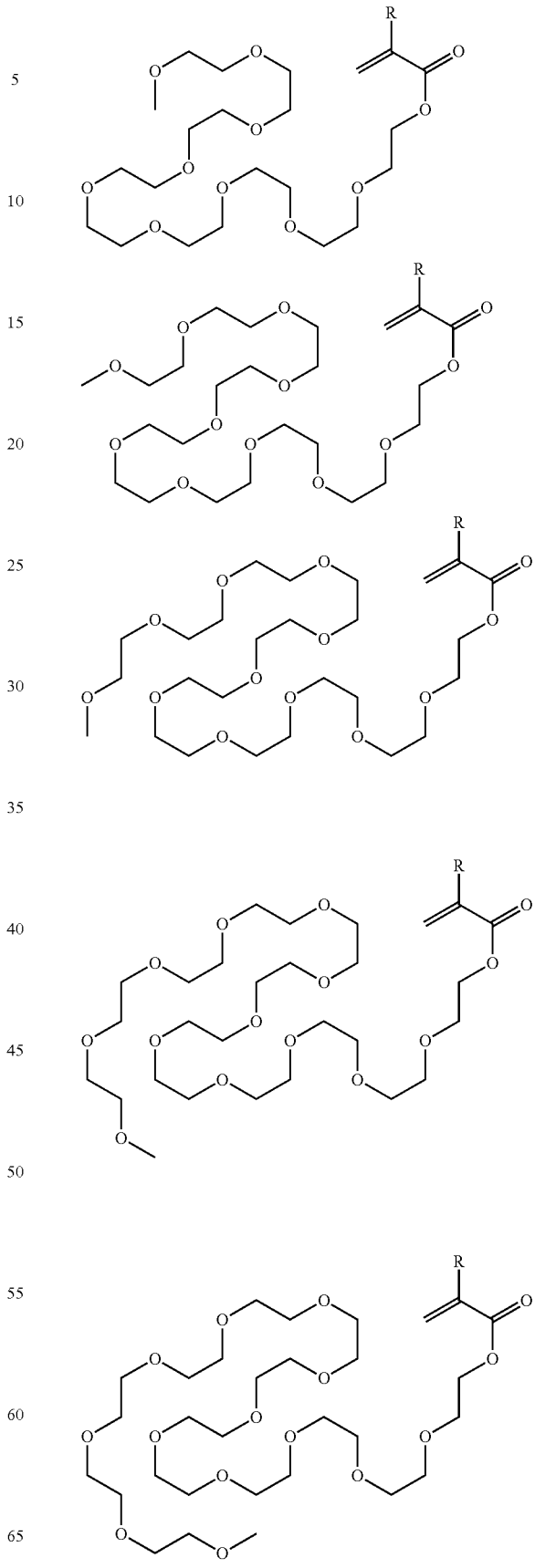

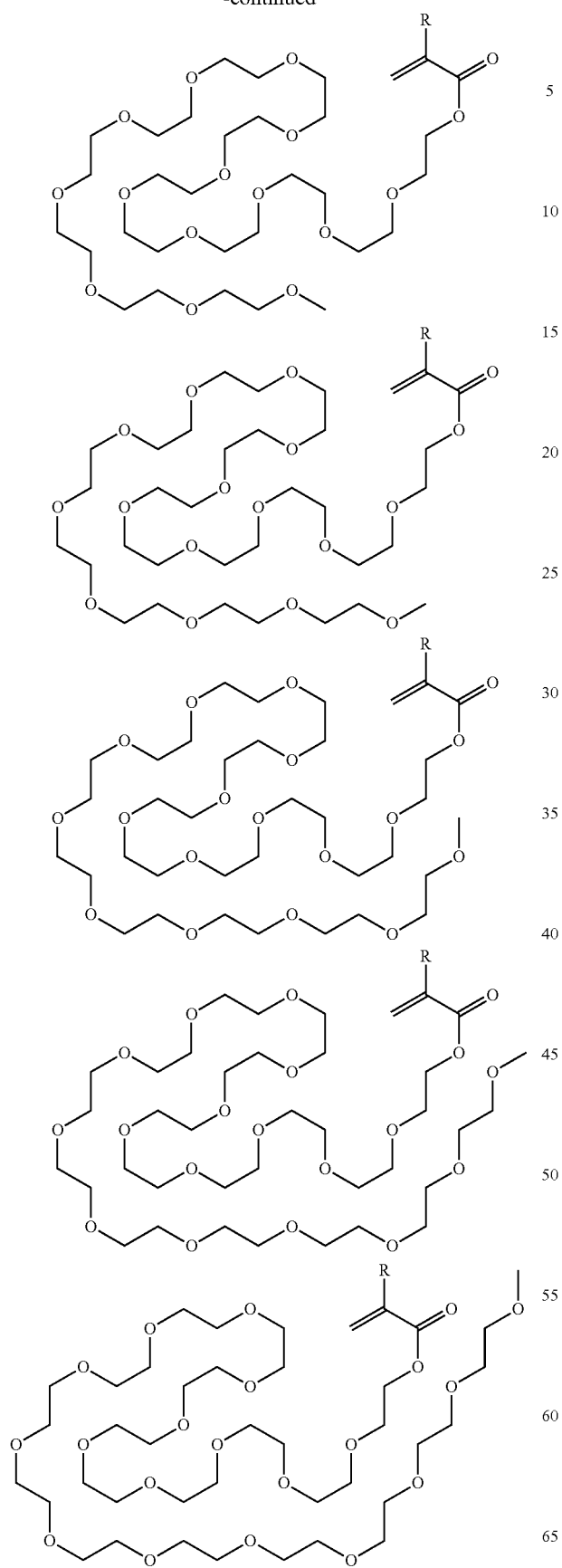
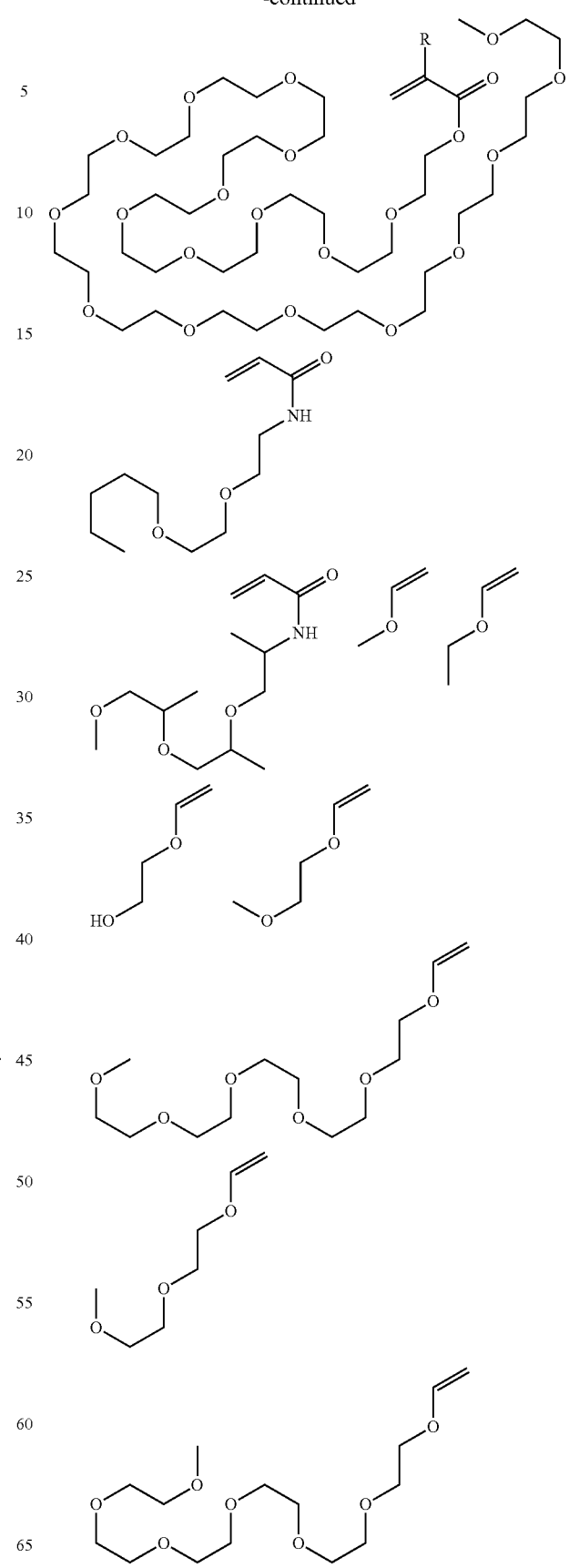

153
-continued
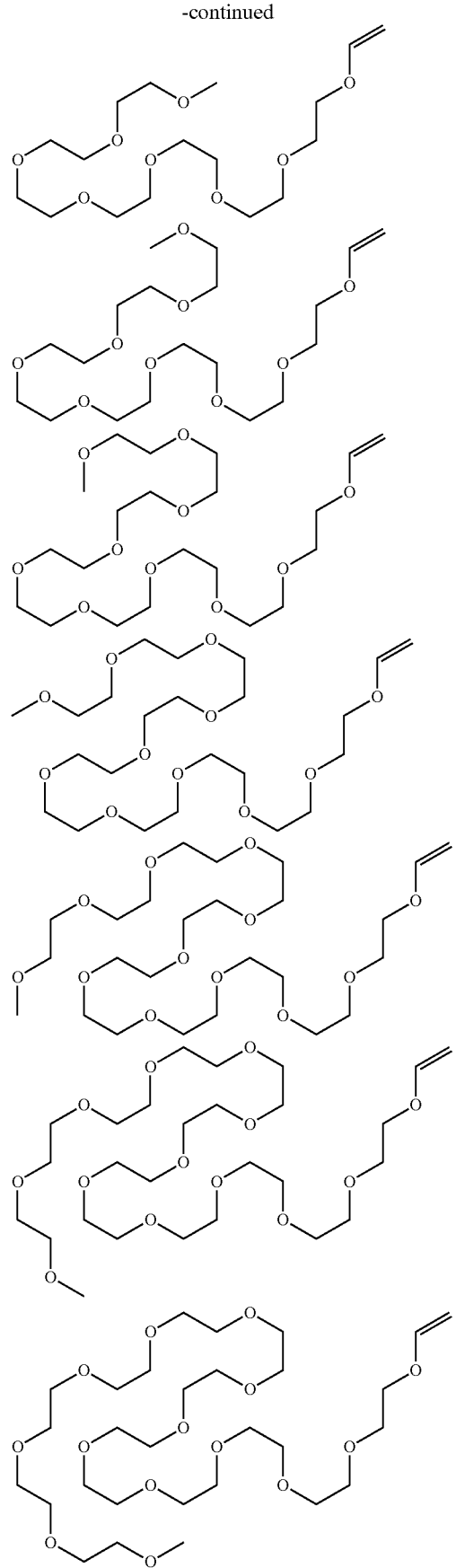
154
-continued
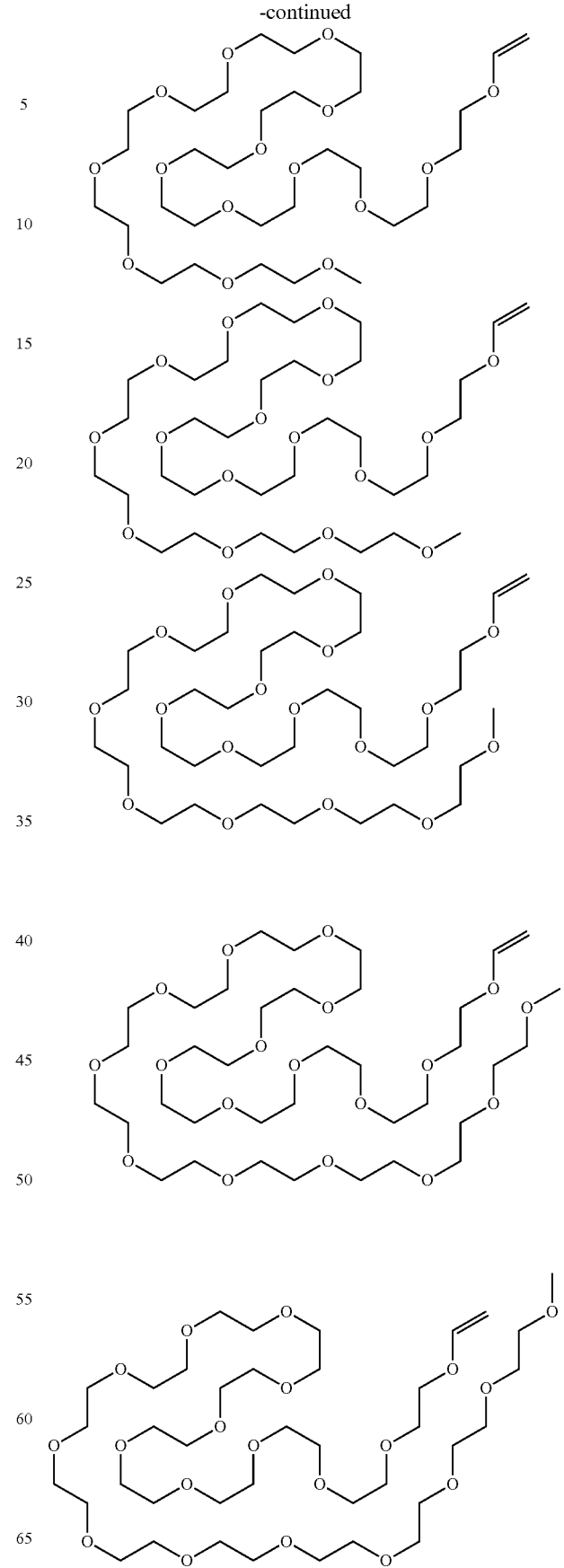

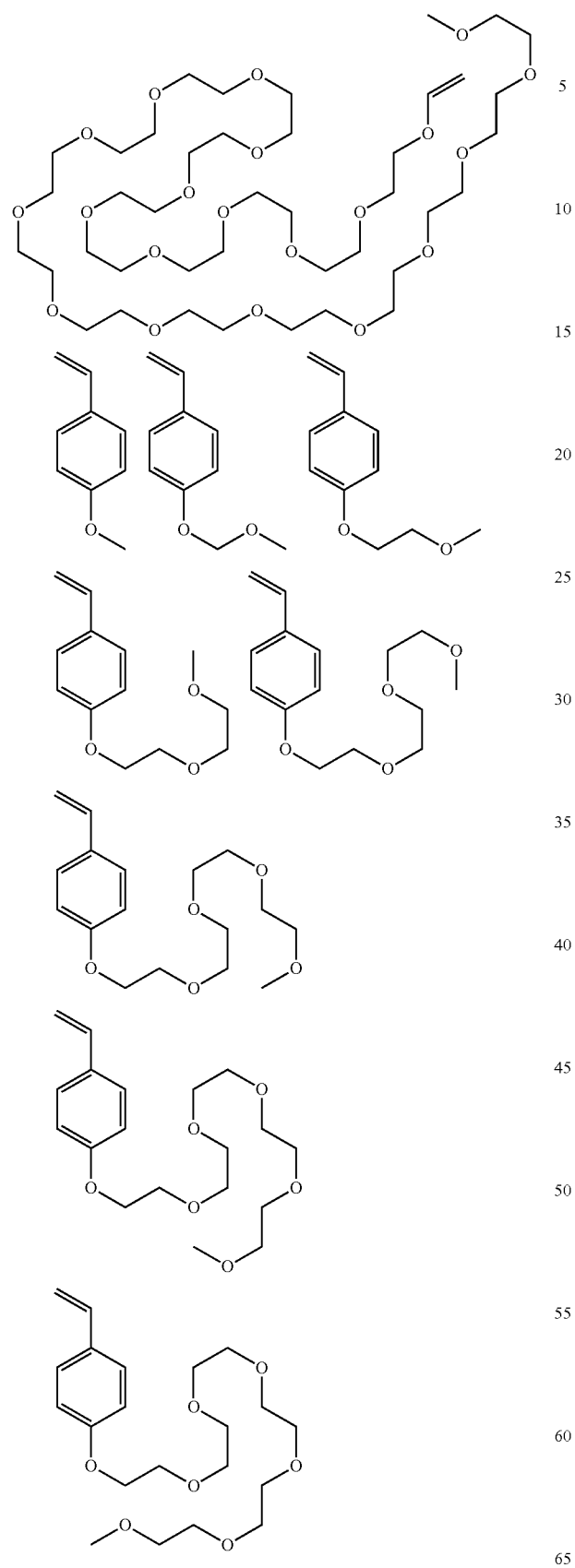
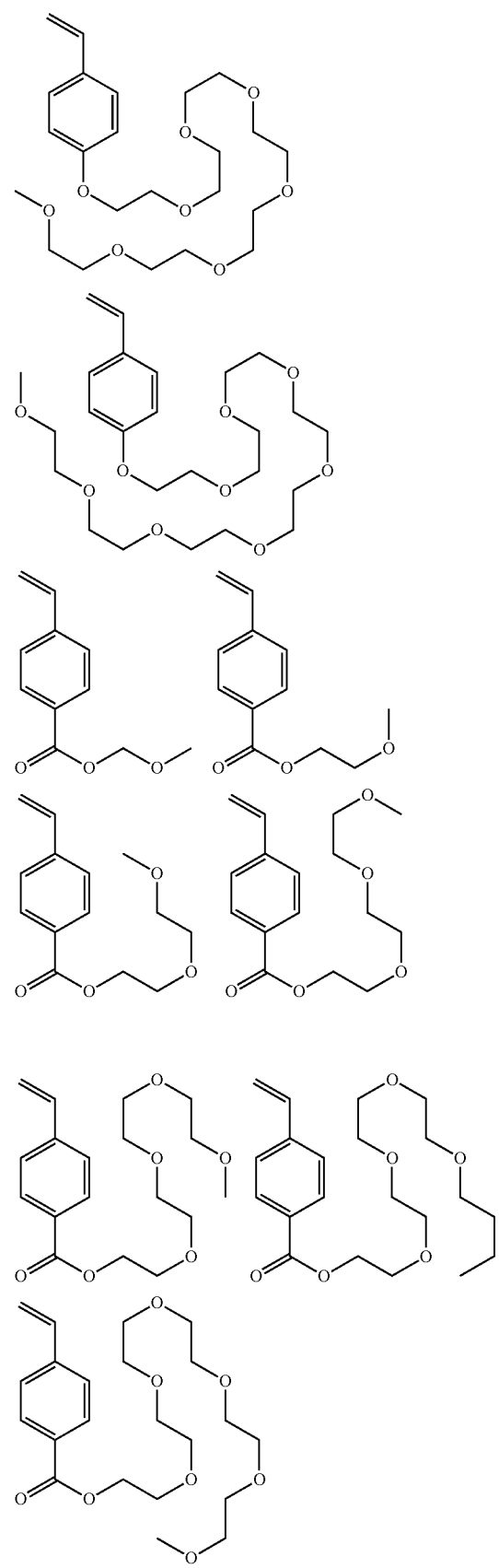

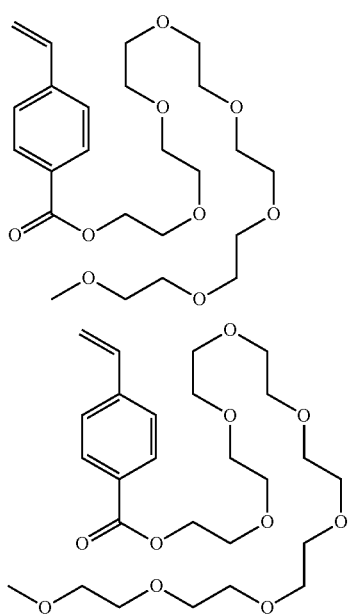

In the formulae, R represents a hydrogen atom or a methyl group.

By bonding an electro-conductive material to be added to the inventive bio-electrode composition and a silsesquioxane-pendant urethane resin to be the base of the bio-electrode, which will be described later, the electro-conductive material and the silsesquioxane-pendant urethane resin are integrated, thereby making it possible to prevent elution of the electro-conductive material. The electro-conductive material and the silsesquioxane-pendant urethane resin can be bonded by the method of copolymerizing a repeating unit e, which has a hydroxy group, an oxirane group, an oxetane group, or an isocyanate group, in the electro-conductive material to form the urethane resin having the silsesquioxane pendant in the presence of the electro-conductive material. The monomer for obtaining the repeating unit e having a hydroxy group, an oxirane group, an oxetane group, or an isocyanate group is not particularly limited, and specific illustrative examples thereof include the following.

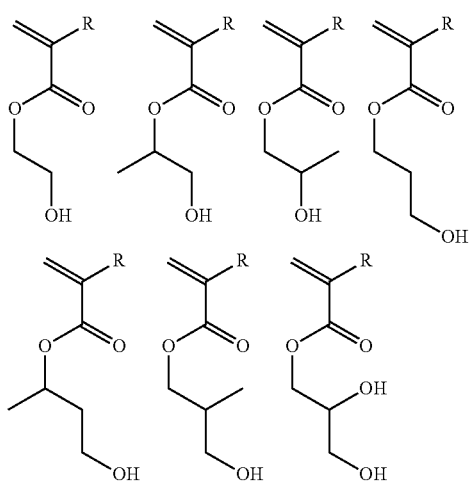

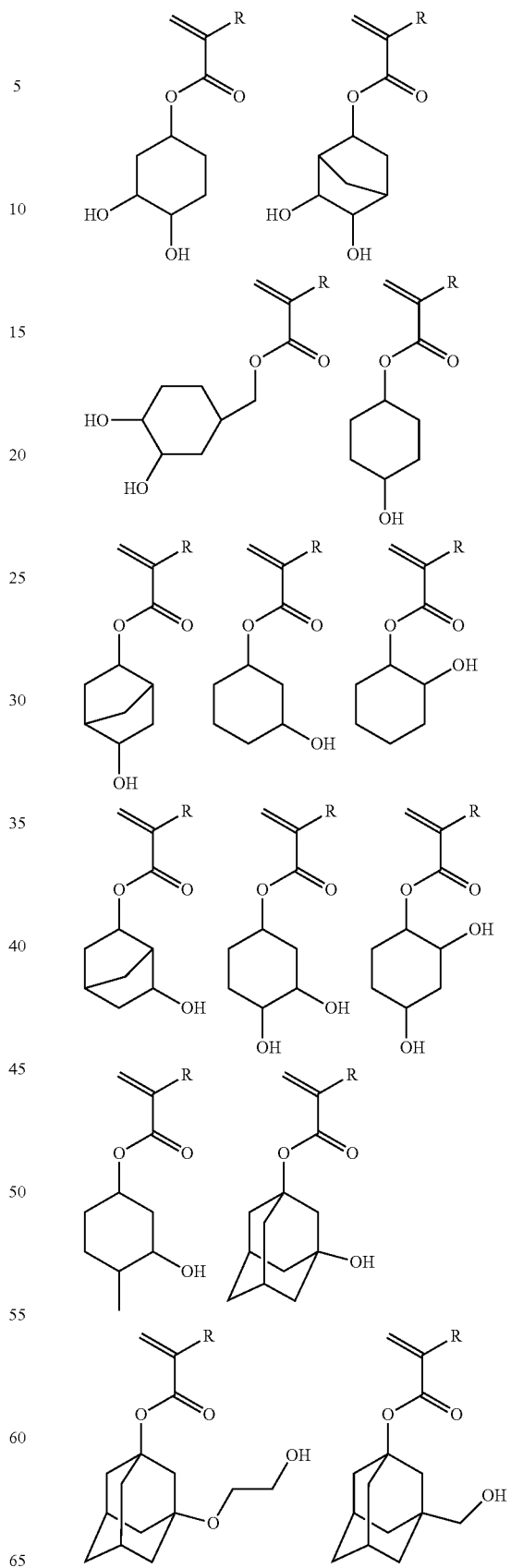

159
-continued
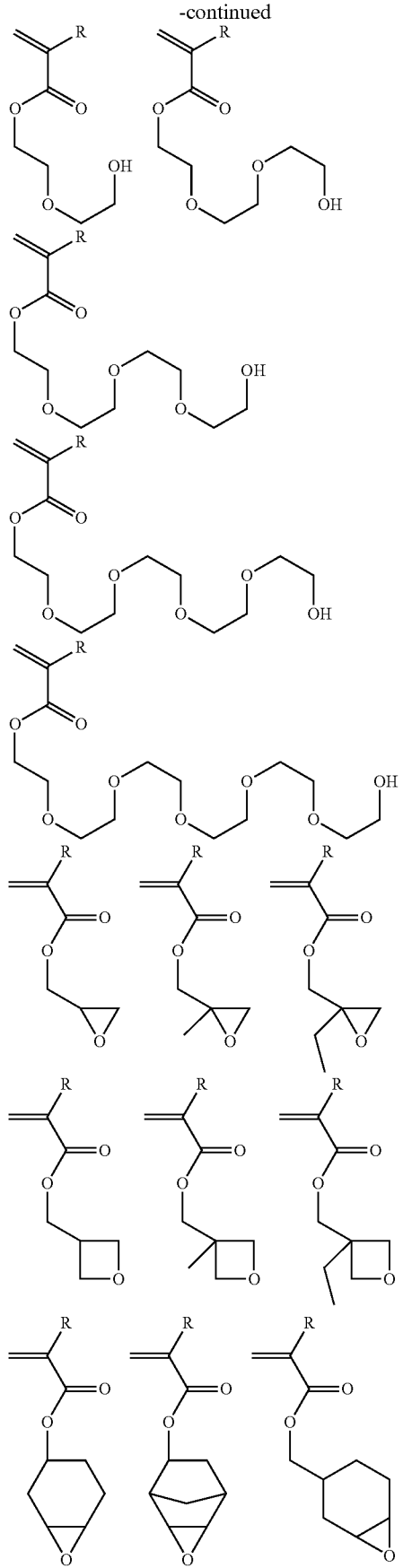
160
-continued
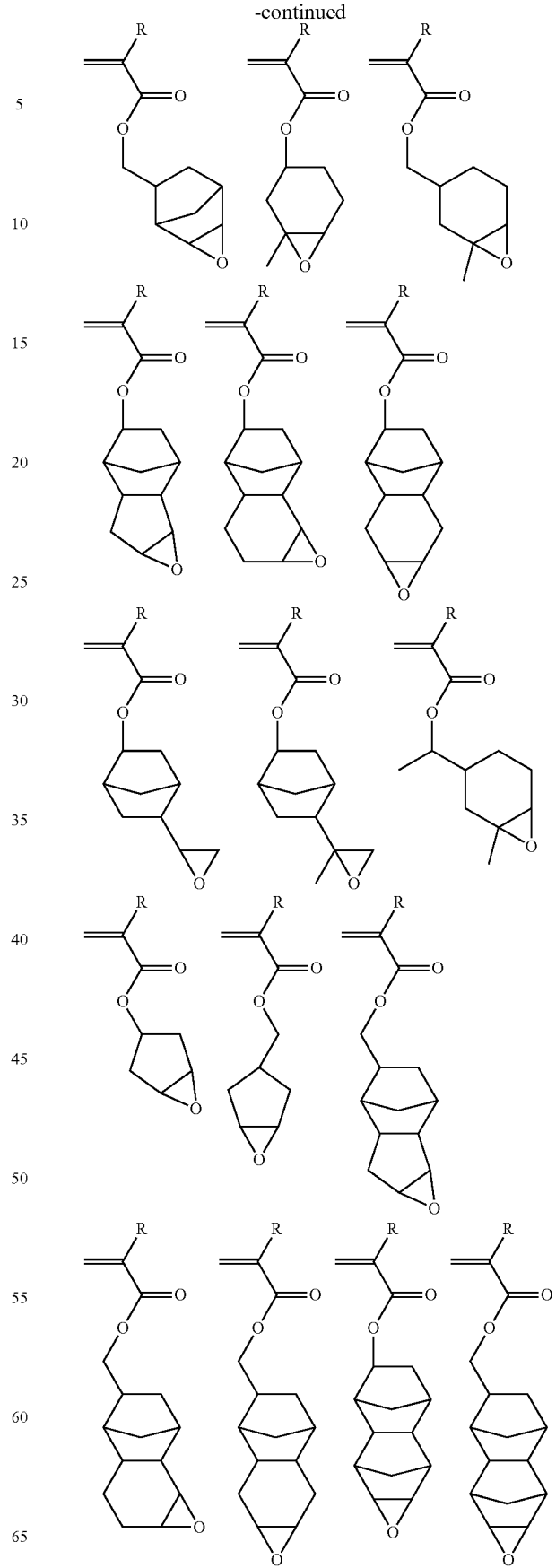

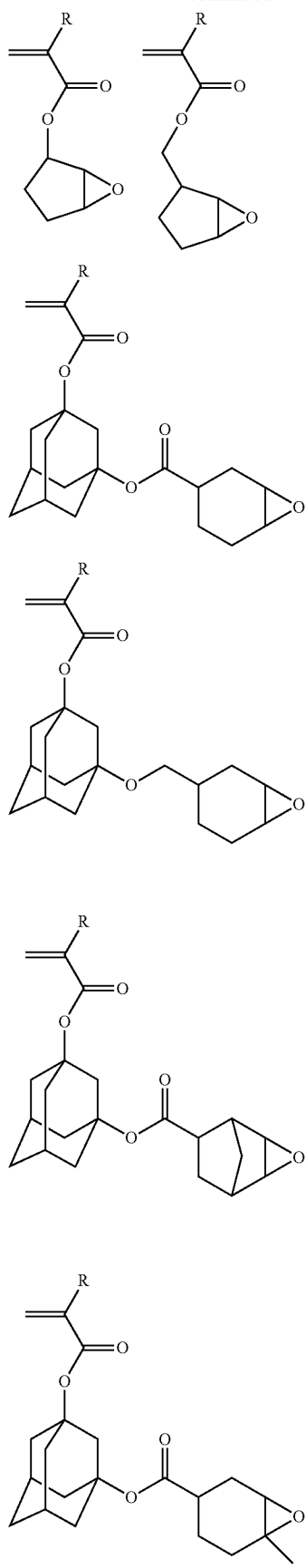
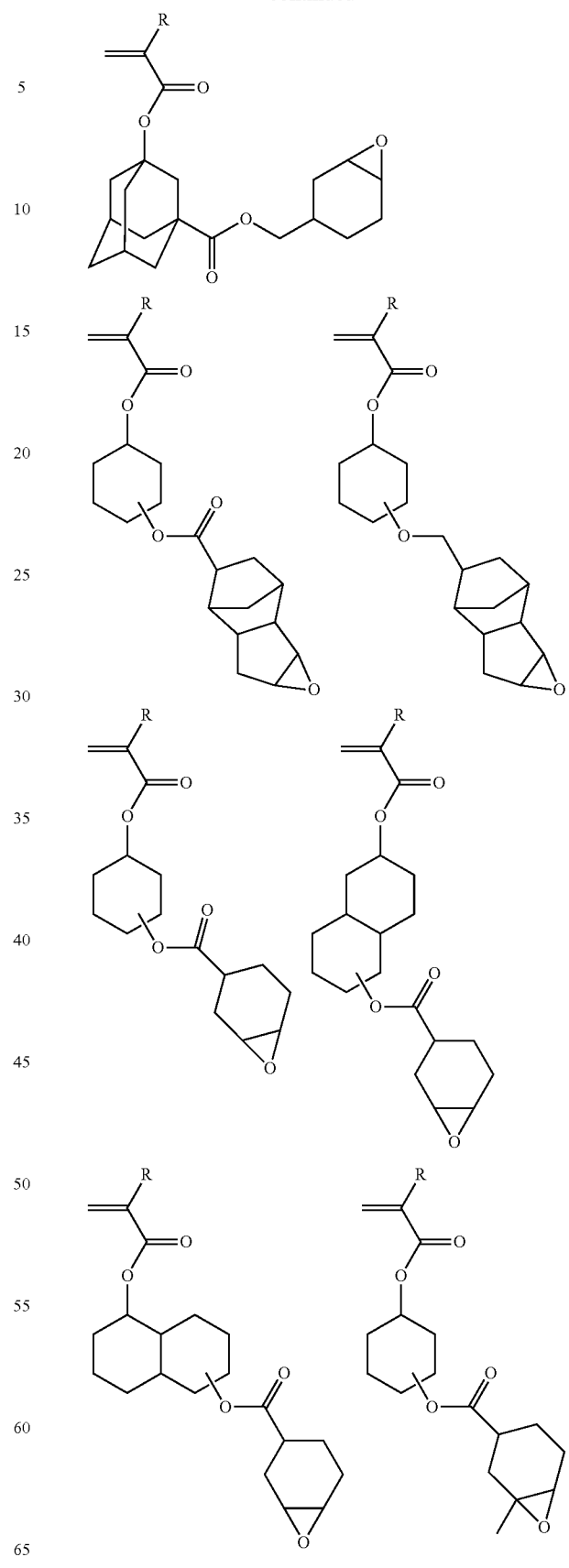

-continued

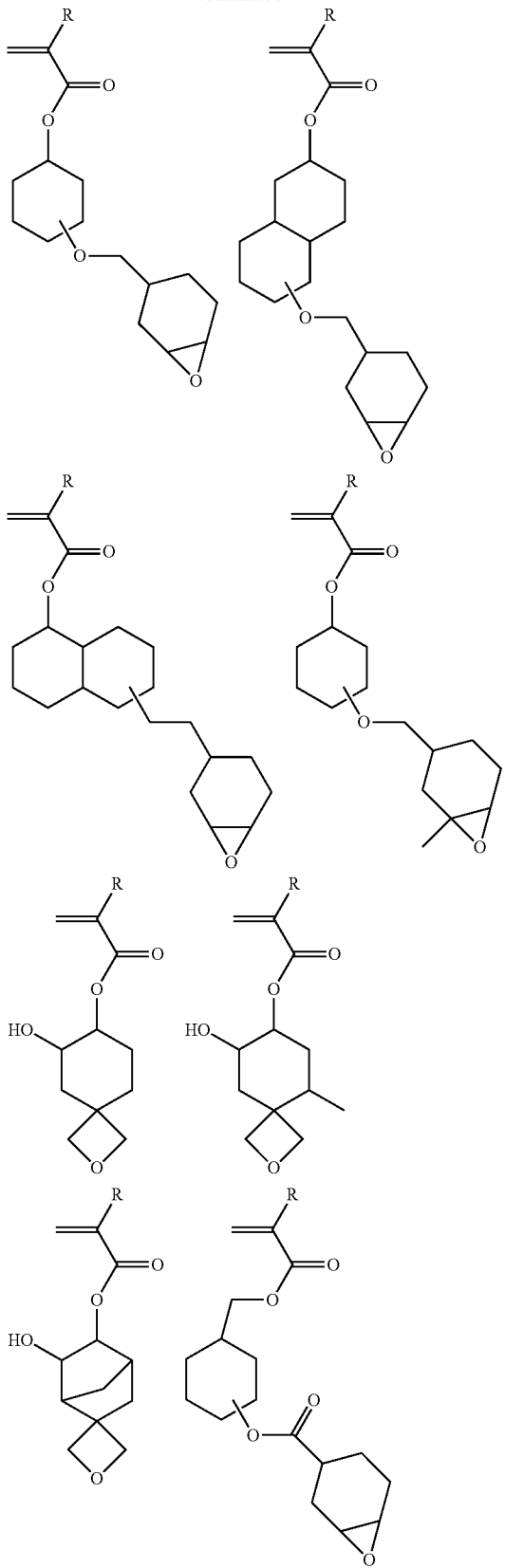

In the formulae, R represents a hydrogen atom or a methyl group.

As the method for synthesizing these polymer compounds to produce the electro-conductive material, heat polymerization can be performed, for example, on a desired monomer(s) that contain one or more repeating units a1 to a7 among the monomers to give the repeating unit(s) a1, a2, a3, a4, a5, a6, a7, "b", "c", "d", and/or "e" by adding a radical polymerization initiator in an organic solvent to give an electro-conductive material as a polymer compound of copolymer.

As the organic solvent used in the polymerization, toluene, benzene, tetrahydrofuran, diethyl ether, dioxane and so on can be exemplified. Illustrative examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide.

The temperature in the heat polymerization is preferably 50 to 80° C. The reaction time is preferably 2 to 100 hours, more preferably 5 to 20 hours.

The ratios of the repeating units a1 to a7, "b", "c", "d", and "e" are preferably $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0 \leq a1+a2+a3+a4+a5+a6+a7 \leq 1.0$, $0 \leq b < 1.0$, $0 \leq c < 1.0$, $0 \leq d < 1.0$, and $0 \leq e < 1.0$; more preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.1 \leq a1+a2+a3+a4+a5+a6+a7 \leq 0.9$, $0 \leq b \leq 0.9$, $0 \leq c \leq 0.9$, $0 \leq d \leq 0.8$, and $0 \leq e \leq 0.5$; and further preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.2 \leq a1+a2+a3+a4+a5+a6+a7 \leq 0.8$, $0 \leq b \leq 0.8$, $0 \leq c \leq 0.8$, $0 \leq d \leq 0.7$, and $0 \leq e \leq 0.5$.

Incidentally, $a1+a2+a3+a4+a5+a6+a7+b+c+d+e=1$, for example, means that the total amount of the repeating units a1 to a7, "b", "c", "d", and "e" is 100 mol % on the basis of the total amount of the whole repeating units in a polymer compound that contains the repeating units a1 to a7, "b", "c", "d", and "e"; and $a1+a2+a3+a4+a5+a6+a7+b+c+d+e<1$ means that the total amount of the repeating units a1 to a7, "b", "c", "d", and "e" is less than 100 mol % on the basis of the total amount of the whole repeating units, and another repeating unit(s) are contained other than the repeating units a1 to a7, "b", "c", "d", and "e".

The molecular weight of the polymer, as a weight average molecular weight, is preferably 500 or more, more preferably in a range of 1000 or more and 1000000 or less, further preferably in a range of 2000 or more and 500000 or less. In case of the presence of a large amount of residual monomers, which are not incorporated into the polymer after polymerization of ionic monomers, they can permeate to skin in a biocompatibility test to cause allergy. Accordingly, the amount of residual monomer(s) has to be decreased. The amount of residual monomer(s) is preferably 10 mass % or less when the whole polymer is 100 parts by mass.

The amount of the ionic polymer blended as an electro-conductive material is preferably in a range of 0.1 to 300 parts by mass, more preferably 1 to 200 parts by mass on the basis of 100 parts by mass of the urethane resin. The ionic polymer blended as an electro-conductive material may be used singly or in admixture of two or more kinds.

As a method for synthesizing the salt shown by a1 to a7 in the formulae (2) when X is a cation having an ammonium structure shown by the formula (1)-5, the method described in JP 2010-113209A can be exemplified, for example. More specifically, it can be obtained by a method in which sodium fluorosulfonate containing the fluorosulfonate anion is mixed with quaternary ammonium chloride containing a cation having one or two quaternary ammonium cation structures described above in an organic solvent, for example. In this case, it is preferable to remove sodium chloride, which is formed as a by-product, by washing with water.

[Resin Containing Urethane Bond in Main Chain and Silsesquioxane in Side Chain (Urethane Resin)]

The resin to be blended in the inventive bio-electrode composition is a component to hold the electro-conductive material and an electric conductivity improver such as carbon to improve the electric conductivity, and has to be soft as well as flexible and stretchable to be in contact with skin in accordance with the motion, and is required to have tackiness in some cases. As such a material, a resin containing a urethane bond in a main chain and a silsesquioxane in a side chain is used. Among them, a resin based on urethane gel (urethane gel composition) is preferably used. In order to exhibit the functions as a bio-electrode without being affected by water, repellency is also necessary. Accordingly, a urethane gel having a silsesquioxane pendant is preferably used.

The urethane gel composition is exemplified by the one that can be obtained by mixing a hydroxy compound and an isocyanate compound, for example, and by adding a catalyst to promote the reaction in some cases. The urethane gel with lower hardness can be obtained by reducing the crosslinking density or totally inhibiting the crosslinking. Accordingly, it is preferable to avoid addition of a cross-linkable hydroxy group-containing compound that has three or more of hydroxy groups in one molecule as possible or to reduce the amount.

The method for forming urethane gel can be exemplified by a one shot method of mixing a hydroxy compound, an isocyanate compound, a diol compound having a silsesquioxane pendant shown by a formula (5), and an ionic polymer, followed by curing thereof by heating, etc. The one shot method has an advantage of higher productivity, but sometimes lowers the strength or stretchability due to remaining of unreacted hydroxy groups or isocyanate groups.

It is also possible to exemplify a prepolymer method in which a hydroxy compound and an isocyanate compound are previously mixed, and then a hydroxy compound, an isocyanate compound, a diol compound having a silsesquioxane pendant shown by the formula (5), and an ionic polymer are additionally mixed, followed by curing. In this case, the hydroxy groups and the isocyanate groups have sufficiently reacted, and there is a feature of lower ratio of residual isocyanate groups. When the prepolymer is prepared, the diol compound having a silsesquioxane pendant shown by the formula (5) can also be mixed not only the hydroxy compound and the isocyanate compound. In case of preparing the prepolymer, it is preferable that excess isocyanate groups have been mixed to make the terminals of prepolymer be isocyanate.

The urethane resin contained as the base resin in the inventive bio-electrode composition is preferably a resin containing a urethane bond in a main chain and a silsesquioxane in a side chain shown by the following formula (3). This makes it possible to improve the repellency and tackiness. Although urethane resin in which silsesquioxane is incorporated into the main chain lowers the strength and stretchability of the film, urethane structure which has a silsesquioxane-pendant(s) entails less lowering of the strength and is usable for a bio-electrode composition favorably.

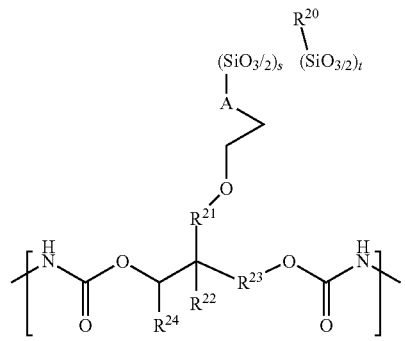

In the formula, $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0 \le s \le 0.2$ and $0.8 \le t < 1.0$.

$R^{20}$ is a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, which may be substituted with a halogen atom, an amino group, a cyano group, or a mercapto group, and may have an ether group, a carbonyl group, an acid anhydride group, an amide group, a nitrogen atom, or a sulfur atom. The aryl group may be substituted with a halogen atom, a nitro group, or a linear, branched, or cyclic alkyl group having 1 to 6 carbon atoms. Specific illustrative examples of $R^{20}$ include a methyl group, an ethyl group, an n-propyl group, an isopropyl group, a 3,3,3-trifluoropropyl group, a 3,3,4,4,5,5,6,6,6-nonafluorohexylmethyl group, an n-butyl group, an isobutyl group, a sec-butyl group, a tert-butyl group, an n-pentyl group, an n-hexyl group, an n-heptyl group, an n-octyl group, an n-nonyl group, an n-decyl group, a dodecyl group, a tridecyl group, an octadecyl group, an eicosyl group, a docosyl group, a cyclopentyl group, a cyclohexyl group, a norbornane group, a norbornene group, a 4-cyclohexenylethyl group, a phenyl group, a 4-chlorophenyl group, a p-tolyl group, a β-phenethyl group, a naphthyl group, an acenaphthyl group, a vinyl group, an allyl group, a benzyl group, an ethynyl group, a 3-cyanopropyl group, a 3-mercaptopropyl group, a 3-aminopropyl group, a 2-aminoethylaminopropyl group, a 3-allylaminopropyl group, a 2-morpholinoethyl group, a 2-piperidinoethyl group, a 2-piperazinoethylthioethyl group, a 4-methylpiperazinopropyl group, a chloromethyl group, a 2-chloroethyl group, a 3-chloropropyl group, a 3-succinimidepropyl group, and a 4-acetylpiperazinopropyl group.

Further, the resin containing a urethane bond in a main chain and a silsesquioxane in a side chain is preferably a resin having a structure containing a polyether main chain shown by the following formula (4). The polyurethane having a polyether main chain makes it possible to form a flexible bio-electrode film and also to improve the ionic conductivity.

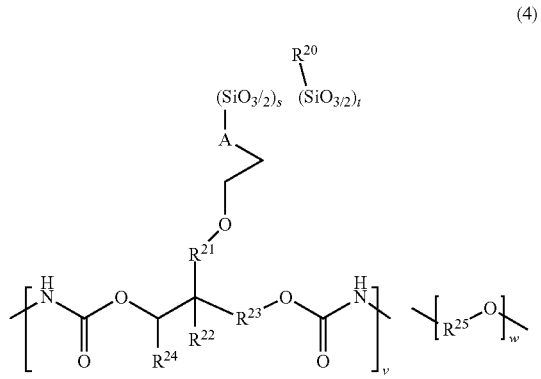

(4)

In the formula, $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; "s" and "t" satisfy $0<s\le 0.2$ and $0.8\le t<1.0$; $R^{25}$ represents a linear, branched, or cyclic alkylene group having 2 to 12 carbon atoms; and "v" and "w" satisfy $0<v<1.0$ and $0<w<1.0$.

The resin containing a urethane bond in a main chain and a silsesquioxane in a side chain is preferably a reaction product of a diol compound bonded to a silsesquioxane shown by the following formula (5), a polyether compound having a hydroxy group at a terminal, and a compound having an isocyanate group. The urethane resin obtained by reacting an isocyanate and a diol having a silsesquioxane pendant has tackiness and is favorably usable as the base resin for a bio-electrode, achieving the object of the present invention.

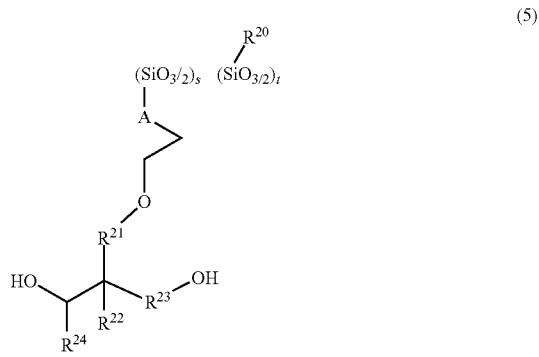

(5)

In the formula, $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{20}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0<s\le 0.2$ and $0.8\le t<1.0$.

The diol compound bonded to the silsesquioxane shown by the formula (5) is not particularly limited, and illustrative examples thereof include the following.

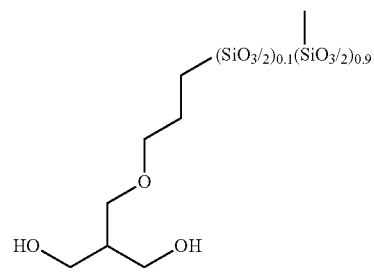

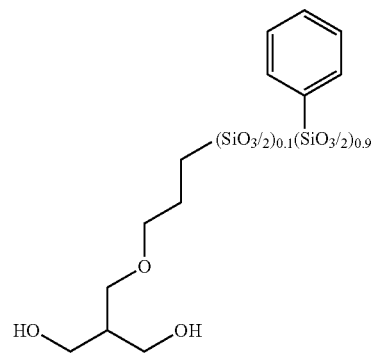

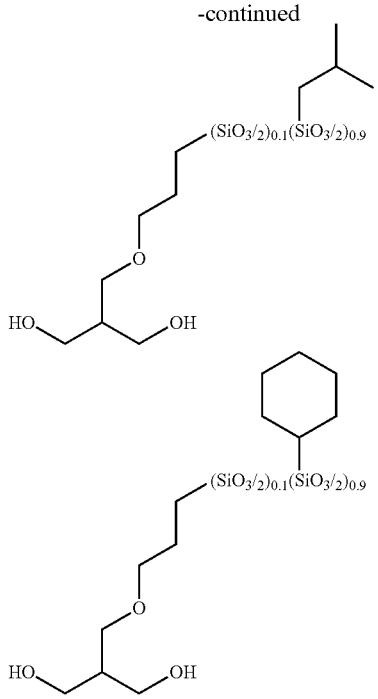

The diol compound bonded to the silsesquioxane shown by the formula (5) is more preferably a compound shown by a formula (6).

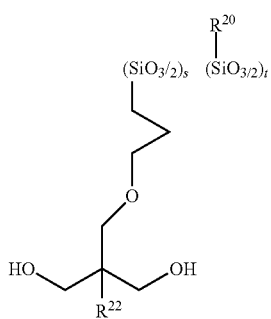

(6)

In the formula, $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{22}$ represents a hydrogen atom or a linear alkyl group having 1 to 4 carbon atoms; and "s" and "t" satisfy $0<s\leq 0.2$ and $0.8\leq t<1.0$.

The diol compound bonded to the silsesquioxane shown by the formula (6) is preferably a reaction product of substances shown by the following formulae (7)-1 and (7)-2. More specifically, the diol compound is preferably synthesized by hydrolysis condensation and ring-opening reaction of the alkoxysilanes shown by the following formulae (7)-1 and (7)-2.

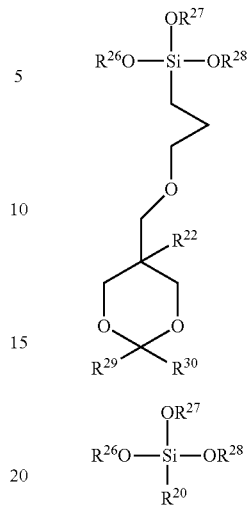

(7)-1

(7)-2

In the formulae, $R^{20}$ and $R^{22}$ have the same meanings as defined above; $R^{26}$ to $R^{28}$ each represent an alkyl group having 1 to 6 carbon atoms; and $R^{29}$ and $R^{30}$ each represent a hydrogen atom, a linear, branched, or cyclic alkyl group having 1 to 20 carbon atoms and optionally bonded to the other to form a ring, or an aryl group having 6 to 10 carbon atoms.

JP H10-87834A described above discloses a method in which after an alkoxysilane bonded to an epoxy ring is condensed to a silsesquioxane, the epoxy ring is opened by using an acid to form a diol. To open the epoxy ring under an acidic condition, a strong acidic condition is required. However, such a strong acidic condition is not preferable because the silsesquioxane bond may be cleaved. Meanwhile, an epoxy group with closed ring, if remaining, reacts with an isocyanate compound in forming the urethane resin, and serves as a crosslinking point, thereby undesirably forming a urethane resin with high hardness. The compound shown by the formula (7)-1 has diol groups substituted with a cyclic acetal group called an acetonide. Since an acetal group has quite high reactivity with an acid in comparison with an epoxy group, it is preferable to produce almost complete diol groups by the ring-opening reaction of the cyclic acetal.

The diol compound bonded to the silsesquioxane shown by the general formula (6) is synthesized also by hydrolysis condensation and ring-opening reaction of alkoxysilanes shown by the following general formulae (7)-3 and (7)-2.

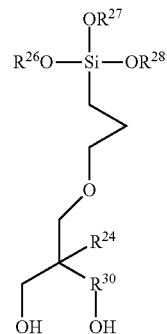

(7)-1

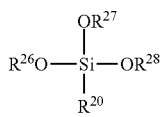

(7)-2

In the formulae, $R^{20}$, $R^{24}$, $R^{26}$ to $R^{28}$ have the same meanings as defined above; $R^{30}$ represents a single bond or a methylene group.

By changing the blending ratios of the formulae (7)-1 and/or (7)-3 and (7)-2, the ratio of the diol in the silsesquioxane can be changed. Given that the total number of moles of the formulae (7)-1, (7)-3, and (7)-2 is the denominator while the number of moles of the formula(e) (7)-1 and/or (7)-3 is the numerator, this ratio is preferably in a range of 0.01 to 0.5. If the number of this ratio is so large that the ratio of the diol is too high, the crosslinking ratio becomes too high when the urethane resin is produced, resulting in a hard film. This is not preferable as a bio-electrode. If the number is too small, the ratio of the silsesquioxane not incorporated into the urethane becomes too high, so that the tackiness is lowered.

In producing the urethane resin contained in the inventive bio-electrode composition, it is preferable to add a compound that has a plurality of hydroxy groups (hydroxy compound), in addition to the silsesquioxane-pendant diol, for extending the chain length or crosslinking. The hydroxy compound more preferably has a polyether structure.

The hydroxy compound is not particularly limited, and specific illustrative examples thereof include the following.

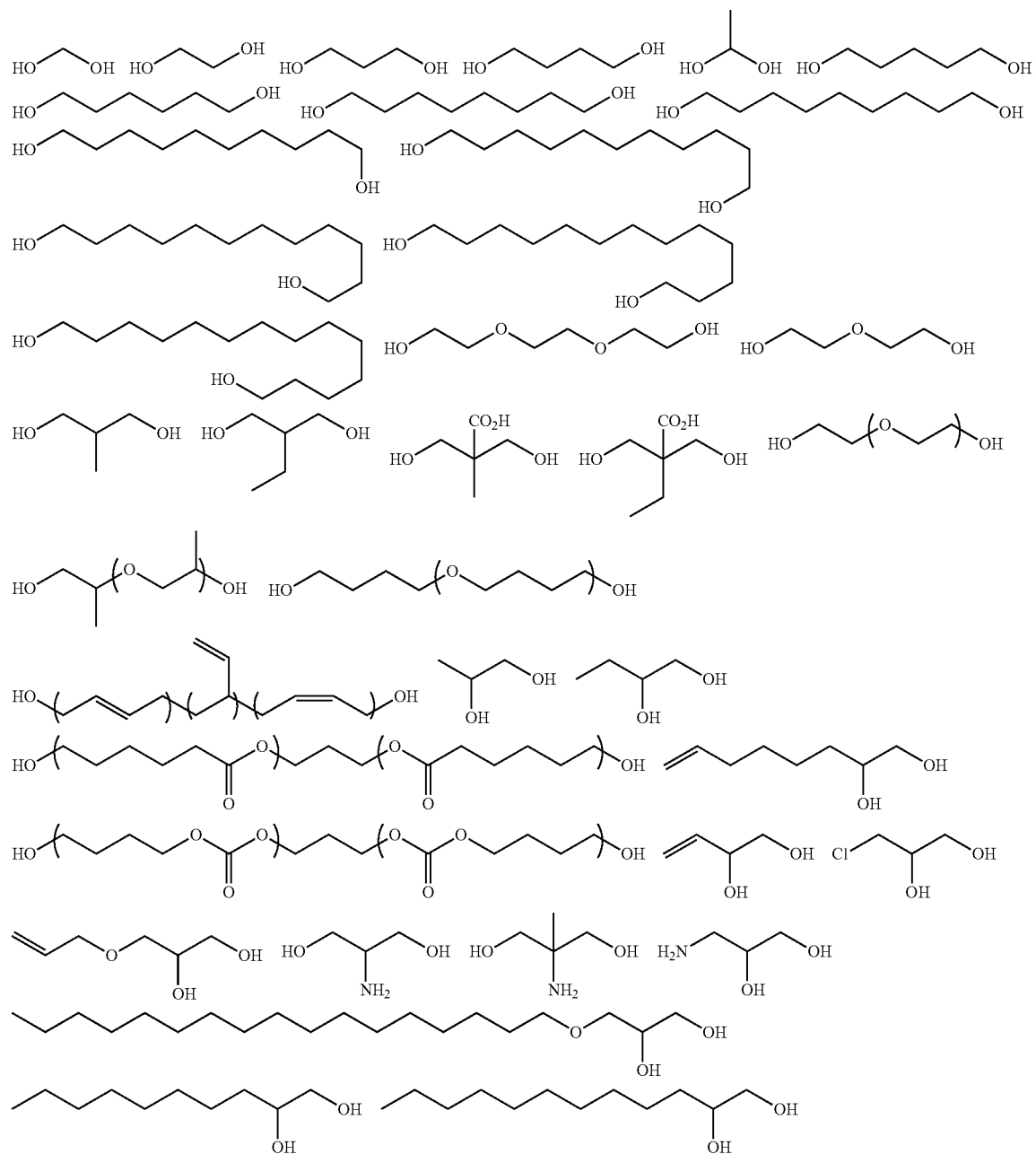

173
-continued
174
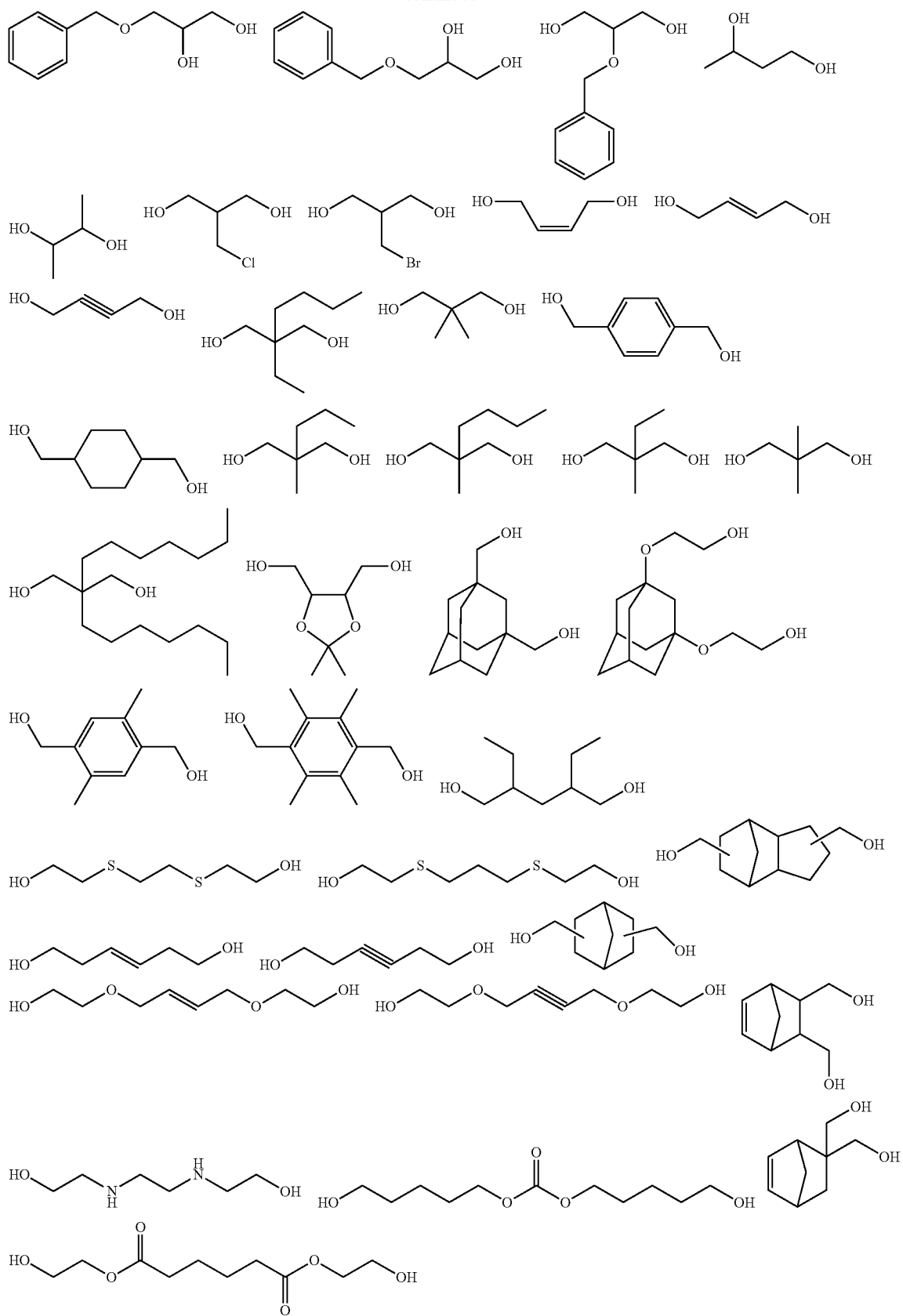

-continued
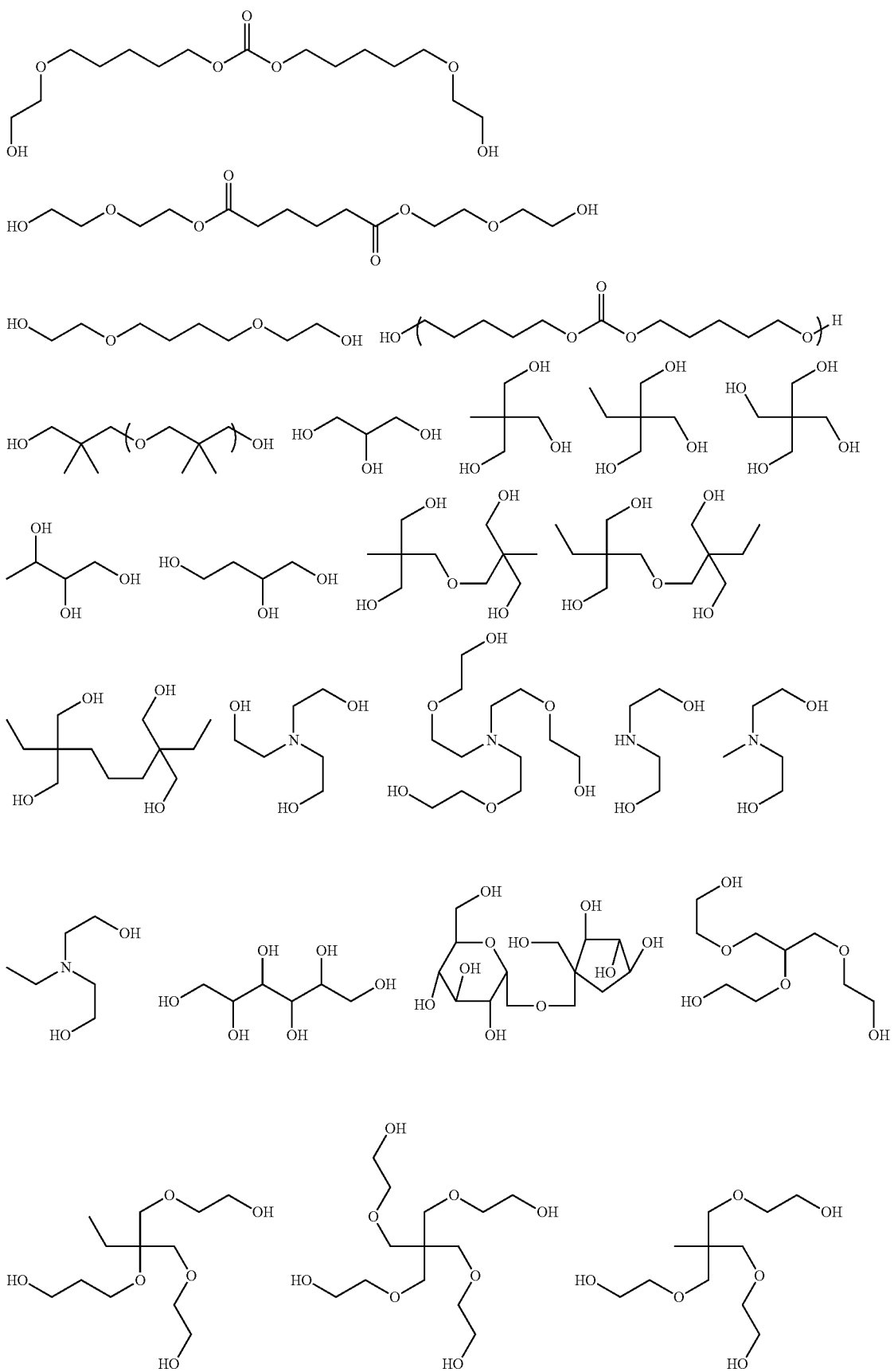

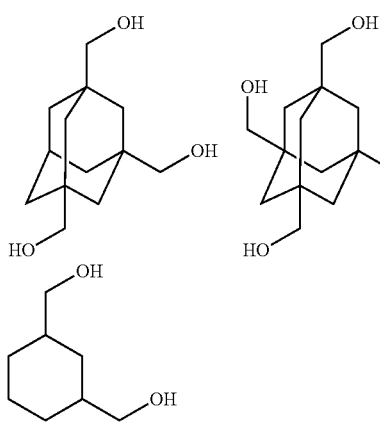
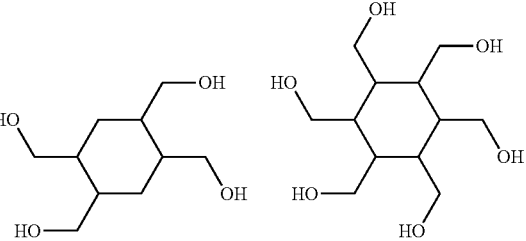
By mixing a hydroxy compound and an isocyanate compound, urethane bonds are formed to promote the reaction for curing, thereby forming a urethane resin.
The isocyanate compound to be used for the reaction with a hydroxy compound is not particularly limited, and specific illustrative examples thereof include the following.
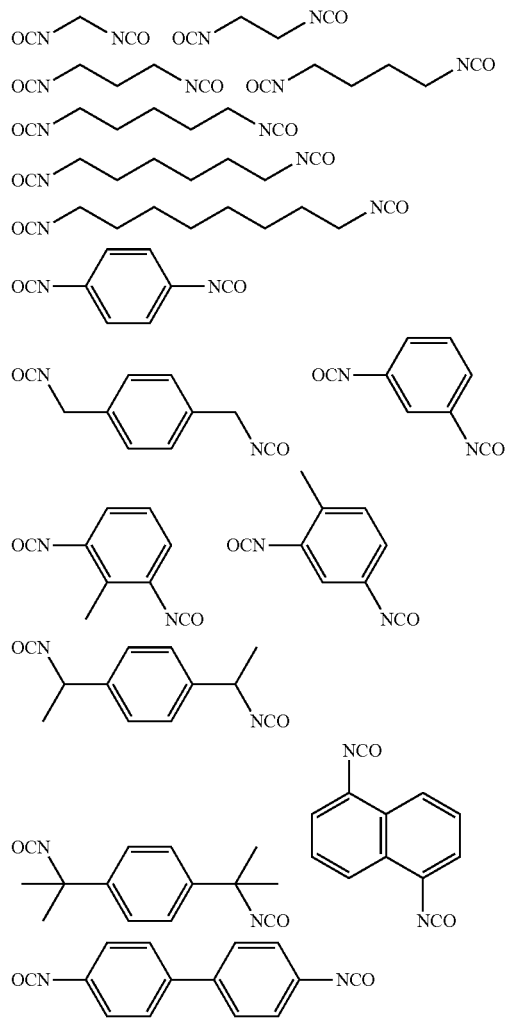
-continued
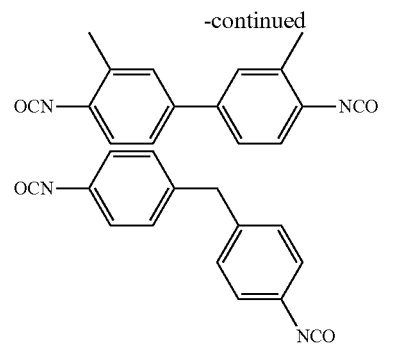
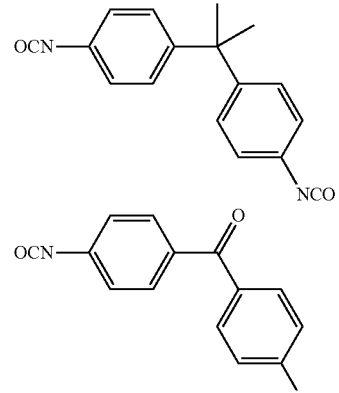
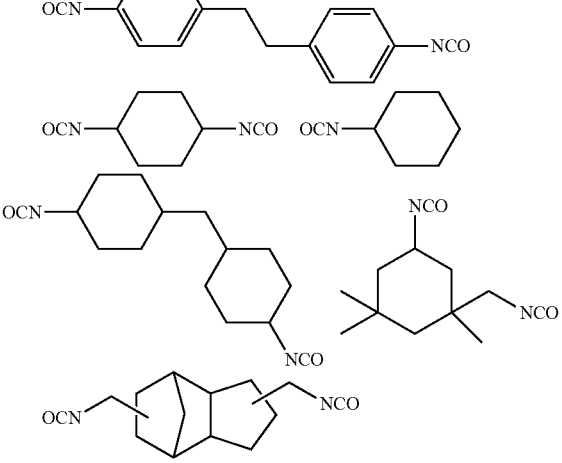

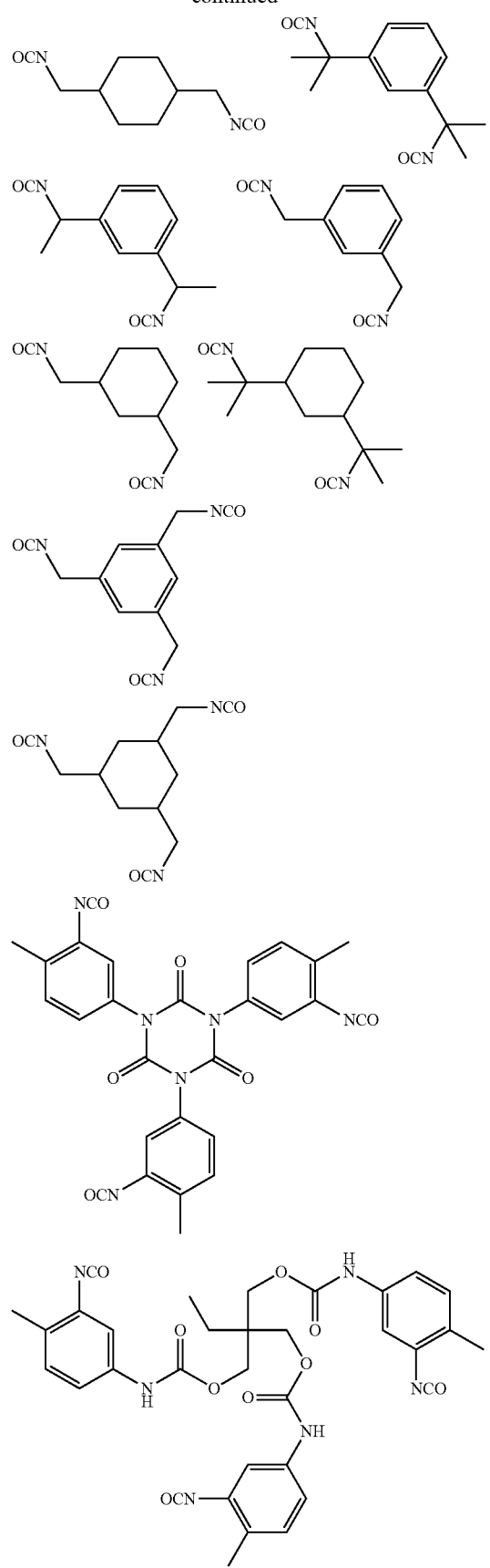
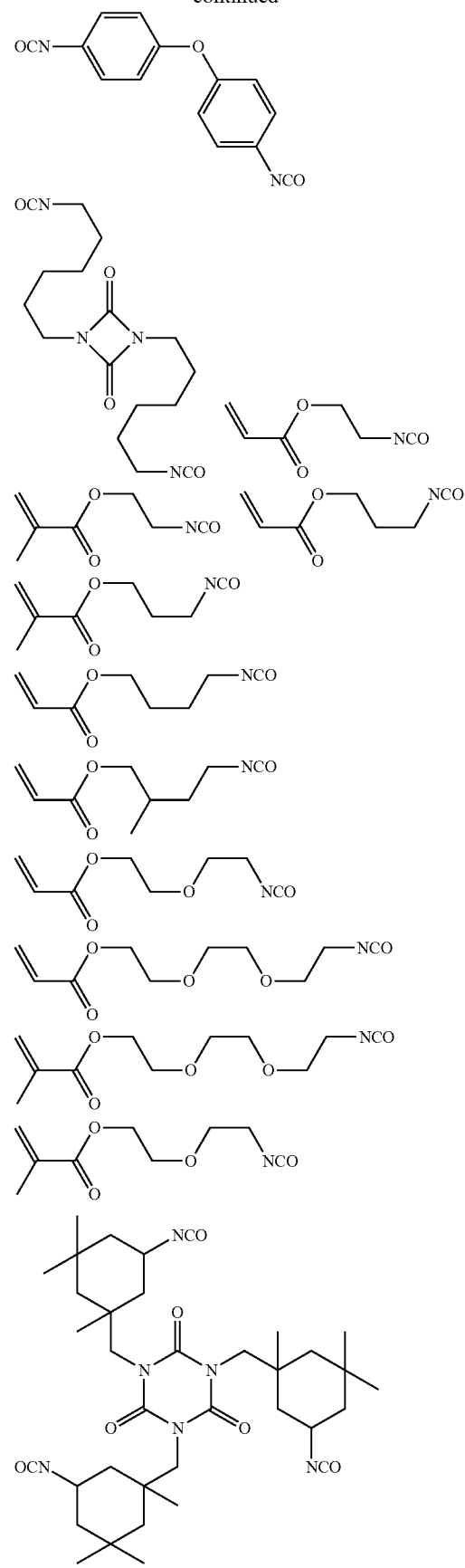

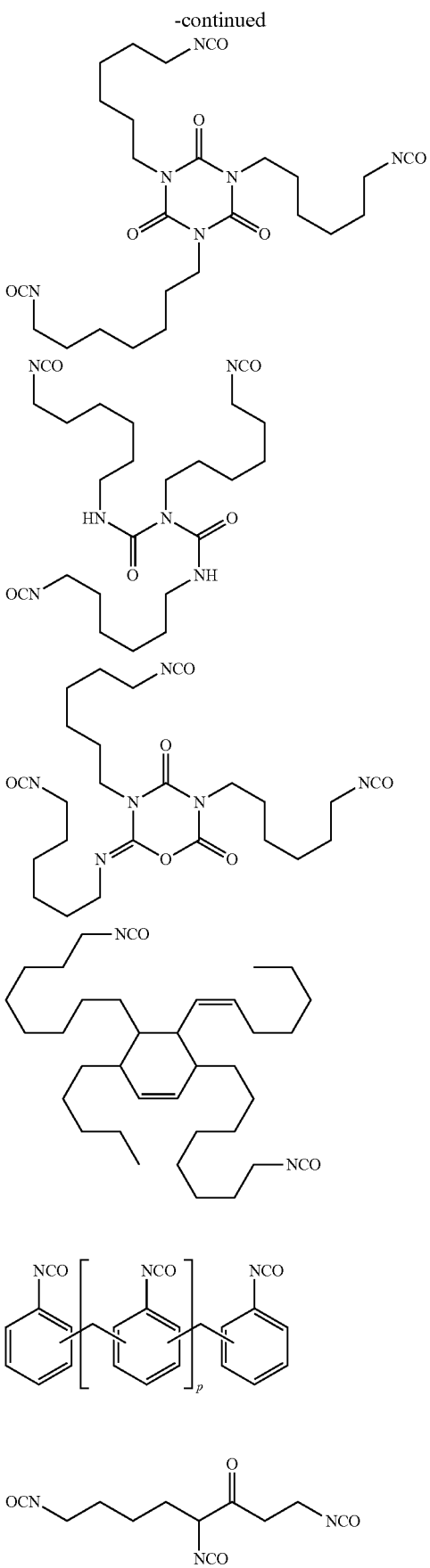

In the formulae, "p" is an integer of 1 or more.

As the isocyanate compound, it is preferable to use a compound having a blocked isocyanate group in which the isocyanate group is protected by a substituent. This facilitates to control the reaction even when the reactivity with the hydroxy group-containing compound is high. The isocyanate compound sometimes reacts with moisture in the air during the storage to cause inactivation of the isocyanate group, and requires full attention such as fully preventing moisture for the storage. In the compound having a blocked isocyanate group, however, these phenomena can be prevented.

The blocked isocyanate group is a group, the blocked group of which is deprotected by heating to be an isocyanate group. Specific illustrative examples thereof include isocyanate groups substituted with alcohol, phenol, thioalcohol, imine, ketimine, amine, lactam, pyrazol, oxime, β-diketone, or the like.

In using a blocked isocyanate compound, a catalyst can be added to decrease the temperature for deprotecting the blocked isocyanate group. This catalyst is not particularly limited, and known examples thereof include organic tin compounds such as dibutyl tin dilaurate, bismuth salts, and zinc carboxylate such as zinc 2-ethylhexanoate and zinc acetate.

It is preferable to use zinc α,β-unsaturated carboxylate as a catalyst for dissociation of blocked isocyanate as described in JP 2012-152725A.

In the synthesis of the urethane resin contained in the inventive bio-electrode composition, it is also possible to add a compound that has an amino group(s). Reaction of an isocyanate group and an amino group forms a urea bond. The parts of urethane bond and urea bond are called hard segments, and their hydrogen bonds improve the strength. It is possible to improve the strength by introducing a urea bond(s) in addition to the urethane bond(s) not only the urethane bond(s) alone.

[Organic Solvent]

The inventive bio-electrode composition may contain an organic solvent. The organic solvent is not particularly limited, and specific illustrative examples thereof include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, 3,9-dodecadiyne, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvent such as γ-butyrolactone; and the like.

The amount of the organic solvent to be added is preferably in a range of 10 to 50,000 parts by mass on the basis of 100 parts by mass of the resin.

[Carbon Material]

The inventive bio-electrode composition can contain a carbon material as an electric conductivity improver to further enhance the electric conductivity. The carbon material may be exemplified by carbon black, carbon nanotube, and the like, and is preferably either or both of them. The carbon nanotube may be either single layer or multilayer, and the surface may be modified with an organic group(s). The amount of the carbon material to be added is preferably in a range of 1 to 50 parts by mass on the basis of 100 parts by mass of the resin.

[Electric Conductivity Improver Other than Carbon Material]

The inventive bio-electrode composition also can contain an electric conductivity improver other than the carbon material. Specific illustrative examples thereof include particles of resin coated with noble metal such as gold, silver, and platinum; nanoparticles of gold, silver, and platinum; particles of metal oxide such as indium-tin oxide (ITO), indium-zinc oxide (IZO), tin oxide, and zinc oxide; as well as silver nanowire.

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. It is possible to improve the electric conductivity still more by adding a carbon material, and to manufacture a particularly soft bio-electrode with high stretchability by combining urethane resin with flexibility and stretchability. Furthermore, it is possible to improve the stretchability and tackiness to skin by additives or the like, and to control the stretchability and tackiness by adjusting the composition of the urethane resin and the thickness of the living body contact layer appropriately.

<Bio-Electrode>

The present invention also provides a bio-electrode comprising an electro-conductive base material and a living body contact layer formed on the electro-conductive base material, wherein the living body contact layer is a cured material of the inventive bio-electrode composition described above.

Hereinafter, the inventive bio-electrode will be specifically described by reference to the drawings, but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the electro-conductive material 4 and the carbon material 5 are dispersed in the urethane resin 6. Incidentally, the carbon material 5 is an optional component.

Figure 2:
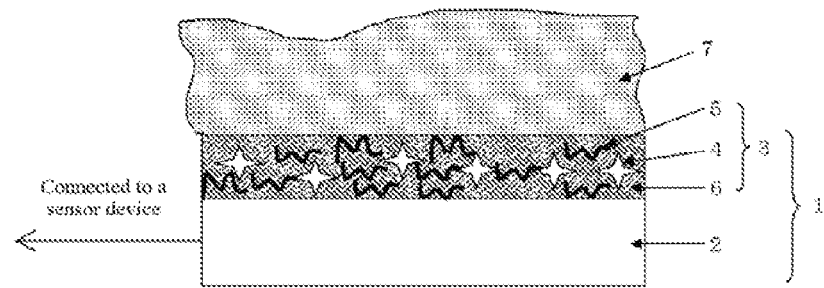
FIG. 2 is a schematic sectional view showing an example of the inventive bio-electrode worn on a living body.

When using the bio-electrode 1 of FIG. 1 like this, electric signals are picked from the living body 7 through the electro-conductive material 4 and the carbon material 5 while bringing the living body contact layer (i.e., the layer in which the electro-conductive material 4 and the carbon material 5 are dispersed in the urethane resin 6) into contact with the living body 7, and then conducted to a sensor device and so on (not shown) through the electro-conductive base material 2 as shown in FIG. 2. As described above, the inventive bio-electrode is capable of coping with both electric conductivity and biocompatibility by using the electro-conductive material described above, improving the electric conductivity further by additionally adding electric conductivity improver such as a carbon material in accordance with needs, and obtaining electric signals from skin stably in high sensitivity because the contact area with skin is kept constant due to the tackiness of the inventive bio-electrode.

Hereinafter, each component composing the inventive bio-electrode will be more specifically described.

[Electro-Conductive Base Material]

The inventive bio-electrode comprises an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be, for example, a hard electro-conductive substrate, an electro-conductive film having flexibility, a cloth with the surface being coated with electro-conductive paste, or a cloth into which electro-conductive polymer is kneaded, without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode comprises a living body contact layer formed on the electro-conductive base material. This living body contact layer is a part to be actually in contact with a living body when using the bio-electrode, and is a urethane resin that has electric conductivity and repellency. The living body contact layer is a cured material of the inventive bio-electrode composition described above, that is to say, a resin layer of the resin containing a urethane bond in a main chain and a silsesquioxane in a side chain, the resin layer containing the resin and the electro-conductive material (salt) described above, together with additives such as a carbon material in accordance with needs.

The living body contact layer of the bio-electrode has a thickness of preferably 1 μm or more and 5 mm or less, more preferably 2 μm or more and 3 mm or less. As the living body contact layer is thinner, the tackiness lowers, but the flexibility is improved, and the weight decreases to improve the compatibility with skin. The thickness of the living body contact layer can be selected based on the balance of flexibility, tackiness, and texture.

The inventive bio-electrode may be provided with a tacky film separately on the living body contact layer as previous bio-electrodes (e.g., the bio-electrode described in JP 2004-033468A) in order to prevent peeling off of the bio-electrode from a living body during the use. When the tacky film is prepared separately, the tacky film may be formed by using a raw material for the tacky film such as an acrylic type, a urethane type, or a silicone type. Particularly, the silicone type is suitable because of: the high oxygen permeability, which allows cutaneous respiration with the silicone pasted; the high water repellency, which decreases lowering of tackiness due to perspiration; and the low irritation to skin. It is to be noted that the inventive bio-electrode does not necessarily require the tacky film that is prepared separately as described above, because peeling off from a living body can be prevented by adding tackifier to the bio-electrode composition or using a resin having good tackiness to a living body.

When the inventive bio-electrode is used as a wearable device, wiring between the bio-electrode and a sensor device, and other components are not limited to particular ones. For example, it is possible to apply the ones described in JP 2004-033468A.

As described above, the inventive bio-electrode is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried, because the living body contact layer is formed from a cured material of the inventive bio-electrode composition described above. It is possible to improve the electric conductivity still more by adding a carbon material, and to manufacture a highly stretchable bio-electrode that is always in contact with skin by combining a urethane resin that has flexibility and stretchability. This urethane resin, having a silsesquioxane in the side chain, has higher repellency to repel perspiration or water to exclude the influences thereof, and also has tackiness together with higher biocompatibility. Additionally, this urethane resin has improved strength since it has a urethane main chain, exhibits higher ionic conductivity since it also has a polyether main chain, and functions as a highly sensitive bio-electrode thereby. It is also possible to improve the stretchability and tackiness to skin by additives or the like, and to control the stretchability and tackiness by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, the bio-electrode composition, etc. used for the inventive method for manufacturing a bio-electrode are the same as those in the inventive bio-electrode described above.

As an example of the method for manufacturing a bio-electrode of the present invention, it is preferable to produce a living body contact layer based on a urethane resin by mixing a silsesquioxane-pendant diol compound, a hydroxy compound, an ionic polymer, an electric conductivity improver, etc., followed by mixing an isocyanate compound. Since the curing reaction occurs when the isocyanate compound is mixed, it is preferable to mix the isocyanate compound at the end. The living body contact layer preferably has no openings due to foaming. Accordingly, it is preferable that the molar ratios of the isocyanate groups and the hydroxy groups be the same or the hydroxy groups be excess.

The bio-electrode composition can be formed from a material in which a hydroxy compound, an isocyanate compound, an ionic polymer, and an electric conductivity improver are mixed with a silsesquioxane-pendant diol compound, for example. In this case, the hydroxy compound and the isocyanate compound may be mixed at one time or may be mixed in stages.

The method for applying the inventive bio-electrode composition onto the electro-conductive base material is not limited to particular ones; and dip coating, spray coating, spin coating, roll coating, flow coating, doctor coating, screen printing, flexographic printing, gravure printing, and inkjet printing are suitable, for example.

The method for curing the bio-electrode composition can be appropriately selected based on a kind of resin used for the bio-electrode composition without being limited to particular methods. For example, the bio-electrode composition is preferably cured by either or both of heat and light. The foregoing bio-electrode composition can also be cured by adding a catalyst to generate acid or base to the bio-electrode composition, which causes a crosslinking reaction.

In case of heating, the temperature may be appropriately selected based on a kind of resin used for the bio-electrode composition without being limited to particular temperature. For example, it is preferable to be about 50 to 250° C., but it is also possible to cure by leaving the composition at room temperature for a long time.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode makes it possible to manufacture the inventive bio-electrode easily and at low cost, which is excellent in electric conductivity and biocompatibility, light in weight, and free from large lowering of the electric conductivity even when it is wetted with water or dried.

EXAMPLES

Hereinafter, the present invention will be more specifically described by showing Examples and Comparative Examples, but the present invention is not limited to the following Examples.

Ionic polymers 1 to 13 blended to solutions of bio-electrode composition as an electro-conductive material were synthesized as follows. Each 30 mass % monomer solution in propylene glycol-1-monomethyl ether-2-acetate (PGMEA) was mixed in a reaction vessel. The reaction vessel was cooled to −70° C. under a nitrogen atmosphere, and subjected to vacuum degassing and nitrogen blowing repeated for three times. After raising the temperature to room temperature, azobisisobutyronitrile (AIBN) was added thereto as a polymerization initiator in an amount of 0.01 moles per 1 mole of the whole monomers, and warmed to a temperature of 60° C. and then allowed to react for 15 hours. The composition of obtained polymer was determined by $^1$H-NMR after drying the solvent, and the Mw and Mw/Mn were determined by gel permeation chromatography (GPC) using tetrahydrofuran (THF) as a solvent.

The following are Ionic polymers 1 to 13 and

Comparative ammonium salts 1, 2 each blended to the bio-electrode composition solution as an electro-conductive material.

Ionic polymer 1

Mw=20,900

Mw/Mn=2.21

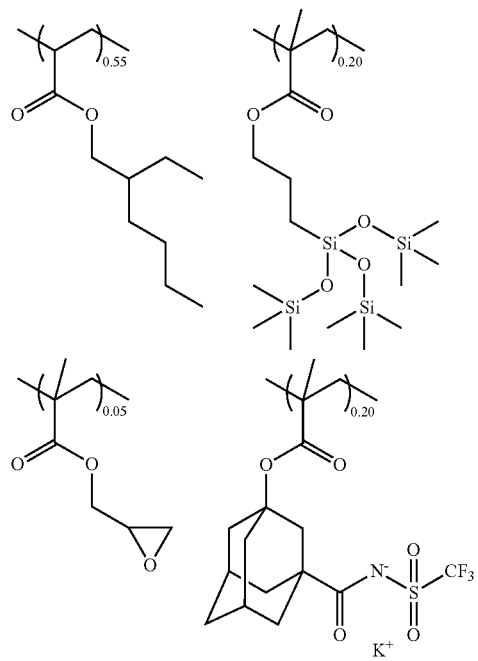

Ionic polymer 2

Mw=23,100

Mw/Mn=2.01

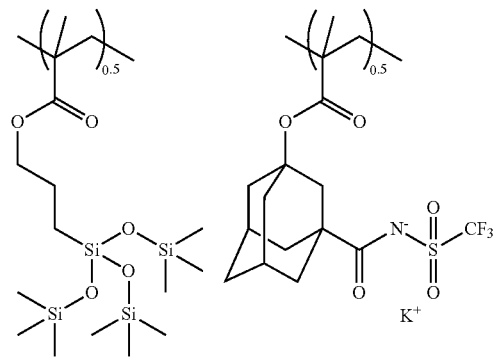

Ionic polymer 3

Mw=27,400

Mw/Mn=1.94

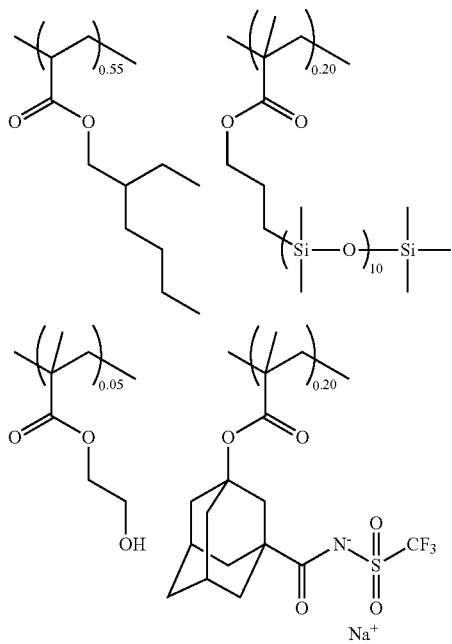
The repeating number in the formula shows the average value.
Ionic polymer 4
Mw=30,600
Mw/Mn=1.88
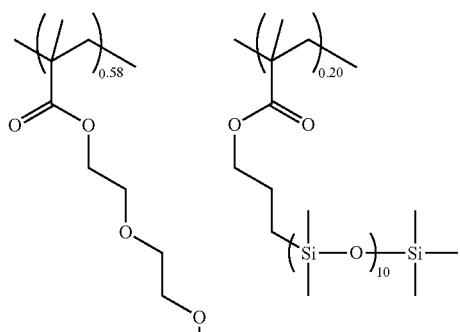
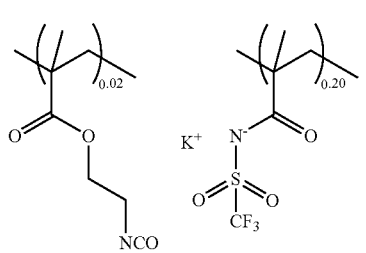
The repeating number in the formula shows the average value.
Ionic polymer 5
Mw=26,600
Mw/Mn=1.86
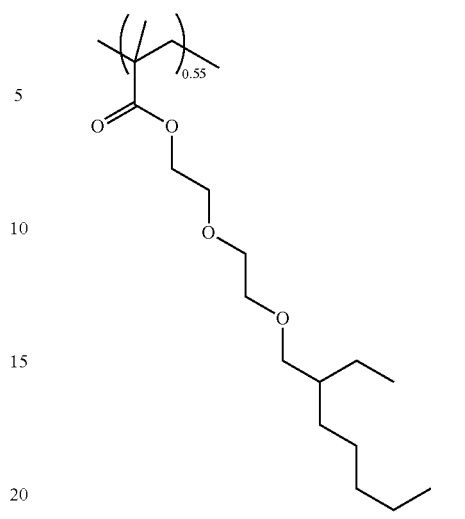
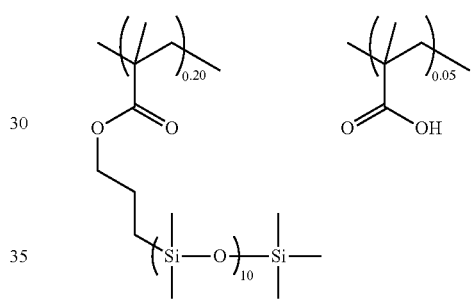
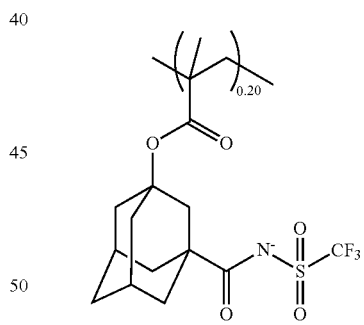
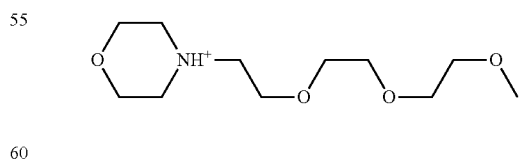
The repeating number in the formula shows the average value.
Ionic polymer 6
Mw=21,900
Mw/Mn=2.10

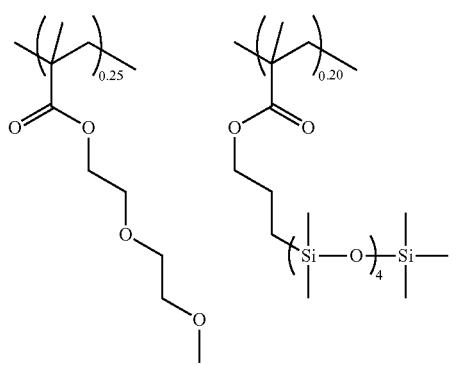
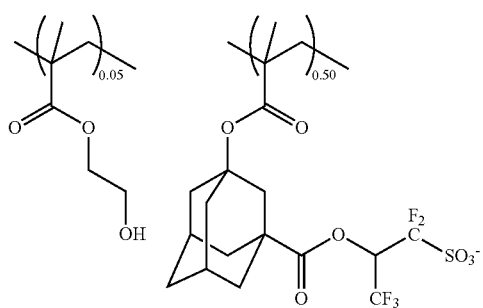
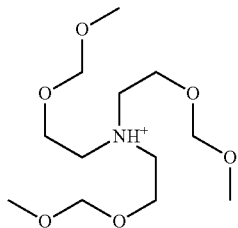
The repeating number in the formula shows the average value.
Ionic polymer 7
Mw=35,700
Mw/Mn=2.33
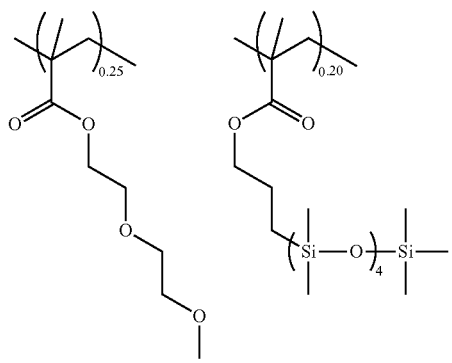
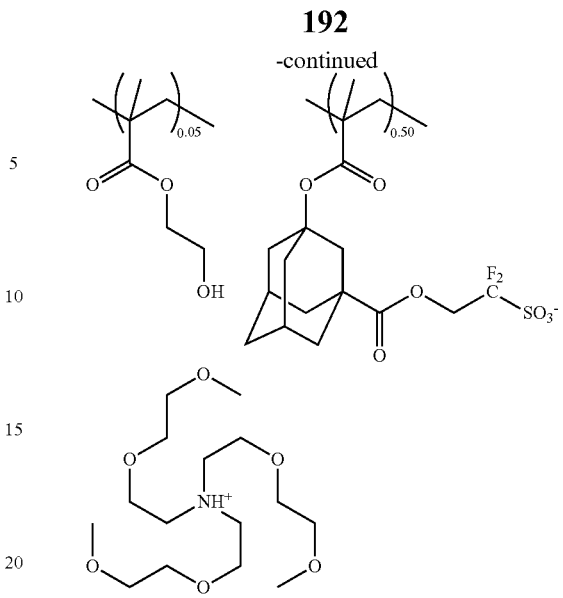
The repeating number in the formula shows the average value.
Ionic polymer 8
Mw=35,700
Mw/Mn=2.33
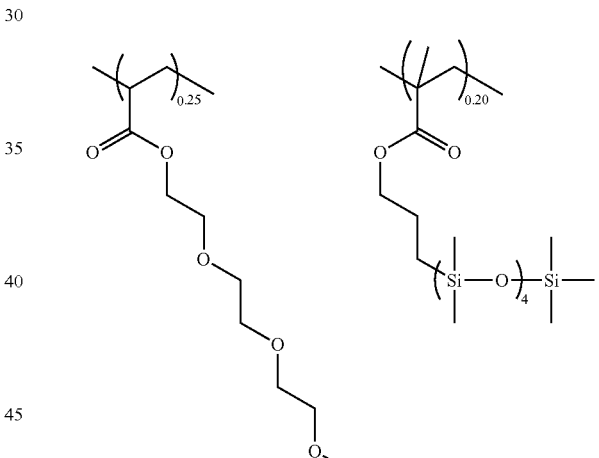
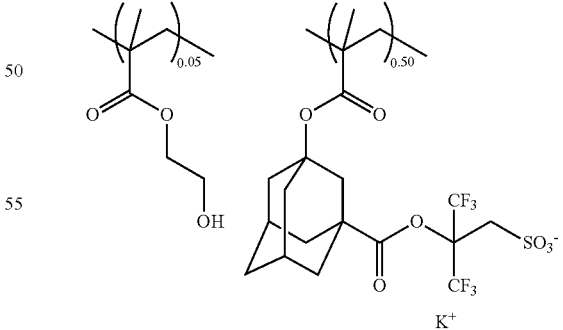
The repeating number in the formula shows the average value.
Ionic polymer 9
Mw=33,100
Mw/Mn=2.02

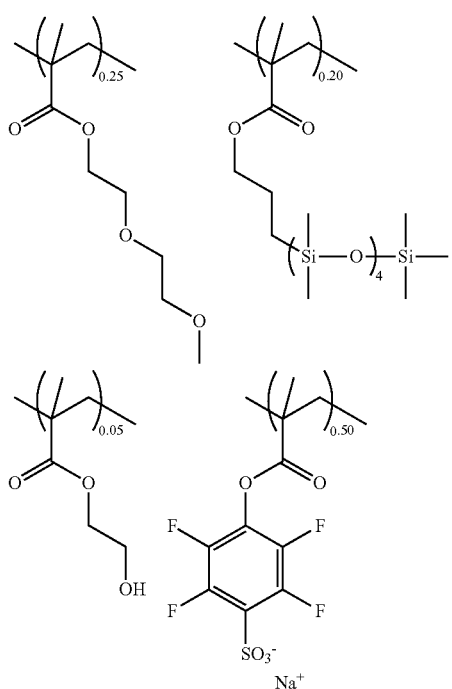
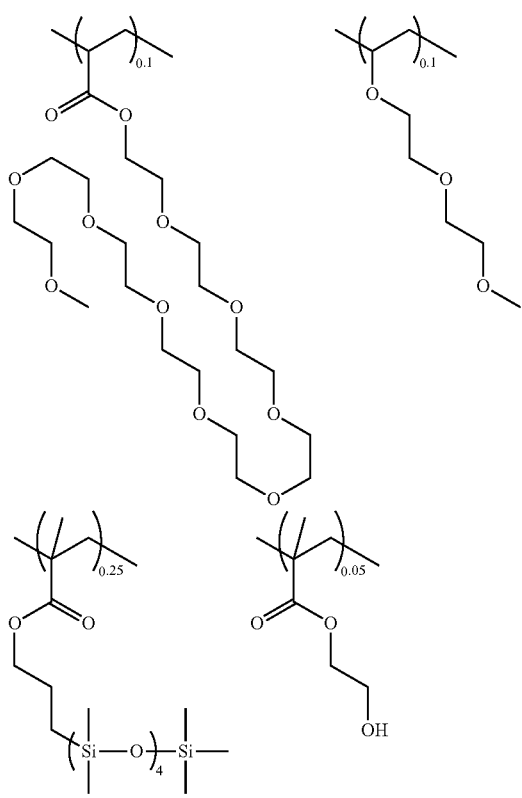
The repeating number in the formula shows the average value.
Ionic polymer 10
Mw=21,500
Mw/Mn=1.96
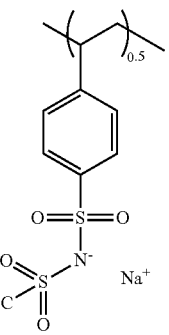
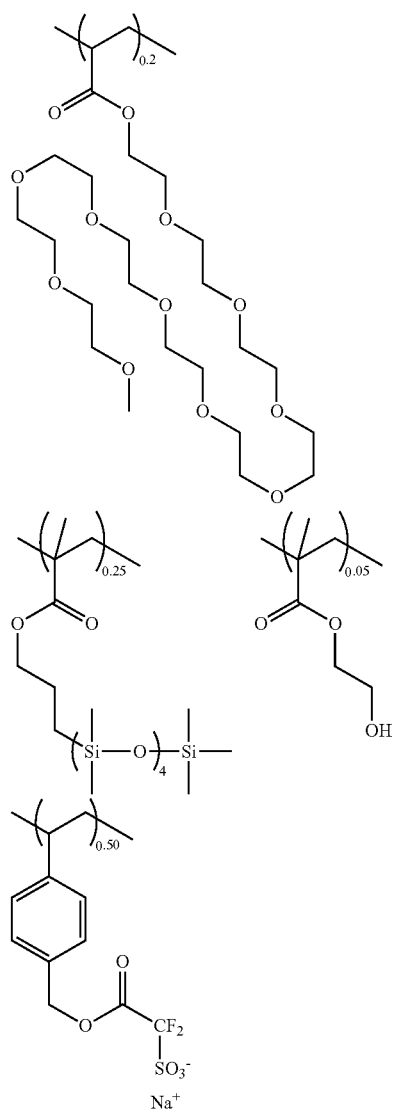
The repeating number in the formula shows the average value.
Ionic polymer 11
Mw=24,500
Mw/Mn=1.91
The repeating number in the formula shows the average value.

Ionic polymer 12
Mw=16,300
Mw/Mn=1.75
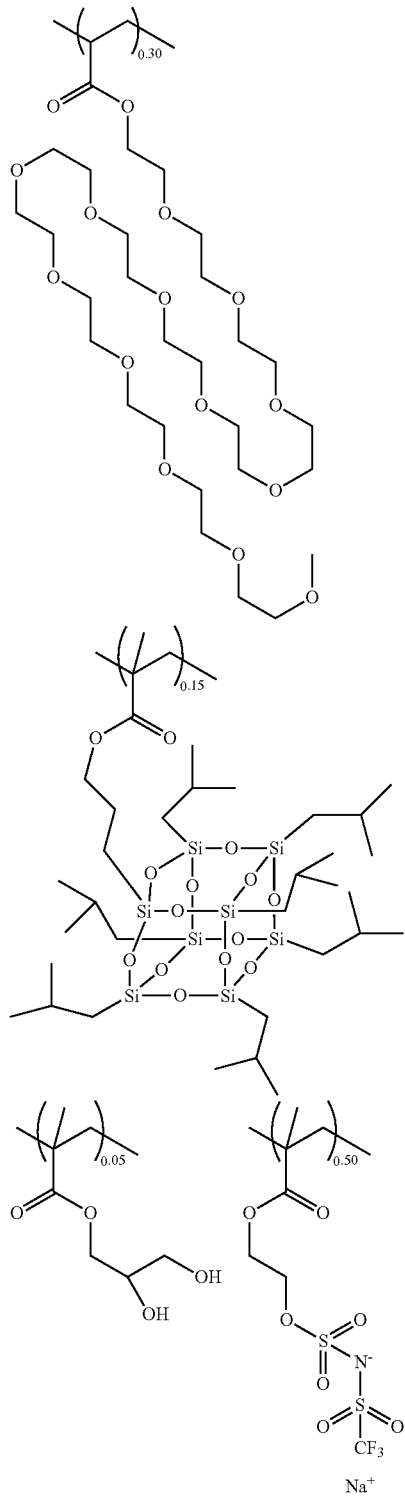
Ionic polymer 13
Mw=26,500
Mw/Mn=1.91
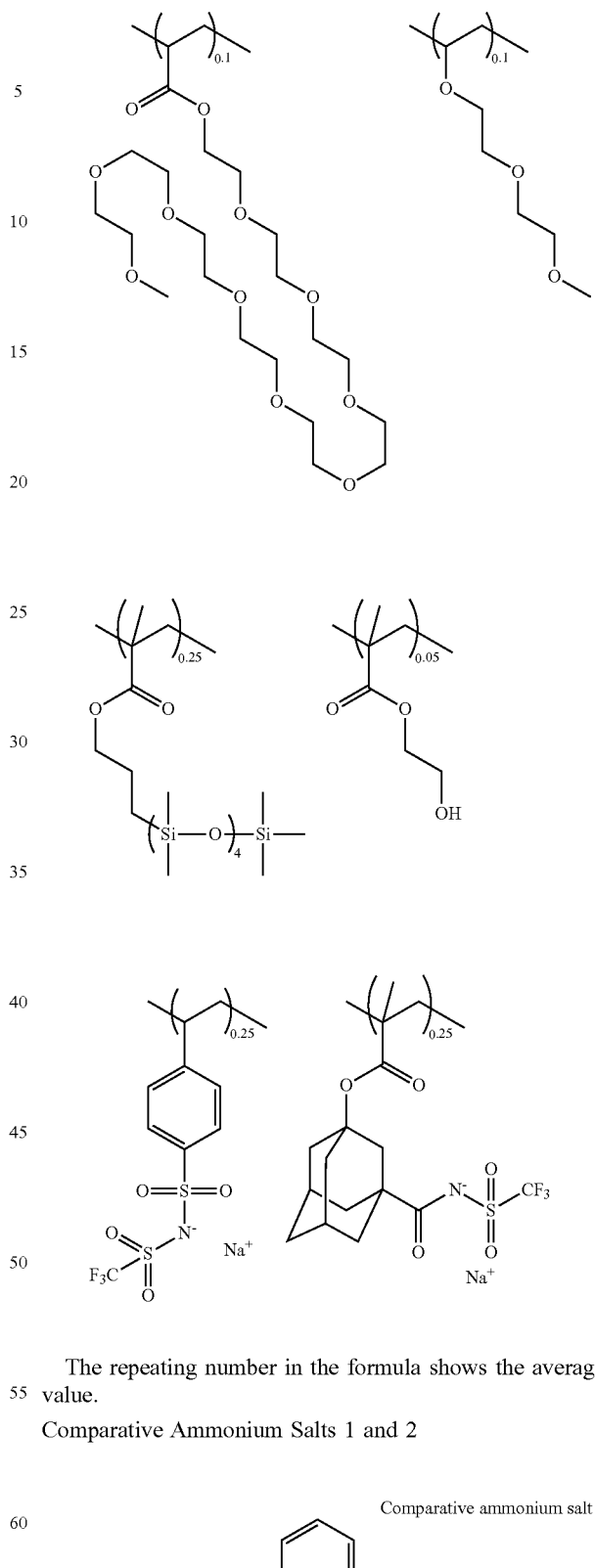
The repeating number in the formula shows the average value.
Comparative Ammonium Salts 1 and 2

-continued

Comparative ammonium salt 2

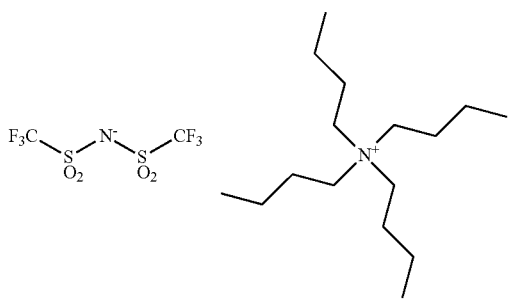

To a solution at 30° C. in which 60 g of acetonitrile was mixed with 1.2 g of oxalic acid, a mixture solution of 6.7 g of the following acetonide-substituted trimethoxysilane monomer with 24.5 g of trimethoxysilane was added dropwise over 1 hour, and stirred for 12 hours to synthesize a silsesquioxane precursor. Simultaneously, diol groups were produced by the ring-opening reaction of the acetal, and 700 g of ethyl acetate was added thereto, followed by liquid separation and water-washing three times. Then, 80 g of dimethyl formamide and 160 g of toluene were added to the resultant, and 1 g of potassium hydroxide was further added. This mixture was heated at 135° C. for 30 minutes, and the residual silanol was condensed.

Subsequently, 500 g of ethyl acetate was added thereto, followed by liquid separation and water-washing three times. A PGMEA solution was added to the resultant, and the other solvents than PGMEA were evaporated at 40° C. Thus, the PGMEA solution containing 30 mass % of a silsesquioxane-pendant diol compound 1 was prepared. PGMEA solutions of the following silsesquioxane-pendant diol compounds 2 to 5 were synthesized by the same method except that the trimethoxysilane monomer was changed to other silane monomers.

Acetonide-Substituted trimethoxysilane Monomer

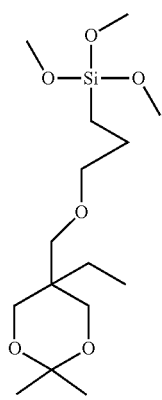 [SMILES: CCC1(COCCC[Si](OC)(OC)OC)COC(C)(C)OC1]

To a solution at 30° C. in which 60 g of acetonitrile was mixed with 1.2 g of oxalic acid, a mixture solution of 5.3 g of the following diol-containing trimethoxysilane monomer with 33.5 g of isobutyltrimethoxysilane was added dropwise over 1 hour, and stirred for 12 hours to synthesize a silsesquioxane precursor. Then, 700 g of ethyl acetate was added thereto, followed by liquid separation and water-washing three times. Subsequently, 80 g of dimethyl formamide and 160 g of toluene were added to the resultant, and 1 g of potassium hydroxide was further added. This mixture was heated at 135° C. for 30 minutes, and the residual silanol was condensed. Thereafter, 500 g of ethyl acetate was added thereto, followed by liquid separation and water-washing three times. A PGMEA solution was added to the resultant, and the other solvents than PGMEA were evaporated at 40° C. Thus, the PGMEA solution containing 30 mass % of a silsesquioxane-pendant diol compound 6 was prepared.

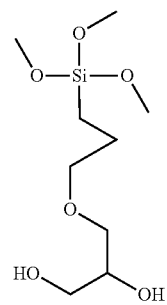

Silsesquioxane-Pendant Diol Compounds 1 to 6

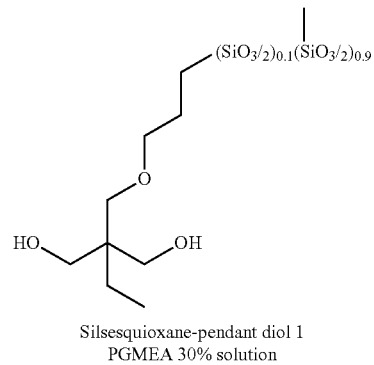

Silsesquioxane-pendant diol 1
PGMEA 30% solution

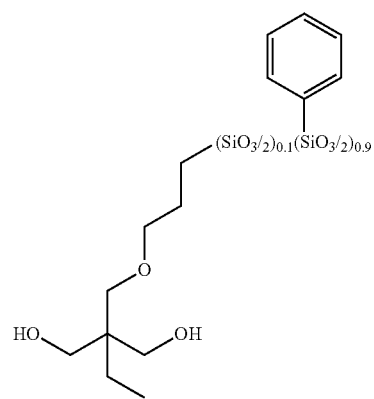

Silsesquioxane-pendant diol 2
PGMEA 30% solution

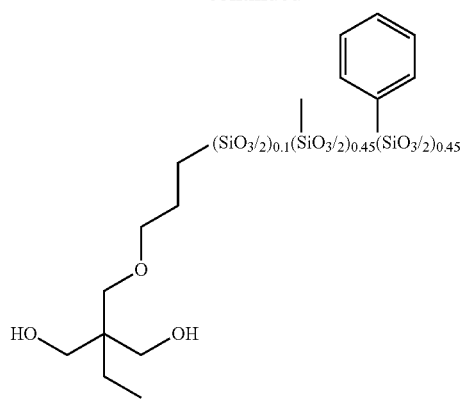

Silsesquioxane-pendant diol 3
PGMEA 30% solution

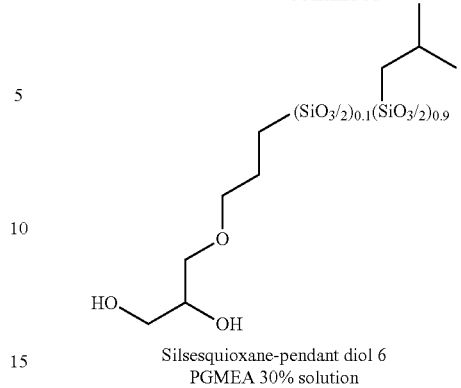

Silsesquioxane-pendant diol 6
PGMEA 30% solution

The following are hydroxy compounds 1 to 7 each blended to the bio-electrode composition.

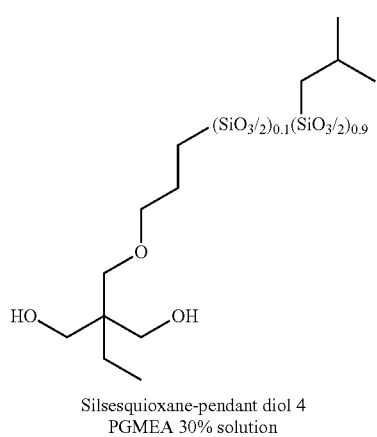

Silsesquioxane-pendant diol 4
PGMEA 30% solution

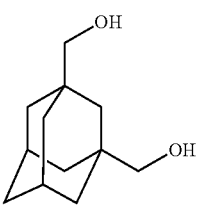

Hydroxy compound 1

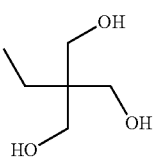

Hydroxy compound 2

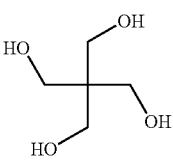

Hydroxy compound 3

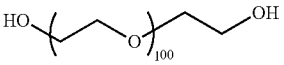

Hydroxy compound 4

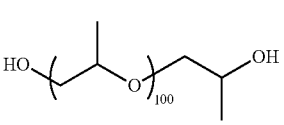

Hydroxy compound 5

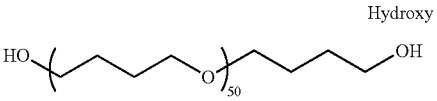

Hydroxy compound 6

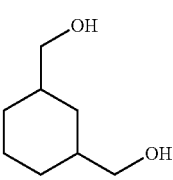

Hydroxy compound 7

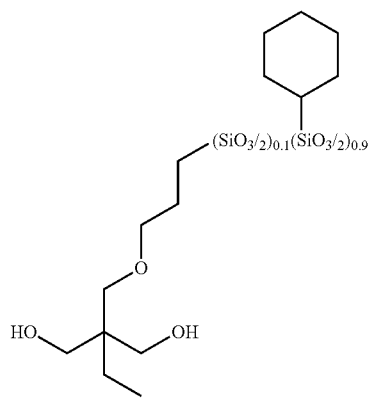

Silsesquioxane-pendant diol 5
PGMEA 30% solution

The repeating numbers in the formulae show the average values.

The following are isocyanate compounds 1 to 4 each blended to the bio-electrode composition.

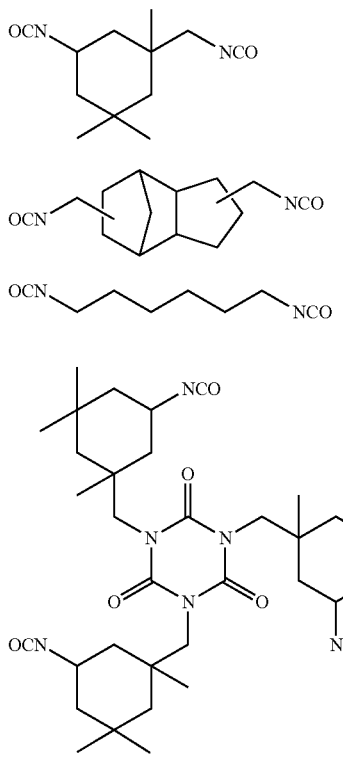

Isocyanate compound 1

Isocyanate compound 2

Isocyanate compound 3

Isocyanate compound 4

The following are electric conductivity improvers (carbon black, multilayer carbon nanotube, Au-coated particle, and Ag-coated particle) blended to the bio-electrode solution as an additive.

Carbon black: DENKA BLACK HS-100 manufactured by Denka Co., Ltd.

Multilayer carbon nanotube: carbon nanotube having a diameter of 0.7 to 1.1 nm and a length of 300 to 2,300 nm manufactured by Sigma-Aldrich Co. LLC.

Au-coated particle: Micropearl AU (the diameter of 3 μm) manufactured by SEKISUI CHEMICAL CO. LTD.

Ag-coated particle: Ag-coated powder (the diameter of 30 μm) manufactured by Mitsubishi Materials Electronic Chemicals Co., Ltd.

Examples 1 to 15, Comparative Examples 1 to 3

On the basis of each composition described in Table 1, the silsesquioxane (SSQ)-pendant diol solutions 1 to 6, the ionic polymer, the hydroxy compound(s), and the additive (electric conductivity improver) were mixed and degassed, and the isocyanate compound(s) were mixed thereto at the end to prepare each bio-electrode solution (Bio-electrode solutions 1 to 15, Comparative bio-electrode solutions 1 to 3).

TABLE 1

| Bio-electrode solution | Electro-conductive meterial (parts by mass) | Hydroxy compound (parts by mass) | Isocyanate compound (parts by mass) | Additive (parts by mass) |
|---|---|---|---|---|
| Bio-electrode solution 1 | Ionic polymer 1 (4) | SSQ-pendant diol 1 solution (9) Hydroxy compound 1 (5) Hydroxy compound 2 (2) Hydroxy compound 4 (10) | Isocyanate compound 1 (12) | Carbon black (2) |
| Bio-electrode solution 2 | Ionic polymer 2 (6) | SSQ-pendant diol 2 solution (12) Hydroxy compound 3 (1) Hydroxy compound 5 (15) | Isocyanate compound 2 (9) | Carbon black (5) |
| Bio-electrode solution 3 | Ionic polymer 5 (5) | SSQ-pendant diol 5 solution (9) Hydroxy compound 3 (1) Hydroxy compound 6 (20) | Isocyanate compound 3 (4) | Carbon black (2) |
| Bio-electrode solution 4 | Ionic polymer 4 (5) | SSQ-pendant diol 4 solution (12) Hydroxy compound 7 (5) Hydroxy compound 3 (1) Hydroxy compound 4 (15) | Isocyanate compound 3 (9) | Carbon black (2) |
| Bio-electrode solution 5 | Ionic polymer 5 (6) | SSQ-pendant diol 5 solution (10) Hydroxy compound 7 (5) Hydroxy compound 3 (1) Hydroxy compound 4 (15) | Isocyanate compound 3 (9) | Carbon black (2) |
| Bio-electrode solution 6 | Ionic polymer 6 (6) | SSQ-pendant diol 4 solution (15) Hydroxy compound 4 (18) | Isocyanate compound 4 (1) Isocyanate compound 3 (2) | Carbon black (2) |
| Bio-electrode solution 7 | Ionic polymer 7 (6) | SSQ-pendant diol 4 solution (15) Hydroxy compound 4 (18) | Isocyanate compound 4 (1) Isocyanate compound 3 (2) | Carbon black (2) |

TABLE 1-continued

| Bio-electrode solution | Electro-conductive meterial (parts by mass) | Hydroxy compound (parts by mass) | Isocyanate compound (parts by mass) | Additive (parts by mass) |
|---|---|---|---|---|
| Bio-electrode solution 8 | Ionic polymer 8 (6) | SSQ-pendant diol 4 solution (15) Hydroxy compound 4 (18) | Isocyanate compound 4 (1) Isocyanate compound 3 (2) | Carbon black (2) |
| Bio-electrode solution 9 | Ionic polymer 9 (6) | SSQ-pendant diol 4 solution (15) Hydroxy compound 4 (18) | Isocyanate compound 4 (1) Isocyanate compound 3 (2) | Multilayer carbon nanotube (2) |
| Bio-electrode solution 10 | Ionic polymer 10 (6) | SSQ-pendant diol 4 solution (15) Hydroxy compound 4 (18) | Isocyanate compound 4 (1) Isocyanate compound 3 (2) | Ag-coated particle (6) |
| Bio-electrode solution 11 | Ionic polymer 11 (8) | SSQ-pendant diol 4 solution (15) Hydroxy compound 4 (18) | Isocyanate compound 4 (1) Isocyanate compound 3 (2) | Ag-coated particle (6) |
| Bio-electrode solution 12 | Ionic polymer 12 (2) | SSQ-pendant diol 4 solution (15) Hydroxy compound 4 (18) | Isocyanate compound 4 (1) Isocyanate compound 3 (2) | Carbon black (2) |
| Bio-electrode solution 13 | Ionic polymer 13 (6) | SSQ-pendant diol 4 solution (15) Hydroxy compound 4 (18) | Isocyanate compound 4 (1) Isocyanate compound 3 (2) | Carbon black (2) |
| Bio-electrode solution 14 | Ionic polymer 5 (6) | SSQ-pendant diol 4 solution (15) Hydroxy compound 4 (18) | Isocyanate compound 4 (1) Isocyanate compound 3 (2) | Carbon black (2) |
| Bio-electrode solution 15 | Ionic polymer 5 (6) | SSQ-pendant diol 6 solution (10) Hydroxy compound 7 (5) Hydroxy compound 3 (1) Hydroxy compound 4 (15) | Isocyanate compound 3 (9) | Carbon black (2) |
| Comparative bio-electrode solution 1 | Comparative ammonium 1 (2) | SSQ-pendant diol 4 solution (15) Hydroxy compound 4 (18) | Isocyanate compound 4 (1) Isocyanate compound 3 (2) | Carbon black (2) |
| Comparative bio-electrode solution 2 | Comparative ammonium 2 (2) | SSQ-pendant diol 4 solution (15) Hydroxy compound 4 (18) | Isocyanate compound 4 (1) Isocyanate compound 3 (2) | Carbon black (2) |
| Comparative bio-electrode solution 3 | Comparative ammonium 1 (4) | Hydroxy compound 4 (10) Hydroxy compound 2 (2) Hydroxy compound 4 (10) | Isocyanate compound 1 (10) | Carbon black (2) |

(Evaluation of Electric Conductivity)

Figure 3A:
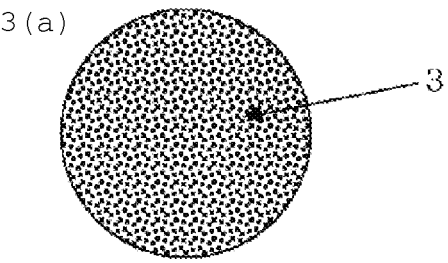
FIG. 3(a) is a schematic view of the bio-electrode produced in Examples of the present invention viewed from the living body contact layer side.
Figure 3B:
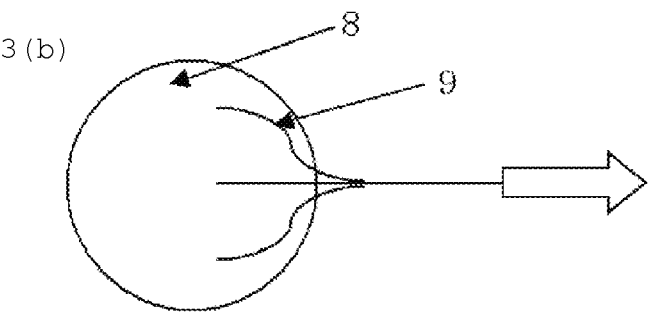
FIG. 3(b) is a schematic view of the bio-electrode produced in Examples of the present invention viewed from the electro-conductive base material side.
Figure 4:
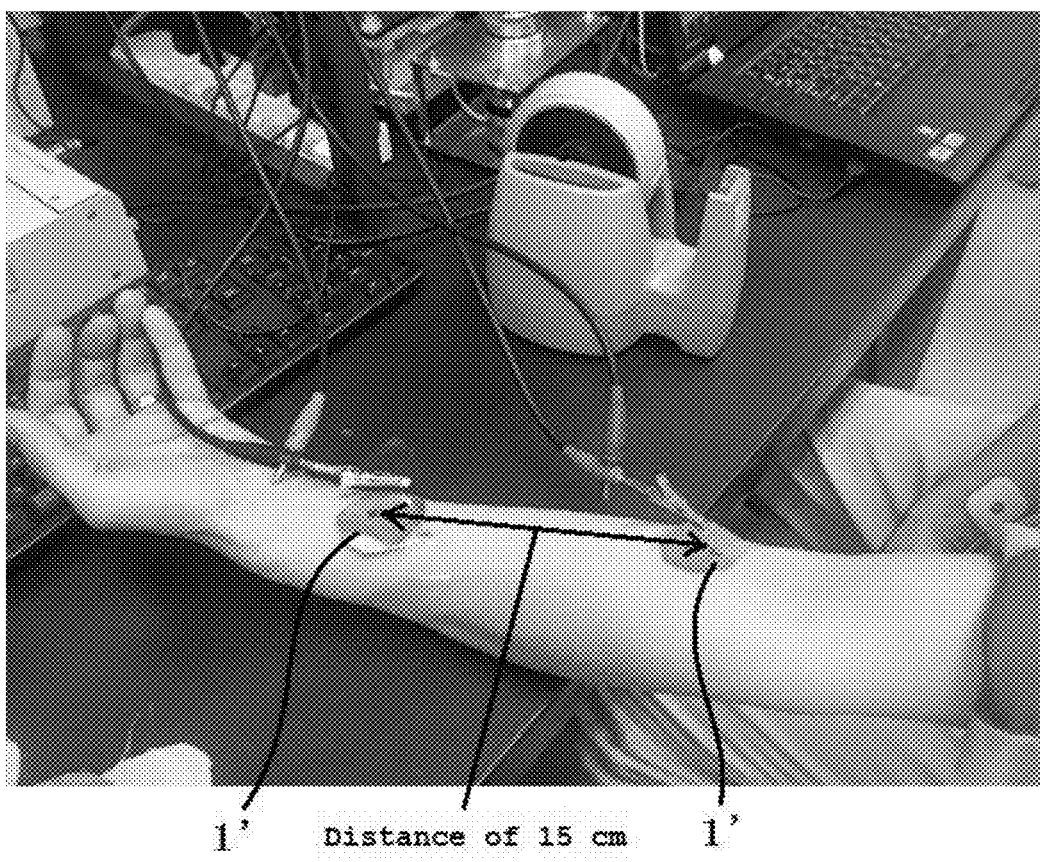
FIG. 4 is a photograph of a scene of measuring impedance on the surface of skin by using the bio-electrode produced in Examples of the present invention.

Each bio-electrode solution was applied onto an aluminum disk having a diameter of 3 cm and a thickness of 0.2 mm by using an applicator. This was baked at 120° C. for 60 minutes under a nitrogen atmosphere by using an oven to be cured, thereby producing four pieces of bio-electrodes for each bio-electrode solution. Thus obtained bio-electrode was provided with the living body contact layer 3 at one side and provided with the aluminum disk 8 at the other side as an electro-conductive base material as shown in FIGS. 3(a) and (b). Then, the copper wiring 9 was pasted on the surface of the aluminum disk 8 with self-adhesive tape at the side that was not coated with the living body contact layer to form a lead-out electrode, which was connected to an impedance measurement apparatus as shown in FIG. 3 (b). Two pieces of the bio-electrodes 1' were pasted on a human arm at a distance of 15 cm from each other such that the side of each living body contact layer was in contact with the skin as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above immediately after the immersion. Each impedance at the frequency of 1,000 Hz is shown in Table 2.

(Measurement of Thickness, Film Surface Tackiness, and Contact Angle of Living Body Contact Layer)

On each bio-electrode produced in the evaluation test of electric conductivity described above, the thickness of the living body contact layer was measured by using a micrometer. The film surface was touched by hand, and whether the film adhered to the hand or not was determined according to the sense of touch. The contact angle with water of the surface of each living body contact layer was measured by using a contact angle meter. The results are shown in Table 2.

magnitude after the water immersion and drying. That is, Examples 1 to 15 each gave a bio-electrode with higher initial electric conductivity without causing large change of the electric conductivity when it was wetted with water or dried. It was verified that incorporating the silsesquioxane-pendant urethane resin according to the present invention improved the tackiness on the film surface, achieving constant adhesion to skin.

On the other hand, each of Comparative Examples 1 and 2, in which the living body contact layer was formed using a bio-electrode containing a conventional salt, caused large increase of the impedance such that the order of magnitude was changed after the water immersion and drying although the initial impedance was low. That is, each of Comparative Examples 1 and 2 only gave a bio-electrode in which the electric conductivity largely lowered when it was wetted with water or dried although the initial electric conductivity was high. Comparative Example 3, in which no silsesquioxane-pendant urethane resin was contained whereas an ionic polymer was contained, exhibited lower contact angle with water, that is, higher hydrophilicity. As a result, the bio-electrode soaked up water after the water immersion to lower the impedance, causing a result that the impedance was changed due to an influence of water.

As described above, it was revealed that the bio-electrode, with the living body contact layer being formed by using the inventive bio-electrode composition, was excellent in electric conductivity, biocompatibility, and adhesion properties to an electro-conductive base material; excellent in holding the electro-conductive materials such as an ionic polymer and carbon black to prevent large lowering of electric conductivity even when it was wetted with water or dried; light in weight; and manufacturable at low cost.

TABLE 2

| Examples | Bio-electrode solution | Thickness of resin (μm) | Film surface tackiness | Contact angle (°) | Initial impedance (Ω) | Impedance after water immersion (Ω) |
| --- | --- | --- | --- | --- | --- | --- |
| Example 1 | Bio-electrode solution 1 | 350 | present | 85 | $5.6E^4$ | $5.5E^4$ |
| Example 2 | Bio-electrode solution 2 | 360 | present | 89 | $6.2E^4$ | $4.0E^4$ |
| Example 3 | Bio-electrode solution 3 | 430 | present | 90 | $7.2E^4$ | $8.3E^4$ |
| Example 4 | Bio-electrode solution 4 | 470 | present | 91 | $4.8E^4$ | $4.5E^4$ |
| Example 5 | Bio-electrode solution 5 | 310 | present | 93 | $6.6E^4$ | $5.5E^4$ |
| Example 6 | Bio-electrode solution 6 | 400 | present | 92 | $5.5E^4$ | $5.5E^4$ |
| Example 7 | Bio-electrode solution 7 | 380 | present | 90 | $6.5E^4$ | $6.6E^4$ |
| Example 8 | Bio-electrode solution 8 | 410 | present | 89 | $9.0E^3$ | $9.6E^3$ |
| Example 9 | Bio-electrode solution 9 | 350 | present | 90 | $6.2E^4$ | $6.1E^4$ |
| Example 10 | Bio-electrode solution 10 | 450 | present | 91 | $3.2E^4$ | $5.3E^4$ |
| Example 11 | Bio-electrode solution 11 | 420 | present | 91 | $4.7E^4$ | $5.1E^4$ |
| Example 12 | Bio-electrode solution 12 | 490 | present | 90 | $5.9E^4$ | $4.8E^4$ |
| Example 13 | Bio-electrode solution 13 | 460 | present | 91 | $6.7E^4$ | $6.1E^4$ |
| Example 14 | Bio-electrode solution 14 | 520 | present | 91 | $5.1E^4$ | $5.3E^4$ |
| Example 15 | Bio-electrode solution 15 | 500 | present | 93 | $6.1E^4$ | $6.3E^4$ |
| Comparative Example 1 | Comparative Bio-electrode solution 1 | 420 | present | 93 | $4.2E^4$ | $5.3E^6$ |
| Comparative Example 2 | Comparative Bio-electrode solution 2 | 430 | present | 93 | $5.2E^4$ | $7.3E^6$ |
| Comparative Example 3 | Comparative Bio-electrode solution 3 | 420 | absent | 70 | $5.1E^4$ | $2.3E^3$ |

As shown in Table 2, each of Examples 1 to 15, in which the inventive bio-electrode film was formed, exhibited higher contact angle with water and lower initial impedance, without causing large increase of impedance by an order of It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A bio-electrode composition comprising:
a resin containing a urethane bond in a main chain and a silsesquioxane in a side chain; and
an electro-conductive material,
wherein the electro-conductive material is a polymer compound having one or more repeating units selected from the group consisting of fluorosulfonic acid salts shown by the following general formulae (1)-1 and (1)-2, sulfonimide salts shown by the following general formula (1)-3, and sulfonamide salts shown by the following general formula (1)-4,

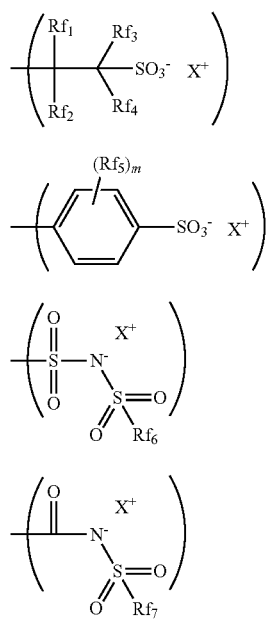

wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

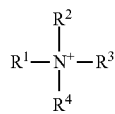 (1)-5 wherein $R^1$ to $R^4$ each represent a hydrogen atom, a linear, branched, or cyclic alkyl group having 1 to 20 carbon atoms, an ether group, a thiol group, an ester group, a carbonyl group, a sulfonyl group, a cyano group, an amino group, a nitro group, or an alkenyl group having 6 to 10 carbon atoms, optionally having a halogen atom, and optionally bonded to each other to form a ring.

2. The bio-electrode composition according to claim 1, wherein the one or more repeating units selected from the group consisting of fluorosulfonic acid salts shown by the general formulae (1)-1 and (1)-2, sulfonimide salts shown by the general formula (1)-3, and sulfonamide salts shown by the general formula (1)-4 are one or more repeating units selected from repeating units a1 to a7 shown by the following general formulae (2),

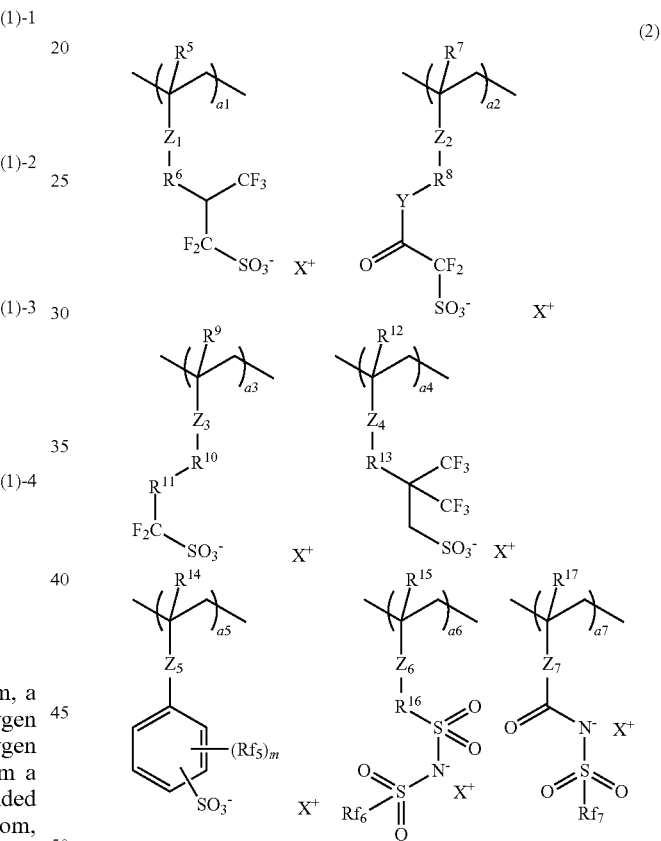

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, and $R^{16}$ each independently represent any of a single bond, an ester group, and a linear, branched, or cyclic hydrocarbon group having 1 to 12 carbon atoms and optionally having either or both of an ether group and an ester group; $R^{11}$ represents a linear or branched alkylene group having 1 to 4 carbon atoms, and one or two of the hydrogen atoms in $R^{11}$ are each optionally substituted with a fluorine atom; $Z_1$, $Z_2$, $Z_3$, $Z_4$, and $Z_6$ each independently represent any of a single bond, a phenylene group, a naphthylene group, an ether group, an ester group, and an amide group; $Z_5$ represents any of a single bond, an ether group, and an ester group; $Z_7$ represents a single bond, an arylene group having 6 to 12 carbon atoms, or —C(=O)—O—$Z^8$—;

Z⁸ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in Z⁸; Y represents an oxygen atom or an —NR¹⁸— group; R¹⁸ represents a hydrogen atom, or a linear or branched alkyl group having 1 to 4 carbon atoms, optionally bonded to R⁸ to form a ring; "m" is an integer of 1 to 4; a1, a2, a3, a4, a5, a6, and a7 satisfy 0≤a1≤1.0, 0≤a2≤1.0, 0≤a3≤1.0, 0≤a4≤1.0, 0≤a5≤1.0, 0≤a6≤1.0, 0≤a7≤1.0, and 0<a1+a2+a3+a4+a5+a6+a7 1.0; and Rf₅, Rf₆, Rf₇, and X⁺ have the same meanings as defined above.

3. The bio-electrode composition according to claim 1, wherein the electro-conductive material is a polymer compound having a repeating unit of a sulfonamide salt shown by the general formula (1)-4.

4. The bio-electrode composition according to claim 2, wherein the electro-conductive material is a polymer compound having a repeating unit of a sulfonamide salt shown by the general formula (1)-4.

5. The bio-electrode composition according to claim 1, wherein the resin containing a urethane bond in a main chain and a silsesquioxane in a side chain has a structure shown by the following general formula (3),

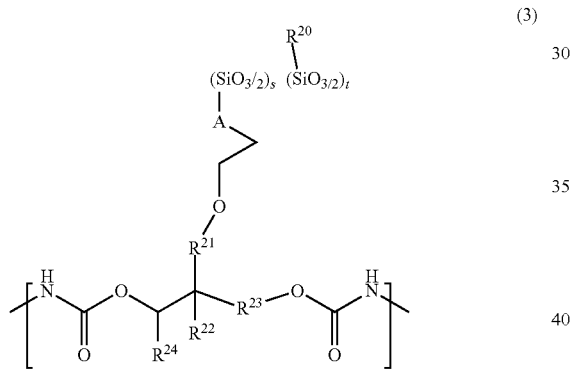

wherein R²⁰ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; R²¹ and R²³ each represent a single bond, a methylene group, or an ethylene group, provided that the total number of carbon atoms of R²¹ and R²³ is 1 or 2; R²² and R²⁴ each represent a hydrogen atom or a linear alkyl group having 1 to 4 carbon atoms; "A" represents a linear or branched alkylene group having 1 to 4 carbon atoms; and "s" and "t" satisfy 0<s≤0.2 and 0.8≤t<1.0.

6. The bio-electrode composition according to claim 2, wherein the resin containing a urethane bond in a main chain and a silsesquioxane in a side chain has a structure shown by the following general formula (3),

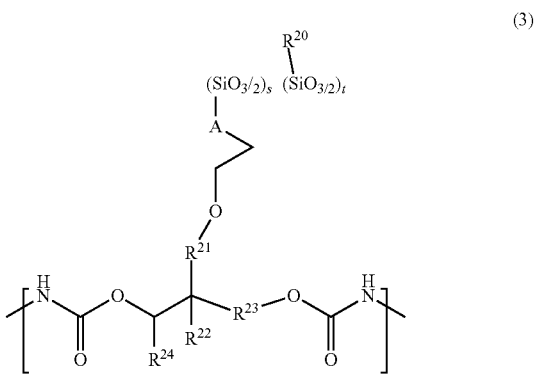

wherein R²⁰ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; R²¹ and R²³ each represent a single bond, a methylene group, or an ethylene group, provided that the total number of carbon atoms of R²¹ and R²³ is 1 or 2; R²² and R²⁴ each represent a hydrogen atom or a linear alkyl group having 1 to 4 carbon atoms; "A" represents a linear or branched alkylene group having 1 to 4 carbon atoms; and "s" and "t" satisfy 0<s≤0.2 and 0.8≤t<1.0.

7. The bio-electrode composition according to claim 1, wherein the resin containing a urethane bond in a main chain and a silsesquioxane in a side chain has a structure containing a polyether main chain shown by the following general formula (4),

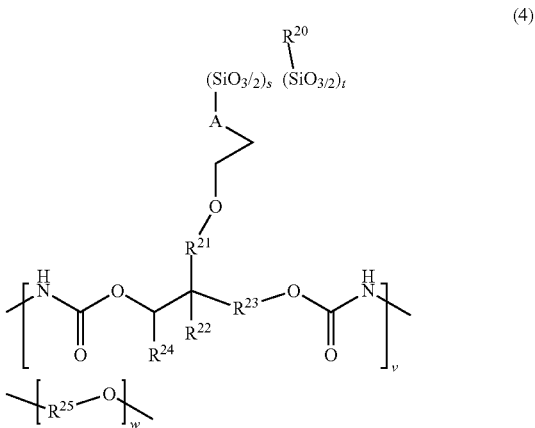

wherein R²⁰ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; "s" and "t" satisfy $0<s\leq0.2$ and $0.8\leq t<1.0$; $R^{25}$ represents a linear, branched, or cyclic alkylene group having 2 to 12 carbon atoms; and "v" and "w" satisfy $0<v<1.0$ and $0<w<1.0$.

8. The bio-electrode composition according to claim 2, wherein the resin containing a urethane bond in a main chain and a silsesquioxane in a side chain has a structure containing a polyether main chain shown by the following general formula (4),

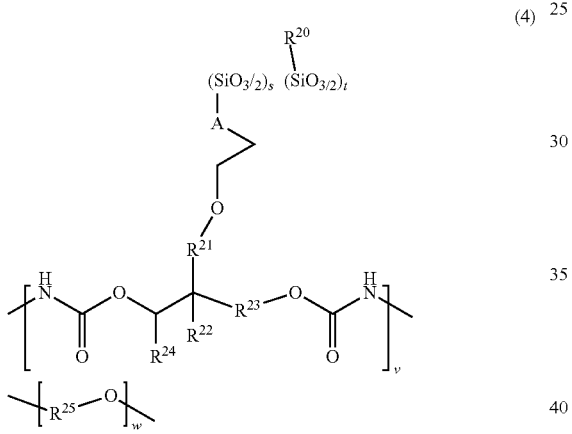

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; "s" and "t" satisfy $0<s\leq0.2$ and $0.8\leq t<1.0$; $R^{25}$ represents a linear, branched, or cyclic alkylene group having 2 to 12 carbon atoms; and "v" and "w" satisfy $0<v<1.0$ and $0<w<1.0$.

9. The bio-electrode composition according to claim 1, wherein the resin containing a urethane bond in a main chain and a silsesquioxane in a side chain is a reaction product of a diol compound shown by the following general formula (5), a polyether compound having a hydroxy group at a terminal, and a compound having an isocyanate group,

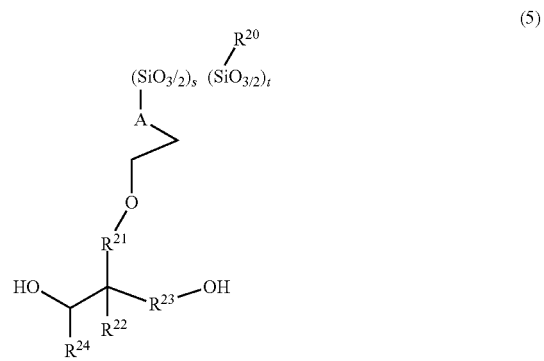

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0<s\leq0.2$ and $0.8\leq t<1.0$.

10. The bio-electrode composition according to claim 2, wherein the resin containing a urethane bond in a main chain and a silsesquioxane in a side chain is a reaction product of a diol compound shown by the following general formula (5), a polyether compound having a hydroxy group at a terminal, and a compound having an isocyanate group,

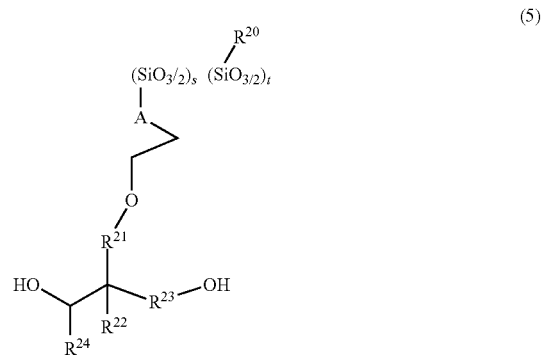

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{21}$ and $R^{23}$ each represent a single bond, a methylene group, or an ethylene group, provided that the total number of carbon atoms of $R^{21}$ and $R^{23}$ is 1 or 2; $R^{22}$ and $R^{24}$ each represent a hydrogen atom or a linear alkyl group having 1 to 4 carbon atoms; "A" represents a linear or branched alkylene group having 1 to 4 carbon atoms; and "s" and "t" satisfy $0<s\leq0.2$ and $0.8\leq t<1.0$.

11. The bio-electrode composition according to claim 1, wherein the resin containing a urethane bond in a main chain and a silsesquioxane in a side chain is a reaction product of a diol compound shown by the following general formula (6) and a compound having an isocyanate group,

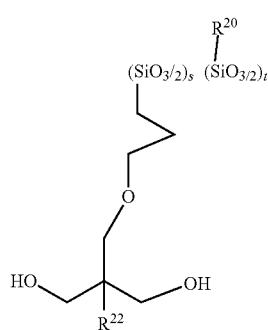

(6)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{22}$ represents a hydrogen atom or a linear alkyl group having 1 to 4 carbon atoms; and "s" and "t" satisfy $0<s\leq0.2$ and $0.8\leq t<1.0$.

12. The bio-electrode composition according to claim 2, wherein the resin containing a urethane bond in a main chain and a silsesquioxane in a side chain is a reaction product of a diol compound shown by the following general formula (6) and a compound having an isocyanate group,

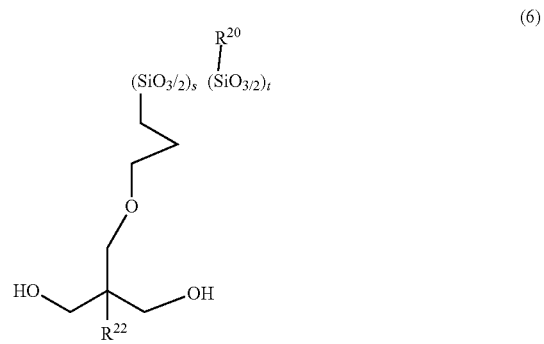

(6)

wherein $R^{20}$ represents a linear, branched, or cyclic alkyl group having 1 to 24 carbon atoms, an alkenyl group having 2 to 10 carbon atoms, an alkynyl group having 2 to 10 carbon atoms, or a substituted or unsubstituted aryl group having 6 to 10 carbon atoms, optionally substituted with a halogen atom, an amino group, a cyano group, or a mercapto group, and optionally having an ether group, a carbonyl group, an acid anhydride group, an amide group, a nitrogen atom, or a sulfur atom, provided that the aryl group is optionally substituted with a halogen atom, a nitro group, or a linear, branched, or cyclic alkyl group having 1 to 6 carbon atoms; $R^{22}$ represents a hydrogen atom or a linear alkyl group having 1 to 4 carbon atoms; and "s" and "t" satisfy $0<s\leq0.2$ and $0.8\leq t<1.0$.

13. The bio-electrode composition according to claim 11, wherein the diol compound shown by the general formula (6) is a reaction product of substances shown by the following general formulae (7)-1 and (7)-2,

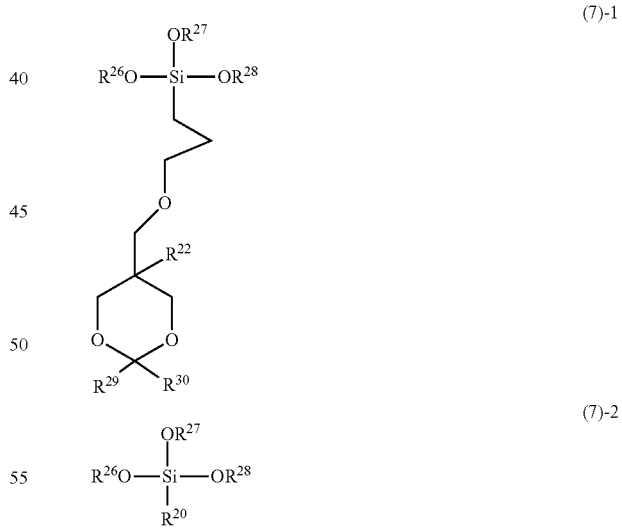

wherein $R^{20}$ and $R^{22}$ have the same meanings as defined above; $R^{26}$ to $R^{28}$ each represent an alkyl group having 1 to 6 carbon atoms; and $R^{29}$ and $R^{30}$ each represent a hydrogen atom, a linear, branched, or cyclic alkyl group having 1 to 20 carbon atoms and optionally bonded to the other to form a ring, or an aryl group having 6 to 10 carbon atoms.

14. The bio-electrode composition according to claim 1, further comprising an organic solvent.

15. The bio-electrode composition according to claim 1, further comprising a carbon material.

16. The bio-electrode composition according to claim 15, wherein the carbon material is either or both of carbon black and carbon nanotube.

17. A bio-electrode comprising an electro-conductive base material and a living body contact layer formed on the electro-conductive base material,
   wherein the living body contact layer is a cured material of the bio-electrode composition according to claim 1.

18. The bio-electrode according to claim 17, wherein the electro-conductive base material comprises one or more species selected from gold, silver, silver chloride, platinum, aluminum, magnesium, tin, tungsten, iron, copper, nickel, stainless steel, chromium, titanium, and carbon.

19. A method for manufacturing a bio-electrode having an electro-conductive base material and a living body contact layer formed on the electro-conductive base material, comprising:
   applying the bio-electrode composition according to claim 1 onto the electro-conductive base material; and
   curing the bio-electrode composition; thereby forming the living body contact layer.

20. The method for manufacturing a bio-electrode according to claim 19, wherein the electro-conductive base material comprises one or more species selected from gold, silver, silver chloride, platinum, aluminum, magnesium, tin, tungsten, iron, copper, nickel, stainless steel, chromium, titanium, and carbon.

* * * * *